US012799527B2

(12) United States Patent
Tan et al.

(10) Patent No.: US 12,799,527 B2
(45) Date of Patent: Nov. 17, 2026

(54) CRISPR-BASED METHODS FOR THE DETECTION OF NUCLEIC ACIDS IN A SAMPLE

(71) Applicants: Nanyang Technological University, Singapore (SG); Agency for Science, Technology and Research, Singapore (SG)

(72) Inventors: Meng How Tan, Singapore (SG); Kean Hean Ooi, Singapore (SG); Jie Wen Douglas Tay, Singapore (SG); Seok Yee Teo, Singapore (SG)

(73) Assignees: Nanyang Technological University, Singapore (SG); Agency for Science, Technology and Research, Singapore (SG)

( * ) Notice: Subject to any disclaimer, the term of this patent is extended or adjusted under 35 U.S.C. 154(b) by 819 days.

(21) Appl. No.: 18/003,126

(22) PCT Filed: Jun. 25, 2021

(86) PCT No.: PCT/SG2021/050371
§ 371 (c)(1),
(2) Date: Dec. 22, 2022

(87) PCT Pub. No.: WO2021/262099
PCT Pub. Date: Dec. 30, 2021

(65) Prior Publication Data

US 2023/0323439 A1 Oct. 12, 2023

(30) Foreign Application Priority Data

Jun. 26, 2020 (SG) .......................... 10202006167W

(51) Int. Cl.
*C12Q 1/68* (2018.01)
*C12N 15/10* (2006.01)
(Continued)

(52) U.S. Cl.
CPC ........... *C12Q 1/6844* (2013.01); *C12N 15/10* (2013.01); *C12Q 1/70* (2013.01); *C12N 2310/20* (2017.05)

(58) Field of Classification Search
None
See application file for complete search history.

(56) References Cited

U.S. PATENT DOCUMENTS 6,410,278 B1 6/2002 Notomi et al.
7,374,913 B2 5/2008 Nagamine
(Continued)

FOREIGN PATENT DOCUMENTS

WO 2018195545 A2 10/2018

OTHER PUBLICATIONS

Abudayyeh et al., "C2c2 is a single-component programmable RNA-guided RNA-targeting CRISPR effector," *Science* 353(6299):557-567, Aug. 5, 2016. (Epub Jun. 2, 2016).
(Continued)

*Primary Examiner* — Aaron A Priest
(74) *Attorney, Agent, or Firm* — Seed Intellectual Property Law Group LLP

(57) ABSTRACT

The present invention is in the field of molecular diagnostics and is directed to the detection of target nucleic acids in a sample using a modified CRISPR-Dx system, typically with prior amplification of the target. The modified CRISPR-Dx system comprising an engineered E174R/S542R/K548R variant of AsCas12a, wherein when get activated indiscriminately cleaves at least one detection reagent to generate signal. In one embodiment, the target nucleic acid is SARS-CoV-2 RNA.

19 Claims, 89 Drawing Sheets

Specification includes a Sequence Listing.

(51) Int. Cl.
*C12Q 1/6844* (2018.01)
*C12Q 1/70* (2006.01)

(56) References Cited

U.S. PATENT DOCUMENTS

| | | | | |
|---|---|---|---|---|
| 10,266,886 B2* | 4/2019 | Abudayyeh | C12N 9/22 |
| 2017/0107549 A1* | 4/2017 | Martineau | C12Q 1/6844 |
| 2019/0010481 A1* | 1/2019 | Joung | C12N 15/62 |
| 2019/0241954 A1* | 8/2019 | Doudna | C12N 15/11 |
| 2020/0254443 A1* | 8/2020 | Zhang | C12Q 1/6816 |
| 2021/0108267 A1* | 4/2021 | Zhang | C12N 15/11 |
| 2021/0292824 A1* | 9/2021 | Zhang | C12N 9/78 |
| 2021/0371926 A1* | 12/2021 | Zhang | C12Q 1/6827 |
| 2022/0073987 A1* | 3/2022 | Freije | C12Q 1/6883 |
| 2023/0203567 A1* | 6/2023 | Kim | C12N 15/1137 435/6.11 |

OTHER PUBLICATIONS

Ackerman et al., "Massively multiplexed nucleic acid detection with Cas13," *Nature* 582:277-303, Jun. 11, 2020.

Altschul et al., "Basic Local Alignment Search Tool," *J. Mol. Biol.* 215:403-410, May 1990.

Altschul et al., "Gapped BLAST and PSI-BLAST: a new generation of protein database search programs," *Nucleic Acids Research* 25(17):3389-3402, Jul. 1997.

Anahtar et al., "Clinical assessment and validation of a rapid and sensitive SARS-CoV-2 test using reverse-transcription loop-mediated isothermal amplification," *medRxiv preprint,* URL= https://doi.org/10.1101/2020.05.12.20095638, posted May 18, 2020.

Azhar et al., "Rapid, field-deployable nucleobase detection and identification using FnCas9," *bioRxiv preprint,* URL= https://doi.org/10.1101/2020.04.07.028167; Apr. 9, 2020. (28 pages).

Baek et al., "Development of a reverse transcription-loop-mediated isothermal amplification as a rapid early-detection method for novel SARS-COV-2," *Emerging Microbes & Infections* 9, May 2020. (11 pages).

Bai et al., "Presumed Asymptomatic Carrier Transmission of COVID-19," *JAMA* 323(14):1406-1407, Apr. 14, 2020. (Epub Feb. 21, 2020).

Ben-Assa et al., "SARS-CoV-2 On-the-Spot Virus Detection Directly from Patients," *medRxiv preprint,* URL= https://doi.org/10.1101/2020.04.22.20072389; posted May 7, 2020, 13 pages.

Bhadra et al., "High-surety isothermal amplification and detection of SARS-CoV-2, including with crude enzymes," *bioRxiv preprint,* URL= https://doi.org/10.1101/2020.04.13.039941, posted Jul. 7, 2020, 15 pages.

Broughton et al., "CRISPR-Cas12-based detection of SARS-CoV-2," *Nature Biotechnology* 38:870-874, Jul. 2020.

Butler et al., "Shotgun Transcriptome and Isothermal Profiling of SARS-CoV-1 2 Infection Reveals Unique 2 Host Responses, Viral Diversification, and Drug Interactions," *bioRxiv preprint,* URL= https://doi.org/10.1101/2020.04.20.048066; May 1, 2020.

Cavallo et al., "D936Y and Other Mutations in the Fusion Core of the SARS-Cov-2 Spike Protein Heptad Repeat 1 Undermine the Post-Fusion Assembly," *bioRxiv preprint,* URL= https://doi.org/10.1101/2020.06.08.140152; posted Jun. 9, 2020, 24 pages.

Chen et al., "CRISPR-Cas12a target binding unleashes indiscriminate single-stranded DNase activity," *Science* 360:436-439, Apr. 27, 2018. (Epub Feb. 15, 2018).

Chenna et al., "Multiple sequence alignment with the Clustal series of programs," *Nucleic Acids Research* 31(13):3497-3500, Mar. 2003.

Dao Thi et al., "Screening for SARS-CoV-2 infections with colorimetric RT-LAMP and LAMP sequencing," *medRxiv preprint,* URL= https://doi.org/10.1101/2020.05.05.20092288; posted May 9, 2020.

Devi et al., "Comparative genomics and diversity of SARS-CoV-2 suggest potential regional virulence," *Research square,* URL= https://doi.org/10.21203/rs.3.rs-29557/v1, May 2020, 23 pages.

Di Giorgio et al., "Evidence for host-dependent RNA editing in the transcriptome of SARS-CoV-2," *Science Advances* 6(eabb5813), Jun. 17, 2020. (8 pages).

Ding et al., "All-in-One Dual CRISPR-Cas12a (AIOD-CRISPR) Assay: A Case for Rapid, Ultrasensitive and Visual Detection of Novel Coronavirus SARS-CoV-2 and HIV virus," *bioRxiv preprint,* URL= https://doi.org/10.1101/2020.03.19.998724; posted Mar. 21, 2020. (19 pages).

East-Seletsky et al., "Two distinct RNase activities of CRISPR-C2c2 enable guide-RNA processing and RNA detection," *Nature* 538:270-286, Oct. 13, 2016.

Elbe et al., "Data, disease and diplomacy: GISAID's innovative contribution to global health," *Data, Disease and Diplomacy*:33-46, Nov. 2017.

El-Tholoth et al., "A Single and Two-Stage, Closed-Tube, Molecular Test for the 2019 Novel Coronavirus (COVID-19) at Home, Clinic, and Points of Entry," doi:10.26434/chemrxiv.11860137.v1, Feb. 2020, 21 pages.

Gandleman et al., "Loop-Mediated Amplification Accelerated by Stem Primers," *Int. J. Mol. Sci.* 12:9108-9124, Dec. 2011.

Gootenberg et al., "Nucleic acid detection with CRISPR-Cas13a/C2c2," *Science* 356:438-442, Apr. 28, 2017. (Epub Apr. 13, 2017).

Gootenberg et al., "Multiplexed and portable nucleic acid detection platform with Cas13, Cas12a, and Csm6," *Science* 360:439-444, Apr. 27, 2018. (6 pages).

Guo et al., "SARS-CoV-2 detection with CRISPR diagnostics," *Cell Discovery* 6(34), Apr. 2020. (4 pages).

Hajian et al., "Detection of unamplified target genes via CRISPR-Cas9 immobilized on a graphene field-effect transistor," *Nature Biomedical Engineering* 3:427-437, Jun. 2019.

Harrington et al., "Programmed DNA destruction by miniature CRISPR-Cas14 enzymes," *Science* 362:839-842, Nov. 16, 2018. (4 pages).

Hou et al., "Development and Evaluation of A CRISPR-based Diagnostic 1 For 2019-novel Coronavirus," *medRxiv preprint,* URL= https://doi.org/10.1101/2020.02.22.20025460; posted Feb. 25, 2020. (22 pages).

Huang et al., "RT-LAMP for rapid diagnosis of coronavirus SARS-CoV-2," *Biotechnology* 13:950-961, Apr. 2020.

Joung et al., "Detection of SARS-COV-2 with SHERLOCK One-Pot Testing," *N Eng J Med* 383, Sep. 2020. (4 pages).

Joung et al., "Point-of-care testing for COVID-19 using SHERLOCK diagnostics," medRxiv preprint (v.20200505), URL= https://doi.org/10.1101/2020.05.04.20091231; posted May 8, 2020. (21 pages).

Kim et al., "The Architecture of SARS-CoV-2 Transcriptome," *Cell* 181:914-921, May 14, 2020.

Klienstiver et al., "Genome-wide specificities of CRISPR-Cas Cpf1 nucleases in human cells," *Nature Biotechnology* 34(8):869-874, Aug. 16, 2016.

Klienstiver et al., "Engineered CRISPR-Cas12a variants with increased activities and improved targeting ranges for gene, epigenetic and base editing," *Nature Biotechnology* 37:276-282, Mar. 2019.

Koyama et al., "Emergence of Drift Variants That May Affect COVID-19 Vaccine Development and Antibody Treatment," *Pathogens* 9(324), Apr. 2020. (7 pages).

Lalli et al., "Rapid and Extraction-Free Detection of SARS-CoV-2 from Saliva by Colorimetric Reverse-Transcription Loop-Mediated Isothermal Amplification," *Clinical Chemistry* 67(2):415-424, Feb. 2021.

Lalli et al., "Rapid and extraction-free detection of SARS-CoV-2 from saliva with colorimetric LAMP," *medRxiv preprint,* URL= https://doi.org/10.1101/2020.05.07.20093542; posted Aug. 6, 2020, 34 pages.

Lamb et al., "Rapid Detection of Novel Coronavirus (COVID-19) by Reverse Transcription-Loop-Mediated Isothermal Amplification," *medRxiv preprint,* URL= https://doi.org/10.1101/2020.02.19.20025155; posted Feb. 24, 2020, 17 pages.

Lapierre et al., "rpoB Targeted Loop-Mediated Isothermal Amplification (LAMP) Assay for Consensus Detection of Mycobacteria Associated With Pulmonary Infections," *Frontiers in Medicine* 5(332), Nov. 2018. (8 pages).

(56) References Cited

OTHER PUBLICATIONS

Li et al., "Early Transmission Dynamics in Wuhan, China, of Novel Coronavirus-Infected Pneumonia," *N Engl J Med* 382(13):1199-1207, Mar. 26, 2020. (Epub Jan. 29, 2020).
Li et al., "Rapid detection of SARS-CoV-2 and other respiratory viruses by using LAMP method with Nanopore Flongle workflow," *bioRxiv preprint,* URL= https://doi.org/10.1101/2020.06.03.131474; posted Jun. 3, 2020, 13 pages.
Lu et al., "Development of a Novel Reverse Transcription Loop-Mediated Isothermal Amplification Method for Rapid Detection of SARS-CoV-2," *Virologica Sinica* 35:344-347, Apr. 2020.
Lucia et al., "An ultrasensitive, rapid, and portable coronavirus SARS-CoV-2 sequence detection method based on CRISPR-Cas12," *medRxiv preprint,* URL= https://doi.org/10.1101/2020.02.29.971127; posted Mar. 2, 2020. (10 pages).
Martineau et al., "Improved Performance of Loop-Mediated Isothermal Amplification Assays via Swarm Priming," *Anal. Chem.* 89:625-632, Jan. 2017.
McMahon et al., "Chemically Modified Cpf1-CRISPR RNAs Mediate Efficient Genome Editing in Mammalian Cells," *Molecular Therapy* 26(5):1228-1240, May 2018.
Mir et al., "Heavily and fully modified RNAs guide efficient SpyCas9-mediated genome editing," *Nature Communications* 9(2641), Jul. 2018. (9 pages).
Moon et al., "Highly efficient genome editing by CRISPR-Cpf1 using CRISPR RNA with a uridinylate-rich 3'-overhang," *Nature Communications* 9(3651), Sep. 2018. (11 pages).
Myhrvold et al., "Field-deployable viral diagnostics using CRISPR-Cas13," *Science* 360:444-448, Apr. 27, 2018.
Nagamine et al., "Accelerated reaction by loop-mediated isothermal amplification using loop primers," *Molecular and Cellular Probes* 16:223-229, Mar. 2002.
Nguyen et al., "Enhancement of trans-cleavage activity of Cas12a with engineered crRNA enables amplified nucleic acid detection," *Nature Communications* 11(4906), Sep. 2020. (13 pages).
Notomi et al., "Loop-mediated isothermal amplification of DNA" *Nucleic Acids Research* 28(12), Apr. 2000. (7 pages).
Notredame et al., "T-Coffee: A Novel Method for Fast and Accurate Multiple Sequence Alignment," *J. Mol. Biol.* 302:205-217, Jul. 2000.
Ooi et al., "An engineered CRISPR-Cas12a variant and DNA-RNA hybrid guides enable robust and rapid COVID-19 testing," *Nature Communications* 12(1739), May 2021. (23 pages).
Ooi et al., "VaNGuard assay protocol for SARS-CoV-2 detection," URL=https://doi.org/10.21203/rs.3.pex-1373/v1, Mar. 2021, 5 pages.
Parida et al., "Loop mediated isothermal amplification (LAMP): a new generation of innovative gene amplification technique; perspectives in clinical diagnosis of infectious diseases," *Rev. Med. Virol.* 18:407-421, Jul. 2008.
Park et al., "Extension of the crRNA enhances Cpf1 gene editing in vitro and in vivo," *Nature Communications* 9(3313), Aug. 2018. (12 pages).
Park et al., "Development of Reverse Transcription Loop-Mediated Isothermal Amplification Assays Targeting Severe Acute Respiratory Syndrome Coronavirus 2 (SARS-CoV-2)," *The Journal of Molecular Diagnostics* 22(6), Jun. 2020. (7 pages).
Piepenburg et al., "DNA Detection Using Recombination Proteins," *PLoS Biology* 4(7), Jul. 2006. (7 pages).
Rahdar et al., "Synthetic CRISPR RNA-Cas9-guided genome editing in human cells," *PNAS*:E7110-E7117, Published Online Nov. 16, 2015, 8 pages.
Rauch et al., "A Scalable, Easy-to-Deploy, Protocol for Cas13-Based Detection of SARS-CoV-2 Genetic Material," *bioRxiv preprint,* URL= https://doi.org/10.1101/2020.04.20.052159; Apr. 21, 2020. (7 pages).
Rothe et al., "Transmission of 2019-nCoV Infection from an Asymptomatic Contact in Germany," *N Engl J Med* 382(10):970-971, Mar. 5, 2020. (Epub Jan. 30, 2020).
Shu et al., "GISAID: Global initiative on sharing all influenza data—from vision to reality," *Euro Surveill* 22(13), Mar. 2017. (3 pages).
Sun et al., "Smartphone-based multiplex 30-minute nucleic acid test of live virus from nasal swab extract†," *Lab Chip* 20:1621-1627, Apr. 2020.
Teng et al., "CDetection: CRISPR-Cas12b-based DNA detection with sub-attomolar sensitivity and single-base specificity," *Genome Biology* 20(132), Jul. 2019. (7 pages).
Van Dorp et al., "Emergence of genomic diversity and recurrent mutations in SARS-CoV-2," *Infection, Genetics and Evolution* 83, Sep. 2020. (9 pages).
Vogels et al., "SalivaDirect: Simple and sensitive molecular diagnostic test for SARS-CoV-2 surveillance," *medRxiv preprint,* URL= https://doi.org/10.1101/2020.08.03.20167791; posted Aug. 4, 2020, 26 pages.
Vincent et al., "Helicase-dependent isothermal DNA amplification," *EMBO reports* 5(8):795-800, Jul. 2004.
Wang et al., "Two Methods for Increased Specificity and Sensitivity in Loop-Mediated Isothermal Amplification," *Molecules* 20:6048-6059, Apr. 2015.
Wang et al., "A novel coronavirus outbreak of global health concern," *The Lancet* 395:470-474, Feb. 14, 2020. (Epub Jan. 24, 2020) URL= https://doi.org/10.1016/S0140-6736(20)30185-9.
Wang et al., "Mutations on COVID-19 diagnostic targets," *Genomics* 112:5204-5213, Nov. 2020.
Wu et al., "Genome Composition and Divergence of the Novel Coronavirus (2019-nCoV) Originating in China," *Cell Host & Microbe* 27:325-328, Mar. 11, 2020.
Yamano et al., "Crystal structure of Cpfl in complex with guide RNA and target DNA," *Cell* 165(4):949-962, May 5, 2016.
Yan et al., "Rapid and visual detection of 2019 novel coronavirus (SARS-CoV-2) by a reverse transcription loop-mediated isothermal amplification assay," *Clinical Microbiology and Infection* 26:773-779, Apr. 2020.
Yang et al., "Genetic cluster analysis of SARS-CoV-2 and the identification of those responsible for the major outbreaks in various countries," *Emerging Microbes & Infections* 9, Jun. 2020. (14 pages).
Yin et al., "Structure-guided chemical modification of guide RNA enables potent non-viral in vivo genome editing," *Nature Biotechnology* 35(12):1179-1190, Dec. 2017.
Yin et al., "Partial DNA-guided Cas9 enables genome editing with reduced off-target activity," *Nature Chemical Biology* 14:311-321, Mar. 2018.
Yu et al., "Rapid detection of COVID-19 coronavirus using a reverse transcriptional loop-mediated isothermal amplification (RT-LAMP) diagnostic platform," *American Association for Clinical Chemistry,* Jul. 2020. (8 pages).
Zhang et al., "Rapid Molecular Detection of SARS-CoV-2 (COVID-19) Virus RNA Using Colorimetric LAMP," *medRxiv preprint,* URL= https://doi.org/10.1101/2020.02.26.20028373; posted Feb. 29, 2020, 14 pages.
Zhang et al., "Enhancing colorimetric loop-mediated isothermal amplification speed and sensitivity with guanidine chloride," *Bio Techniques* 69:179-185, Sep. 2020.
Zhou et al., "A pneumonia outbreak associated with a new coronavirus of probable bat origin," *Nature* 579: 270-289, Mar. 12, 2020. (Epub Feb. 3, 2020).
Zhou et al., "A Mismatch-Tolerant Reverse Transcription Loop-Mediated Isothermal Amplification Method and Its Application on Simultaneous Detection of All Four Serotype of Dengue Viruses," *Frontiers in Microbiology* 10(1056), May 2019. (13 pages).
Zhu et al., "A Novel Coronavirus from Patients with Pneumonia in China, 2019," *N Engl J Med* 382(8):727-733, Feb. 20, 2020.

* cited by examiner b b

F3

| | |
|---|---|
| PM | TTAATTTAGTGCGTGATCTCC |
| MM1 | TTAATTTAGTGCGTGATCTCA |
| MM2 | TTAATTTAGTGCGTGATCTAC |
| MM3 | TTAATTTAGTGCGTGATCGCC |

B3

| | |
|---|---|
| PM | AGCATCTGTAATGGTTCCAT |
| MM1 | AGCATCTGTAATGGTTCCAG |
| MM2 | AGCATCTGTAATGGTTCCCT |
| MM3 | AGCATCTGTAATGGTTCAAT |

FIP

| | |
|---|---|
| PM | TGTAAAGCAAGTAAAGTTTGAAACCCTCAGGGTTTTTCGGCT |
| MM1 (3') | TGTAAAGCAAGTAAAGTTTGAAACCCTCAGGGTTTTTCGGCG |
| MM2 (3') | TGTAAAGCAAGTAAAGTTTGAAACCCTCAGGGTTTTTCGGAT |
| MM3 (3') | TGTAAAGCAAGTAAAGTTTGAAACCCTCAGGGTTTTTCGTCT |
| MM1 (5') | GGTAAAGCAAGTAAAGTTTGAAACCCTCAGGGTTTTTCGGCT |
| MM2 (5') | TTTAAAGCAAGTAAAGTTTGAAACCCTCAGGGTTTTTCGGCT |
| MM3 (5') | TGGAAAGCAAGTAAAGTTTGAAACCCTCAGGGTTTTTCGGCT |
| tPM-3 | TGTAAAGCAAGTAAAGTTTGAAACCCTCAGGGTTTTTCGGC |
| tPM-5 | GTAAAGCAAGTAAAGTTTGAAACCCTCAGGGTTTTTCGGCT |

BIP

| | |
|---|---|
| PM | TGGACAGCTGGTGCTAATAGAAAAGTCCTAGGTTGAAG |
| MM1 (3') | TGGACAGCTGGTGCTAATAGAAAAGTCCTAGGTTGAAT |
| MM2 (3') | TGGACAGCTGGTGCTAATAGAAAAGTCCTAGGTTGACG |
| MM3 (3') | TGGACAGCTGGTGCTAATAGAAAAGTCCTAGGTTGCAG |
| MM1 (5') | GGGACAGCTGGTGCTAATAGAAAAGTCCTAGGTTGAAG |
| MM2 (5') | TTGACAGCTGGTGCTAATAGAAAAGTCCTAGGTTGAAG |
| MM3 (5') | TGTACAGCTGGTGCTAATAGAAAAGTCCTAGGTTGAAG |
| tPM-3 | TGGACAGCTGGTGCTAATAGAAAAGTCCTAGGTTGAA |

Figure 21 (cont.)

| | | | | | | | |
|---|---|---|---|---|---|---|---|
| F3 | 0.2 | 0.2 | 0.4 | 0.2 | 0.2 | 0.2 | 0.2 |
| B3 | 0.2 | 0.2 | 0.2 | 0.4 | 0.2 | 0.2 | 0.2 |
| FIP (PM) | 1.6 | 0.8 | 0.8 | 0.8 | 1.6 | 0.8 | 0.8 |
| FIP (tPM-3) | - | 0.8 | 0.8 | 0.8 | 1.6 | 0.8 | 0.8 |
| BIP (PM) | 1.6 | 0.8 | 0.8 | 0.8 | 0.8 | 1.6 | 0.8 |
| BIP (tPM-3) | - | 0.8 | 0.8 | 0.8 | 0.8 | 1.6 | 0.8 |
| LF | 0.8 | 0.8 | 0.8 | 0.8 | 0.8 | 0.8 | 0.8 |
| LB | 0.8 | 0.8 | 0.8 | 0.8 | 0.8 | 0.8 | 0.8 |

a

| | Spacer |
|---|---|
| Original | UAAUUUCUACUCUUGUAGAUACUCCUGGUGAUUCUUCUUC |
| 5'ext(+4) | UGGAUAAUUUCUACUCUUGUAGAUACUCCUGGUGAUUCUUCUUC |
| 5'ext(+9) | GGGAAUGGAUAAUUUCUACUCUUGUAGAUACUCCUGGUGAUUCUUCUUC |
| Chem mod | mC*U*UAAUUUCUACUCUUGUAGAUACUCCUGGUGAUUCUUCUUC |
| 2DNA-RNA | UAAUUUCUACUCUUGUAGAUACUCCUGGUGAUUCUUCUTC |
| 4DNA-RNA | UAAUUUCUACUCUUGUAGAUACUCCUGGUGAUUCUUCUTC |

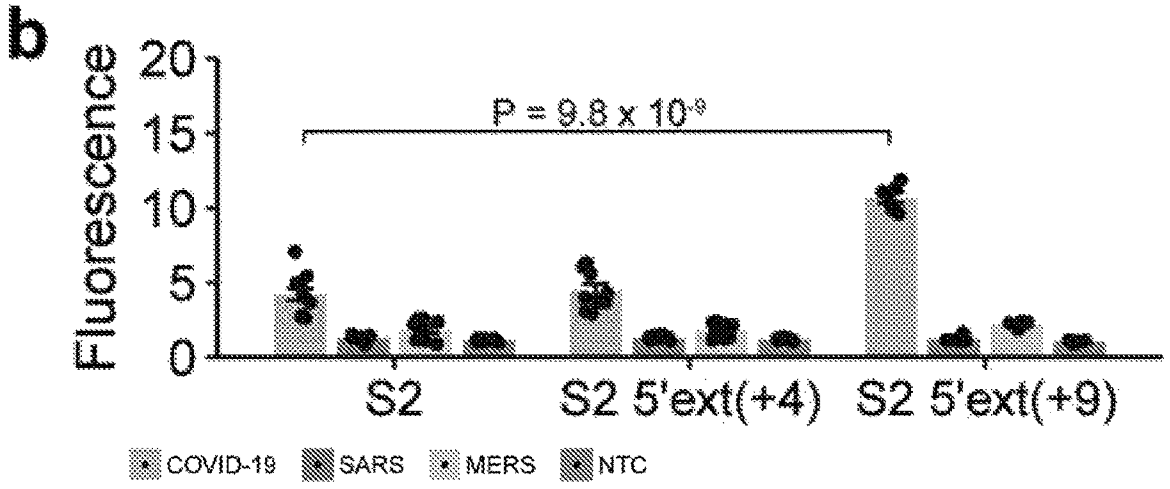

Figure 49 d

SEQUENCE LISTING

<160> NUMBER OF SEQ ID NOS: 290

<210> SEQ ID NO 1
<211> LENGTH: 1307
<212> TYPE: PRT
<213> ORGANISM: Artificial
<220> FEATURE:
<223> OTHER INFORMATION: engineered AsCas12a

<400> SEQUENCE: 1

Met Thr Gln Phe Glu Gly Phe Thr Asn Leu Tyr Gln Val Ser Lys Thr
1 5 10 15

Leu Arg Phe Glu Leu Ile Pro Gln Gly Lys Thr Leu Lys His Ile Gln
20 25 30

Glu Gln Gly Phe Ile Glu Glu Asp Lys Ala Arg Asn Asp His Tyr Lys
35 40 45

Glu Leu Lys Pro Ile Ile Asp Arg Ile Tyr Lys Thr Tyr Ala Asp Gln
50 55 60

Cys Leu Gln Leu Val Gln Leu Asp Trp Glu Asn Leu Ser Ala Ala Ile
65 70 75 80

Asp Ser Tyr Arg Lys Glu Lys Thr Glu Glu Thr Arg Asn Ala Leu Ile
85 90 95

Glu Glu Gln Ala Thr Tyr Arg Asn Ala Ile His Asp Tyr Phe Ile Gly
100 105 110

Arg Thr Asp Asn Leu Thr Asp Ala Ile Asn Lys Arg His Ala Glu Ile
115 120 125

Tyr Lys Gly Leu Phe Lys Ala Glu Leu Phe Asn Gly Lys Val Leu Lys
130 135 140

Gln Leu Gly Thr Val Thr Thr Thr Glu His Glu Asn Ala Leu Leu Arg
145 150 155 160

Ser Phe Asp Lys Phe Thr Thr Tyr Phe Ser Gly Phe Tyr Arg Asn Arg
165 170 175

Lys Asn Val Phe Ser Ala Glu Asp Ile Ser Thr Ala Ile Pro His Arg
180 185 190

Ile Val Gln Asp Asn Phe Pro Lys Phe Lys Glu Asn Cys His Ile Phe
195 200 205

Thr Arg Leu Ile Thr Ala Val Pro Ser Leu Arg Glu His Phe Glu Asn
210 215 220

Val Lys Lys Ala Ile Gly Ile Phe Val Ser Thr Ser Ile Glu Glu Val
225 230 235 240

Phe Ser Phe Pro Phe Tyr Asn Gln Leu Leu Thr Gln Thr Gln Ile Asp
245 250 255

```
Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Arg Gly Trp
    530                 535                 540

Asp Val Asn Arg Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
```

```
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys  Ser Lys Arg Thr Gly  Ile Ala Glu
        995                 1000                1005

Lys Ala  Val Tyr Gln Gln Phe  Glu Lys Met Leu Ile  Asp Lys Leu
    1010                1015                1020

Asn Cys  Leu Val Leu Lys Asp  Tyr Pro Ala Glu Lys  Val Gly Gly
    1025                1030                1035

Val Leu  Asn Pro Tyr Gln Leu  Thr Asp Gln Phe Thr  Ser Phe Ala
    1040                1045                1050

Lys Met  Gly Thr Gln Ser Gly  Phe Leu Phe Tyr Val  Pro Ala Pro
    1055                1060                1065

Tyr Thr  Ser Lys Ile Asp Pro  Leu Thr Gly Phe Val  Asp Pro Phe
    1070                1075                1080

Val Trp  Lys Thr Ile Lys Asn  His Glu Ser Arg Lys  His Phe Leu
    1085                1090                1095
```

```
Glu Gly  Phe Asp Phe Leu His  Tyr Asp Val Lys Thr  Gly Asp Phe
    1100                 1105                 1110

Ile Leu  His Phe Lys Met Asn  Arg Asn Leu Ser Phe  Gln Arg Gly
    1115                 1120                 1125

Leu Pro  Gly Phe Met Pro Ala  Trp Asp Ile Val Phe  Glu Lys Asn
    1130                 1135                 1140

Glu Thr  Gln Phe Asp Ala Lys  Gly Thr Pro Phe Ile  Ala Gly Lys
    1145                 1150                 1155

Arg Ile  Val Pro Val Ile Glu  Asn His Arg Phe Thr  Gly Arg Tyr
    1160                 1165                 1170

Arg Asp  Leu Tyr Pro Ala Asn  Glu Leu Ile Ala Leu  Leu Glu Glu
    1175                 1180                 1185

Lys Gly  Ile Val Phe Arg Asp  Gly Ser Asn Ile Leu  Pro Lys Leu
    1190                 1195                 1200

Leu Glu  Asn Asp Asp Ser His  Ala Ile Asp Thr Met  Val Ala Leu
    1205                 1210                 1215

Ile Arg  Ser Val Leu Gln Met  Arg Asn Ser Asn Ala  Ala Thr Gly
    1220                 1225                 1230

Glu Asp  Tyr Ile Asn Ser Pro  Val Arg Asp Leu Asn  Gly Val Cys
    1235                 1240                 1245

Phe Asp  Ser Arg Phe Gln Asn  Pro Glu Trp Pro Met  Asp Ala Asp
    1250                 1255                 1260

Ala Asn  Gly Ala Tyr His Ile  Ala Leu Lys Gly Gln  Leu Leu Leu
    1265                 1270                 1275

Asn His  Leu Lys Glu Ser Lys  Asp Leu Lys Leu Gln  Asn Gly Ile
    1280                 1285                 1290

Ser Asn  Gln Asp Trp Leu Ala  Tyr Ile Gln Glu Leu  Arg Asn
    1295                 1300                 1305
```

<210> SEQ ID NO 2
<211> LENGTH: 1307
<212> TYPE: PRT
<213> ORGANISM: Acidaminococcus sp. BV3L6

<400> SEQUENCE: 2

```
Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
```

```
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575
```

```
Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990
```

```
Glu Asn Leu Asn Phe Gly Phe Lys  Ser Lys Arg Thr Gly  Ile Ala Glu
        995                 1000                 1005

Lys Ala  Val Tyr Gln Gln Phe  Glu Lys Met Leu Ile  Asp Lys Leu
    1010                 1015                 1020

Asn Cys  Leu Val Leu Lys Asp  Tyr Pro Ala Glu Lys  Val Gly Gly
    1025                 1030                 1035

Val Leu  Asn Pro Tyr Gln Leu  Thr Asp Gln Phe Thr  Ser Phe Ala
    1040                 1045                 1050

Lys Met  Gly Thr Gln Ser Gly  Phe Leu Phe Tyr Val  Pro Ala Pro
    1055                 1060                 1065

Tyr Thr  Ser Lys Ile Asp Pro  Leu Thr Gly Phe Val  Asp Pro Phe
    1070                 1075                 1080

Val Trp  Lys Thr Ile Lys Asn  His Glu Ser Arg Lys  His Phe Leu
    1085                 1090                 1095

Glu Gly  Phe Asp Phe Leu His  Tyr Asp Val Lys Thr  Gly Asp Phe
    1100                 1105                 1110

Ile Leu  His Phe Lys Met Asn  Arg Asn Leu Ser Phe  Gln Arg Gly
    1115                 1120                 1125

Leu Pro  Gly Phe Met Pro Ala  Trp Asp Ile Val Phe  Glu Lys Asn
    1130                 1135                 1140

Glu Thr  Gln Phe Asp Ala Lys  Gly Thr Pro Phe Ile  Ala Gly Lys
    1145                 1150                 1155

Arg Ile  Val Pro Val Ile Glu  Asn His Arg Phe Thr  Gly Arg Tyr
    1160                 1165                 1170

Arg Asp  Leu Tyr Pro Ala Asn  Glu Leu Ile Ala Leu  Leu Glu Glu
    1175                 1180                 1185

Lys Gly  Ile Val Phe Arg Asp  Gly Ser Asn Ile Leu  Pro Lys Leu
    1190                 1195                 1200

Leu Glu  Asn Asp Asp Ser His  Ala Ile Asp Thr Met  Val Ala Leu
    1205                 1210                 1215

Ile Arg  Ser Val Leu Gln Met  Arg Asn Ser Asn Ala  Ala Thr Gly
    1220                 1225                 1230

Glu Asp  Tyr Ile Asn Ser Pro  Val Arg Asp Leu Asn  Gly Val Cys
    1235                 1240                 1245

Phe Asp  Ser Arg Phe Gln Asn  Pro Glu Trp Pro Met  Asp Ala Asp
    1250                 1255                 1260

Ala Asn  Gly Ala Tyr His Ile  Ala Leu Lys Gly Gln  Leu Leu Leu
    1265                 1270                 1275

Asn His  Leu Lys Glu Ser Lys  Asp Leu Lys Leu Gln  Asn Gly Ile
    1280                 1285                 1290

Ser Asn  Gln Asp Trp Leu Ala  Tyr Ile Gln Glu Leu  Arg Asn
    1295                 1300                 1305
```

<210> SEQ ID NO 3
<211> LENGTH: 1228
<212> TYPE: PRT
<213> ORGANISM: Lachnospiraceae bacterium ND2006

<400> SEQUENCE: 3

```
Ala Ala Ser Lys Leu Glu Lys Phe Thr Asn Cys Tyr Ser Leu Ser Lys
1               5                   10                  15

Thr Leu Arg Phe Lys Ala Ile Pro Val Gly Lys Thr Gln Glu Asn Ile
            20                  25                  30

Asp Asn Lys Arg Leu Leu Val Glu Asp Glu Lys Arg Ala Glu Asp Tyr
        35                  40                  45
```

```
Lys Gly Val Lys Lys Leu Leu Asp Arg Tyr Tyr Leu Ser Phe Ile Asn
    50                  55                  60

Asp Val Leu His Ser Ile Lys Leu Lys Asn Leu Asn Asn Tyr Ile Ser
65                  70                  75                  80

Leu Phe Arg Lys Lys Thr Arg Thr Glu Lys Glu Asn Lys Glu Leu Glu
                85                  90                  95

Asn Leu Glu Ile Asn Leu Arg Lys Glu Ile Ala Lys Ala Phe Lys Gly
            100                 105                 110

Ala Ala Gly Tyr Lys Ser Leu Phe Lys Lys Asp Ile Ile Glu Thr Ile
        115                 120                 125

Leu Pro Glu Ala Ala Asp Asp Lys Asp Glu Ile Ala Leu Val Asn Ser
    130                 135                 140

Phe Asn Gly Phe Thr Thr Ala Phe Thr Gly Phe Phe Asp Asn Arg Glu
145                 150                 155                 160

Asn Met Phe Ser Glu Glu Ala Lys Ser Thr Ser Ile Ala Phe Arg Cys
                165                 170                 175

Ile Asn Glu Asn Leu Thr Arg Tyr Ile Ser Asn Met Asp Ile Phe Glu
            180                 185                 190

Lys Val Asp Ala Ile Phe Asp Lys His Glu Val Gln Glu Ile Lys Glu
        195                 200                 205

Lys Ile Leu Asn Ser Asp Tyr Asp Val Glu Asp Phe Phe Glu Gly Glu
    210                 215                 220

Phe Phe Asn Phe Val Leu Thr Gln Glu Gly Ile Asp Val Tyr Asn Ala
225                 230                 235                 240

Ile Ile Gly Gly Phe Val Thr Glu Ser Gly Glu Lys Ile Lys Gly Leu
                245                 250                 255

Asn Glu Tyr Ile Asn Leu Tyr Asn Ala Lys Thr Lys Gln Ala Leu Pro
            260                 265                 270

Lys Phe Lys Pro Leu Tyr Lys Gln Val Leu Ser Asp Arg Glu Ser Leu
        275                 280                 285

Ser Phe Tyr Gly Glu Gly Tyr Thr Ser Asp Glu Glu Val Leu Glu Val
    290                 295                 300

Phe Arg Asn Thr Leu Asn Lys Asn Ser Glu Ile Phe Ser Ser Ile Lys
305                 310                 315                 320

Lys Leu Glu Lys Leu Phe Lys Asn Phe Asp Glu Tyr Ser Ser Ala Gly
                325                 330                 335

Ile Phe Val Lys Asn Gly Pro Ala Ile Ser Thr Ile Ser Lys Asp Ile
            340                 345                 350

Phe Gly Glu Trp Asn Leu Ile Arg Asp Lys Trp Asn Ala Glu Tyr Asp
        355                 360                 365

Asp Ile His Leu Lys Lys Lys Ala Val Val Thr Glu Lys Tyr Glu Asp
    370                 375                 380

Asp Arg Arg Lys Ser Phe Lys Lys Ile Gly Ser Phe Ser Leu Glu Gln
385                 390                 395                 400

Leu Gln Glu Tyr Ala Asp Ala Asp Leu Ser Val Val Glu Lys Leu Lys
                405                 410                 415

Glu Ile Ile Ile Gln Lys Val Asp Glu Ile Tyr Lys Val Tyr Gly Ser
            420                 425                 430

Ser Glu Lys Leu Phe Asp Ala Asp Phe Val Leu Glu Lys Ser Leu Lys
        435                 440                 445

Lys Asn Asp Ala Val Val Ala Ile Met Lys Asp Leu Leu Asp Ser Val
    450                 455                 460
```

```
Lys Ser Phe Glu Asn Tyr Ile Lys Ala Phe Phe Gly Glu Gly Lys Glu
465                 470                 475                 480

Thr Asn Arg Asp Glu Ser Phe Tyr Gly Asp Phe Val Leu Ala Tyr Asp
                485                 490                 495

Ile Leu Leu Lys Val Asp His Ile Tyr Asp Ala Ile Arg Asn Tyr Val
            500                 505                 510

Thr Gln Lys Pro Tyr Ser Lys Asp Lys Phe Lys Leu Tyr Phe Gln Asn
        515                 520                 525

Pro Gln Phe Met Gly Gly Trp Asp Lys Asp Lys Glu Thr Asp Tyr Arg
    530                 535                 540

Ala Thr Ile Leu Arg Tyr Gly Ser Lys Tyr Tyr Leu Ala Ile Met Asp
545                 550                 555                 560

Lys Lys Tyr Ala Lys Cys Leu Gln Lys Ile Asp Lys Asp Asp Val Asn
                565                 570                 575

Gly Asn Tyr Glu Lys Ile Asn Tyr Lys Leu Leu Pro Gly Pro Asn Lys
            580                 585                 590

Met Leu Pro Lys Val Phe Phe Ser Lys Lys Trp Met Ala Tyr Tyr Asn
        595                 600                 605

Pro Ser Glu Asp Ile Gln Lys Ile Tyr Lys Asn Gly Thr Phe Lys Lys
    610                 615                 620

Gly Asp Met Phe Asn Leu Asn Asp Cys His Lys Leu Ile Asp Phe Phe
625                 630                 635                 640

Lys Asp Ser Ile Ser Arg Tyr Pro Lys Trp Ser Asn Ala Tyr Asp Phe
                645                 650                 655

Asn Phe Ser Glu Thr Glu Lys Tyr Lys Asp Ile Ala Gly Phe Tyr Arg
            660                 665                 670

Glu Val Glu Glu Gln Gly Tyr Lys Val Ser Phe Glu Ser Ala Ser Lys
        675                 680                 685

Lys Glu Val Asp Lys Leu Val Glu Glu Gly Lys Leu Tyr Met Phe Gln
    690                 695                 700

Ile Tyr Asn Lys Asp Phe Ser Asp Lys Ser His Gly Thr Pro Asn Leu
705                 710                 715                 720

His Thr Met Tyr Phe Lys Leu Leu Phe Asp Glu Asn Asn His Gly Gln
                725                 730                 735

Ile Arg Leu Ser Gly Gly Ala Glu Leu Phe Met Arg Arg Ala Ser Leu
            740                 745                 750

Lys Lys Glu Glu Leu Val Val His Pro Ala Asn Ser Pro Ile Ala Asn
        755                 760                 765

Lys Asn Pro Asp Asn Pro Lys Lys Thr Thr Thr Leu Ser Tyr Asp Val
    770                 775                 780

Tyr Lys Asp Lys Arg Phe Ser Glu Asp Gln Tyr Glu Leu His Ile Pro
785                 790                 795                 800

Ile Ala Ile Asn Lys Cys Pro Lys Asn Ile Phe Lys Ile Asn Thr Glu
                805                 810                 815

Val Arg Val Leu Leu Lys His Asp Asp Asn Pro Tyr Val Ile Gly Ile
            820                 825                 830

Asp Arg Gly Glu Arg Asn Leu Leu Tyr Ile Val Val Val Asp Gly Lys
        835                 840                 845

Gly Asn Ile Val Glu Gln Tyr Ser Leu Asn Glu Ile Ile Asn Asn Phe
    850                 855                 860

Asn Gly Ile Arg Ile Lys Thr Asp Tyr His Ser Leu Leu Asp Lys Lys
865                 870                 875                 880

Glu Lys Glu Arg Phe Glu Ala Arg Gln Asn Trp Thr Ser Ile Glu Asn
```

```
                885                 890                 895

Ile Lys Glu Leu Lys Ala Gly Tyr Ile Ser Gln Val Val His Lys Ile
            900                 905                 910

Cys Glu Leu Val Glu Lys Tyr Asp Ala Val Ile Ala Leu Glu Asp Leu
        915                 920                 925

Asn Ser Gly Phe Lys Asn Ser Arg Val Lys Val Glu Lys Gln Val Tyr
    930                 935                 940

Gln Lys Phe Glu Lys Met Leu Ile Asp Lys Leu Asn Tyr Met Val Asp
945                 950                 955                 960

Lys Lys Ser Asn Pro Cys Ala Thr Gly Gly Ala Leu Lys Gly Tyr Gln
                965                 970                 975

Ile Thr Asn Lys Phe Glu Ser Phe Lys Ser Met Ser Thr Gln Asn Gly
            980                 985                 990

Phe Ile Phe Tyr Ile Pro Ala Trp  Leu Thr Ser Lys Ile  Asp Pro Ser
        995                 1000                1005

Thr Gly  Phe Val Asn Leu Leu  Lys Thr Lys Tyr Thr  Ser Ile Ala
    1010                1015                1020

Asp Ser  Lys Lys Phe Ile Ser  Ser Phe Asp Arg Ile  Met Tyr Val
    1025                1030                1035

Pro Glu  Glu Asp Leu Phe Glu  Phe Ala Leu Asp Tyr  Lys Asn Phe
    1040                1045                1050

Ser Arg  Thr Asp Ala Asp Tyr  Ile Lys Lys Trp Lys  Leu Tyr Ser
    1055                1060                1065

Tyr Gly  Asn Arg Ile Arg Ile  Phe Ala Ala Ala Lys  Lys Asn Asn
    1070                1075                1080

Val Phe  Ala Trp Glu Glu Val  Cys Leu Thr Ser Ala  Tyr Lys Glu
    1085                1090                1095

Leu Phe  Asn Lys Tyr Gly Ile  Asn Tyr Gln Gln Gly  Asp Ile Arg
    1100                1105                1110

Ala Leu  Leu Cys Glu Gln Ser  Asp Lys Ala Phe Tyr  Ser Ser Phe
    1115                1120                1125

Met Ala  Leu Met Ser Leu Met  Leu Gln Met Arg Asn  Ser Ile Thr
    1130                1135                1140

Gly Arg  Thr Asp Val Asp Phe  Leu Ile Ser Pro Val  Lys Asn Ser
    1145                1150                1155

Asp Gly  Ile Phe Tyr Asp Ser  Arg Asn Tyr Glu Ala  Gln Glu Asn
    1160                1165                1170

Ala Ile  Leu Pro Lys Asn Ala  Asp Ala Asn Gly Ala  Tyr Asn Ile
    1175                1180                1185

Ala Arg  Lys Val Leu Trp Ala  Ile Gly Gln Phe Lys  Lys Ala Glu
    1190                1195                1200

Asp Glu  Lys Leu Asp Lys Val  Lys Ile Ala Ile Ser  Asn Lys Glu
    1205                1210                1215

Trp Leu  Glu Tyr Ala Gln Thr  Ser Val Lys
    1220                1225
```

<210> SEQ ID NO 4
<211> LENGTH: 42
<212> TYPE: DNA
<213> ORGANISM: Artificial
<220> FEATURE:
<223> OTHER INFORMATION: FIP LAMP Primer

<400> SEQUENCE: 4
tgtaaagcaa gtaaagtttg aaaccctcag ggtttttcgg ct 42

<210> SEQ ID NO 5
<211> LENGTH: 38
<212> TYPE: DNA
<213> ORGANISM: Artificial
<220> FEATURE:
<223> OTHER INFORMATION: BIP LAMP Primer

<400> SEQUENCE: 5
tggacagctg gtgctaatag aaaagtccta ggttgaag 38

<210> SEQ ID NO 6
<211> LENGTH: 21
<212> TYPE: DNA
<213> ORGANISM: Artificial
<220> FEATURE:
<223> OTHER INFORMATION: F3 LAMP Primer

<400> SEQUENCE: 6
ttaatttagt gcgtgatctc c 21

<210> SEQ ID NO 7
<211> LENGTH: 20
<212> TYPE: DNA
<213> ORGANISM: Artificial
<220> FEATURE:
<223> OTHER INFORMATION: B3 LAMP Primer

<400> SEQUENCE: 7
agcatctgta atggttccat 20

<210> SEQ ID NO 8
<211> LENGTH: 23
<212> TYPE: DNA
<213> ORGANISM: Artificial
<220> FEATURE:
<223> OTHER INFORMATION: LF LAMP Primer

<400> SEQUENCE: 8
ggcaaatcta ccaatggttc taa 23

<210> SEQ ID NO 9
<211> LENGTH: 21
<212> TYPE: DNA
<213> ORGANISM: Artificial
<220> FEATURE:
<223> OTHER INFORMATION: LB LAMP Primer

<400> SEQUENCE: 9
gcagcttatt atgtgggtta t 21

<210> SEQ ID NO 10
<211> LENGTH: 25
<212> TYPE: DNA
<213> ORGANISM: Artificial
<220> FEATURE:
<223> OTHER INFORMATION: F1c LAMP swarm Primer

<400> SEQUENCE: 10
tgtaaagcaa gtaaagtttg aaacc 25

<210> SEQ ID NO 11
<211> LENGTH: 15
<212> TYPE: DNA
<213> ORGANISM: Artificial
<220> FEATURE:

<223> OTHER INFORMATION: B1c LAMP swarm Primer

<400> SEQUENCE: 11
tggacagctg gtgct 15

<210> SEQ ID NO 12
<211> LENGTH: 20
<212> TYPE: RNA
<213> ORGANISM: Artificial
<220> FEATURE:
<223> OTHER INFORMATION: gRNA spacer sequence

<400> SEQUENCE: 12
acuccuggug auucuucuuc 20

<210> SEQ ID NO 13
<211> LENGTH: 20
<212> TYPE: RNA
<213> ORGANISM: Artificial
<220> FEATURE:
<223> OTHER INFORMATION: gRNA spacer sequence

<400> SEQUENCE: 13
aaaccuagug auguuaauac 20

<210> SEQ ID NO 14
<211> LENGTH: 20
<212> TYPE: RNA
<213> ORGANISM: SARS-CoV-2

<400> SEQUENCE: 14
gaagaagaau caccaggagu 20

<210> SEQ ID NO 15
<211> LENGTH: 20
<212> TYPE: RNA
<213> ORGANISM: SARS-CoV-2

<400> SEQUENCE: 15
guauuaacau cacuagguuu 20

<210> SEQ ID NO 16
<211> LENGTH: 20
<212> TYPE: RNA
<213> ORGANISM: Artificial
<220> FEATURE:
<223> OTHER INFORMATION: gRNA Cas12a binding sequence

<400> SEQUENCE: 16
uaauuucuac ucuuguagau 20

<210> SEQ ID NO 17
<211> LENGTH: 500
<212> TYPE: DNA
<213> ORGANISM: SARS-CoV-2

<400> SEQUENCE: 17
gctttgggct aagcgcaaca ttaaaccagt accagaggtg aaaatactca ataatttggg 60
tgtggacatt gctgctaata ctgtgatctg ggactacaaa agagatgctc cagcacatat 120
atctactatt ggtgtttgtt ctatgactga catagccaag aaaccaactg aaacgatttg 180
tgcaccactc actgtctttt ttgatggtag agttgatggt caagtagact tatttagaaa 240
tgcccgtaat ggtgttctta ttacagaagg tagtgttaaa ggtttacaac catctgtagg 300
tcccaaacaa gctagtctta atggagtcac attaattgga gaagccgtaa aaacacagtt 360
caattattat aagaaagttg atggtgttgt ccaacaatta cctgaaactt actttactca 420
gagtagaaat ttacaagaat ttaaacccag gagtcaaatg gaaattgatt tcttagaatt 480
agctatggat gaattcattg 500

<210> SEQ ID NO 18
<211> LENGTH: 490
<212> TYPE: DNA
<213> ORGANISM: SARS-CoV-2

<400> SEQUENCE: 18
aaacagggta atttcaaaaa tcttagggaa tttgtgttta agaatattga tggttatttt 60
aaaatatatt ctaagcacac gcctattaat ttagtgcgtg atctccctca gggtttttcg 120
gctttagaac cattggtaga tttgccaata ggtattaaca tcactaggtt tcaaacttta 180
cttgctttac atagaagtta tttgactcct ggtgattctt cttcaggttg gacagctggt 240
gctgcagctt attatgtggg ttatcttcaa cctaggactt ttctattaaa atataatgaa 300
aatggaacca ttacagatgc tgtagactgt gcacttgacc ctctctcaga aacaaagtgt 360
acgttgaaat ccttcactgt agaaaaagga atctatcaaa cttctaactt tagagtccaa 420
ccaacagaat ctattgttag atttcctaat attacaaact tgtgcccttt tggtgaagtt 480
tttaacgcca 490

<210> SEQ ID NO 19
<211> LENGTH: 490
<212> TYPE: DNA
<213> ORGANISM: SARS-CoV-2

<400> SEQUENCE: 19
cttctaagaa gcctcggcaa aaacgtactg ccactaaagc atacaatgta acacaagctt 60
tcggcagacg tggtccagaa caaacccaag gaaattttgg ggaccaggaa ctaatcagac 120
aaggaactga ttacaaacat tggccgcaaa ttgcacaatt tgcccccagc gcttcagcgt 180
tcttcggaat gtcgcgcatt ggcatggaag tcacaccttc gggaacgtgg ttgacctaca 240
caggtgccat caaattggat gacaaagatc caaatttcaa agatcaagtc attttgctga 300
ataagcatat tgacgcatac aaaacattcc caccaacaga gcctaaaaag gacaaaaaga 360
agaaggctga tgaaactcaa gccttaccgc agagacagaa gaaacagcaa actgtgactc 420
ttcttcctgc tgcagatttg gatgatttct ccaaacaatt gcaacaatcc atgagcagtg 480
ctgactcaac 490

<210> SEQ ID NO 20
<211> LENGTH: 500
<212> TYPE: DNA
<213> ORGANISM: SARS-CoV

<400> SEQUENCE: 20
gctttgggct aagcgtaaca ttaaaccagt gccagagatt aagatactca ataatttggg 60
tgttgatatc gctgctaata ctgtaatctg ggactacaaa agagaagccc cagcacatgt 120
atctacaata ggtgtctgca caatgactga cattgccaag aaacctactg agagtgcttg 180
ttcttcactt actgtcttgt ttgatggtag agtggaagga caggtagacc tttttagaaa 240
cgcccgtaat ggtgttttaa taacagaagg ttcagtcaaa ggtctaacac cttcaaaggg 300
accagcacaa gctagcgtca atggagtcac attaattgga gaatcagtaa aaacacagtt 360
taactacttt aagaaagtag acggcattat tcaacagttg cctgaaacct actttactca 420
gagcagagac ttagaggatt ttaagcccag atcacaaatg gaaactgact ttctcgagct 480
cgctatggat gaattcatac 500

<210> SEQ ID NO 21
<211> LENGTH: 482
<212> TYPE: DNA
<213> ORGANISM: SARS-CoV

<400> SEQUENCE: 21
aagtcaggta attttaaaca cttacgagag tttgtgttta aaaataaaga tgggtttctc 60
tatgtttata agggctatca acctatagat gtagttcgtg atctaccttc tggttttaac 120
actttgaaac ctatttttaa gttgcctctt ggtattaaca ttacaaattt tagagccatt 180
cttacagcct tttcacctgc tcaagacatt tggggcacgt cagctgcagc ctattttgtt 240
ggctatttaa agccaactac atttatgctc aagtatgatg aaaatggtac aatcacagat 300
gctgttgatt gttctcaaaa tccacttgct gaactcaaat gctctgttaa gagctttgag 360
attgacaaag gaatttacca gacctctaat ttcagggttg ttccctcagg agatgttgtg 420
agattcccta atattacaaa cttgtgtcct tttggagagg tttttaatgc tactaaattc 480
cc 482

<210> SEQ ID NO 22
<211> LENGTH: 496
<212> TYPE: DNA
<213> ORGANISM: SARS-CoV

<400> SEQUENCE: 22
catctaaaaa gcctcgccaa aaacgtactg ccacaaaaca gtacaacgtc actcaagcat 60
ttgggagacg tggtccagaa caaacccaag gaaatttcgg ggaccaagac ctaatcagac 120
aaggaactga ttacaaacat tggccgcaaa ttgcacaatt tgctccaagt gcctctgcat 180
tctttggaat gtcacgcatt ggcatggaag tcacaccttc gggaacatgg ctgacttatc 240
atggagccat taaattggat gacaaagatc cacaattcaa agacaacgtc atactgctga 300
acaagcacat tgacgcatac aaaacattcc caccaacaga gcctaaaaag gacaaaaaga 360
aaaagactga tgaagctcag cctttgccgc agagacaaaa gaagcagccc actgtgactc 420
ttcttcctgc ggctgacatg gatgatttct ccagacaact tcaaaattcc atgagtggag 480
cttctgctga ttcaac 496

<210> SEQ ID NO 23
<211> LENGTH: 491
<212> TYPE: DNA
<213> ORGANISM: MERS-CoV

<400> SEQUENCE: 23
actctatgct aagcgtgctg tacgctcgca tcccgatttc aaattgctac acaatttaca 60
agcagacatt tgctacaagt tcgtcctttg ggattatgaa cgtagcaata tttatggtac 120
tgctactatt ggtgtatgta agtacactga tattgatgtt aattcagctt tgaatatatg 180
ttttgacata cgcgataatt gttcattgga gaagttcatg tctactccca atgccatctt 240
tatttctgat agaaaaatca agaaataccc ttgtatggta ggtcctgatt atgcttactt 300
caatggtgct atcatccgtg atagtgatgt tgttaaacaa ccagtgaagt tctacttgta 360
taagaaagtc aataatgagt ttattgatcc tactgagtgt atttacactc agagtcgctc 420
ttgtagtgac ttcctacccc tttctgacat ggagaaagac tttctatctt ttgatagtga 480
tgttttcatt a 491

<210> SEQ ID NO 24
<211> LENGTH: 587
<212> TYPE: DNA
<213> ORGANISM: MERS-CoV

<400> SEQUENCE: 24
aattcctata cttcttttgc cacttatcac actcctgcaa cagattgttc tgatggcaat 60
tacaatcgta atgccagtct gaactctttt aaggagtatt ttaatttacg taactgcacc 120
tttatgtaca cttataacat taccgaagat gagattttag agtggtttgg cattacacaa 180
actgctcaag gtgttcacct cttctcatct cggtatgttg atttgtacgg cggcaatatg 240
tttcaatttg ccaccttgcc tgtttatgat actattaagt attattctat cattcctcac 300
agtattcgtt ctatccaaag tgatagaaaa gcttgggctg ccttctacgt atataaactt 360
caaccgttaa ctttcctgtt ggatttttct gttgatggtt atatacgcag agctatagac 420
tgtggtttta atgatttgtc acaactccac tgctcatatg aatccttcga tgttgaatct 480
ggagtttatt cagtttcgtc tttcgaagca aaaccttctg gctcagttgt ggaacaggct 540
gaaggtgttg aatgtgattt ttcacctctt ctgtctggca cacctcc 587

<210> SEQ ID NO 25
<211> LENGTH: 484
<212> TYPE: DNA
<213> ORGANISM: MERS-CoV

<400> SEQUENCE: 25
ctaaaaataa gatgcgccac aagcgcactt ccaccaaaag tttcaacatg gtgcaagctt 60
ttggtcttcg cggaccagga gacctccagg gaaactttgg tgatcttcaa ttgaataaac 120
tcggcactga ggacccacgt tggccccaaa ttgctgagct tgctcctaca gccagtgctt 180
ttatgggtat gtcgcaattt aaacttaccc atcagaacaa tgatgatcat ggcaaccctg 240
tgtacttcct tcggtacagt ggagccatta aacttgaccc aaagaatccc aactacaata 300
agtggttgga gcttcttgag caaaatattg atgcctacaa aaccttccct aagaaggaaa 360
agaaacaaaa ggcaccaaaa gaagaatcaa cagaccaaat gtctgaacct ccaaaggagc 420
agcgtgtgca aggtagcatc actcagcgca ctcgcacccg tccaagtgtt cagcctggtc 480
caat 484

<210> SEQ ID NO 26
<211> LENGTH: 19
<212> TYPE: DNA
<213> ORGANISM: Artificial
<220> FEATURE:
<223> OTHER INFORMATION: T7 promoter

<400> SEQUENCE: 26
taatacgact cactatagg 19

<210> SEQ ID NO 27
<211> LENGTH: 39
<212> TYPE: DNA
<213> ORGANISM: Artificial
<220> FEATURE:

<223> OTHER INFORMATION: oligonucleotide

<400> SEQUENCE: 27
taatacgact cactataggt aatttctact cttgtagat 39

<210> SEQ ID NO 28
<211> LENGTH: 40
<212> TYPE: DNA
<213> ORGANISM: Artificial
<220> FEATURE:
<223> OTHER INFORMATION: oligonucleotide

<400> SEQUENCE: 28
taatacgact cactataggt aatttctact aagtgtagat 40

<210> SEQ ID NO 29
<211> LENGTH: 20
<212> TYPE: DNA
<213> ORGANISM: Artificial
<220> FEATURE:
<223> OTHER INFORMATION: spacer

<400> SEQUENCE: 29
tgcaccactc actgtctttt 20

<210> SEQ ID NO 30
<211> LENGTH: 53
<212> TYPE: DNA
<213> ORGANISM: Artificial
<220> FEATURE:
<223> OTHER INFORMATION: oligonucleotide

<400> SEQUENCE: 30
aaaagacagt gagtggtgca atctacaaga gtagaaatta cctatagtga gtc 53

<210> SEQ ID NO 31
<211> LENGTH: 20
<212> TYPE: DNA
<213> ORGANISM: Artificial
<220> FEATURE:
<223> OTHER INFORMATION: spacer

<400> SEQUENCE: 31
caaccatctg taggtcccaa 20

<210> SEQ ID NO 32
<211> LENGTH: 53
<212> TYPE: DNA
<213> ORGANISM: Artificial
<220> FEATURE:
<223> OTHER INFORMATION: oligonucleotide

<400> SEQUENCE: 32
ttgggaccta cagatggttg atctacaaga gtagaaatta cctatagtga gtc 53

<210> SEQ ID NO 33
<211> LENGTH: 20
<212> TYPE: DNA
<213> ORGANISM: Artificial
<220> FEATURE:
<223> OTHER INFORMATION: spacer

<400> SEQUENCE: 33
cttgctttac atagaagtta 20

<210> SEQ ID NO 34
<211> LENGTH: 53
<212> TYPE: DNA
<213> ORGANISM: Artificial
<220> FEATURE:
<223> OTHER INFORMATION: oligonucleotide

<400> SEQUENCE: 34
taacttctat gtaaagcaag atctacaaga gtagaaatta cctatagtga gtc 53

<210> SEQ ID NO 35
<211> LENGTH: 20
<212> TYPE: DNA
<213> ORGANISM: Artificial
<220> FEATURE:
<223> OTHER INFORMATION: spacer

<400> SEQUENCE: 35
actcctggtg attcttcttc 20

<210> SEQ ID NO 36
<211> LENGTH: 53
<212> TYPE: DNA
<213> ORGANISM: Artificial
<220> FEATURE:
<223> OTHER INFORMATION: oligonucleotide

<400> SEQUENCE: 36
gaagaagaat caccaggagt atctacaaga gtagaaatta cctatagtga gtc 53

<210> SEQ ID NO 37
<211> LENGTH: 20
<212> TYPE: DNA
<213> ORGANISM: Artificial
<220> FEATURE:
<223> OTHER INFORMATION: spacer

<400> SEQUENCE: 37
gagtccaacc aacagaatct 20

<210> SEQ ID NO 38
<211> LENGTH: 53
<212> TYPE: DNA
<213> ORGANISM: Artificial
<220> FEATURE:
<223> OTHER INFORMATION: oligonucleotide

<400> SEQUENCE: 38
agattctgtt ggttggactc atctacaaga gtagaaatta cctatagtga gtc 53

<210> SEQ ID NO 39
<211> LENGTH: 20
<212> TYPE: DNA
<213> ORGANISM: Artificial
<220> FEATURE:
<223> OTHER INFORMATION: spacer

<400> SEQUENCE: 39
aaactttact tgctttacat 20

<210> SEQ ID NO 40
<211> LENGTH: 53
<212> TYPE: DNA
<213> ORGANISM: Artificial
<220> FEATURE:
<223> OTHER INFORMATION: oligonucleotide

<400> SEQUENCE: 40
atgtaaagca agtaaagttt atctacaaga gtagaaatta cctatagtga gtc 53

<210> SEQ ID NO 41
<211> LENGTH: 20
<212> TYPE: DNA
<213> ORGANISM: Artificial
<220> FEATURE:
<223> OTHER INFORMATION: spacer

<400> SEQUENCE: 41
catagaagtt atttgactcc 20

<210> SEQ ID NO 42
<211> LENGTH: 53
<212> TYPE: DNA
<213> ORGANISM: Artificial
<220> FEATURE:
<223> OTHER INFORMATION: oligonucleotide

<400> SEQUENCE: 42
ggagtcaaat aacttctatg atctacaaga gtagaaatta cctatagtga gtc 53

<210> SEQ ID NO 43
<211> LENGTH: 20
<212> TYPE: DNA
<213> ORGANISM: Artificial
<220> FEATURE:
<223> OTHER INFORMATION: spacer

<400> SEQUENCE: 43
aaacctagtg atgttaatac 20

<210> SEQ ID NO 44
<211> LENGTH: 53
<212> TYPE: DNA
<213> ORGANISM: Artificial
<220> FEATURE:
<223> OTHER INFORMATION: oligonucleotide

<400> SEQUENCE: 44
gtattaacat cactaggttt atctacaaga gtagaaatta cctatagtga gtc 53

<210> SEQ ID NO 45
<211> LENGTH: 20
<212> TYPE: DNA
<213> ORGANISM: Artificial
<220> FEATURE:
<223> OTHER INFORMATION: spacer

<400> SEQUENCE: 45
ccaataggta ttaacatcac 20

<210> SEQ ID NO 46
<211> LENGTH: 53
<212> TYPE: DNA
<213> ORGANISM: Artificial
<220> FEATURE:
<223> OTHER INFORMATION: oligonucleotide

<400> SEQUENCE: 46
gtgatgttaa tacctattgg atctacaaga gtagaaatta cctatagtga gtc 53

<210> SEQ ID NO 47
<211> LENGTH: 20

<212> TYPE: DNA
<213> ORGANISM: Artificial
<220> FEATURE:
<223> OTHER INFORMATION: spacer

<400> SEQUENCE: 47
gaaccattgg tagatttgcc 20

<210> SEQ ID NO 48
<211> LENGTH: 53
<212> TYPE: DNA
<213> ORGANISM: Artificial
<220> FEATURE:
<223> OTHER INFORMATION: oligonucleotide

<400> SEQUENCE: 48
ggcaaatcta ccaatggttc atctacaaga gtagaaatta cctatagtga gtc 53

<210> SEQ ID NO 49
<211> LENGTH: 20
<212> TYPE: DNA
<213> ORGANISM: Artificial
<220> FEATURE:
<223> OTHER INFORMATION: spacer

<400> SEQUENCE: 49
gaaccattgg tagatttgcc 20

<210> SEQ ID NO 50
<211> LENGTH: 53
<212> TYPE: DNA
<213> ORGANISM: Artificial
<220> FEATURE:
<223> OTHER INFORMATION: oligonucleotide

<400> SEQUENCE: 50
ctaccaatgg ttctaaagcc atctacaaga gtagaaatta cctatagtga gtc 53

<210> SEQ ID NO 51
<211> LENGTH: 20
<212> TYPE: DNA
<213> ORGANISM: Artificial
<220> FEATURE:
<223> OTHER INFORMATION: spacer

<400> SEQUENCE: 51
atagaaaagt cctaggttga 20

<210> SEQ ID NO 52
<211> LENGTH: 53
<212> TYPE: DNA
<213> ORGANISM: Artificial
<220> FEATURE:
<223> OTHER INFORMATION: oligonucleotide

<400> SEQUENCE: 52
tcaacctagg acttttctat atctacaaga gtagaaatta cctatagtga gtc 53

<210> SEQ ID NO 53
<211> LENGTH: 20
<212> TYPE: DNA
<213> ORGANISM: Artificial
<220> FEATURE:
<223> OTHER INFORMATION: spacer

<400> SEQUENCE: 53
tgagagaggg tcaagtgcac 20

<210> SEQ ID NO 54
<211> LENGTH: 53
<212> TYPE: DNA
<213> ORGANISM: Artificial
<220> FEATURE:
<223> OTHER INFORMATION: oligonucleotide

<400> SEQUENCE: 54
gtgcacttga ccctctctca atctacaaga gtagaaatta cctatagtga gtc 53

<210> SEQ ID NO 55
<211> LENGTH: 20
<212> TYPE: DNA
<213> ORGANISM: Artificial
<220> FEATURE:
<223> OTHER INFORMATION: spacer

<400> SEQUENCE: 55
tttctgagag agggtcaagt 20

<210> SEQ ID NO 56
<211> LENGTH: 53
<212> TYPE: DNA
<213> ORGANISM: Artificial
<220> FEATURE:
<223> OTHER INFORMATION: oligonucleotide

<400> SEQUENCE: 56
acttgaccct ctctcagaaa atctacaaga gtagaaatta cctatagtga gtc 53

<210> SEQ ID NO 57
<211> LENGTH: 20
<212> TYPE: DNA
<213> ORGANISM: Artificial
<220> FEATURE:
<223> OTHER INFORMATION: spacer

<400> SEQUENCE: 57
aacgtacact ttgtttctga 20

<210> SEQ ID NO 58
<211> LENGTH: 53
<212> TYPE: DNA
<213> ORGANISM: Artificial
<220> FEATURE:
<223> OTHER INFORMATION: oligonucleotide

<400> SEQUENCE: 58
tcagaaacaa agtgtacgtt atctacaaga gtagaaatta cctatagtga gtc 53

<210> SEQ ID NO 59
<211> LENGTH: 20
<212> TYPE: DNA
<213> ORGANISM: Artificial
<220> FEATURE:
<223> OTHER INFORMATION: spacer

<400> SEQUENCE: 59
tacagtgaag gatttcaacg 20

<210> SEQ ID NO 60
<211> LENGTH: 53
<212> TYPE: DNA
<213> ORGANISM: Artificial

<220> FEATURE:
<223> OTHER INFORMATION: oligonucleotide

<400> SEQUENCE: 60
cgttgaaatc cttcactgta atctacaaga gtagaaatta cctatagtga gtc 53

<210> SEQ ID NO 61
<211> LENGTH: 20
<212> TYPE: DNA
<213> ORGANISM: Artificial
<220> FEATURE:
<223> OTHER INFORMATION: spacer

<400> SEQUENCE: 61
gtgcgtgatc tccctcaggg 20

<210> SEQ ID NO 62
<211> LENGTH: 53
<212> TYPE: DNA
<213> ORGANISM: Artificial
<220> FEATURE:
<223> OTHER INFORMATION: oligonucleotide

<400> SEQUENCE: 62
ccctgaggga gatcacgcac atctacaaga gtagaaatta cctatagtga gtc 53

<210> SEQ ID NO 63
<211> LENGTH: 20
<212> TYPE: DNA
<213> ORGANISM: Artificial
<220> FEATURE:
<223> OTHER INFORMATION: spacer

<400> SEQUENCE: 63
aaagatcaag tcattttgct 20

<210> SEQ ID NO 64
<211> LENGTH: 53
<212> TYPE: DNA
<213> ORGANISM: Artificial
<220> FEATURE:
<223> OTHER INFORMATION: oligonucleotide

<400> SEQUENCE: 64
agcaaaatga cttgatcttt atctacaaga gtagaaatta cctatagtga gtc 53

<210> SEQ ID NO 65
<211> LENGTH: 20
<212> TYPE: DNA
<213> ORGANISM: Artificial
<220> FEATURE:
<223> OTHER INFORMATION: spacer

<400> SEQUENCE: 65
cccccagcgc ttcagcgttc 20

<210> SEQ ID NO 66
<211> LENGTH: 55
<212> TYPE: DNA
<213> ORGANISM: Artificial
<220> FEATURE:
<223> OTHER INFORMATION: oligonucleotide

<400> SEQUENCE: 66
gaacgctgaa gcgctggggg atctacaaga gtagaaatta cctatagtga gtcgt 55

<210> SEQ ID NO 67
<211> LENGTH: 20
<212> TYPE: DNA
<213> ORGANISM: Artificial
<220> FEATURE:
<223> OTHER INFORMATION: spacer

<400> SEQUENCE: 67
tgcaccactc actgtctttt 20

<210> SEQ ID NO 68
<211> LENGTH: 52
<212> TYPE: DNA
<213> ORGANISM: Artificial
<220> FEATURE:
<223> OTHER INFORMATION: oligonucleotide

<400> SEQUENCE: 68
aaaagacagt gagtggtgca atctacactt agtagaaatt acctatagtg ag 52

<210> SEQ ID NO 69
<211> LENGTH: 20
<212> TYPE: DNA
<213> ORGANISM: Artificial
<220> FEATURE:
<223> OTHER INFORMATION: spacer

<400> SEQUENCE: 69
caaccatctg taggtcccaa 20

<210> SEQ ID NO 70
<211> LENGTH: 52
<212> TYPE: DNA
<213> ORGANISM: Artificial
<220> FEATURE:
<223> OTHER INFORMATION: oligonucleotide

<400> SEQUENCE: 70
ttgggaccta cagatggttg atctacactt agtagaaatt acctatagtg ag 52

<210> SEQ ID NO 71
<211> LENGTH: 20
<212> TYPE: DNA
<213> ORGANISM: Artificial
<220> FEATURE:
<223> OTHER INFORMATION: spacer

<400> SEQUENCE: 71
cttgctttac atagaagtta 20

<210> SEQ ID NO 72
<211> LENGTH: 52
<212> TYPE: DNA
<213> ORGANISM: Artificial
<220> FEATURE:
<223> OTHER INFORMATION: oligonucleotide

<400> SEQUENCE: 72
taacttctat gtaaagcaag atctacactt agtagaaatt acctatagtg ag 52

<210> SEQ ID NO 73
<211> LENGTH: 20
<212> TYPE: DNA
<213> ORGANISM: Artificial
<220> FEATURE:
<223> OTHER INFORMATION: spacer

<400> SEQUENCE: 73
actcctggtg attcttcttc 20

<210> SEQ ID NO 74
<211> LENGTH: 52
<212> TYPE: DNA
<213> ORGANISM: Artificial
<220> FEATURE:
<223> OTHER INFORMATION: oligonucleotide

<400> SEQUENCE: 74
gaagaagaat caccaggagt atctacactt agtagaaatt acctatagtg ag 52

<210> SEQ ID NO 75
<211> LENGTH: 20
<212> TYPE: DNA
<213> ORGANISM: Artificial
<220> FEATURE:
<223> OTHER INFORMATION: spacer

<400> SEQUENCE: 75
gagtccaacc aacagaatct 20

<210> SEQ ID NO 76
<211> LENGTH: 52
<212> TYPE: DNA
<213> ORGANISM: Artificial
<220> FEATURE:
<223> OTHER INFORMATION: oligonucleotide

<400> SEQUENCE: 76
agattctgtt ggttggactc atctacactt agtagaaatt acctatagtg ag 52

<210> SEQ ID NO 77
<211> LENGTH: 20
<212> TYPE: DNA
<213> ORGANISM: Artificial
<220> FEATURE:
<223> OTHER INFORMATION: spacer

<400> SEQUENCE: 77
aaagatcaag tcattttgct 20

<210> SEQ ID NO 78
<211> LENGTH: 52
<212> TYPE: DNA
<213> ORGANISM: Artificial
<220> FEATURE:
<223> OTHER INFORMATION: oligonucleotide

<400> SEQUENCE: 78
agcaaaatga cttgatcttt atctacactt agtagaaatt acctatagtg ag 52

<210> SEQ ID NO 79
<211> LENGTH: 20
<212> TYPE: DNA
<213> ORGANISM: Artificial
<220> FEATURE:
<223> OTHER INFORMATION: spacer

<400> SEQUENCE: 79
cccccagcgc ttcagcgttc 20

<210> SEQ ID NO 80

<211> LENGTH: 55
<212> TYPE: DNA
<213> ORGANISM: Artificial
<220> FEATURE:
<223> OTHER INFORMATION: oligonucleotide

<400> SEQUENCE: 80
gaacgctgaa gcgctggggg atctacactt agtagaaatt acctatagtg agtcg 55

<210> SEQ ID NO 81
<211> LENGTH: 18
<212> TYPE: DNA
<213> ORGANISM: Artificial
<220> FEATURE:
<223> OTHER INFORMATION: spacer

<400> SEQUENCE: 81
actcctggtg attcttct 18

<210> SEQ ID NO 82
<211> LENGTH: 52
<212> TYPE: DNA
<213> ORGANISM: Artificial
<220> FEATURE:
<223> OTHER INFORMATION: oligonucleotide

<400> SEQUENCE: 82
agaagaatca ccaggagtat ctacaagagt agaaattacc tatagtgagt cg 52

<210> SEQ ID NO 83
<211> LENGTH: 18
<212> TYPE: DNA
<213> ORGANISM: Artificial
<220> FEATURE:
<223> OTHER INFORMATION: spacer

<400> SEQUENCE: 83
actcctggtg attcttct 18

<210> SEQ ID NO 84
<211> LENGTH: 52
<212> TYPE: DNA
<213> ORGANISM: Artificial
<220> FEATURE:
<223> OTHER INFORMATION: oligonucleotide

<400> SEQUENCE: 84
agaagaatca ccaggagtat ctacacttag tagaaattac ctatagtgag tc 52

<210> SEQ ID NO 85
<211> LENGTH: 18
<212> TYPE: DNA
<213> ORGANISM: Artificial
<220> FEATURE:
<223> OTHER INFORMATION: spacer

<400> SEQUENCE: 85
cccccagcgc ttcagcgt 18

<210> SEQ ID NO 86
<211> LENGTH: 50
<212> TYPE: DNA
<213> ORGANISM: Artificial
<220> FEATURE:
<223> OTHER INFORMATION: oligonucleotide

<400> SEQUENCE: 86
acgctgaagc gctgggggat ctacaagagt agaaattacc tatagtgagt 50

<210> SEQ ID NO 87
<211> LENGTH: 18
<212> TYPE: DNA
<213> ORGANISM: Artificial
<220> FEATURE:
<223> OTHER INFORMATION: spacer

<400> SEQUENCE: 87
cccccagcgc ttcagcgt 18

<210> SEQ ID NO 88
<211> LENGTH: 50
<212> TYPE: DNA
<213> ORGANISM: Artificial
<220> FEATURE:
<223> OTHER INFORMATION: oligonucleotide

<400> SEQUENCE: 88
acgctgaagc gctgggggat ctacacttag tagaaattac ctatagtgag 50

<210> SEQ ID NO 89
<211> LENGTH: 19
<212> TYPE: DNA
<213> ORGANISM: Artificial
<220> FEATURE:
<223> OTHER INFORMATION: spacer

<400> SEQUENCE: 89
actcctggtg attcttctt 19

<210> SEQ ID NO 90
<211> LENGTH: 50
<212> TYPE: DNA
<213> ORGANISM: Artificial
<220> FEATURE:
<223> OTHER INFORMATION: oligonucleotide

<400> SEQUENCE: 90
aagaagaatc accaggagta tctacaagag tagaaattac ctatagtgag 50

<210> SEQ ID NO 91
<211> LENGTH: 19
<212> TYPE: DNA
<213> ORGANISM: Artificial
<220> FEATURE:
<223> OTHER INFORMATION: spacer

<400> SEQUENCE: 91
actcctggtg attcttctt 19

<210> SEQ ID NO 92
<211> LENGTH: 50
<212> TYPE: DNA
<213> ORGANISM: Artificial
<220> FEATURE:
<223> OTHER INFORMATION: oligonucleotide

<400> SEQUENCE: 92
aagaagaatc accaggagta tctacactta gtagaaatta cctatagtga 50

<210> SEQ ID NO 93
<211> LENGTH: 19
<212> TYPE: DNA

```
<213> ORGANISM: Artificial
<220> FEATURE:
<223> OTHER INFORMATION: spacer

<400> SEQUENCE: 93

cccccagcgc ttcagcgtt                                                    19


<210> SEQ ID NO 94
<211> LENGTH: 54
<212> TYPE: DNA
<213> ORGANISM: Artificial
<220> FEATURE:
<223> OTHER INFORMATION: oligonucleotide

<400> SEQUENCE: 94

aacgctgaag cgctggggga tctacaagag tagaaattac ctatagtgag tcgt             54


<210> SEQ ID NO 95
<211> LENGTH: 19
<212> TYPE: DNA
<213> ORGANISM: Artificial
<220> FEATURE:
<223> OTHER INFORMATION: spacer

<400> SEQUENCE: 95

cccccagcgc ttcagcgtt                                                    19


<210> SEQ ID NO 96
<211> LENGTH: 54
<212> TYPE: DNA
<213> ORGANISM: Artificial
<220> FEATURE:
<223> OTHER INFORMATION: oligonucleotide

<400> SEQUENCE: 96

aacgctgaag cgctggggga tctacactta gtagaaatta cctatagtga gtcg             54


<210> SEQ ID NO 97
<211> LENGTH: 20
<212> TYPE: DNA
<213> ORGANISM: Artificial
<220> FEATURE:
<223> OTHER INFORMATION: spacer

<400> SEQUENCE: 97

accccagcgc ttcagcgttc                                                   20


<210> SEQ ID NO 98
<211> LENGTH: 50
<212> TYPE: DNA
<213> ORGANISM: Artificial
<220> FEATURE:
<223> OTHER INFORMATION: oligonucleotide

<400> SEQUENCE: 98

gaacgctgaa gcgctggggt atctacaaga gtagaaatta cctatagtga                 50


<210> SEQ ID NO 99
<211> LENGTH: 20
<212> TYPE: DNA
<213> ORGANISM: Artificial
<220> FEATURE:
<223> OTHER INFORMATION: spacer

<400> SEQUENCE: 99

ccaccagcgc ttcagcgttc                                                   20
```

<210> SEQ ID NO 100
<211> LENGTH: 50
<212> TYPE: DNA
<213> ORGANISM: Artificial
<220> FEATURE:
<223> OTHER INFORMATION: oligonucleotide

<400> SEQUENCE: 100
gaacgctgaa gcgctggtgg atctacaaga gtagaaatta cctatagtga 50

<210> SEQ ID NO 101
<211> LENGTH: 20
<212> TYPE: DNA
<213> ORGANISM: Artificial
<220> FEATURE:
<223> OTHER INFORMATION: spacer

<400> SEQUENCE: 101
ccccaagcgc ttcagcgttc 20

<210> SEQ ID NO 102
<211> LENGTH: 50
<212> TYPE: DNA
<213> ORGANISM: Artificial
<220> FEATURE:
<223> OTHER INFORMATION: oligonucleotide

<400> SEQUENCE: 102
gaacgctgaa gcgcttgggg atctacaaga gtagaaatta cctatagtga 50

<210> SEQ ID NO 103
<211> LENGTH: 20
<212> TYPE: DNA
<213> ORGANISM: Artificial
<220> FEATURE:
<223> OTHER INFORMATION: spacer

<400> SEQUENCE: 103
cccccatcgc ttcagcgttc 20

<210> SEQ ID NO 104
<211> LENGTH: 50
<212> TYPE: DNA
<213> ORGANISM: Artificial
<220> FEATURE:
<223> OTHER INFORMATION: oligonucleotide

<400> SEQUENCE: 104
gaacgctgaa gcgatggggg atctacaaga gtagaaatta cctatagtga 50

<210> SEQ ID NO 105
<211> LENGTH: 20
<212> TYPE: DNA
<213> ORGANISM: Artificial
<220> FEATURE:
<223> OTHER INFORMATION: spacer

<400> SEQUENCE: 105
cccccagctc ttcagcgttc 20

<210> SEQ ID NO 106
<211> LENGTH: 50
<212> TYPE: DNA
<213> ORGANISM: Artificial
<220> FEATURE:

<223> OTHER INFORMATION: oligonucleotide

<400> SEQUENCE: 106
gaacgctgaa gagctggggg atctacaaga gtagaaatta cctatagtga 50

<210> SEQ ID NO 107
<211> LENGTH: 20
<212> TYPE: DNA
<213> ORGANISM: Artificial
<220> FEATURE:
<223> OTHER INFORMATION: spacer

<400> SEQUENCE: 107
cccccagcgc gtcagcgttc 20

<210> SEQ ID NO 108
<211> LENGTH: 50
<212> TYPE: DNA
<213> ORGANISM: Artificial
<220> FEATURE:
<223> OTHER INFORMATION: oligonucleotide

<400> SEQUENCE: 108
gaacgctgac gcgctggggg atctacaaga gtagaaatta cctatagtga 50

<210> SEQ ID NO 109
<211> LENGTH: 20
<212> TYPE: DNA
<213> ORGANISM: Artificial
<220> FEATURE:
<223> OTHER INFORMATION: spacer

<400> SEQUENCE: 109
cccccagcgc ttaagcgttc 20

<210> SEQ ID NO 110
<211> LENGTH: 50
<212> TYPE: DNA
<213> ORGANISM: Artificial
<220> FEATURE:
<223> OTHER INFORMATION: oligonucleotide

<400> SEQUENCE: 110
gaacgcttaa gcgctggggg atctacaaga gtagaaatta cctatagtga 50

<210> SEQ ID NO 111
<211> LENGTH: 20
<212> TYPE: DNA
<213> ORGANISM: Artificial
<220> FEATURE:
<223> OTHER INFORMATION: spacer

<400> SEQUENCE: 111
cccccagcgc ttcatcgttc 20

<210> SEQ ID NO 112
<211> LENGTH: 50
<212> TYPE: DNA
<213> ORGANISM: Artificial
<220> FEATURE:
<223> OTHER INFORMATION: oligonucleotide

<400> SEQUENCE: 112
gaacgatgaa gcgctggggg atctacaaga gtagaaatta cctatagtga 50

<210> SEQ ID NO 113
<211> LENGTH: 20
<212> TYPE: DNA
<213> ORGANISM: Artificial
<220> FEATURE:
<223> OTHER INFORMATION: spacer

<400> SEQUENCE: 113
cccccagcgc ttcagcattc 20

<210> SEQ ID NO 114
<211> LENGTH: 50
<212> TYPE: DNA
<213> ORGANISM: Artificial
<220> FEATURE:
<223> OTHER INFORMATION: oligonucleotide

<400> SEQUENCE: 114
gaatgctgaa gcgctggggg atctacaaga gtagaaatta cctatagtga 50

<210> SEQ ID NO 115
<211> LENGTH: 20
<212> TYPE: DNA
<213> ORGANISM: Artificial
<220> FEATURE:
<223> OTHER INFORMATION: spacer

<400> SEQUENCE: 115
cccccagcgc ttcagcgtgc 20

<210> SEQ ID NO 116
<211> LENGTH: 55
<212> TYPE: DNA
<213> ORGANISM: Artificial
<220> FEATURE:
<223> OTHER INFORMATION: oligonucleotide

<400> SEQUENCE: 116
gcacgctgaa gcgctggggg atctacaaga gtagaaatta cctatagtga gtcgt 55

<210> SEQ ID NO 117
<211> LENGTH: 20
<212> TYPE: DNA
<213> ORGANISM: Artificial
<220> FEATURE:
<223> OTHER INFORMATION: spacer

<400> SEQUENCE: 117
accccagcgc ttcagcgttc 20

<210> SEQ ID NO 118
<211> LENGTH: 50
<212> TYPE: DNA
<213> ORGANISM: Artificial
<220> FEATURE:
<223> OTHER INFORMATION: oligonucleotide

<400> SEQUENCE: 118
gaacgctgaa gcgctggggt atctacactt agtagaaatt acctatagtg 50

<210> SEQ ID NO 119
<211> LENGTH: 20
<212> TYPE: DNA
<213> ORGANISM: Artificial
<220> FEATURE:
<223> OTHER INFORMATION: spacer

<400> SEQUENCE: 119
ccaccagcgc ttcagcgttc 20

<210> SEQ ID NO 120
<211> LENGTH: 50
<212> TYPE: DNA
<213> ORGANISM: Artificial
<220> FEATURE:
<223> OTHER INFORMATION: oligonucleotide

<400> SEQUENCE: 120
gaacgctgaa gcgctggtgg atctacactt agtagaaatt acctatagtg 50

<210> SEQ ID NO 121
<211> LENGTH: 20
<212> TYPE: DNA
<213> ORGANISM: Artificial
<220> FEATURE:
<223> OTHER INFORMATION: spacer

<400> SEQUENCE: 121
ccccaagcgc ttcagcgttc 20

<210> SEQ ID NO 122
<211> LENGTH: 50
<212> TYPE: DNA
<213> ORGANISM: Artificial
<220> FEATURE:
<223> OTHER INFORMATION: oligonucleotide

<400> SEQUENCE: 122
gaacgctgaa gcgcttgggg atctacactt agtagaaatt acctatagtg 50

<210> SEQ ID NO 123
<211> LENGTH: 20
<212> TYPE: DNA
<213> ORGANISM: Artificial
<220> FEATURE:
<223> OTHER INFORMATION: spacer

<400> SEQUENCE: 123
cccccatcgc ttcagcgttc 20

<210> SEQ ID NO 124
<211> LENGTH: 50
<212> TYPE: DNA
<213> ORGANISM: Artificial
<220> FEATURE:
<223> OTHER INFORMATION: oligonucleotide

<400> SEQUENCE: 124
gaacgctgaa gcgatggggg atctacactt agtagaaatt acctatagtg 50

<210> SEQ ID NO 125
<211> LENGTH: 20
<212> TYPE: DNA
<213> ORGANISM: Artificial
<220> FEATURE:
<223> OTHER INFORMATION: spacer

<400> SEQUENCE: 125
cccccagctc ttcagcgttc 20

<210> SEQ ID NO 126
<211> LENGTH: 50

<212> TYPE: DNA
<213> ORGANISM: Artificial
<220> FEATURE:
<223> OTHER INFORMATION: oligonucleotide

<400> SEQUENCE: 126
gaacgctgaa gagctggggg atctacactt agtagaaatt acctatagtg 50

<210> SEQ ID NO 127
<211> LENGTH: 20
<212> TYPE: DNA
<213> ORGANISM: Artificial
<220> FEATURE:
<223> OTHER INFORMATION: spacer

<400> SEQUENCE: 127
cccccagcgc gtcagcgttc 20

<210> SEQ ID NO 128
<211> LENGTH: 50
<212> TYPE: DNA
<213> ORGANISM: Artificial
<220> FEATURE:
<223> OTHER INFORMATION: oligonucleotide

<400> SEQUENCE: 128
gaacgctgac gcgctggggg atctacactt agtagaaatt acctatagtg 50

<210> SEQ ID NO 129
<211> LENGTH: 20
<212> TYPE: DNA
<213> ORGANISM: Artificial
<220> FEATURE:
<223> OTHER INFORMATION: spacer

<400> SEQUENCE: 129
cccccagcgc ttaagcgttc 20

<210> SEQ ID NO 130
<211> LENGTH: 50
<212> TYPE: DNA
<213> ORGANISM: Artificial
<220> FEATURE:
<223> OTHER INFORMATION: oligonucleotide

<400> SEQUENCE: 130
gaacgcttaa gcgctggggg atctacactt agtagaaatt acctatagtg 50

<210> SEQ ID NO 131
<211> LENGTH: 20
<212> TYPE: DNA
<213> ORGANISM: Artificial
<220> FEATURE:
<223> OTHER INFORMATION: spacer

<400> SEQUENCE: 131
cccccagcgc ttcatcgttc 20

<210> SEQ ID NO 132
<211> LENGTH: 50
<212> TYPE: DNA
<213> ORGANISM: Artificial
<220> FEATURE:
<223> OTHER INFORMATION: oligonucleotide

<400> SEQUENCE: 132
gaacgatgaa gcgctggggg atctacactt agtagaaatt acctatagtg 50

<210> SEQ ID NO 133
<211> LENGTH: 20
<212> TYPE: DNA
<213> ORGANISM: Artificial
<220> FEATURE:
<223> OTHER INFORMATION: spacer

<400> SEQUENCE: 133
cccccagcgc ttcagcattc 20

<210> SEQ ID NO 134
<211> LENGTH: 50
<212> TYPE: DNA
<213> ORGANISM: Artificial
<220> FEATURE:
<223> OTHER INFORMATION: oligonucleotide

<400> SEQUENCE: 134
gaatgctgaa gcgctggggg atctacactt agtagaaatt acctatagtg 50

<210> SEQ ID NO 135
<211> LENGTH: 20
<212> TYPE: DNA
<213> ORGANISM: Artificial
<220> FEATURE:
<223> OTHER INFORMATION: spacer

<400> SEQUENCE: 135
cccccagcgc ttcagcgtgc 20

<210> SEQ ID NO 136
<211> LENGTH: 55
<212> TYPE: DNA
<213> ORGANISM: Artificial
<220> FEATURE:
<223> OTHER INFORMATION: oligonucleotide

<400> SEQUENCE: 136
gcacgctgaa gcgctggggg atctacactt agtagaaatt acctatagtg agtcg 55

<210> SEQ ID NO 137
<211> LENGTH: 20
<212> TYPE: DNA
<213> ORGANISM: Artificial
<220> FEATURE:
<223> OTHER INFORMATION: spacer

<400> SEQUENCE: 137
cctcctggtg attcttcttc 20

<210> SEQ ID NO 138
<211> LENGTH: 55
<212> TYPE: DNA
<213> ORGANISM: Artificial
<220> FEATURE:
<223> OTHER INFORMATION: oligonucleotide

<400> SEQUENCE: 138
gaagaagaat caccaggagg atctacaaga gtagaaatta cctatagtga gtcgt 55

<210> SEQ ID NO 139
<211> LENGTH: 20
<212> TYPE: DNA
<213> ORGANISM: Artificial

<220> FEATURE:
<223> OTHER INFORMATION: spacer

<400> SEQUENCE: 139
acgcctggtg attcttcttc 20

<210> SEQ ID NO 140
<211> LENGTH: 55
<212> TYPE: DNA
<213> ORGANISM: Artificial
<220> FEATURE:
<223> OTHER INFORMATION: oligonucleotide

<400> SEQUENCE: 140
gaagaagaat caccaggcgt atctacaaga gtagaaatta cctatagtga gtcgt 55

<210> SEQ ID NO 141
<211> LENGTH: 20
<212> TYPE: DNA
<213> ORGANISM: Artificial
<220> FEATURE:
<223> OTHER INFORMATION: spacer

<400> SEQUENCE: 141
actcatggtg attcttcttc 20

<210> SEQ ID NO 142
<211> LENGTH: 55
<212> TYPE: DNA
<213> ORGANISM: Artificial
<220> FEATURE:
<223> OTHER INFORMATION: oligonucleotide

<400> SEQUENCE: 142
gaagaagaat caccatgagt atctacaaga gtagaaatta cctatagtga gtcgt 55

<210> SEQ ID NO 143
<211> LENGTH: 20
<212> TYPE: DNA
<213> ORGANISM: Artificial
<220> FEATURE:
<223> OTHER INFORMATION: spacer

<400> SEQUENCE: 143
actccttgtg attcttcttc 20

<210> SEQ ID NO 144
<211> LENGTH: 55
<212> TYPE: DNA
<213> ORGANISM: Artificial
<220> FEATURE:
<223> OTHER INFORMATION: oligonucleotide

<400> SEQUENCE: 144
gaagaagaat cacaaggagt atctacaaga gtagaaatta cctatagtga gtcgt 55

<210> SEQ ID NO 145
<211> LENGTH: 20
<212> TYPE: DNA
<213> ORGANISM: Artificial
<220> FEATURE:
<223> OTHER INFORMATION: spacer

<400> SEQUENCE: 145
actcctgggg attcttcttc 20

<210> SEQ ID NO 146
<211> LENGTH: 55
<212> TYPE: DNA
<213> ORGANISM: Artificial
<220> FEATURE:
<223> OTHER INFORMATION: oligonucleotide

<400> SEQUENCE: 146
gaagaagaat ccccaggagt atctacaaga gtagaaatta cctatagtga gtcgt 55

<210> SEQ ID NO 147
<211> LENGTH: 20
<212> TYPE: DNA
<213> ORGANISM: Artificial
<220> FEATURE:
<223> OTHER INFORMATION: spacer

<400> SEQUENCE: 147
actcctggtg cttcttcttc 20

<210> SEQ ID NO 148
<211> LENGTH: 55
<212> TYPE: DNA
<213> ORGANISM: Artificial
<220> FEATURE:
<223> OTHER INFORMATION: oligonucleotide

<400> SEQUENCE: 148
gaagaagaag caccaggagt atctacaaga gtagaaatta cctatagtga gtcgt 55

<210> SEQ ID NO 149
<211> LENGTH: 20
<212> TYPE: DNA
<213> ORGANISM: Artificial
<220> FEATURE:
<223> OTHER INFORMATION: spacer

<400> SEQUENCE: 149
actcctggtg atgcttcttc 20

<210> SEQ ID NO 150
<211> LENGTH: 55
<212> TYPE: DNA
<213> ORGANISM: Artificial
<220> FEATURE:
<223> OTHER INFORMATION: oligonucleotide

<400> SEQUENCE: 150
gaagaagcat caccaggagt atctacaaga gtagaaatta cctatagtga gtcgt 55

<210> SEQ ID NO 151
<211> LENGTH: 20
<212> TYPE: DNA
<213> ORGANISM: Artificial
<220> FEATURE:
<223> OTHER INFORMATION: spacer

<400> SEQUENCE: 151
actcctggtg attcgtcttc 20

<210> SEQ ID NO 152
<211> LENGTH: 55
<212> TYPE: DNA
<213> ORGANISM: Artificial
<220> FEATURE:
<223> OTHER INFORMATION: oligonucleotide

<400> SEQUENCE: 152
gaagacgaat caccaggagt atctacaaga gtagaaatta cctatagtga gtcgt 55

<210> SEQ ID NO 153
<211> LENGTH: 20
<212> TYPE: DNA
<213> ORGANISM: Artificial
<220> FEATURE:
<223> OTHER INFORMATION: spacer

<400> SEQUENCE: 153
actcctggtg attcttattc 20

<210> SEQ ID NO 154
<211> LENGTH: 55
<212> TYPE: DNA
<213> ORGANISM: Artificial
<220> FEATURE:
<223> OTHER INFORMATION: oligonucleotide

<400> SEQUENCE: 154
gaataagaat caccaggagt atctacaaga gtagaaatta cctatagtga gtcgt 55

<210> SEQ ID NO 155
<211> LENGTH: 20
<212> TYPE: DNA
<213> ORGANISM: Artificial
<220> FEATURE:
<223> OTHER INFORMATION: spacer

<400> SEQUENCE: 155
actcctggtg attcttctgc 20

<210> SEQ ID NO 156
<211> LENGTH: 55
<212> TYPE: DNA
<213> ORGANISM: Artificial
<220> FEATURE:
<223> OTHER INFORMATION: oligonucleotide

<400> SEQUENCE: 156
gcagaagaat caccaggagt atctacaaga gtagaaatta cctatagtga gtcgt 55

<210> SEQ ID NO 157
<211> LENGTH: 20
<212> TYPE: DNA
<213> ORGANISM: Artificial
<220> FEATURE:
<223> OTHER INFORMATION: spacer

<400> SEQUENCE: 157
cctcctggtg attcttcttc 20

<210> SEQ ID NO 158
<211> LENGTH: 55
<212> TYPE: DNA
<213> ORGANISM: Artificial
<220> FEATURE:
<223> OTHER INFORMATION: oligonucleotide

<400> SEQUENCE: 158
gaagaagaat caccaggagg atctacactt agtagaaatt acctatagtg agtcg 55

<210> SEQ ID NO 159

<211> LENGTH: 20
<212> TYPE: DNA
<213> ORGANISM: Artificial
<220> FEATURE:
<223> OTHER INFORMATION: spacer

<400> SEQUENCE: 159
acgcctggtg attcttcttc 20

<210> SEQ ID NO 160
<211> LENGTH: 55
<212> TYPE: DNA
<213> ORGANISM: Artificial
<220> FEATURE:
<223> OTHER INFORMATION: oligonucleotide

<400> SEQUENCE: 160
gaagaagaat caccaggcgt atctacactt agtagaaatt acctatagtg agtcg 55

<210> SEQ ID NO 161
<211> LENGTH: 20
<212> TYPE: DNA
<213> ORGANISM: Artificial
<220> FEATURE:
<223> OTHER INFORMATION: spacer

<400> SEQUENCE: 161
actcatggtg attcttcttc 20

<210> SEQ ID NO 162
<211> LENGTH: 55
<212> TYPE: DNA
<213> ORGANISM: Artificial
<220> FEATURE:
<223> OTHER INFORMATION: oligonucleotide

<400> SEQUENCE: 162
gaagaagaat caccatgagt atctacactt agtagaaatt acctatagtg agtcg 55

<210> SEQ ID NO 163
<211> LENGTH: 20
<212> TYPE: DNA
<213> ORGANISM: Artificial
<220> FEATURE:
<223> OTHER INFORMATION: spacer

<400> SEQUENCE: 163
actccttgtg attcttcttc 20

<210> SEQ ID NO 164
<211> LENGTH: 55
<212> TYPE: DNA
<213> ORGANISM: Artificial
<220> FEATURE:
<223> OTHER INFORMATION: oligonucleotide

<400> SEQUENCE: 164
gaagaagaat cacaaggagt atctacactt agtagaaatt acctatagtg agtcg 55

<210> SEQ ID NO 165
<211> LENGTH: 20
<212> TYPE: DNA
<213> ORGANISM: Artificial
<220> FEATURE:
<223> OTHER INFORMATION: spacer

<400> SEQUENCE: 165
actcctgggg attcttcttc 20

<210> SEQ ID NO 166
<211> LENGTH: 55
<212> TYPE: DNA
<213> ORGANISM: Artificial
<220> FEATURE:
<223> OTHER INFORMATION: oligonucleotide

<400> SEQUENCE: 166
gaagaagaat ccccaggagt atctacactt agtagaaatt acctatagtg agtcg 55

<210> SEQ ID NO 167
<211> LENGTH: 20
<212> TYPE: DNA
<213> ORGANISM: Artificial
<220> FEATURE:
<223> OTHER INFORMATION: spacer

<400> SEQUENCE: 167
actcctggtg cttcttcttc 20

<210> SEQ ID NO 168
<211> LENGTH: 55
<212> TYPE: DNA
<213> ORGANISM: Artificial
<220> FEATURE:
<223> OTHER INFORMATION: oligonucleotide

<400> SEQUENCE: 168
gaagaagaag caccaggagt atctacactt agtagaaatt acctatagtg agtcg 55

<210> SEQ ID NO 169
<211> LENGTH: 20
<212> TYPE: DNA
<213> ORGANISM: Artificial
<220> FEATURE:
<223> OTHER INFORMATION: spacer

<400> SEQUENCE: 169
actcctggtg atgcttcttc 20

<210> SEQ ID NO 170
<211> LENGTH: 55
<212> TYPE: DNA
<213> ORGANISM: Artificial
<220> FEATURE:
<223> OTHER INFORMATION: oligonucleotide

<400> SEQUENCE: 170
gaagaagcat caccaggagt atctacactt agtagaaatt acctatagtg agtcg 55

<210> SEQ ID NO 171
<211> LENGTH: 20
<212> TYPE: DNA
<213> ORGANISM: Artificial
<220> FEATURE:
<223> OTHER INFORMATION: spacer

<400> SEQUENCE: 171
actcctggtg attcgtcttc 20

<210> SEQ ID NO 172
<211> LENGTH: 55
<212> TYPE: DNA

<213> ORGANISM: Artificial
<220> FEATURE:
<223> OTHER INFORMATION: oligonucleotide

<400> SEQUENCE: 172
gaagacgaat caccaggagt atctacactt agtagaaatt acctatagtg agtcg 55

<210> SEQ ID NO 173
<211> LENGTH: 20
<212> TYPE: DNA
<213> ORGANISM: Artificial
<220> FEATURE:
<223> OTHER INFORMATION: spacer

<400> SEQUENCE: 173
actcctggtg attcttattc 20

<210> SEQ ID NO 174
<211> LENGTH: 55
<212> TYPE: DNA
<213> ORGANISM: Artificial
<220> FEATURE:
<223> OTHER INFORMATION: oligonucleotide

<400> SEQUENCE: 174
gaataagaat caccaggagt atctacactt agtagaaatt acctatagtg agtcg 55

<210> SEQ ID NO 175
<211> LENGTH: 20
<212> TYPE: DNA
<213> ORGANISM: Artificial
<220> FEATURE:
<223> OTHER INFORMATION: spacer

<400> SEQUENCE: 175
actcctggtg attcttctgc 20

<210> SEQ ID NO 176
<211> LENGTH: 55
<212> TYPE: DNA
<213> ORGANISM: Artificial
<220> FEATURE:
<223> OTHER INFORMATION: oligonucleotide

<400> SEQUENCE: 176
gcagaagaat caccaggagt atctacactt agtagaaatt acctatagtg agtcg 55

<210> SEQ ID NO 177
<211> LENGTH: 20
<212> TYPE: DNA
<213> ORGANISM: Artificial
<220> FEATURE:
<223> OTHER INFORMATION: spacer

<400> SEQUENCE: 177
tagtccaacc aacagaatct 20

<210> SEQ ID NO 178
<211> LENGTH: 50
<212> TYPE: DNA
<213> ORGANISM: Artificial
<220> FEATURE:
<223> OTHER INFORMATION: oligonucleotide

<400> SEQUENCE: 178
agattctgtt ggttggacta atctacaaga gtagaaatta cctatagtga 50

<210> SEQ ID NO 179
<211> LENGTH: 20
<212> TYPE: DNA
<213> ORGANISM: Artificial
<220> FEATURE:
<223> OTHER INFORMATION: spacer

<400> SEQUENCE: 179
gattccaacc aacagaatct 20

<210> SEQ ID NO 180
<211> LENGTH: 50
<212> TYPE: DNA
<213> ORGANISM: Artificial
<220> FEATURE:
<223> OTHER INFORMATION: oligonucleotide

<400> SEQUENCE: 180
agattctgtt ggttggaatc atctacaaga gtagaaatta cctatagtga 50

<210> SEQ ID NO 181
<211> LENGTH: 20
<212> TYPE: DNA
<213> ORGANISM: Artificial
<220> FEATURE:
<223> OTHER INFORMATION: spacer

<400> SEQUENCE: 181
gagtacaacc aacagaatct 20

<210> SEQ ID NO 182
<211> LENGTH: 50
<212> TYPE: DNA
<213> ORGANISM: Artificial
<220> FEATURE:
<223> OTHER INFORMATION: oligonucleotide

<400> SEQUENCE: 182
agattctgtt ggttgtactc atctacaaga gtagaaatta cctatagtga 50

<210> SEQ ID NO 183
<211> LENGTH: 20
<212> TYPE: DNA
<213> ORGANISM: Artificial
<220> FEATURE:
<223> OTHER INFORMATION: spacer

<400> SEQUENCE: 183
gagtcccacc aacagaatct 20

<210> SEQ ID NO 184
<211> LENGTH: 50
<212> TYPE: DNA
<213> ORGANISM: Artificial
<220> FEATURE:
<223> OTHER INFORMATION: oligonucleotide

<400> SEQUENCE: 184
agattctgtt ggtgggactc atctacaaga gtagaaatta cctatagtga 50

<210> SEQ ID NO 185
<211> LENGTH: 20
<212> TYPE: DNA
<213> ORGANISM: Artificial
<220> FEATURE:

<223> OTHER INFORMATION: spacer

<400> SEQUENCE: 185
gagtccaaac aacagaatct 20

<210> SEQ ID NO 186
<211> LENGTH: 50
<212> TYPE: DNA
<213> ORGANISM: Artificial
<220> FEATURE:
<223> OTHER INFORMATION: oligonucleotide

<400> SEQUENCE: 186
agattctgtt gtttggactc atctacaaga gtagaaatta cctatagtga 50

<210> SEQ ID NO 187
<211> LENGTH: 20
<212> TYPE: DNA
<213> ORGANISM: Artificial
<220> FEATURE:
<223> OTHER INFORMATION: spacer

<400> SEQUENCE: 187
gagtccaacc cacagaatct 20

<210> SEQ ID NO 188
<211> LENGTH: 50
<212> TYPE: DNA
<213> ORGANISM: Artificial
<220> FEATURE:
<223> OTHER INFORMATION: oligonucleotide

<400> SEQUENCE: 188
agattctgtg ggttggactc atctacaaga gtagaaatta cctatagtga 50

<210> SEQ ID NO 189
<211> LENGTH: 20
<212> TYPE: DNA
<213> ORGANISM: Artificial
<220> FEATURE:
<223> OTHER INFORMATION: spacer

<400> SEQUENCE: 189
gagtccaacc aaaagaatct 20

<210> SEQ ID NO 190
<211> LENGTH: 50
<212> TYPE: DNA
<213> ORGANISM: Artificial
<220> FEATURE:
<223> OTHER INFORMATION: oligonucleotide

<400> SEQUENCE: 190
agattctttt ggttggactc atctacaaga gtagaaatta cctatagtga 50

<210> SEQ ID NO 191
<211> LENGTH: 20
<212> TYPE: DNA
<213> ORGANISM: Artificial
<220> FEATURE:
<223> OTHER INFORMATION: spacer

<400> SEQUENCE: 191
gagtccaacc aacataatct 20

<210> SEQ ID NO 192
<211> LENGTH: 50
<212> TYPE: DNA
<213> ORGANISM: Artificial
<220> FEATURE:
<223> OTHER INFORMATION: oligonucleotide

<400> SEQUENCE: 192
agattatgtt ggttggactc atctacaaga gtagaaatta cctatagtga 50

<210> SEQ ID NO 193
<211> LENGTH: 20
<212> TYPE: DNA
<213> ORGANISM: Artificial
<220> FEATURE:
<223> OTHER INFORMATION: spacer

<400> SEQUENCE: 193
gagtccaacc aacagactct 20

<210> SEQ ID NO 194
<211> LENGTH: 50
<212> TYPE: DNA
<213> ORGANISM: Artificial
<220> FEATURE:
<223> OTHER INFORMATION: oligonucleotide

<400> SEQUENCE: 194
agagtctgtt ggttggactc atctacaaga gtagaaatta cctatagtga 50

<210> SEQ ID NO 195
<211> LENGTH: 20
<212> TYPE: DNA
<213> ORGANISM: Artificial
<220> FEATURE:
<223> OTHER INFORMATION: spacer

<400> SEQUENCE: 195
gagtccaacc aacagaatat 20

<210> SEQ ID NO 196
<211> LENGTH: 50
<212> TYPE: DNA
<213> ORGANISM: Artificial
<220> FEATURE:
<223> OTHER INFORMATION: oligonucleotide

<400> SEQUENCE: 196
atattctgtt ggttggactc atctacaaga gtagaaatta cctatagtga 50

<210> SEQ ID NO 197
<211> LENGTH: 20
<212> TYPE: DNA
<213> ORGANISM: Artificial
<220> FEATURE:
<223> OTHER INFORMATION: spacer

<400> SEQUENCE: 197
tagtccaacc aacagaatct 20

<210> SEQ ID NO 198
<211> LENGTH: 50
<212> TYPE: DNA
<213> ORGANISM: Artificial
<220> FEATURE:
<223> OTHER INFORMATION: oligonucleotide

<400> SEQUENCE: 198
agattctgtt ggttggacta atctacactt agtagaaatt acctatagtg 50

<210> SEQ ID NO 199
<211> LENGTH: 20
<212> TYPE: DNA
<213> ORGANISM: Artificial
<220> FEATURE:
<223> OTHER INFORMATION: spacer

<400> SEQUENCE: 199
gattccaacc aacagaatct 20

<210> SEQ ID NO 200
<211> LENGTH: 50
<212> TYPE: DNA
<213> ORGANISM: Artificial
<220> FEATURE:
<223> OTHER INFORMATION: oligonucleotide

<400> SEQUENCE: 200
agattctgtt ggttggaatc atctacactt agtagaaatt acctatagtg 50

<210> SEQ ID NO 201
<211> LENGTH: 20
<212> TYPE: DNA
<213> ORGANISM: Artificial
<220> FEATURE:
<223> OTHER INFORMATION: spacer

<400> SEQUENCE: 201
gagtacaacc aacagaatct 20

<210> SEQ ID NO 202
<211> LENGTH: 50
<212> TYPE: DNA
<213> ORGANISM: Artificial
<220> FEATURE:
<223> OTHER INFORMATION: oligonucleotide

<400> SEQUENCE: 202
agattctgtt ggttgtactc atctacactt agtagaaatt acctatagtg 50

<210> SEQ ID NO 203
<211> LENGTH: 20
<212> TYPE: DNA
<213> ORGANISM: Artificial
<220> FEATURE:
<223> OTHER INFORMATION: spacer

<400> SEQUENCE: 203
gagtcccacc aacagaatct 20

<210> SEQ ID NO 204
<211> LENGTH: 50
<212> TYPE: DNA
<213> ORGANISM: Artificial
<220> FEATURE:
<223> OTHER INFORMATION: oligonucleotide

<400> SEQUENCE: 204
agattctgtt ggtgggactc atctacactt agtagaaatt acctatagtg 50

<210> SEQ ID NO 205
<211> LENGTH: 20

<212> TYPE: DNA
<213> ORGANISM: Artificial
<220> FEATURE:
<223> OTHER INFORMATION: spacer

<400> SEQUENCE: 205
gagtccaaac aacagaatct 20

<210> SEQ ID NO 206
<211> LENGTH: 50
<212> TYPE: DNA
<213> ORGANISM: Artificial
<220> FEATURE:
<223> OTHER INFORMATION: oligonucleotide

<400> SEQUENCE: 206
agattctgtt gtttggactc atctacactt agtagaaatt acctatagtg 50

<210> SEQ ID NO 207
<211> LENGTH: 20
<212> TYPE: DNA
<213> ORGANISM: Artificial
<220> FEATURE:
<223> OTHER INFORMATION: spacer

<400> SEQUENCE: 207
gagtccaacc cacagaatct 20

<210> SEQ ID NO 208
<211> LENGTH: 50
<212> TYPE: DNA
<213> ORGANISM: Artificial
<220> FEATURE:
<223> OTHER INFORMATION: oligonucleotide

<400> SEQUENCE: 208
agattctgtg ggttggactc atctacactt agtagaaatt acctatagtg 50

<210> SEQ ID NO 209
<211> LENGTH: 20
<212> TYPE: DNA
<213> ORGANISM: Artificial
<220> FEATURE:
<223> OTHER INFORMATION: spacer

<400> SEQUENCE: 209
gagtccaacc aaaagaatct 20

<210> SEQ ID NO 210
<211> LENGTH: 50
<212> TYPE: DNA
<213> ORGANISM: Artificial
<220> FEATURE:
<223> OTHER INFORMATION: oligonucleotide

<400> SEQUENCE: 210
agattctttt ggttggactc atctacactt agtagaaatt acctatagtg 50

<210> SEQ ID NO 211
<211> LENGTH: 20
<212> TYPE: DNA
<213> ORGANISM: Artificial
<220> FEATURE:
<223> OTHER INFORMATION: spacer

<400> SEQUENCE: 211
gagtccaacc aacataatct 20

<210> SEQ ID NO 212
<211> LENGTH: 50
<212> TYPE: DNA
<213> ORGANISM: Artificial
<220> FEATURE:
<223> OTHER INFORMATION: oligonucleotide

<400> SEQUENCE: 212
agattatgtt ggttggactc atctacactt agtagaaatt acctatagtg 50

<210> SEQ ID NO 213
<211> LENGTH: 20
<212> TYPE: DNA
<213> ORGANISM: Artificial
<220> FEATURE:
<223> OTHER INFORMATION: spacer

<400> SEQUENCE: 213
gagtccaacc aacagactct 20

<210> SEQ ID NO 214
<211> LENGTH: 50
<212> TYPE: DNA
<213> ORGANISM: Artificial
<220> FEATURE:
<223> OTHER INFORMATION: oligonucleotide

<400> SEQUENCE: 214
agagtctgtt ggttggactc atctacactt agtagaaatt acctatagtg 50

<210> SEQ ID NO 215
<211> LENGTH: 20
<212> TYPE: DNA
<213> ORGANISM: Artificial
<220> FEATURE:
<223> OTHER INFORMATION: spacer

<400> SEQUENCE: 215
gagtccaacc aacagaatat 20

<210> SEQ ID NO 216
<211> LENGTH: 50
<212> TYPE: DNA
<213> ORGANISM: Artificial
<220> FEATURE:
<223> OTHER INFORMATION: oligonucleotide

<400> SEQUENCE: 216
atattctgtt ggttggactc atctacactt agtagaaatt acctatagtg 50

<210> SEQ ID NO 217
<211> LENGTH: 18
<212> TYPE: DNA
<213> ORGANISM: Artificial
<220> FEATURE:
<223> OTHER INFORMATION: primer

<400> SEQUENCE: 217
gctttgggct aagcgcaa 18

<210> SEQ ID NO 218
<211> LENGTH: 23
<212> TYPE: DNA
<213> ORGANISM: Artificial

<220> FEATURE:
<223> OTHER INFORMATION: primer

<400> SEQUENCE: 218
aaacagggta atttcaaaaa tct 23

<210> SEQ ID NO 219
<211> LENGTH: 18
<212> TYPE: DNA
<213> ORGANISM: Artificial
<220> FEATURE:
<223> OTHER INFORMATION: primer

<400> SEQUENCE: 219
cttctaagaa gcctcggc 18

<210> SEQ ID NO 220
<211> LENGTH: 18
<212> TYPE: DNA
<213> ORGANISM: Artificial
<220> FEATURE:
<223> OTHER INFORMATION: primer

<400> SEQUENCE: 220
gctttgggct aagcgtaa 18

<210> SEQ ID NO 221
<211> LENGTH: 25
<212> TYPE: DNA
<213> ORGANISM: Artificial
<220> FEATURE:
<223> OTHER INFORMATION: primer

<400> SEQUENCE: 221
aagtcaggta attttaaaca cttac 25

<210> SEQ ID NO 222
<211> LENGTH: 19
<212> TYPE: DNA
<213> ORGANISM: Artificial
<220> FEATURE:
<223> OTHER INFORMATION: primer

<400> SEQUENCE: 222
catctaaaaa gcctcgcca 19

<210> SEQ ID NO 223
<211> LENGTH: 18
<212> TYPE: DNA
<213> ORGANISM: Artificial
<220> FEATURE:
<223> OTHER INFORMATION: primer

<400> SEQUENCE: 223
actctatgct aagcgtgc 18

<210> SEQ ID NO 224
<211> LENGTH: 25
<212> TYPE: DNA
<213> ORGANISM: Artificial
<220> FEATURE:
<223> OTHER INFORMATION: primer

<400> SEQUENCE: 224
aattcctata cttcttttgc cactt 25

<210> SEQ ID NO 225
<211> LENGTH: 23
<212> TYPE: DNA
<213> ORGANISM: Artificial
<220> FEATURE:
<223> OTHER INFORMATION: primer

<400> SEQUENCE: 225
ctaaaaataa gatgcgccac aag 23

<210> SEQ ID NO 226
<211> LENGTH: 30
<212> TYPE: DNA
<213> ORGANISM: Artificial
<220> FEATURE:
<223> OTHER INFORMATION: primer

<400> SEQUENCE: 226
caatgaattc atccatagct aattctaaga 30

<210> SEQ ID NO 227
<211> LENGTH: 20
<212> TYPE: DNA
<213> ORGANISM: Artificial
<220> FEATURE:
<223> OTHER INFORMATION: primer

<400> SEQUENCE: 227
tggcgttaaa aacttcacca 20

<210> SEQ ID NO 228
<211> LENGTH: 20
<212> TYPE: DNA
<213> ORGANISM: Artificial
<220> FEATURE:
<223> OTHER INFORMATION: primer

<400> SEQUENCE: 228
gttgagtcag cactgctcat 20

<210> SEQ ID NO 229
<211> LENGTH: 22
<212> TYPE: DNA
<213> ORGANISM: Artificial
<220> FEATURE:
<223> OTHER INFORMATION: primer

<400> SEQUENCE: 229
gtatgaattc atccatagcg ag 22

<210> SEQ ID NO 230
<211> LENGTH: 24
<212> TYPE: DNA
<213> ORGANISM: Artificial
<220> FEATURE:
<223> OTHER INFORMATION: primer

<400> SEQUENCE: 230
gggaatttag tagcattaaa aacc 24

<210> SEQ ID NO 231
<211> LENGTH: 20
<212> TYPE: DNA
<213> ORGANISM: Artificial
<220> FEATURE:
<223> OTHER INFORMATION: primer

<400> SEQUENCE: 231
gttgaatcag cagaagctcc 20

<210> SEQ ID NO 232
<211> LENGTH: 26
<212> TYPE: DNA
<213> ORGANISM: Artificial
<220> FEATURE:
<223> OTHER INFORMATION: primer

<400> SEQUENCE: 232
taatgaaaac atcactatca aaagat 26

<210> SEQ ID NO 233
<211> LENGTH: 18
<212> TYPE: DNA
<213> ORGANISM: Artificial
<220> FEATURE:
<223> OTHER INFORMATION: primer

<400> SEQUENCE: 233
ggaggtgtgc cagacaga 18

<210> SEQ ID NO 234
<211> LENGTH: 19
<212> TYPE: DNA
<213> ORGANISM: Artificial
<220> FEATURE:
<223> OTHER INFORMATION: primer

<400> SEQUENCE: 234
attggaccag gctgaacac 19

<210> SEQ ID NO 235
<211> LENGTH: 37
<212> TYPE: DNA
<213> ORGANISM: Artificial
<220> FEATURE:
<223> OTHER INFORMATION: primer

<400> SEQUENCE: 235
taatacgact cactataggg ctttgggcta agcgcaa 37

<210> SEQ ID NO 236
<211> LENGTH: 42
<212> TYPE: DNA
<213> ORGANISM: Artificial
<220> FEATURE:
<223> OTHER INFORMATION: primer

<400> SEQUENCE: 236
taatacgact cactatagga aacagggtaa tttcaaaaat ct 42

<210> SEQ ID NO 237
<211> LENGTH: 37
<212> TYPE: DNA
<213> ORGANISM: Artificial
<220> FEATURE:
<223> OTHER INFORMATION: primer

<400> SEQUENCE: 237
taatacgact cactataggc ttctaagaag cctcggc 37

<210> SEQ ID NO 238

<211> LENGTH: 18
<212> TYPE: DNA
<213> ORGANISM: Artificial
<220> FEATURE:
<223> OTHER INFORMATION: primer

<400> SEQUENCE: 238
aacacaagct ttcggcag 18

<210> SEQ ID NO 239
<211> LENGTH: 22
<212> TYPE: DNA
<213> ORGANISM: Artificial
<220> FEATURE:
<223> OTHER INFORMATION: primer

<400> SEQUENCE: 239
gaaatttgga tctttgtcat cc 22

<210> SEQ ID NO 240
<211> LENGTH: 41
<212> TYPE: DNA
<213> ORGANISM: Artificial
<220> FEATURE:
<223> OTHER INFORMATION: primer

<400> SEQUENCE: 240
tgcggccaat gtttgtaatc agccaaggaa attttgggga c 41

<210> SEQ ID NO 241
<211> LENGTH: 39
<212> TYPE: DNA
<213> ORGANISM: Artificial
<220> FEATURE:
<223> OTHER INFORMATION: primer

<400> SEQUENCE: 241
cgcattggca tggaagtcac tttgatggca cctgtgtag 39

<210> SEQ ID NO 242
<211> LENGTH: 19
<212> TYPE: DNA
<213> ORGANISM: Artificial
<220> FEATURE:
<223> OTHER INFORMATION: primer

<400> SEQUENCE: 242
ttccttgtct gattagttc 19

<210> SEQ ID NO 243
<211> LENGTH: 18
<212> TYPE: DNA
<213> ORGANISM: Artificial
<220> FEATURE:
<223> OTHER INFORMATION: primer

<400> SEQUENCE: 243
accttcggga acgtggtt 18

<210> SEQ ID NO 244
<211> LENGTH: 21
<212> TYPE: DNA
<213> ORGANISM: Artificial
<220> FEATURE:
<223> OTHER INFORMATION: primer

<400> SEQUENCE: 244
ttaatttagt gcgtgatctc c 21

<210> SEQ ID NO 245
<211> LENGTH: 20
<212> TYPE: DNA
<213> ORGANISM: Artificial
<220> FEATURE:
<223> OTHER INFORMATION: primer

<400> SEQUENCE: 245
agcatctgta atggttccat 20

<210> SEQ ID NO 246
<211> LENGTH: 39
<212> TYPE: DNA
<213> ORGANISM: Artificial
<220> FEATURE:
<223> OTHER INFORMATION: primer

<400> SEQUENCE: 246
gcaagtaaag tttgaaacct agctcagggt ttttcggct 39

<210> SEQ ID NO 247
<211> LENGTH: 40
<212> TYPE: DNA
<213> ORGANISM: Artificial
<220> FEATURE:
<223> OTHER INFORMATION: primer

<400> SEQUENCE: 247
aagcaagtaa agtttgaaac ctactcaggg tttttcggct 40

<210> SEQ ID NO 248
<211> LENGTH: 42
<212> TYPE: DNA
<213> ORGANISM: Artificial
<220> FEATURE:
<223> OTHER INFORMATION: primer

<400> SEQUENCE: 248
tgtaaagcaa gtaaagtttg aaaccctcag ggtttttcgg ct 42

<210> SEQ ID NO 249
<211> LENGTH: 38
<212> TYPE: DNA
<213> ORGANISM: Artificial
<220> FEATURE:
<223> OTHER INFORMATION: primer

<400> SEQUENCE: 249
tggacagctg gtgctaatag aaaagtccta ggttgaag 38

<210> SEQ ID NO 250
<211> LENGTH: 23
<212> TYPE: DNA
<213> ORGANISM: Artificial
<220> FEATURE:
<223> OTHER INFORMATION: primer

<400> SEQUENCE: 250
ggcaaatcta ccaatggttc taa 23

<210> SEQ ID NO 251
<211> LENGTH: 21
<212> TYPE: DNA

<213> ORGANISM: Artificial
<220> FEATURE:
<223> OTHER INFORMATION: primer

<400> SEQUENCE: 251
gcagcttatt atgtgggtta t 21

<210> SEQ ID NO 252
<211> LENGTH: 25
<212> TYPE: DNA
<213> ORGANISM: Artificial
<220> FEATURE:
<223> OTHER INFORMATION: primer

<400> SEQUENCE: 252
tgtaaagcaa gtaaagtttg aaacc 25

<210> SEQ ID NO 253
<211> LENGTH: 15
<212> TYPE: DNA
<213> ORGANISM: Artificial
<220> FEATURE:
<223> OTHER INFORMATION: primer

<400> SEQUENCE: 253
tggacagctg gtgct 15

<210> SEQ ID NO 254
<211> LENGTH: 22
<212> TYPE: DNA
<213> ORGANISM: Artificial
<220> FEATURE:
<223> OTHER INFORMATION: primer

<400> SEQUENCE: 254
agaagttatt tgactcctgg tg 22

<210> SEQ ID NO 255
<211> LENGTH: 20
<212> TYPE: DNA
<213> ORGANISM: Artificial
<220> FEATURE:
<223> OTHER INFORMATION: primer

<400> SEQUENCE: 255
cctgaagaag aatcaccagg 20

<210> SEQ ID NO 256
<211> LENGTH: 22
<212> TYPE: DNA
<213> ORGANISM: Artificial
<220> FEATURE:
<223> OTHER INFORMATION: primer

<400> SEQUENCE: 256
caccaggagt caaataactt ct 22

<210> SEQ ID NO 257
<211> LENGTH: 21
<212> TYPE: DNA
<213> ORGANISM: Artificial
<220> FEATURE:
<223> OTHER INFORMATION: primer

<400> SEQUENCE: 257
actcctggtg attcttcttc a 21

<210> SEQ ID NO 258
<211> LENGTH: 20
<212> TYPE: DNA
<213> ORGANISM: Artificial
<220> FEATURE:
<223> OTHER INFORMATION: primer sequence

<400> SEQUENCE: 258
taatttctac tcttgtagat 20

<210> SEQ ID NO 259
<211> LENGTH: 20
<212> TYPE: DNA
<213> ORGANISM: Artificial
<220> FEATURE:
<223> OTHER INFORMATION: primer sequence

<400> SEQUENCE: 259
aatttctact aagtgtagat 20

<210> SEQ ID NO 260
<211> LENGTH: 21
<212> TYPE: DNA
<213> ORGANISM: Artificial
<220> FEATURE:
<223> OTHER INFORMATION: primer

<400> SEQUENCE: 260
ttaatttagt gcgtgatctc a 21

<210> SEQ ID NO 261
<211> LENGTH: 21
<212> TYPE: DNA
<213> ORGANISM: Artificial
<220> FEATURE:
<223> OTHER INFORMATION: primer

<400> SEQUENCE: 261
ttaatttagt gcgtgatcta c 21

<210> SEQ ID NO 262
<211> LENGTH: 21
<212> TYPE: DNA
<213> ORGANISM: Artificial
<220> FEATURE:
<223> OTHER INFORMATION: primer

<400> SEQUENCE: 262
ttaatttagt gcgtgatcgc c 21

<210> SEQ ID NO 263
<211> LENGTH: 20
<212> TYPE: DNA
<213> ORGANISM: Artificial
<220> FEATURE:
<223> OTHER INFORMATION: primer

<400> SEQUENCE: 263
agcatctgta atggttccag 20

<210> SEQ ID NO 264
<211> LENGTH: 20
<212> TYPE: DNA
<213> ORGANISM: Artificial
<220> FEATURE:

<223> OTHER INFORMATION: primer

<400> SEQUENCE: 264
agcatctgta atggttccct 20

<210> SEQ ID NO 265
<211> LENGTH: 20
<212> TYPE: DNA
<213> ORGANISM: Artificial
<220> FEATURE:
<223> OTHER INFORMATION: primer

<400> SEQUENCE: 265
agcatctgta atggttcaat 20

<210> SEQ ID NO 266
<211> LENGTH: 42
<212> TYPE: DNA
<213> ORGANISM: Artificial
<220> FEATURE:
<223> OTHER INFORMATION: primer

<400> SEQUENCE: 266
tgtaaagcaa gtaaagtttg aaaccctcag ggtttttcgg cg 42

<210> SEQ ID NO 267
<211> LENGTH: 42
<212> TYPE: DNA
<213> ORGANISM: Artificial
<220> FEATURE:
<223> OTHER INFORMATION: primer

<400> SEQUENCE: 267
tgtaaagcaa gtaaagtttg aaaccctcag ggtttttcgg at 42

<210> SEQ ID NO 268
<211> LENGTH: 42
<212> TYPE: DNA
<213> ORGANISM: Artificial
<220> FEATURE:
<223> OTHER INFORMATION: primer

<400> SEQUENCE: 268
tgtaaagcaa gtaaagtttg aaaccctcag ggtttttcgt ct 42

<210> SEQ ID NO 269
<211> LENGTH: 42
<212> TYPE: DNA
<213> ORGANISM: Artificial
<220> FEATURE:
<223> OTHER INFORMATION: primer

<400> SEQUENCE: 269
ggtaaagcaa gtaaagtttg aaaccctcag ggtttttcgg ct 42

<210> SEQ ID NO 270
<211> LENGTH: 42
<212> TYPE: DNA
<213> ORGANISM: Artificial
<220> FEATURE:
<223> OTHER INFORMATION: primer

<400> SEQUENCE: 270
tttaaagcaa gtaaagtttg aaaccctcag ggtttttcgg ct 42

<210> SEQ ID NO 271
<211> LENGTH: 42
<212> TYPE: DNA
<213> ORGANISM: Artificial
<220> FEATURE:
<223> OTHER INFORMATION: primer

<400> SEQUENCE: 271
tggaaagcaa gtaaagtttg aaaccctcag ggtttttcgg ct 42

<210> SEQ ID NO 272
<211> LENGTH: 41
<212> TYPE: DNA
<213> ORGANISM: Artificial
<220> FEATURE:
<223> OTHER INFORMATION: primer

<400> SEQUENCE: 272
tgtaaagcaa gtaaagtttg aaaccctcag ggtttttcgg c 41

<210> SEQ ID NO 273
<211> LENGTH: 41
<212> TYPE: DNA
<213> ORGANISM: Artificial
<220> FEATURE:
<223> OTHER INFORMATION: primer

<400> SEQUENCE: 273
gtaaagcaag taaagtttga aaccctcagg gtttttcggc t 41

<210> SEQ ID NO 274
<211> LENGTH: 38
<212> TYPE: DNA
<213> ORGANISM: Artificial
<220> FEATURE:
<223> OTHER INFORMATION: primer

<400> SEQUENCE: 274
tggacagctg gtgctaatag aaaagtccta ggttgaat 38

<210> SEQ ID NO 275
<211> LENGTH: 38
<212> TYPE: DNA
<213> ORGANISM: Artificial
<220> FEATURE:
<223> OTHER INFORMATION: primer

<400> SEQUENCE: 275
tggacagctg gtgctaatag aaaagtccta ggttgacg 38

<210> SEQ ID NO 276
<211> LENGTH: 38
<212> TYPE: DNA
<213> ORGANISM: Artificial
<220> FEATURE:
<223> OTHER INFORMATION: primer

<400> SEQUENCE: 276
tggacagctg gtgctaatag aaaagtccta ggttgcag 38

<210> SEQ ID NO 277
<211> LENGTH: 38
<212> TYPE: DNA
<213> ORGANISM: Artificial
<220> FEATURE:
<223> OTHER INFORMATION: primer

<400> SEQUENCE: 277
gggacagctg gtgctaatag aaaagtccta ggttgaag 38

<210> SEQ ID NO 278
<211> LENGTH: 38
<212> TYPE: DNA
<213> ORGANISM: Artificial
<220> FEATURE:
<223> OTHER INFORMATION: primer

<400> SEQUENCE: 278
ttgacagctg gtgctaatag aaaagtccta ggttgaag 38

<210> SEQ ID NO 279
<211> LENGTH: 38
<212> TYPE: DNA
<213> ORGANISM: Artificial
<220> FEATURE:
<223> OTHER INFORMATION: primer

<400> SEQUENCE: 279
tgtacagctg gtgctaatag aaaagtccta ggttgaag 38

<210> SEQ ID NO 280
<211> LENGTH: 37
<212> TYPE: DNA
<213> ORGANISM: Artificial
<220> FEATURE:
<223> OTHER INFORMATION: primer

<400> SEQUENCE: 280
tggacagctg gtgctaatag aaaagtccta ggttgaa 37

<210> SEQ ID NO 281
<211> LENGTH: 40
<212> TYPE: RNA
<213> ORGANISM: Artificial
<220> FEATURE:
<223> OTHER INFORMATION: gRNA

<400> SEQUENCE: 281
uaauuucuac ucuuguagau acuccuggug auucuucuuc 40

<210> SEQ ID NO 282
<211> LENGTH: 44
<212> TYPE: RNA
<213> ORGANISM: Artificial
<220> FEATURE:
<223> OTHER INFORMATION: gRNA

<400> SEQUENCE: 282
uggauaauuu cuacucuugu agauacuccu ggugauucuu cuuc 44

<210> SEQ ID NO 283
<211> LENGTH: 49
<212> TYPE: RNA
<213> ORGANISM: Artificial
<220> FEATURE:
<223> OTHER INFORMATION: gRNA

<400> SEQUENCE: 283
gggaauggau aauuucuacu cuuguagaua cuccugguga uucuucuuc 49

<210> SEQ ID NO 284
<211> LENGTH: 42

```
<212> TYPE: RNA
<213> ORGANISM: Artificial
<220> FEATURE:
<223> OTHER INFORMATION: gRNA
<220> FEATURE:
<221> NAME/KEY: misc_feature
<222> LOCATION: (1)..(1)
<223> OTHER INFORMATION: 2'-O-methyl-C, phosphorothioate linkage
<220> FEATURE:
<221> NAME/KEY: misc_feature
<222> LOCATION: (2)..(2)
<223> OTHER INFORMATION: phosphorothioate linkage

<400> SEQUENCE: 284

cuuaauuucu acucuuguag auacuccugg ugauucuucu uc                        42


<210> SEQ ID NO 285
<211> LENGTH: 40
<212> TYPE: DNA
<213> ORGANISM: Artificial
<220> FEATURE:
<223> OTHER INFORMATION: gRNA/DNA hybrid
<220> FEATURE:
<221> NAME/KEY: misc_feature
<222> LOCATION: (1)..(38)
<223> OTHER INFORMATION: RNA nucleotides

<400> SEQUENCE: 285

uaauuucuac ucuuguagau acuccuggug auucuucutc                           40


<210> SEQ ID NO 286
<211> LENGTH: 40
<212> TYPE: DNA
<213> ORGANISM: Artificial
<220> FEATURE:
<223> OTHER INFORMATION: rRNA/DNA hybrid
<220> FEATURE:
<221> NAME/KEY: misc_feature
<222> LOCATION: (1)..(20)
<223> OTHER INFORMATION: RNA nucleotide
<220> FEATURE:
<221> NAME/KEY: misc_feature
<222> LOCATION: (21)..(21)
<223> OTHER INFORMATION: DNA nucleotide
<220> FEATURE:
<221> NAME/KEY: misc_feature
<222> LOCATION: (22)..(27)
<223> OTHER INFORMATION: RNA nucleotide
<220> FEATURE:
<221> NAME/KEY: misc_feature
<222> LOCATION: (28)..(28)
<223> OTHER INFORMATION: DNA nucleotide
<220> FEATURE:
<221> NAME/KEY: misc_feature
<222> LOCATION: (29)..(38)
<223> OTHER INFORMATION: RNA nucleotide
<220> FEATURE:
<221> NAME/KEY: misc_feature
<222> LOCATION: (39)..(40)
<223> OTHER INFORMATION: DNA nucleotide

<400> SEQUENCE: 286

uaauuucuac ucuuguagau acuccuggug auucuucutc                           40


<210> SEQ ID NO 287
<211> LENGTH: 40
<212> TYPE: RNA
<213> ORGANISM: Artificial
<220> FEATURE:
<223> OTHER INFORMATION: gRNA

<400> SEQUENCE: 287
```

-continued

```
uaauuucuac ucuuguagau aaaccuagug auguuaauac                             40


<210> SEQ ID NO 288
<211> LENGTH: 44
<212> TYPE: RNA
<213> ORGANISM: Artificial
<220> FEATURE:
<223> OTHER INFORMATION: gRNA

<400> SEQUENCE: 288

uggauaauuu cuacucuugu agauaaaccu agugauguua auac                        44


<210> SEQ ID NO 289
<211> LENGTH: 49
<212> TYPE: RNA
<213> ORGANISM: Artificial
<220> FEATURE:
<223> OTHER INFORMATION: gRNA

<400> SEQUENCE: 289

gggaauggau aauuucuacu cuuguagaua aaccuaguga uguuaauac                   49


<210> SEQ ID NO 290
<211> LENGTH: 40
<212> TYPE: DNA
<213> ORGANISM: Artificial
<220> FEATURE:
<223> OTHER INFORMATION: gRNA/DNA hybrid
<220> FEATURE:
<221> NAME/KEY: misc_feature
<222> LOCATION: (1)..(20)
<223> OTHER INFORMATION: RNA nucleotide
<220> FEATURE:
<221> NAME/KEY: misc_feature
<222> LOCATION: (21)..(21)
<223> OTHER INFORMATION: DNA nucleotide
<220> FEATURE:
<221> NAME/KEY: misc_feature
<222> LOCATION: (22)..(27)
<223> OTHER INFORMATION: RNA nucleotide
<220> FEATURE:
<221> NAME/KEY: misc_feature
<222> LOCATION: (28)..(28)
<223> OTHER INFORMATION: DNA nucleotide
<220> FEATURE:
<221> NAME/KEY: misc_feature
<222> LOCATION: (29)..(38)
<223> OTHER INFORMATION: RNA nucleotide
<220> FEATURE:
<221> NAME/KEY: misc_feature
<222> LOCATION: (39)..(40)
<223> OTHER INFORMATION: DNA nucleotide

<400> SEQUENCE: 290

uaauuucuac ucuuguagau aaaccuagug auguuaauac                             40
```

CRISPR-BASED METHODS FOR THE DETECTION OF NUCLEIC ACIDS IN A SAMPLE

REFERENCE TO AN ELECTRONIC SEQUENCE LISTING

The contents of the electronic sequence listing (693148_401USPC_SeqListing.txt; Size: 90,432 bytes; and Date of Creation: Dec. 22, 2022) is herein incorporated by reference in its entirety.

CROSS-REFERENCE TO RELATED APPLICATION

This application claims the benefit of priority of Singapore Patent Application No. 10202006167W filed 26 Jun. 2020, the contents of which being hereby incorporated by reference in its entirety for all purposes.

FIELD OF THE INVENTION

The present invention is in the field of molecular diagnostics and is directed to the detection of target nucleic acids in a sample using a modified CRISPR-Dx system, typically with prior amplification of the target.

BACKGROUND OF THE INVENTION

CRISPR-Cas has emerged as a powerful technology that can potentially drive next-generation diagnostic platforms. After binding to and cutting a specific target substrate, certain Cas enzymes are then hyperactivated to cleave all neighbouring nucleic acids indiscriminately (Chen, J. S. et al. (2018) Science 360, 436-439, doi:10.1126/science.aar6245). By programming the Cas nuclease to recognize desired sequences, such as those containing cancer mutations or from pathogens-of-interest, and providing single-stranded DNA (ssDNA) or RNA reporter molecules in the reaction mix, various groups have successfully developed CRISPR-based diagnostics (CRISPR-Dx) for a range of applications (Gootenberg et al. (2017) Science 356, 438-442, doi:10.1126/science.aam9321; Gootenberg et al. (2018) Science 360, 439-444, doi:10.1126/science.aaq0179; Harrington et al. (2018) Science 362, 839-842, doi:10.1126/science.aav4294; Teng et al. (2019) Genome Biol 20, 132, doi:10.1186/s13059-019-1742-z; Myhrvold et al. (2018) Science 360, 444-448, doi:10.1126/science.aas8836). Unsurprisingly, it has also not escaped attention that the same technology can be quickly applied to tackle the ongoing COVID-19 pandemic. Within a few months, multiple CRISPR-based assays for the disease have been announced (Broughton et al. (2020) Nat Biotechnol, doi:10.1038/s41587-020-0513-4; Ackerman et al. (2020) Nature, doi:10.1038/s41586-020-2279-8; Guo et al. (2020) Cell Discov 6, 34, doi:10.1038/s41421-020-0174-y; Joung et al. (2020) doi:10.1101/2020.05.04.20091231; Hou et al. (2020) doi:10.1101/2020.02.22.20025460; Lucia et al. (2020) doi:10.1101/2020.02.29.971127; Ding et al. (2020) doi:10.1101/2020.03.19.998724; Azhar et al. (2020) doi:10.1101/2020.04.07.028167; Rauch et al. (2020) doi:10.1101/2020.04.20.052159), underscoring the ease-of-use and versatility of the technology.

While promising, existing CRISPR-Dx have not considered the possibility that the viral sequences may be altered over time or in human cells. Viruses are known to mutate especially under selective pressure. Using SARS-CoV-2 as an example: Thousands of SARS-CoV-2 genomes have been sequenced and deposited in the GISAID database and analysis of their sequences revealed numerous mutations, suggesting an ongoing adaptation of the coronavirus to its novel human host. In particular, mutations had been discovered in the target sites of many current COVID-19 diagnostic tests and could affect the performance of these qRT-PCR tests (Wang et al. (2020) arXiv e-prints, arXiv:2005.02188 https://ui.adsabs.harvard.edu/abs/2020arXiv200502188W). Similarly, mutations in the SARS-CoV-2 genome may also create mismatches in the guide RNA (gRNA) binding site and consequently affect the Cas ribonucleoprotein (RNP) complex's ability to recognize its target. In addition, ADAR and APOBEC deaminases form part of the human host's innate immune responses to viral infection and had recently been shown to edit SARS-CoV-2 RNA. The respective adenosine-to-inosine and cytosine-to-uracil changes may also affect the ability of the CRISPR-Cas system to detect the virus.

Besides a lack of robustness to variations that commonly occur in pathogens, in particular viruses, there are other shortcomings of existing CRISPR-based assays. First, the duration of reported tests is generally around 40 min or so. In point-of-need scenarios, the waiting time should ideally be as short as possible. Hence, it is desirable if the CRISPR reaction can be sped up. Second, to boost sensitivity, CRISPR-Cas detection is typically combined with an isothermal amplification step, of which there are several options. Due to supply chain issues in the ongoing pandemic, reverse transcription loop-mediated isothermal amplification (RT-LAMP) is the method-of-choice for COVID-19 applications. However, with the exception of AapCas12b and the TtCsm complex, the operating temperature for most Cas enzymes used in diagnostics is narrowly centered around 37° C., while the RT-LAMP reaction is performed at 60-65° C. Consequently, two heat blocks are required for many CRISPR diagnostics and time is also wasted in cooling the sample tubes. It is currently unclear if there are additional Cas enzymes that will allow the entire workflow to be performed at a single temperature. Third, most reported tests have only been evaluated on purified RNA samples. Consequently, it is unclear how well they will work on unpurified clinical specimens. Moreover, the process of RNA isolation adds at least 15 min to the test duration. Fourth, most reported tests do not have a built-in human internal control, which is essential for confirming that a negative result is not due to an insufficient amount of patient material. In the DETECTR system (Broughton et al., supra), separate reaction tubes are utilized for the human control and the actual (SARS-CoV-2) test, but this setup is not ideal since one has to infer that the tube for the viral test contains the correct amount of sample input.

There is thus demand in the art for alternative CRISPR-Dx systems that allow mitigating the loss in signal caused by genomic mutations or RNA editing.

SUMMARY OF THE INVENTION

The present invention is based on the inventors' finding upon screening several different Cas12a enzymes that enAsCas12a, an engineered E174R/S542R/K548R variant of AsCas12a (Kleinstiver, et al. (2019) *Nat Biotechnol* 37, 276-282, doi:10.1038/s41587-018-0011-0), was able to tolerate mismatches at the target site better than other (wild-type) Cas12a nucleases. Furthermore, they could demonstrate that incorporation of two gRNAs into the CRISPR-Cas system resulted in partial rescue of the output signal when a variant nucleotide was present in the substrate. Notably, while the developed assay could tolerate single nucleotide variations (SNVs) in the target sites, it still maintained high specificity and, using a SARS-CoV-2 as a proof-of-concept example, was able to distinguish SARS-CoV-2 from SARS-CoV and MERS-CoV reliably.

The inventors further discovered that the use of modified guides improves reaction kinetics. Hybrid DNA-RNA guides work particularly well at the selected sites, increasing the on-target signal significantly compared to regular gRNAs while suppressing off-target background to negligible levels. Moreover, the inventors found that enAsCas12a exhibits an unexpectedly wide range of operating temperatures and is active from 37 to 65° C. This property allows to perform the entire RT-LAMP-CRISPR workflow in a single heat block.

It was further demonstrated that such an assay can successfully be applied on nasopharyngeal (NP) specimens directly without an extra RNA purification step, thereby improving its ease-of-use, and also allows incorporation of a human internal control into the same reaction tube, thereby simplifying the workflow even further.

Taken together, the newly developed VaNGuard (Variant Nucleotide Guard) test holds the potential to address the need for a robust and rapid diagnostic assay that can be used to arrest viral spread in pandemic scenarios. While the various strategies presented here use SARS-CoV-2 as a proof-of-concept, it is understood that they may easily be adapted for use in future pandemics.

In a first aspect, the present invention is directed to a method for detecting the presence or amount of a target nucleic acid in a sample, comprising:

(a) contacting the target nucleic acid and/or an amplicon thereof with a nucleic acid detection system, said nucleic acid detection system comprising (1) at least one Cas12a enzyme, (2) at least one guide RNA (gRNA), and (3) at least one detection reagent; wherein said at least one Cas12a enzyme (1) is LbCas12a or AsCas12a or a variant thereof; and
  wherein said at least one gRNA (2) comprises a spacer sequence of at least 20 nucleotides in length that specifically recognizes and binds a target sequence in the target nucleic acid, under conditions that allow binding of the complex of the Cas12a enzyme and the at least one gRNA to the target sequence and resultant activation of the Cas12a enzyme;
  wherein the activated Cas12a enzyme generates, by interaction with the at least one detection reagent (3), a detectable, and optionally quantifiable, signal; and
(b) detecting and optionally quantifying said detectable signal.

In various embodiments of the methods described herein, the Cas12a enzyme is LbCas12a, AsCas12a or a variant, such as an engineered variant thereof. In specific embodiments, the Cas12a enzyme comprises or consists of the amino acid sequence set forth in SEQ ID NO:3 (LbCas12a) or SEQ ID NO:2 (AsCas12a) or a variant thereof that retains Cas12a functionality and has at least 80% sequence identity to SEQ ID NO:2 or 3.

In various embodiments, the Cas12a enzyme is AsCas12a, preferably comprising or consisting of the amino acid sequence set forth in SEQ ID NO:2, or a variant thereof that retains Cas12a functionality and has at least 80% sequence identity to SEQ ID NO:2, preferably a variant comprising or consisting of the amino acid sequence set forth in SEQ ID NO:1.

In various embodiments, the at least one gRNA molecule comprises a 5'-terminal extension of at least 2, preferably 4 to 9 nucleotides. Alternatively or additionally, the at least one gRNA sequence may comprise at least one chemical modification of a nucleotide selected from 2'-O-methyl RNA, 2'-fluoro base nucleotide and phosphorothioate linkage.

In various embodiments, the at least one gRNA is a DNA-RNA hybrid and comprises at least 1 DNA nucleotide, preferably 2 to 4 DNA nucleotides, preferably in the spacer sequence, the rest being RNA nucleotides. Said DNA nucleotides may be are located (1) at the 3' terminus of the spacer sequence, preferably the 3'-terminal and/or the 3'-penultimate nucleotide, and/or (2) at the 5' end of the spacer sequence, such as in position 1 of the spacer sequence and/or (3) at any of positions 2, 3, 4, 5, 6, 7, 8, 9, 10, 11 and 12 of the spacer sequence, for example at position 8, with positional numbering being based on the spacer sequence (not the complete gRNA sequence) in 5' to 3' orientation.

In various embodiments, the at least one gRNA comprises at least two gRNAs. Said at least two gRNA may be directed to different target sites in the same target nucleic acid.

In various embodiments, the target nucleic acid may be RNA or DNA. It may be derived from a pathogenic organism, such as a virus. In some embodiments, it is viral nucleic acid, such as SARS-CoV-2 nucleic acid. In such embodiments, where the target nucleic acid is SARS-CoV-2 RNA the spacer sequence of the at least one gRNA may comprise or consist of the nucleotide sequence ACUCCUGGUGAUUCUUCUUC (SEQ ID NO:12), AAACCUAGUGAUGUUAAUAC (SEQ ID NO:13) or a variant thereof that shares at least 85% sequence identity with SEQ ID NO:12 or 13. In embodiments where at least two gRNAs are used, the first gRNA may comprise a spacer sequence comprising or consisting of the nucleotide sequence ACUCCUGGUGAUUCUUCUUC (SEQ ID NO:12) or a variant thereof having at least 85% sequence identity to SEQ ID NO:12, and the second gRNA may comprise a spacer sequence comprising or consisting of the nucleotide sequence AAACCUAGUGAUGUUAAUAC (SEQ ID NO:13) or a variant thereof having at least 85% sequence identity to SEQ ID NO:13.

In various embodiments, the target nucleic acid is SARS-CoV-2 RNA or a DNA amplicon thereof obtained in step (a) and the SARS-CoV-2 target sequence comprises or consists of the nucleotide sequence GAAGAAGAAUCACCAGGAGU (SEQ ID NO:14) or GUAUUAACAUCACUAGGUUU (SEQ ID NO:15) or a variant thereof that shares at least 85% sequence identity with SEQ ID NO:14 or 15.

In various embodiments, the CRISPR-Dx nucleic acid detection system comprises at least two different gRNAs that bind to two different, non-overlapping target sequences in the same target nucleic acid.

In various embodiments, the method further comprises the step of amplifying the target nucleic acid to obtain an amplicon thereof. This then also means that in the contacting step the amplicons of the target nucleic acid and, optionally, also the original target nucleic acid are contacted with the nucleic acid detection system. The amplifying step may be carried out using an isothermal amplification method, such as recombinase polymerase amplification (RPA) and loop-mediated isothermal amplification (LAMP), with the latter being particularly preferred. If the target nucleic acid is an RNA, said amplification method may comprise a reverse transcription step to generate template DNA from the target RNA. Accordingly, the amplification method may be reverse transcription loop-mediated isothermal amplification (RT-LAMP).

In various embodiments of the inventive methods, the amplicon obtained by said amplification step is a DNA amplicon.

In various embodiments where LAMP is used as the amplification method, the LAMP method comprises the use of two internal primers (FIP and BIP), two displacement primers (F3 and B3) and optionally (two) loop primers (LF and LB). In some embodiments, the LAMP method may further comprise the use of at least one swarm primer set or at least one stem primer set, preferably a swarm primer set.

In various embodiments, the target nucleic acid is a SARS-CoV-2 nucleic acid and the first internal primer (FIP) has the nucleotide sequence set forth in SEQ ID NO:4, the second internal primer (BIP) has the nucleotide sequence set forth in SEQ ID NO:5, the first displacement primer (F3) has the nucleotide sequence set forth in SEQ ID NO:6, and/or the second displacement primer (B3) has the nucleotide sequence set forth in SEQ ID NO:7. If loop primers are used, the first loop primer (LF) may have the nucleotide sequence set forth in SEQ ID NO:8 and/or the second loop primer (LB) may have the nucleotide sequence set forth in SEQ ID NO:9. If swarm primers are used, the first swarm primer may have the nucleotide sequence set forth in SEQ ID NO:10 and/or the second swarm primer may have the nucleotide sequence set forth in SEQ ID NO:11.

Amplification may be carried out in the presence of agents that improve amplification results, such as glycine, taurine or guanidine, preferably guanidine. Amplification may be carried out isothermally at a temperature of 60 to 65° C. and/or for a time period of 10 to 60 minutes, preferably 12 to 22 minutes.

In various embodiments, the LAMP method further comprises the use of 3' or 5' truncated internal primers that differ from the internal primers by a truncation of one nucleotide at the 3' or 5' end of their target-complementary sequence.

In various embodiments, the LAMP method further comprises the use of a high fidelity DNA polymerase with a proofreading capability, preferably with a 3'-to-5'-exonuclease activity.

In the methods described herein, the detection step (b) may be conducted at a temperature of at least 37° C., preferably at a temperature in the range of from 37° C. to 65° C. In various embodiments, said temperature range for the detection step should be compatible with the temperature used for the optional amplification step, preferably those should overlap to a certain extent.

In various embodiments, the detection reagent is an oligonucleotide, such as an RNA oligonucleotide or a ssDNA molecule. It has been found that activated Cas12a enzymes indiscriminately cleave single-stranded DNA molecules. ssDNA molecules are thus a suitable detection reagent for activated Cas12a enzyme, which becomes activated upon target complex formation with the gRNA and the target nucleic acid. In various embodiments, the ssDNA molecule is designed such that upon cleavage by the activated Cas12a enzyme it generates a detectable signal. This may be achieved by using a detectable tag or signaling moiety coupled to the ssDNA that becomes activated or detectable upon cleavage of the ssDNA molecule. Exemplary signaling moieties comprise the two members of a FRET pair, such as two fluorophores (donor and acceptor fluorophore) or a fluorophore (donor) and a quencher (acceptor), wherein upon cleavage of the oligonucleotide, one member of the FRET pair, typically the donor fluorophore, generates a detectable signal or the signal is detectably different between the intact and the cleaved oligonucleotide, such as in case two fluorophores are used that allow energy transfer between them in the intact molecule only. Fluorophore/quencher pairs that are in sufficient proximity to complex may also be used.

In various embodiments, the detection reagent therefore is an ssDNA molecule and/or comprises a donor fluorophore/acceptor or fluorophore/quencher pair, wherein upon cleavage of the oligonucleotide, the (donor) fluorophore generates a detectable signal. The ssDNA may be 5 to 15 nucleotides in length and may have, without limitation, the nucleotide sequence TTATT or TTATTATT.

In a second aspect, the present invention relates to a nucleic acid detection system comprising:

at least one Cas12a enzyme, at least one gRNA, and at least one detection reagent;

wherein said at least one Cas12a enzyme is LbCas12a or AsCas12a or a variant thereof; and wherein said at least one gRNA comprises a spacer sequence of at least 20 nucleotides in length that specifically recognizes and binds a target sequence in the target nucleic acid, wherein said binding of the target nucleic acid results in activation of the Cas12a enzyme and the activated Cas12a generates, by interaction with the at least one detection reagent, a detectable, and optionally quantifiable, signal;

wherein (1) the Cas12a enzyme is AsCas12a or a variant thereof or a variant thereof that retains Cas12a functionality and has at least 80% sequence identity to SEQ ID NO:2, preferably a variant comprising the amino acid sequence set forth in SEQ ID NO:1; and/or (2) the gRNA is a DNA-RNA hybrid and comprises at least 1 DNA nucleotide, preferably 2 to 4 DNA nucleotides, preferably in the spacer sequence, the rest being RNA nucleotides; and/or (3) said spacer sequence of the at least one gRNA comprises or consists of the nucleotide sequence ACUCCUGGUGAUUCUUCUUC (SEQ ID NO:12), AAACCUAGUGAUGUUAAUAC (SEQ ID NO:13) or a variant thereof that shares at least 85% sequence identity with SEQ ID NO:12 or 13; and/or (4) the CRISPR-Dx nucleic acid detection system comprises at least two different gRNAs that bind to two different, non-overlapping target sequences in the same target nucleic acid.

In various embodiments, the nucleic acid detection system further comprises nucleic acid amplification reagents to amplify target nucleic acid molecules in a sample. Said reagents may be reagents for an isothermal amplification method, such as LAMP, in particular RT-LAMP.

In various embodiments, the at least one guide RNA (gRNA) is designed to bind to one or more target nucleic acids that are diagnostic for a disease state and/or presence of a pathogen and/or resistance to a specific drug, such as a chemotherapeutic drug. The disease state may be an infection, an autoimmune disease, cancer or any other disease.

In various embodiments, the at least one detection reagent is an oligonucleotide, such as an RNA oligonucleotide or ssDNA oligonucleotide, to which a detectable ligand is attached. The detectable ligand may comprise a signaling component and a masking component. Exemplary signaling components include chromophores and fluorophores. Exemplary masking components include quenchers. The detectable ligand may comprise two members of a FRET pair, such as two fluorophores or a fluorophore and a quencher, wherein upon cleavage of oligonucleotide, one member of the FRET pair, typically the fluorophore, generates a detectable signal (as it is no longer in vicinity to the quencher) or the signal is detectably different between the intact and the cleaved ssDNA, such as in case two fluorophores are used that allow energy transfer between them in the intact molecule only.

In various embodiments, the nucleic acid detection system is designed to detect one or more viral targets and may optionally be used in combination with anti-viral therapeutics. It may be designed such that it detects novel mutations in the viral target nucleic acid.

BRIEF DESCRIPTION OF THE DRAWINGS

In the following description, various embodiments of the invention are described with reference to the following drawings.

FIG. 1*a* shows a schematic of a fluorescence trans-cleavage assay. Here, the reporter comprises a fluorophore linked to a quencher by a short piece of ssDNA. The gRNA is programmed to recognize a particular locus of the SARS-CoV-2 genome. In the absence of the virus, the reporter molecule is intact and thus no fluorescence is observed. However, when the virus is present, the Cas12a RNP will bind to and cleave its programmed target, become hyperactivated, and cut the linker between the fluorophore and quencher, thereby generating a fluorescence signal. FIG. 1*b* shows the organization of the SARS-CoV-2 genome.

FIG. 4*a* shows time courses of the fluorescence intensity in the trans-cleavage assays for various Cas12a nucleases complexed with perfect matched (PM) N-Mam gRNAs of three different spacer lengths. The assays were performed at 24° C. and 1E11 copies of purified DNA template were used as input. All the measurements were normalized to the no-template control (NTC) at the start of the experiment. Data represent mean±s.e.m. (n=3 biological replicates). FIG. 4*b* shows fluorescence measurements using a microplate reader after 30 minutes of cleavage reaction. 1E11 copies of DNA template corresponding to one of the coronaviruses were present in a 50 μl reaction. Spacers of three different lengths targeting the N-Mam locus were tested. There was no cross-reactivity for SARS-CoV or MERS-CoV as expected. All the measurements were normalized to the no-template control (NTC) at the start of the experiment. Data represent mean±s.e.m. (n=3 biological replicates).

FIG. 6*a* shows sequences of perfect matched (PM) or mismatched (MM) spacers targeting the N-Mam locus. Each mismatched position is indicated by a bold letter. The respective sequences are set forth in SEQ ID Nos. 65, 97, 99, 101, 103, 105, 107, 109, 111, 113 and 115. FIG. 6*b* is a heatmap showing the tolerance of various Cas12a enzymes to mismatched N-Mam gRNAs. The fluorescence readings are scaled between 0 and 1, where 1 is the highest measurement obtained and 0 is the background signal for NTC at the start of the experiment.

FIG. 8*a* shows sequences of perfect matched (PM) or mismatched (MM) spacers targeting the S2 locus. Each mismatched position is indicated by a bold letter. The respective sequences are set forth in SEQ ID Nos. 35, 137, 139, 141, 143, 145, 147, 149, 151, 153, and 155. FIG. 8*b* is a heatmap showing the tolerance of various Cas12a enzymes to mismatched S2 gRNAs. The fluorescence readings are scaled between 0 and 1, where 1 is the highest measurement obtained and 0 is the background signal for NTC at the start of the experiment.

FIG. 10*a* shows sequences of perfect matched (PM) or mismatched (MM) spacers targeting the S3 locus. Each mismatched position is indicated by a bold letter. The respective sequences are set forth in SEQ ID Nos. 75, 197, 199, 201, 203, 205, 207, 209, 211, 213, and 215. FIG. 10*b* shows time courses of the fluorescence intensity in our trans-cleavage assays for LbCas12a complexed with S3 MM gRNAs. The assays were performed at 24° C. and 1E11 copies of DNA template were used as input. Data represent mean±s.e.m. (n=3 biological replicates). FIG. 10*c* shows a summary of LbCas12a's collateral activity when complexed with a S3 PM or MM gRNA. The fluorescence measurements here were taken after 30 minutes of cleavage reaction using amicroplate reader and all the readings were normalized to the NTC at the start of the experiment. Data represent mean±s.e.m. (n=3 biological replicates).

FIG. 21*a* shows a schematic of LAMP. Six distinct regions in the target locus (F1, F2, F3, B1, B2, and B3) are recognized by four core primers, which have a black arrow at their 3' ends to represent extension by the DNA polymerase. The letter "c" appended to each region name indicates the reverse complementary sequence. After our LAMP optimization process, swarm primers have been incorporated, whose sequences are equivalent to F1c and B1c. Moreover, to demonstrate how a mismatch at the 5' end of FIP can affect the LAMP reaction, an asterisk has been added to track the progression of the mismatch. FIG. 21*b* shows sequences of LAMP primers tested. The mismatches are indicated by bold letters. The sequences are set forth in SEQ ID Nos. 244, 245, 248, 249, 260-280. FIG. 21*c* shows a strip chart showing how mismatches between LAMP primers and their binding sites affected the rate of isothermal amplification. RT-LAMP was performed at 65° C. in a real-time instrument with 20,000 copies of synthetic RNA corresponding to the S-gene of SARS-CoV-2. Cycle threshold (Ct) values were given by the instrument using default settings. The black horizontal bars among the data points in the strip chart represent the mean (n=3 [F3 MM, B3 MM] or 4 [PM, FIP (3') MM, BIP (3') MM, FIP (5') MM, BIP (5') MM, NTC] biological replicates). P values were calculated using one-sided Student's t-test. FIG. 21*d* shows a strip chart showing rescue of the LAMP reaction by truncated primers and a Q5 high-fidelity DNA polymerase in the presence of mismatches at the 3' ends of FIP and BIP. RT-LAMP was performed at 65° C. with 20,000 copies of RNA template. The black horizontal bars among the data points in the strip chart represent the mean (n=4 [FIP PM+tPM+Q5, BIP PM+tPM+Q5], 5 [PM, PM+Q5, FIP MM+tPM+Q5, FIP PM+tPM, BIP MM+tPM+Q5, BIP PM+tPM], or 6 [FIP MM, FIP MM+Q5, FIP MM+tPM, BIP MM, BIP MM+Q5, BIP MM+tPM, NTC] biological replicates). P values were calculated using one-sided Student's t-test. FIG. 21*e* shows a strip chart showing rescue of the LAMP reaction by truncated primers and a Q5 high-fidelity DNA polymerase in the presence of a mismatch at the 5' end of FIP. RT-LAMP was performed at 65° C. with 20,000 copies of RNA template. The black horizontal bars among the data points in the strip chart represent the mean (n=4 biological replicates). P values were calculated using one-sided Student's t-test.

FIG. 25*a* shows a strip chart showing how the kinetics of the LAMP module was altered by the addition of either 0.1 M glycine or 50 mM taurine. The RT-LAMP reaction was carried out at 65° C. in a real-time instrument with 20,000 copies of SARS-CoV-2 synthetic RNA template. The black horizontal bars among the data points in the strip chart represent the mean (n=4 biological replicates). P values were calculated using one-sided Student's t-test. FIG. 25*b* shows a strip chart showing the sensitivity of the LAMP module in the presence of 0.1 M glycine (G) or 50 mM taurine(T). The RT-LAMP reaction was carried out at 65° C. in a real-time instrument with variable copies of SARS-CoV-2 RNA template. The black horizontal bars among the data points in the strip chart represent the mean (n=5 [glycine] or 6 [taurine] biological replicates).

FIG. 26*a* shows a strip chart showing how LAMP sensitivity was altered by the use of swarm or stem primers. The box demarcates the four core primers, which were included in every experiment. The concentrations of each displacement primer, internal primer, loop primer, swarm primer, and stem primer were 0.2, 1.6, 0.8, 1.6, and 1.6 μM respectively. RT-LAMP was performed at 65° C. with 20,000 copies of RNA template. The black horizontal bars among the data points in the strip chart represent the mean (n=5 [swarm, $stem_{in}$, loop+$stem_{in}$, NTC for loop+swarm] or 7 [loop, loop+swarm, NTC for loop] biological replicates). P value was calculated using one-sided Student's t-test. FIG. 26*b* shows further dissection of stem primers. The strip chart shows the impact of various stem primers on LAMP sensitivity. Here, every reaction contained the displacement primers (0.2 μM each), internal primers (1.6 μM each), and loop primers (0.8 μM each). Furthermore, it could also contain either two additional swarm primers or one or two additional stem primers (with the concentration of each extra primer being 1.6 μM). RT-LAMP was performed at 65° C. with 20,000 copies of RNA template. The black horizontal bars among the data points in the strip chart represent the mean (n=3 [NTC] or 4 [with template] biological replicates). P values were calculated using one-sided Student's t-test.

FIG. 29*a* shows time courses of the fluorescence intensity in the trans-cleavage assays for enAsCas12a complexed with both the S6 gRNA and either the perfect matched (PM) or a mismatched (MM10) S2 gRNA. Before the Cas detection step, various copies of synthetic SARS-CoV-2 RNA fragments (see legend) were used as input to RT-LAMP, which was performed at 65° C. for 15 minutes. The LAMP reaction conditions were optimized and encompassed 0.2 μM of F3, 0.4 μM of B3, 1.6 μM of each full-length and 1nt-truncated internal primer, 0.8 μM of each loop primer, 1.6 μM of each swarm primer, 0.15 U of Q5 high-fidelity DNA polymerase, and 0.1 M glycine. Subsequently, 4 μl of LAMP products were used for the trans-cleavage assays, which were performed at 37° C. Fluorescence measurements were taken using a microplate reader at five-minute intervals. Data represent mean±s.e.m. (n=5 [2E6] or 6 [other copy numbers] biological replicates). FIG. 29*b* shows robust detection of a SARS-CoV-2 S-gene sequence using a lateral flow assay. The enAsCas12a enzyme was complexed with both the S6 gRNA and either the perfect matched (PM) or a mismatched (MM10) S2 gRNA. Different copies of synthetic RNA fragments were used as input to the RT-LAMP reaction, which was performed at 65° C. for 15 minutes under optimized conditions. Next, the Cas detection reaction was carried out at 37° C. for 10 minutes before a dipstick was added to each reaction tube. Bands appeared on the dipstick by 2 minutes. The higher arrow indicates the test bands, while the lower arrow indicates the control bands.

FIG. 43. Optimizing reaction conditions for enAsCas12a. FIG. 43*a* shows the evaluation of various experimental conditions, including different concentrations of enAsCas12a and different durations of the cleavage reaction. 1× specifies 65 nM. 2E6 copies of synthetic wildtype SARS-CoV-2 RNA served as input to RT-LAMP. FIG. 43*b* shows the detection of wildtype or S254F mutant SARS-CoV-2 sequence using S2 and S6 gRNAs. Different copies of SARS-CoV-2 RNA fragments were used as input to RT-LAMP, which was performed at 65° C. for 15 minutes. Next, the Cas detection reaction was carried out at 37° C. for 10 minutes in Buffer 2.1 with DTT before a dipstick was added to each reaction tube. FIG. 43*c* shows the systematic testing of different reaction buffers and temperatures for the Cas detection step. Here, enAsCas12a complexed with the S2 gRNA was only utilized in a 50 μl trans-cleavage assay with 2E11 copies of DNA template corresponding to SARS-CoV-2 S-gene. Data represent mean±s.e.m. (n=3 [41° C., 45° C., 50° C., 55° C. Tango alone, 60° C. no DTT and NTC], 4 [37° C., 55° C. all but Tango alone], or 6 [60° C. with DTT] biological replicates).

FIG. 46*a* shows time courses of the fluorescence intensity in the trans-cleavage assays, which were carried out at either 37° C. or 41° C. in a 50 μl reaction volume. 2E11 copies of synthetic DNA template corresponding to the S-gene of SARS-CoV-2 were used. Data represent mean±s.e.m. (n=3 [41° C.] or 4 [37° C.] biological replicates). FIG. 46*b* shows the effect of DTT on the collateral activity of enAsCas12a with the S6 gRNA. Fluorescence measurements here were taken using a microplate reader after 10 minutes of cleavage reaction. DTT significantly improved the activity of enAsCas12a in CutSmart buffer at 37° C. Data represent mean±s.e.m. (n=3 [41° C.] or 4 [37° C.] biological replicates). P value was calculated using two-sided Student's t-test.

FIG. 47. Optimizing reaction conditions for enAsCas12a. FIG. 47*a* shows the preliminary evaluation of our VaNGuard test with leftover patient samples. A Ct value of 30 was estimated to be equivalent to 500 copies of the virus. RT-LAMP was performed at 65° C. for 15 minutes before the Cas detection reaction was carried out at 37° C. for 10 minutes in CutSmart with DTT. Each clinical sample was tested twice using dipsticks. FIG. 47*b* shows re-testing the pilot set of clinical RNA samples using a fluorescence readout. RT-LAMP was performed at 65° C. for 15 minutes. Subsequently, 4 μl LAMP products (out of 25 μl) were used for the trans-cleavage assay, which was performed at 37° C. in a real-time instrument where measurements were taken every minute. The fluorescence readings for all six clinically negative samples remained low over the duration of the experiment. Additionally, the fluorescence readings for five out of the six clinically positive samples showed a clear exponential increase with time. The remaining positive sample (RP6), which contained 14 copies of the virus, gave fluorescence signals that were only slightly above those of the negative samples.

FIG. 49. Guide engineering to enhance the CRISPR detection module. FIG. 49*a* shows sequences of the original S2-targeting gRNA and the modified guides evaluated in this work. 2'-O-methyl ribonucleotides (2'OMe RNA) are indicated by an extra lower-case m before the relevant nucleotide. Phosphorothioate (PS) bonds are marked by asterisks. The respective sequences are set forth in SEQ ID Nos. 281-286. FIG. 49*b* shows the comparison of 5'-extended gRNAs with the original S2-targeting gRNA at 37° C. for enAsCas12a. Fluorescence measurements here were taken using a microplate reader after 5 minutes of cleavage reaction with 2E11 copies of synthetic DNA. Data represent mean±s.e.m. (n=6 [S2 5'ext(+9)] or 11 [S2, S2 5'ext(+4)] biological replicates). P value was calculated using one-sided Student's t-test.

FIG. 55*a* shows sequences of the original S6-targeting gRNA and the modified guides evaluated in this work. The respective sequences are set forth in SEQ ID Nos. 287-290. FIG. 55*b* shows the comparison of 5'-extended gRNAs and a DNA-RNA hybrid guide with the original S6-targeting gRNA at 37° C. for enAsCas12a. Data represent mean±s.e.m. (n=3 [S6 4DNA] or 4 [S6, S6 5'ext(+4), S6 5'ext(+9)] biological replicates). P values were calculated using one-sided Student's t-test.

FIG. 62*a* shows time courses of the fluorescence intensity in our trans-cleavage assays for enAsCas12a complexed with both the S2 4DNA hybrid guide and the S6 9nt 5'-extended gRNA. Prior to the Cas detection step, RT-LAMP was performed at 65° C. for 15 minutes with 20,000 copies of synthetic SARS-CoV-2 RNA template as input. Different amounts of LAMP products (4 μl, 8 μl, 12 μl, or 25 μl) were added into the CRISPR reaction mix before the cleavage assays were carried out at either 37° C. or 60° C. CutSmart buffer with DTT was used. Fluorescence readings were taken at 5-minute intervals using a microplate reader and were then normalized to NTC at the 0 min timepoint. Data represent mean±s.e.m. (n=3 [37° C.], 4 [60° C. 25 μl and NTC], or 5 [60° C. 4-12 μl and quasi] biological replicates). FIG. 62*b* shows a summary of enAsCas12a's collateral activity when different amounts of LAMP products were added into the CRISPR reaction mix. "Quasi" refers to the setup where the CRISPR mix was added into the LAMP reaction tube instead. The fluorescence measurements here were taken after 5 minutes of cleavage reaction. Data represent mean±s.e.m. (n=3 [37° C.], 4 [60° C. 25 μl and NTC], or 5 [60° C. 4-12 μl and quasi] biological replicates). P values were calculated using two-sided Student's t-test.

FIG. 63*a* shows an analytical LoD based on the original workflow. Different copies of synthetic SARS-CoV-2 RNA were used as input to RT-LAMP, which was performed at 65° C. for 15 minutes. The cleavage reaction was then carried out on only 4 μl LAMP products at 60° C., with fluorescence measurements here taken after 10 minutes using a microplate reader. Data represent mean±s.e.m. (n=3 biological replicates). FIG. 63*b* shows an Analytical LoD when all LAMP products were utilized. After RT-LAMP was completed, 50 μl CRISPR reagents were added directly into each sample tube for the cleavage reaction. Data represent mean±s.e.m. (n=3 biological replicates).

FIG. 66*a* shows a strip chart showing how LAMP sensitivity was altered by substituting 0.1 M glycine (Gly) with 40 mM guanidine (Gua). RT-LAMP was performed at 65° C. in a real-time instrument with variable copies of synthetic RNA. The black horizontal bars among the data points in the strip chart represent the mean (n=5 biological replicates). P values were calculated using one-sided Student's t-test. FIG. 66*b* is a comparison of the assay sensitivity between glycine and guanidine. Different copies of synthetic SARS-CoV-2 RNA were used as input to RT-LAMP, which was performed at 65° C. for 15 minutes. Subsequently, 50 μl CRISPR reagents were added directly into each sample tube and the cleavage reaction was carried out at 60° C., with fluorescence measurements here taken after 10 minutes using a microplate reader. Data represent mean±s.e.m. (n=8 biological replicates).

FIG. 68*a* shows lateral flow assays to assess cleavage reaction kinetics with guanidine in the assay mix. The enAsCas12a enzyme was complexed with both the S2 hybrid guide and the S6 5'-extended gRNA. After RT-LAMP was completed, the Cas detection reaction was performed at 60° C. for 5, 7, or 10 minutes before a dipstick was added to each sample tube. FIG. 68*b* shows lateral flow assays to evaluate VaNGuard test sensitivity with guanidine in the assay mix. Different copies of synthetic SARS-CoV-2 RNA were used as input to RT-LAMP, which was performed at 65° C. for 15 minutes. The Cas detection reaction was then carried out at 60° C. for 5 minutes before a dipstick was added to each sample tube.

FIG. 69*a* shows the collateral activity of enAsCas12a complexed with both the S2 and S6 4DNA hybrid guides at 60-65° C. Prior to the Cas detection step, RT-LAMP was carried out at 65° C. for 15 minutes with 20 copies of synthetic SARS-CoV-2 RNA template as input. Subsequently, 50 μl CRISPR reagents in Tango buffer were added directly into the LAMP reaction tube and the Cas detection reaction was then carried out at 60, 63, or 65° C., with fluorescence measurements taken every minute using a real-time instrument. FIG. 69*b* shows the sensitivity of our assay with RT-LAMP performed at a slightly lower temperature of 63° C. Different copies of synthetic SARS-CoV-2 RNA were used as input to the RT-LAMP reaction, which was performed at 63° C. for 15 or 17 minutes. Subsequently, 50 μl CRISPR reagents in Tango buffer were added directly into the LAMP reaction tube and the Cas detection reaction was then carried out at 60° C., with fluorescence measurements taken at five-minute intervals using a microplate reader. All readings were normalized to NTC at the 0 min timepoint. Data represent mean±s.e.m. (n=4 biological replicates for 2E3-2E6 copies and n=15 biological replicates for the other lower copy numbers). FIG. 69*c* shows the detection of SARS-CoV-2 using a lateral flow assay where both RT-LAMP and the Cas detection reaction were performed at 63° C. The enAsCas12a enzyme was complexed with the S2 and S6 4DNA hybrid guides. Different copies of synthetic viral RNA template were used as input to RT-LAMP, which was performed for 22 minutes. Subsequently, the trans-cleavage reaction was carried out for 5, 7, or 10 minutes before a dipstick was added to each reaction tube. The higher arrow indicates the test bands, while the lower arrow indicates the control bands. FIG. 69*d* shows the detection of SARS-CoV-2 using a lateral flow assay where both RT-LAMP and the Cas detection reaction were performed at 60° C. The cleavage reaction was performed for 5 minutes before a dipstick was added to each reaction tube.

FIG. 72*a* Evaluating the specificity of the VaNGuard test. The enAsCas12a enzyme was complexed with both the S2 and S6 hybrid guides. 1E6 copies of synthetic RNA from different respiratory viruses were used as input to the quasi-one-pot reaction. Fluorescence measurements were taken at 5-minute intervals using a microplate reader. Data represent mean±s.e.m. (n=3 biological replicates). FIG. 72*b* shows the evaluation with clinical RNA samples. Ct values were obtained using the Fortitude Kit. The enAsCas12a enzyme was complexed with both the S2 and S6 hybrid guides. 2 μl of each RNA sample was used as input to the quasi-one pot reaction. The Cas detection reaction was performed for 5 minutes before a dipstick was added to each sample tube. A ratio of less than 0.15 was considered to be negative in our test. Hence, for the purified RNA samples, the lateral flow assay gave 0 false positives and 8 false negatives (RP6, RP45-51). FIG. 72*c* shows a strip chart summarizing the results from the clinical evaluation of our VaNGuard test using purified RNA samples. "Yes" indicates that the samples emerged positive in our test, while "No" indicates that the samples emerged negative.

FIG. 74*a* shows a strip chart showing the effect of proteinase K and heat treatment on RT-LAMP when different copies of S-gene-expressing lentivirus spiked into saliva were used as input. The black horizontal bars among the data points in the strip chart represent the mean (no PK+no heat: n=5 [4E5-4E6], 7 [4-4E2], 10 [4E4], or 12 [4E3 and NTC]; no PK+heat: n=7 [4E5], 9 [4E6], 10 [4-4E2], 15 [4E4], or 17 [4E3 and NTC]; PK+heat: n=7 [4-4E2], 11 [4E5], 13 [4E6], 15 [4E4], 18 [4E3], or 20 [NTC] biological replicates). FIG. 74*b* Evaluating VaNGuard test sensitivity to unpurified pseudovirus. The enAsCas12a enzyme was complexed with both the S2 and S6 hybrid guides. Different copies of lentivirus spiked into saliva were treated with proteinase K and heat before being used as input to the quasi-one-pot reaction. Fluorescence measurements were taken at 5-minute intervals using a microplate reader. Data represent mean±s.e.m. (n=4 biological replicates). FIG. 74*c* Evaluating VaNGuard test sensitivity to unpurified SARS-CoV-2. The enAsCas12a enzyme was complexed with both the S2 and S6 hybrid guides. Different copies of the coronavirus produced in Vero E6 cells were spiked into clinically negative UTM, treated with proteinase K and heat, and then used as input to the quasi-one-pot reaction. The Cas detection step was carried out for 5 minutes before a dipstick was added to each reaction tube. FIG. 74*d* Clinical evaluation with NP swab samples. A Ct value of 30 was estimated to be equivalent to 500 copies of the virus. The enAsCas12a enzyme was complexed with both the S2 and S6 hybrid guides. Each sample was treated with proteinase K and heat before 2 μl was used as input to the quasi-one-pot reaction. The Cas detection step was carried out for 5 minutes before a dipstick was added to each reaction tube. FIG. 74*e* shows the re-test of misclassified NP swab samples using twice the reaction volume. 4 μl of each sample was used as input to the quasi-one-pot reaction. Overall, for the direct patient samples, the lateral flow assay gave 0 false positives and 4 false negatives (DP16, DP18, DP20, and DP21). FIG. 74*f* shows a strip chart summarizing the results from the clinical evaluation of our VaNGuard test using unpurified NP swab samples. "Yes" indicates that the samples emerged positive in our test, while "No" indicates that the samples emerged negative.

FIG. 75*a* shows a strip chart showing the efficacy of different sets of LAMP primers targeting the human POP7, ACTB, or GAPDH gene. The primers labelled with "Set1", "Set2", or "Set3" are newly designed, while the primers labelled with "Pub" have been published (Broughton et al. (2020) *Nat Biotechnol*, doi:10.1038/s41587-020-0513-4; Anahtar et al. (2020) doi:10.1101/2020.05.12.20095638; Li, et al. (2020) doi:10.1101/2020.06.03.131474). 2 μl heat-treated saliva was used as sample input to RT-LAMP, which was performed at 65° C. over 40 minutes in a real-time instrument. The black horizontal bars among the data points in the strip chart represent the mean (n=6 [POP7 Pub and Set1-2, ACTB Set2-3, GAPDH Set2-3], 8 [ACTB Set1, GAPDH Pub and Set1], or 14 [ACTB Pub] biological replicates). Comparisons were done relative to the POP7 Pub primers (Broughton et al. (2020) *Nat Biotechnol*, doi:10.1038/s41587-020-0513-4). P values were calculated using one-sided Student's t-test. FIG. 75*b* shows a strip chart showing the effect of different human primer sets on isothermal amplification of the SARS-CoV-2 S-gene. Different copies of synthetic SARS-CoV-2 RNA were used as sample input to RT-LAMP, which was performed at 65° C. over 40 minutes in a real-time instrument. The black horizontal bars among the data points in the strip chart represent the mean (n=3 [POP7 Pub 2E5] or 6 [POP7 Pub all except 2E5, ACTB Set2] biological replicates).

FIG. 77*a* shows time courses of the fluorescence intensity in the trans-cleavage assays for enAsCas12a complexed with the S2 gRNA. The assays were performed at 60° C. and 2E11 copies of DNA template were used as input. All readings were normalized to NTC at the 0 min timepoint. Data represent mean±s.e.m. (n=3 biological replicates). FIG. 77*b* shows an analytical LoD of the prototype VaNGuard assay with a human internal control. Different copies of synthetic SARS-CoV-2 RNA were spiked into heat-treated healthy donor saliva before being used as input to RT-LAMP, whose reaction mix contained a generic DNA-binding dye (such as SYBR Green or EvaGreen), enabling green fluorescence measurements to be taken every minute (left panel). After 22 minutes of RT-LAMP reaction, 50 μl CRISPR reagents containing the Cy5-quencher reporter in Tango buffer were added directly into the LAMP reaction tube. Red fluorescence measurements were then taken every 5 minutes (right panel). Here, the enAsCas12a enzyme was complexed with both the S2 and S6 hybrid guides.

FIG. 79*a* shows the performance of isothermal amplification using a WarmStart LAMP Kit from New England Biolabs together with variable amounts (0-2 U) of pyrophosphatase. 2E4 copies of synthetic SARS-CoV-2 RNA were used as sample input to RT-LAMP, which was performed at 65° C. over 40 minutes in a real-time instrument. The black horizontal bars among the data points in the strip chart represent the mean (n=2 [1-2 U, NTC], 3 [0.5 U], or 5[0 U] biological replicates). FIG. 79*b* since the master mix from the WarmStart LAMP Kit contained some unknown components, it has also been performed an isothermal amplification using Bst2.0 in a chemically defined buffer (20 mM Tris-HCl, 10 mM $(NH_4)_2SO_4$, 50 mM KCl, 8 mM $MgSO_4$, and 0.1 Tween) together with variable amounts (0-2 U) of pyrophosphatase. The black horizontal bars among the data points in the strip chart represent the mean (n=2 [0.5-2 U] or 4 [0 U, NTC] biological replicates).

FIG. 83*a* shows the evaluation of the assay with various amounts of human primers and pyrophosphatase. Different copies of synthetic RNA spiked into heat-treated saliva were used as input to the quasi-one-pot reaction. Fluorescence measurements were taken at 5-minute intervals using a microplate reader. Data represent mean±s.e.m. (n=3 biological replicates). FIG. 83*b* shows a clinical evaluation of the optimized VaNGuard assay containing a human internal control. 2 μl of each proteinase K- and heat-treated NP swab sample was used as input.

FIG. 84*a* shows exemplary fluorescence curves from a real-time instrument for RT-LAMP experiments. Four replicates are shown, where + indicates 20,000 copies of RNA have been added and − indicates NTC (no template control). While the majority of NTC setups showed no amplification, some of the NTC reactions gave late amplifications (high Ct values). FIG. 84*b* shows a gel electrophoresis of LAMP products. In the first two experiments, the NTC reactions showed late amplifications in the real-time instrument, while for the third experiment, the NTC reaction did not give any amplification after 40 cycles (minutes). The different samples have then be subjected to gel electrophoresis. As shown in the gel image, products from all the + reactions appear as staggered bands, which are characteristic of successful LAMP. In contrast, products from the first two − reactions appear as smears on the agarose gel, indicating that they are a result of spurious amplification. The three RT-LAMP experiments shown are independent of one another. Overall, it has been observed that around 10% of the NTCs (7 out of 69 replicates) showed late amplification for our set of S-gene LAMP primers.

FIG. 91*a* shows an overview of a prototypical CRISPR-Dx workflow. While a microplate reader can allow up to 96 samples to be processed at once, it is not amenable to point-of-care testing. In contrast, a lateral flow strip proves a simple visual readout akin to an off-the-shelf pregnancy test. FIG. 91*b* is the detection of SARS-CoV-2 sequence using gRNAs targeting the S-gene. Different copies of synthetic SARS-CoV-2 RNA fragments were used as input to the RT-LAMP reaction, which was performed at 65° C. for 15 minutes. Next, the Cas detection reaction was carried out at 37° C. for 10 minutes before a dipstick was added to each reaction tube. The bands on the dipstick appeared by 2 minutes. In total, the VaNGuard assay was completed in under 30 minutes.

DETAILED DESCRIPTION OF THE INVENTION

Figure 1:
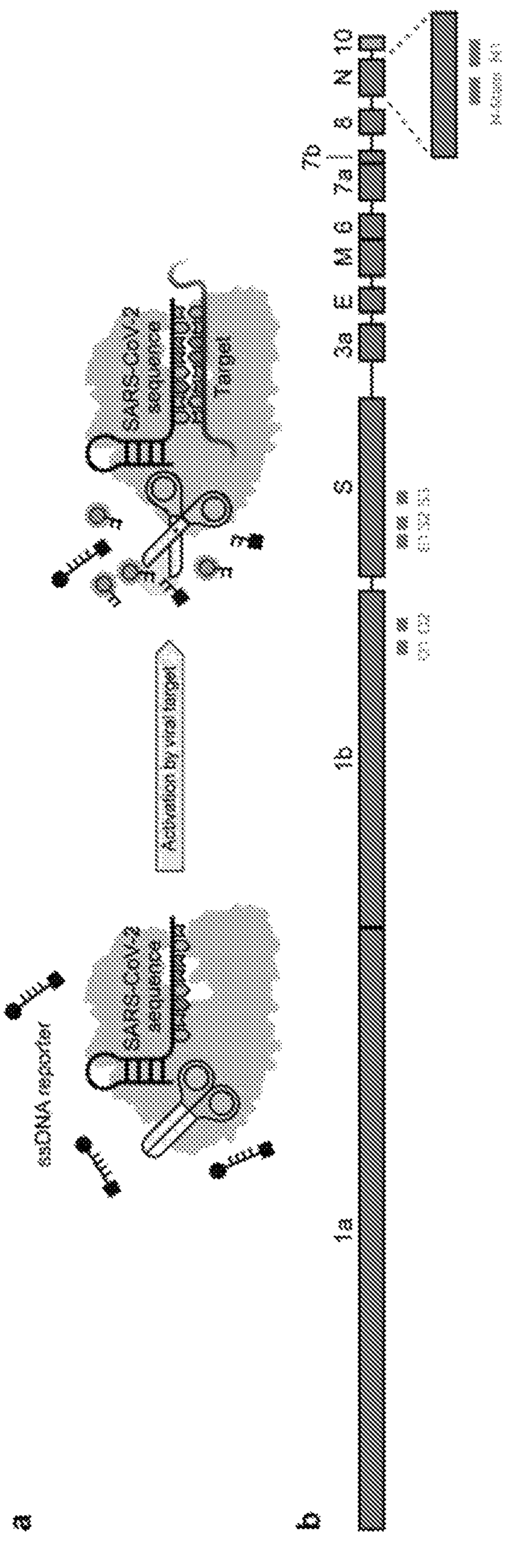
FIG. 1. Evaluation of different Cas12a-gRNA combinations at room temperature (24° C.).
Figure 2:
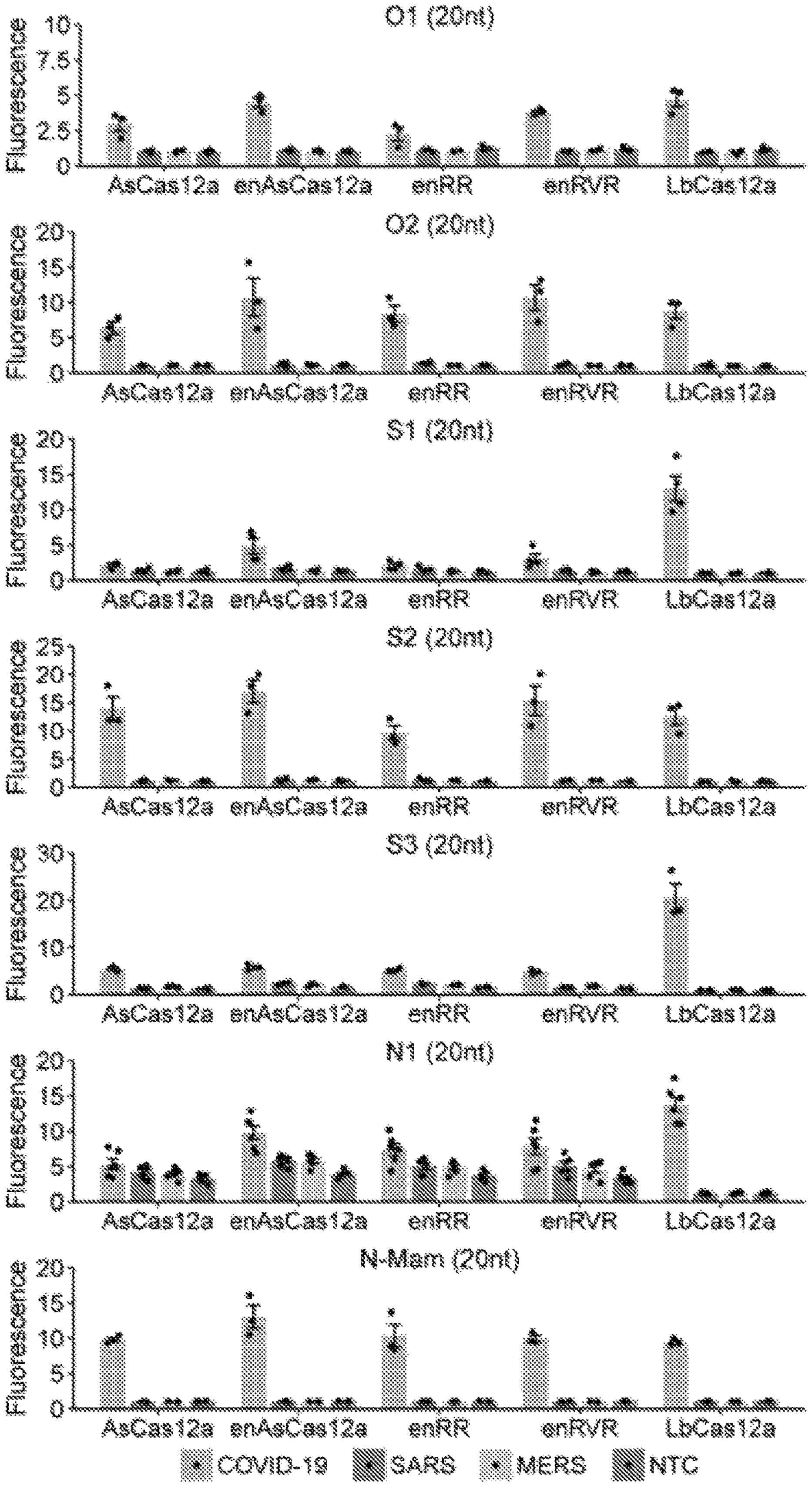
FIG. 2. Evaluation of different Cas12a-gRNA combinations at room temperature (24° C.). The figure shows fluorescence measurements using a microplate reader after 30 minutes of cleavage reaction. 1E11 copies of the relevant DNA target were present in a 50 μl reaction. All readings were normalized to the no template control (NTC) at the start of the experiment. The N1 gRNA gave an unexpected result, whereby it triggered the collateral activity of AsCas12a and its variants without a template. Data represent mean±s.e.m. (n=3 [N-Mam, O1, O2, S2, S3], 4 [S1], or 6 [N1] biological replicates).

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2$^{nd}$ edition (1989) (Sambrook, Fritsch, and Maniatis); Molecular Cloning: A Laboratory Manual, 4$^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2$^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2$^{nd}$ edition (2011)

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−,10% or less, +/−m5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

"At least one", as used herein, means one or more, for example 2, 3, 4, 5, 6, 7, 8, 9 or more. If used in relation to a component or agent, the term does not relate to the total number of molecules of the respective component or agent but rather to the number of different species of said component or agent that fall within the definition of broader term.

"Isolated" as used herein in relation to a molecule means that said molecule has been at least partially separated from other molecules it naturally associates with or other cellular components. "Isolated" may mean that the molecule has been purified to separate it from other molecules and components, such as other proteins and nucleic acids and cellular debris, in particular those that accompany it due to its recombinant production in host cells.

"Nucleic acid" as used herein includes all natural forms of nucleic acids, such as DNA and RNA. Preferably, the nucleic acid molecules of the invention are DNA.

If reference to "sequence identity" of nucleic acid or amino acid sequences is made herein, the determination of the sequence identity of nucleic acid or amino acid sequences can be done by a sequence alignment based on well-established and commonly used BLAST algorithms (See, e.g. Altschul, S. F., Gish, W., Miller, W., Myers, E. W. & Lipman, D. J. (1990) "Basic local alignment search tool." J. Mol. Biol. 215:403-410, and Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs"; Nucleic Acids Res., 25, S.3389-3402). Such an alignment is based on aligning similar nucleotide or amino acid sequences stretches with each other. Another algorithm known in the art for said purpose is the FASTA algorithm. Alignments, in particular multiple sequence comparisons, are typically done by using computer programs. Commonly used are the Clustal series (See, e.g., Chenna et al. (2003): Multiple sequence alignment with the Clustal series of programs. Nucleic Acid Research 31, 3497-3500), T-Coffee (See, e.g., Notredame et al. (2000): T-Coffee: A novel method for multiple sequence alignments. J. Mol. Biol. 302, 205-217) or programs based on these known programs or algorithms. Also possible are sequence alignments using the computer program Vector NTI® Suite 10.3 (Invitrogen Corporation, 1600 Faraday Avenue, Carlsbad, CA, USA) with the set standard parameters, with the AlignX module for sequence comparisons being based on the ClustalW. If not indicated otherwise, the sequence identity is determined using the BLAST algorithm. Such a comparison also allows determination of the similarity of the compared sequences. Said similarity is typically expressed in percent identify, i.e. the portion of identical nucleotides/amino acids at the same or corresponding (in an alignment) sequence positions relative to the total number of the aligned nucleotides/amino acids. For example, if in an alignment 90nt of a 100nt long query sequence are identical to the nucleotides in corresponding positions of a template sequence, the sequence identity is 90%. If not indicated otherwise, sequence identity relates to the entire length of the aligned sequence.

In the context of the present invention, the feature that an amino acid position corresponds to a numerically defined position in a reference sequence means that the respective position correlates to the numerically defined position in said reference sequence in an alignment obtained as described above.

The present invention is directed to the detection of target nucleic acids in a sample using a modified CRISPR-Dx system, typically with prior amplification of the target. It is based on the inventors' finding that the methods described herein allow detection of target nucleic acids in a sample with high accuracy and even accommodate for mutations in the target nucleic acid without significant loss of detection sensitivity.

The embodiments disclosed herein can detect both DNA and RNA with comparable levels of sensitivity and can differentiate targets from non-targets based on single base pair differences. Moreover, the embodiments disclosed herein can be prepared in freeze-dried format for convenient distribution and point-of-care (POC) applications, Such embodiments are useful in multiple scenarios in human health including, for example, viral detection, bacterial strain typing, sensitive genotyping, and detection of disease-associated cell free DNA.

In a first aspect, the present invention is directed to a method for detecting the presence or amount of a target nucleic acid in a sample, comprising:

(a) contacting the target nucleic acid and/or an amplicon thereof with a nucleic acid detection system, said nucleic acid detection system comprising (1) at least one Cas12a enzyme, (2) at least one guide RNA (gRNA), and (3) at least one detection reagent;
    wherein said at least one Cas12a enzyme (1) is LbCas12a or AsCas12a or a variant thereof; and
    wherein said at least one gRNA (2) comprises a spacer sequence of at least 20 nucleotides in length that specifically recognizes and binds a target sequence in the target nucleic acid, under conditions that allow binding of the complex of the Cas12a enzyme and the at least one gRNA to the target sequence and resultant activation of the Cas12a enzyme;
    wherein the activated Cas12a enzyme generates, by interaction with the at least one detection reagent (3), a detectable, and optionally quantifiable, signal; and
(b) detecting and optionally quantifying said detectable signal.

The term "Cas12a" enzyme, as used herein, relates to CRISPR-associated endonucleases. Also referred to as Cpf1, they are single RNA-guided endonucleases lacking a small trans-encoded RNA (a tracrRNA) but instead use a T-rich protospacer adjacent motif (also known as PAM) that is 5' of the target site consisting of a 2-6 base pair DNA sequence immediately following the DNA sequence targeted by the Cas9 nuclease in the CRISPR bacterial adaptive immune system. Generally, these enzymes require only a shorter, typically about 40nt long, guide RNA, also called CRISPR-RNA (crRNA), instead of the about 100nt long guide RNA required for Cas9. The gRNA is used to bind complementary sequences in the target which is then cleaved. The enzymes cleave dsDNA and generate a sticky end with a 5' overhang of 4-5 nucleotides about 18 or 22-23 nucleotides downstream of the PAM motif. The enzymes thus form a complex with the gRNA and the target nucleic acid. It has been found that once activated by binding of the gRNA and the target, after cleavage of the target the enzyme gets hyperactivated and then indiscriminately cleaves also ssDNA.

In various embodiments of the methods described herein, the Cas12a enzyme is a bacterial enzyme or derived from a bacterial enzyme. Suitable Cas12a enzymes include, without limitation, those of *Lachnospiraceae bacterium* (LbCas12a), *Acidaminococcus* sp. BV3 L6 (AsCas12a), *Francisella novicida* (FnCas12a), *Coprococcus eutactus* (CeCas12a), and the like. In various embodiments, the enzyme is an engineered variant of a wildtype Cas12a enzyme. These typically retain full functionality but have one or more mutations and share a sequence identity of at least 80%, for example at least 81, 82, 83, 84, 85, 86, 87, 88, 89, 90, 91, 92, 93, 94, 95, 96, 97, 98 or 99%, over their entire length with the respective wildtype enzyme they are derived from.

The enzyme may be selected from LbCas12a, AsCas12a or a variant, such as an engineered variant thereof. Said enzymes may comprise or consist of the amino acid sequence set forth in SEQ ID NO:3 (LbCas12a) or SEQ ID NO:2 (AsCas12a) or may be variants thereof as defined above that retain Cas12a functionality and have the above-indicated sequence identity to SEQ ID NO:2 or 3. Preferred are AsCas12a, preferably comprising or consisting of the amino acid sequence set forth in SEQ ID NO:2, or a variant thereof that retains Cas12a functionality, in particular an artificially engineered variant thereof. Such variants are as defined above and have at least 80% sequence identity, for example at least 81, 82, 83, 84, 85, 86, 87, 88, 89, 90, 91, 92, 93, 94, 95, 96, 97, 98 or 99%, over their entire length to SEQ ID NO:2. Said engineered variant of AsCas12a may comprise any one or more of the amino substitutions 174R, 542R, and 548R relative to SEQ ID NO:14 and also using the positional numbering of SEQ ID NO:2. Particularly preferred are variants comprising all of the above amino acid substitutions E174R, S542R, and K548R. The variant may comprise or consist of the amino acid sequence set forth in SEQ ID NO:1. The AsCas12a variant having the amino acid sequence of SEQ ID NO:1 is also known enAsCas12a and is an engineered variant of AsCas12a comprising the amino acid substitutions E174R, S542R, and K548R that has originally been described by Kleinstiver, et al.(supra). This variant was found to be able to tolerate mismatches at the target site better than other (wildtype) Cas12a nucleases. In various embodiments, the at least one Cas12a enzyme thus has the amino acid sequence set forth in SEQ ID NO:1 or a variant thereof.

"Variant", as used herein in relation to the Cas12a enzymes, relate to polypeptides that differ from a given template sequence by one or more amino acid residues. As described above, this may mean that a variant has a sequence identity to a reference sequence of at least 80%, for example at least 81, 82, 83, 84, 85, 86, 87, 88, 89, 90, 91, 92, 93, 94, 95, 96, 97, 98, 98.1, 98.2, 98.3, 98.4, 98.5, 98.6, 98.7, 98.8, 98.9, 99.0, 99.1, 99.2, 99.3, 99.4, 99.5, 99.6, 99.7, 99.8 or 99.9%, over their entire length. Said variants retain the functionality of the reference sequence and, in various embodiments, have at least the same or even higher activity than the sequence they are derived from. Said term does not only encompass mutants that comprise one or more amino acid substitutions relative to the starting sequence but also truncated versions of the enzyme that lack one or more amino acids from their C- or N-terminal end. Such truncations may be up to 50 or more amino acids in length, but may also be only 1, 2, 3, 4, 5, 6, 7, 9 or 10 amino acids. Generally, such truncated versions retain the core sequence responsible for activity.

As used herein, the terms "crRNA" or "guide RNA" or "single guide RNA," "gRNA", as used interchangeably, refer to a polynucleotide comprising any polynucleotide sequence having sufficient complementarity with a target nucleic acid sequence to hybridize with the target nucleic add sequence and to direct sequence-specific binding of a targeting complex comprising the gRNA and the Cas12a enzyme to the target nucleic acid sequence. In general, a gRNA may be any polynucleotide sequence (i) being able to form a complex with a Cas12a enzyme and (H) comprising a sequence having sufficient complementarity with a target polynucleotide sequence to hybridize with the target sequence and direct sequence-specific binding of a CRISPR complex to the target sequence. As used herein the term "capable of forming a complex with the Cas12a enzyme" refers to the gRNA having a structure that allows specific binding by the Cas12a protein to the gRNA such that a complex is formed that is capable of binding to a target nucleic acid in a sequence specific manner and that can exert a function on said target nucleic acid. Structural components of the gRNA may include direct repeats and a guide sequence (or spacer). The sequence specific binding to the target nucleic acid is mediated by a part of the gRNA, the "guide sequence" or "spacer sequence", being complementary to the target. As used herein the term "wherein the guide sequence is capable of hybridizing" refers to a subsection of the gRNA having sufficient complementarity to the target sequence to hybridize thereto and to mediate binding of a Cas12a protein to the target. In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 80%, 85%, 90%, 95%, 97.5%, 99%, or more.

In various embodiments, the at least one guide RNA (gRNA) is designed to bind to one or more target nucleic acids that are diagnostic for a disease state and/or presence of a pathogen and/or resistance to a specific drug, such as a chemotherapeutic drug. The disease state may be an infection, an autoimmune disease, cancer or any other disease. The selection of the gRNA is thus decisive for the desired application and needs to be tailored to be specific for the target nucleic acid selected.

The at least one gRNA comprises a spacer sequence of at least 20 nucleotides in length that specifically recognizes and binds a target sequence in the target nucleic acid. The spacer sequence may be longer, for example of up to 40, up to 35, up to 32, up to 30, up to 28, up to 27, up to 26, up to 25, up to 24, up to 23 or up to 22 nucleotides in length. In addition to the spacer sequence, the at least one gRNA for the Cas12a enzyme also comprises at least one additional sequence portion that facilitates the binding of the Cas12a enzyme which is typically located 5' to the spacer sequence and is about 20 to 35 nucleotides in length, typically 20 to 30 nucleotides in length. The total length of the at least one gRNA molecule is, in various embodiments, up to 60, typically up to 55, up to 50, up to 45, or about 40 nucleotides. In various embodiments, the at least one gRNA comprises a spacer of 20 nucleotides and an enzyme binding sequence 5' to the spacer of also 20 nucleotides in length. The enzyme binding sequence may have the nucleotide sequence UAAUUUCUACUCUUGUAGAU (SEQ ID NO:16). The spacer sequence may be selected based on the intended target sequence.

In various embodiments, the at least one gRNA molecule comprises a 5'-terminal extension of at least 2, preferably 3, 4, 5, 6, 7, 8, 9 or more nucleotides, for example 4 to 9 nucleotides. These extensions are additional nucleotides 5' to the Cas12a binding sequence. These may have the sequence UGGA or GGGAAUGGA or 3' fragments thereof. It has been found that such 5' extensions on the gRNA, in particular a gRNA comprising a Cas12a binding sequence about 20 nucleotides in length and a spacer sequence of about 20 nucleotides in length, can improve the activity and/or efficiency of the cleavage reaction.

Alternatively or additionally, the at least one gRNA sequence may comprise at least one chemically modified nucleotide. Such chemically modified nucleotides comprise 2'-O-methyl modifications, 2'-fluoro modifications and phosphorothioate linkages as well as so-called locked nucleic acid (LNA) nucleotides comprising a methylene bridge between the 2' and 4' ring of the ribose ring. It has been found that such modifications may also improve the activity and/or efficiency of the cleavage reaction.

In various embodiments, the at least one gRNA is a DNA-RNA hybrid. In such embodiments, the gRNA molecule comprises at least 1 DNA nucleotide, preferably 2 to 4 DNA nucleotides, preferably in the spacer sequence, the rest being RNA nucleotides. In such DNA-RNA hybrid molecules the majority of nucleotides are typically still RNA nucleotides, in particular the sequence stretch that facilitates binding to the Cas12a enzyme is typically a full RNA sequence. It may be preferred that the gRNA comprises up to 10, or up to 8, or up to 6, up to 5, or up to 4 DNA nucleotides, that may be exclusively located in the spacer sequence. If such DNA nucleotides are present, these may be located at the 3' terminus of the spacer sequence, preferably the 3'-terminal, the 3'-penultimate nucleotide, or both may be DNA nucleotides. Another favorable location is the 5' end of the spacer sequence, i.e. position 1 of the spacer sequence, that means the first nucleotide downstream of the sequence that facilitates Cas12a binding. In addition to position 1 of the spacer sequence or alternatively, any of positions 2, 3, 4, 5, 6, 7, 8, 9, 10, 11 and 12 of the spacer sequence may be a DNA nucleotide, for example position 8. In these embodiments, positional numbering is based on the spacer sequence alone, i.e. not the complete gRNA sequence, in 5' to 3' orientation.

Such embodiments in which the gRNA is a DNA-RNA hybrid have been found to be particularly advantageous with respect to efficiency. In various embodiments, the gRNA is thus a DNA-RNA hybrid as described above. It is understood that such a hybrid may also comprise 5' extensions and chemical nucleotide modifications as described above. In general, all possible modifications of the gRNA described herein may be used individually or in any possible combination.

In various embodiments, the at least one gRNA comprises at least two gRNAs. In such embodiments, the at least two gRNA are preferably directed to different target sites in the same target nucleic acid. Said different target sites are, in various embodiments, non-overlapping and although they may b e directly adjacent to each other, in various embodiments they are separated by more than 10 nucleotides, for example more than 50 or more than 100 nucleotides. It is thus possible that both gRNA are directed to completely different target sites within the target nucleic acid.

The target nucleic acid may be RNA or DNA, including RNA molecules selected from the group consisting of messenger RNA (mRNA), pre-mRNA, ribosomal RNA (rRNA), transfer RNA (tRNA), micro-RNA (miRNA), small interfering RNA (siRNA), small nuclear RNA (snRNA), small nuclear RNA (snoRNA), double stranded RNA (dsRNA), non coding RNA (ncRNA), long non-coding RNA (lncRNA), and small cytoplasmic RNA (scRNA). It may be derived from any particular source or organism. In various embodiments, the target nucleic acid is derived from a pathogen. Such pathogenic organisms may include, without limitation, bacteria, fungi, parasites and viruses. In other embodiments, it is derived from a subject or organism that is suspected to suffer from a disease or disorder that is not caused by a pathogen, with the target nucleic acid being related to the cause of the disease or disorder. While in the following the concept of the invention is demonstrated by reference to a viral target nucleic acid, it is understood that this serves as proof-of-principle only and the invention is by no means limited thereto. The skilled person would rather understand that the methods and systems described herein can be practiced with virtually any nucleic acid of sufficient length.

The term "target sequence", as used herein, refers to a sequence within the target nucleic acid to which a guide sequence is designed to have complementarity, where hybridization between a target sequence and a guide sequence promotes the formation of a CRISPR complex.

In some embodiments described herein as proof-of-principle, the target nucleic acid is viral nucleic acid. Again, the target nucleic acid may be derived from any known virus, but herein the efficacy of the claimed methods and systems is demonstrated using SARS-CoV-2 nucleic acid as a target.

In such embodiments, where the target nucleic acid is SARS-CoV-2 RNA the spacer sequence of the at least one gRNA may comprise or consist of the nucleotide sequence ACUCCUGGUGAUUCUUCUUC (SEQ ID NO:12), AAACCUAGUGAUGUUAAUAC (SEQ ID NO:13) or a variant thereof that shares at least 85% sequence identity with SEQ ID NO:12 or 13. The sequence identity may be higher, for example, 90, 95, or 100%, over the entire length of the variants. In embodiments where at least two gRNAs are used and the target nucleic acid is SARS-CoV-2 nucleic acid, the first gRNA may comprise a spacer sequence comprising or consisting of the nucleotide sequence ACUCCUGGUGAUUCUUCUUC (SEQ ID NO:12) or a variant thereof having at least 85%, 90%, or 95% sequence identity to SEQ ID NO:12, and the second gRNA may comprise a spacer sequence comprising or consisting of the nucleotide sequence AAACCUAGUGAUGUUAAUAC (SEQ ID NO:13) or a variant thereof having at least 85%, 90% or 95% sequence identity to SEQ ID NO:13.

In various embodiments, where the target nucleic acid is SARS-CoV-2 RNA the SARS-CoV-2 target sequence comprises or consists of the nucleotide sequence GAAGAAGAAUCACCAGGAGU (SEQ ID NO:14) or GUAUUAACAUCACUAGGUUU (SEQ ID NO:15) or a naturally occurring variant thereof that shares at least 85%, 90% or 95% sequence identity with SEQ ID NO:14 or 15.

If the target nucleic acid is RNA, it may first be reverse transcribed into the corresponding DNA sequence. This is generally preferred for the enzymes of the present invention. Techniques for such reverse transcription of RNA targets are known to those skilled in the art and routinely practiced.

In various embodiments, the method further comprises the step of amplifying the target nucleic acid before it is detected by means of the steps and systems described herein. Such amplification may serve to generate amplicons of the target nucleic acid. The amplification may also entail a reverse transcription step if the target is an RNA molecule. In various embodiments of the inventive methods, the amplicon obtained by said amplification step is therefore a DNA amplicon.

The use of such amplification techniques to generate amplicons of the target means that in the contacting step the amplicons of the target nucleic acid and, optionally and depending on the type of amplification used and whether the template stays intact, also the original target nucleic acid are contacted with the nucleic acid detection system described.

In various embodiments, the amplifying step may be carried out using an isothermal amplification method, including but not limited to nucleic-acid sequenced-based amplification (NASBA), recombinase polymerase amplification (RPA), loop-mediated isothermal amplification (LAMP), strand displacement amplification (SDA), helicase-dependent amplification (HDA), or nicking enzyme amplification reaction (NEAR). In certain example embodiments, non-isothermal amplification methods may be used which include, but are not limited to, PCR, multiple displacement amplification (MDA), rolling circle amplification (RCA), ligase chain reaction (LCR), or ramification amplification method (RAM). In various embodiments, the amplification method is however an isothermal amplification method, such as recombinase polymerase amplification (RPA) or loop-mediated isothermal amplification (LAMP), with the latter being particularly preferred. As described above, if the target nucleic acid is an RNA, said amplification method may comprise a reverse transcription step to generate template DNA from the target RNA. Accordingly, the amplification method may be reverse transcription loop-mediated isothermal amplification (RT-LAMP).

As used herein, the terms “LAMP” or “loop mediated isothermal amplification”, refer to an isothermal amplification method, i.e. a method that is performed at an essential constant temperature without the need for a thermocycler. In LAMP, the target sequence is typically amplified at 60 to 65° C. using at least two sets of primers (i.e. at least 4 primers) and a polymerase with high strand displacement activity in addition to a replication activity. DNA polymerase with strand displacement activity/properties is known to those skilled in the art as an ability of the polymerase to displace the downstream DNA strand encountered during synthesis along the target strand. Typically, 4 different primers are used to identify 6 distinct regions on the target gene, which adds highly to the specificity. An additional “loop primer” or pair of “loop primers” can further accelerate the reaction. Due to the specific nature of the action of these primers, the amount of DNA produced in LAMP is considerably higher than PCR based amplification. The LAMP method is generally described in U.S. Pat. Nos. 6,410,278 B1 and 7,374,913 B2. Generally, the method uses two inner or internal primers (forward inner/internal primer=FIP and backward inner/internal primer=BIP), two outer primers or displacement primers (F3 and B3), and optionally one or two, preferably two, loop primers (loop forward=LF and/or loop backward=LB). If two loop primers are used, one is preferably a loop forward primer and the other a loop backward primer. The inner primers comprise a target complementary region (typically referred to as F2 and B2) that facilitates hybridization and, 5' to said target complementary region, a sequence that is identical to a sequence in the target nucleic acid located upstream (5') relative to the sequence of the target bound by the target complementary region of the inner primer (typically referred to as F1c and B1c). Elongation of the inner primer by the polymerase thus creates a sequence comprising regions of self-complementarity in that the target-identical sequence on the 5' end of the inner primer (B1c) can, after elongation, bind to the synthesized sequence downstream of the target-complementary region of the inner primer (referred to as B1) and act as a primer for further extension. The outer primers bind to a target region in the target nucleic acid that lies downstream (i.e. 3') to the target region bound by the inner primers (referred to as F3c and B3c) and thus are responsible for the displacement of the elongated inner primer sequences from the template strand. The elongated inner primers are recognized and hybridized by the other primer of the inner primer pair and thus the dumbbell structured starting amplicons are generated. The dumbbell structures are then used for the following amplification, with the amplicons taking the form of concatemers. The principles of LAMP are for example disclosed by Eiken Chemical Co., Ltd. at http://loopamp.eiken.co.jp/e/lamp/principle.html and http://loopamp.eiken.co.jp/e/lamp/loop.html, in the publications of Nagamine et al. (Mol. Cell. Probes (2002) 16:223-229) and Notomi et al. (Nucleic Acids Res. (2000), 28 (12): e63).

The target nucleic acid (DNA) sequence stretches for LAMP can thus be schematically shown as:

5'-F3c-F2c-F1c-B1-B2-B3-3'

3'-F3-F2-F1-B1c-B2c-B3c-5'

The inner primers comprise the sequence elements 5'-F1c-F2-3' and 5'-B1c-B2-3'

The outer primers comprise the sequence elements 5'-F3-3' and 5'-B3-3'

The loop primer(s) typically target(s) a sequence in the loops between F2 and F1 and/or B2 and B1.

The principle of LAMP amplification is also schematically shown in Parida et al. (Rev. Med. Virol. (2008) 18:407-21) and is common general knowledge for those skilled in the art.

The LAMP method may further comprise the use of at least one swarm primer set or at least one stem primer set, preferably a swarm primer set.

If LAMP is used for amplification of the target, the term “target”, as used herein, further encompasses the amplicons and concatemers produced by the LAMP reaction. Accordingly, when reference is made to a target that is bound by the Cas12a/gRNA complex, this term typically relates to the amplicons and concatemers as produced in the LAMP reaction, as these are more prevalent than the original target nucleic acid. “Amplicons” or “concatemers”, as used interchangeable herein, relate to the amplified products generated starting from the template, i.e. the original target nucleic acid, and dumbbell starting structure produced from the inner primers in a first part of the LAMP reaction. These structures contain multiple repeats of the relevant sequence elements described above.

The term “sample”, as used herein, includes any suitable sample and includes environmental samples, such as soil or water samples, as well as biological samples, such as tissue or biological fluids, including blood, plasma, serum, saliva and the like. The sample may be derived from a subject, suffering from or suspected of suffering from a disease, for example an infectious disease, the subject preferably being a mammal, for example a human. Alternatively, the subject may also be an animal or plant. If the method is used for pathogen detection, any sample type useful and known for such purpose may be used.

In accordance with the established principles of LAMP, the LAMP reaction mixture as used in the methods of the invention comprises a LAMP primer set of at least 4 primers, typically at least 6 primers, comprising two inner/internal primers (FIP and BIP), two outer/displacement primers (F3 and B3), and optionally one or two loop primers (LF and/or LB) and a pair of swarm or stem primers or both. While it is known that the loop primer(s) increase(s) amplification efficiency, these are optional and not essential for carrying out the LAMP method. It is however preferred that one or two, preferably two, loop primers are included in the methods of the invention. The same applies to the swarm and stem primers, with swarm primers having been found to be advantageous for the methods described herein if also combined with the loop primer set.

The two inner primers used in the methods thus each comprise a target complementary region on their 3' end (F2 and B2) and a target identical region on their 5' end (F1c and B1c), where in the target nucleic acid the sequence recognized by the target complementary region of the inner primers (termed F2c or B2c) lies 3' to the sequence identical to the target identical sequence on the 5' end of the inner primers (said sequence in the target termed F1c and B1c).

Accordingly, the two outer primers each comprise a target complementary region (F3 and B3), wherein in the target nucleic acid the sequence targeted by the target complementary region of the outer primers (termed F3c and B3c) are located 3' to the sequence of the target nucleic acid targeted by the target complementary region of the inner primers. This allows displacement of the elongated inner primers necessary for generation of the dumbbell shaped starting structures needed for concatemer formation in the later stages of LAMP.

The one or two optional loop primers each comprise a target complementary region that recognizes a sequence between the target complementary region on the 3' end of the inner primers or the complement thereof (i.e. the F2 or B2 region) and the sequence complementary to the target identical sequence on the 5' end of the inner primers or the complement thereof (i.e. the F1 or B1 region). The forward loop primers preferably bind between F1 and F2. Similarly, preferred binding for the backward loop primers is thus between B1 and B2. It may be preferred that the loop primer set comprises loop primers that bind between the F1 and F2 and loop primers that bind between the B1 and B2 regions of the amplicons.

In various embodiments, the target nucleic acid is a SARS-CoV-2 nucleic acid and the first internal primer (FIP) has the nucleotide sequence set forth in SEQ ID NO:4, the second internal primer (BIP) has the nucleotide sequence set forth in SEQ ID NO:5, the first displacement primer (F3) has the nucleotide sequence set forth in SEQ ID NO:6, and/or the second displacement primer (B3) has the nucleotide sequence set forth in SEQ ID NO:7. If loop primers are used, the first loop primer (LF) may have the nucleotide sequence set forth in SEQ ID NO:8 and/or the second loop primer (LB) may have the nucleotide sequence set forth in SEQ ID NO:9. If swarm primers are used, the first swarm primer may have the nucleotide sequence set forth in SEQ ID NO:10 and/or the second swarm primer may have the nucleotide sequence set forth in SEQ ID NO:11.

It has been found that amplification can be advantageously influenced by the presence of certain additives, in particular glycine, taurine and/or guanidine. In various embodiments, amplification is thus carried out in the presence of such agents that improve amplification results, in particular any one or more of glycine, taurine and guanidine, preferably guanidine.

As described above, amplification is typically carried out isothermally at a temperature of 60 to 65° C. Typical amplification times are 10 to 60 minutes, preferably 12 to 30 or 12 to 22 minutes.

In various embodiments, the LAMP method further comprises the use of 3' or 5' truncated internal primers that differ from the internal primers by a truncation of one nucleotide at the 3' or 5' end of their target-complementary sequence.

In various embodiments, the LAMP method further comprises the use of a high fidelity DNA polymerase with a proofreading capability, preferably with a 3'-to-5'-exonuclease activity.

In the methods described herein, the detection step (b) may be conducted at a temperature of at least 37° C., preferably at a temperature in the range of from 37° C. to 65° C. In various embodiments, said temperature range for the detection step should be compatible with the temperature used for the optional amplification step, preferably those should overlap to a certain extent. In various embodiments, the detection can thus also be carried out at a temperature of about 60 to 65° C.

In various embodiments, the detection reagent is an oligonucleotide, such as an RNA oligonucleotide or a ssDNA molecule. It has been found that activated Cas12a enzymes indiscriminately cleave single-stranded DNA molecules. ssDNA molecules are thus a suitable detection reagent for activated Cas12a enzyme, which becomes activated upon target complex formation with the gRNA and the target nucleic acid. In various embodiments, the oligonucleotide used as the detection reagent is designed such that upon cleavage by the activated Cas12a enzyme it generates a detectable signal. This may be achieved by using a detectable tag or signaling moiety coupled thereto that becomes activated or detectable upon cleavage. Exemplary signaling moieties are described below.

The oligonucleotide may be an interfering RNA involved in an RNA interference pathway, such as siRNA. While present, such an oligonucleotide will suppress expression of a gene product. The gene product may be encoded by a reporter construct that is added to the sample. The gene product may be a fluorescent protein or other RNA transcript or proteins that would otherwise be detectable by a labeled probe or antibody but for the presence of the oligonucleotide. Upon activation of the Cas12a enzyme the oligonucleotide is cleaved allowing for expression and detection of the gene product as a positive detectable signal.

In certain other embodiments, the oligonucleotide may comprise a detectable label and a masking agent of that detectable label. An example of such a detectable label/masking agent pair is a fluorophore and a quencher of the fluorophore. Quenching of the fluorophore can occur as the result of the formation of a non-fluorescent complex between the fluorophore and another fluorophore or non-fluorescent molecule. This mechanism is known as ground-state complex formation, static quenching or contact quenching. Accordingly, the oligonucleotide may be designed such that the fluorophore and quencher are in sufficient proximity for contact quenching to occur. Fluorophores and their cognate quenchers are known in the art and can be selected for this purpose by one having ordinary skill in the art. The particular fluorophore/quencher pair is not critical in the context of this invention, it is only relevant that the selection of the pairs ensures masking of the fluorophore as long as the oligonucleotide is intact. Upon activation of the at least one Cas12a enzyme used as an effector protein herein, the oligonucleotide is cleaved thereby severing the proximity between the fluorophore and the quencher needed to maintain the contact quenching effect. Accordingly, detection of the fluorophore may be used to determine the presence or amount of a target in a sample.

In various example embodiments, fluorescence energy transfer (FRET) may be used to generate a detectable positive signal. FRET is a non-radiative process by which a photon from an energetically excited fluorophore (i.e. the donor fluorophore) raises the energy state of an electron in another molecule (i.e. the acceptor) to higher vibrational levels of the excited singlet state. The donor fluorophore returns to the ground state without emitting a fluoresce characteristic of that fluorophore. The acceptor can be another fluorophore or non-fluorescent molecule. If the acceptor is another fluorophore, the transferred energy is emitted as fluorescence characteristic of that fluorophore. If the acceptor is a non-fluorescent molecule the absorbed energy is lost as heat. Thus in the embodiments disclosed herein, the fluorophore/quencher pair is replaced with a donor fluorophore/acceptor pair attached to the oligonucleotide molecule. When intact, the oligonucleotide generates a first signal as detected by the fluorescence or heat emitted from the acceptor (negative signal). Upon activation of the Cas12a enzymes disclosed herein, the oligonucleotide is cleaved and FRET is disrupted so that fluorescence of the donor fluorophore may now be detected (positive signal).

In various embodiments, the methods described herein may also comprise a step of enriching the target nucleic acid prior to, optional amplification and, detection. This may be achieved by binding the target nucleic acid to a specific binding agent for said target, such as capture probes, antibodies or CRISPR effector systems, such as the Cas12a complex systems described herein.

The present invention also relates to the nucleic acid detection systems described above in the context of the inventive methods. These typically comprise:

at least one Cas12a enzyme, at least one gRNA, and at least one detection reagent;

wherein said at least one Cas12a enzyme is LbCas12a or AsCas12a or a variant thereof; and wherein said at least one gRNA comprises a spacer sequence of at least 20 nucleotides in length that specifically recognizes and binds a target sequence in the target nucleic acid, wherein said binding of the target nucleic acid results in activation of the Cas12a enzyme and the activated Cas12a generates, by interaction with the at least one detection reagent, a detectable, and optionally quantifiable, signal.

All embodiments described above in relation to the inventive methods similarly apply to these systems and vice versa.

In various embodiments of said systems, the at least one Cas12a enzyme is defined as for the methods described herein. In various sample embodiments, the enzyme is thus AsCas12a or a variant thereof that retains Cas12a functionality and has at least 80% sequence identity to SEQ ID NO:2, preferably a variant comprising the amino acid sequence set forth in SEQ ID NO:1.

In various embodiments of said systems, the at least one gRNA is as defined above in context with the methods of the invention. In particular, the gRNA may be a DNA-RNA hybrid and comprises at least 1 DNA nucleotide, preferably 2 to 4 DNA nucleotides, preferably in the spacer sequence, the rest being RNA nucleotides.

In various embodiments, the nucleic acid detection system comprises at least two different gRNAs that bind to two different, non-overlapping target sequences in the same target nucleic acid.

Generally, the at least one guide RNA (gRNA) is designed and selected to bind to one or more target nucleic acids of choice. As disclosed above, these target nucleic acids may be diagnostic for a disease state and/or presence of a pathogen and/or resistance to a specific drug, such as a chemotherapeutic drug. The disease state may be an infection, an autoimmune disease, cancer or any other disease.

In various embodiments of said nucleic acid detection system, the spacer sequence of the at least one gRNA comprises or consists of the nucleotide sequence ACUCCUGGUGAUUCUUCUUC (SEQ ID NO:12), AAACCUAGUGAUGUUAAUAC (SEQ ID NO:13) or a variant thereof that shares at least 85% sequence identity with SEQ ID NO:12 or 13. Such systems are then designed for the detection of SARS-CoV-2 in a sample.

The nucleic acid detection systems may further comprise reagents for amplification of the target nucleic prior to detection. Said reagents are typically adapted for the amplification method of choice. If the amplification method is LAMP or RT-LAMP, the system may comprise the necessary enzymes, primers and/or buffers.

In various embodiments of the described systems, the at least one detection reagent is an oligonucleotide, such as an RNA oligonucleotide or ssDNA oligonucleotide. Suitable detection reagents have been described above in the context of the inventive methods.

In various embodiments, the nucleic acid detection system is designed to detect one or more viral targets and may optionally be used in combination with anti-viral therapeutics. It may be designed such that it detects novel mutations in the viral target nucleic acid. The viral target may be SARS-CoV-2, which is also used as a proof-of-principle target herein.

The present invention is further illustrated by the following examples. However, it should be understood, that the invention is not limited to the exemplified embodiments.

EXAMPLES

All sequences referred to in the examples and figures are set forth in Table 1 below.

Example 1

1. Characterization of Cas12a Enzymes with Different gRNAs

Figure 3:
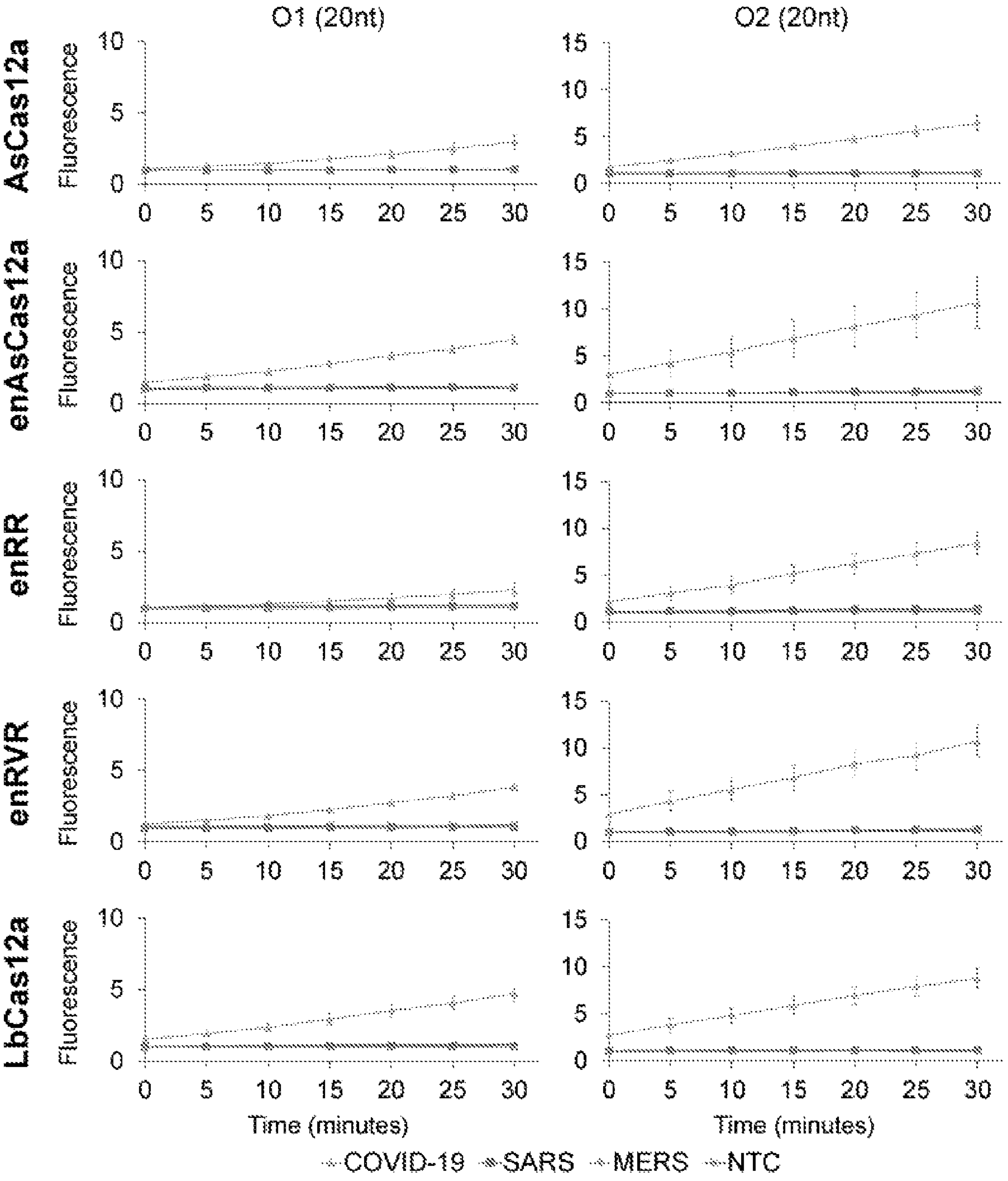
FIG. 3. Time courses of the fluorescence intensity in the trans-cleavage assays for various Cas12a nucleases complexed with perfect matched (PM) gRNAs targeting the O1, O2, S1, S3, and N1 loci of the SARS-CoV-2 genome. The assays were performed at 24° C. and approximately 1E11 copies of purified DNA template were used as input. All the measurements were normalized to the no-template control (NTC) at the start of the experiment. Data represent mean±s.e.m. (n=3[O1, O2, S3], 4 [S1], or 6 [N1] biological replicates).
Figure 3:
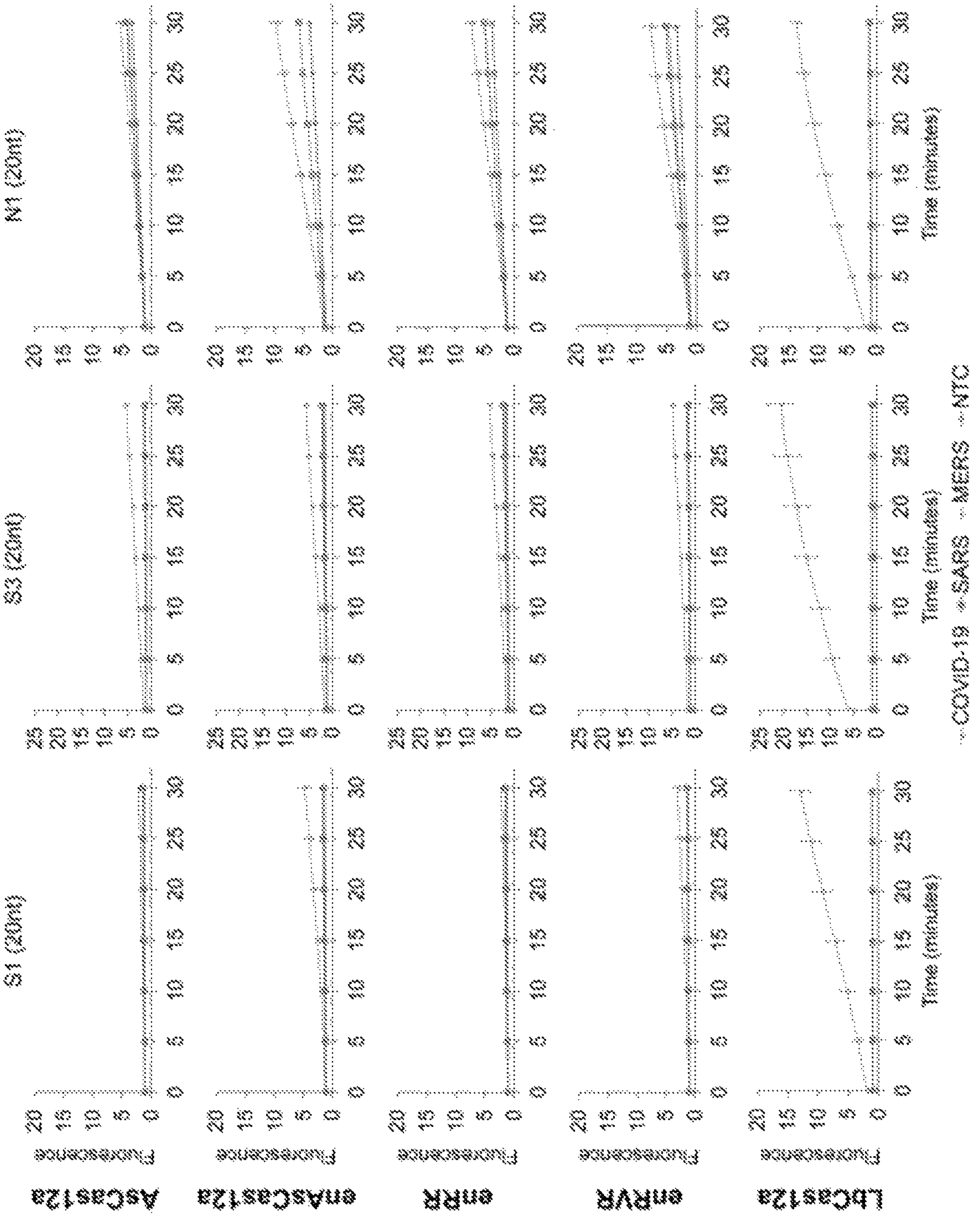
Figure 4:
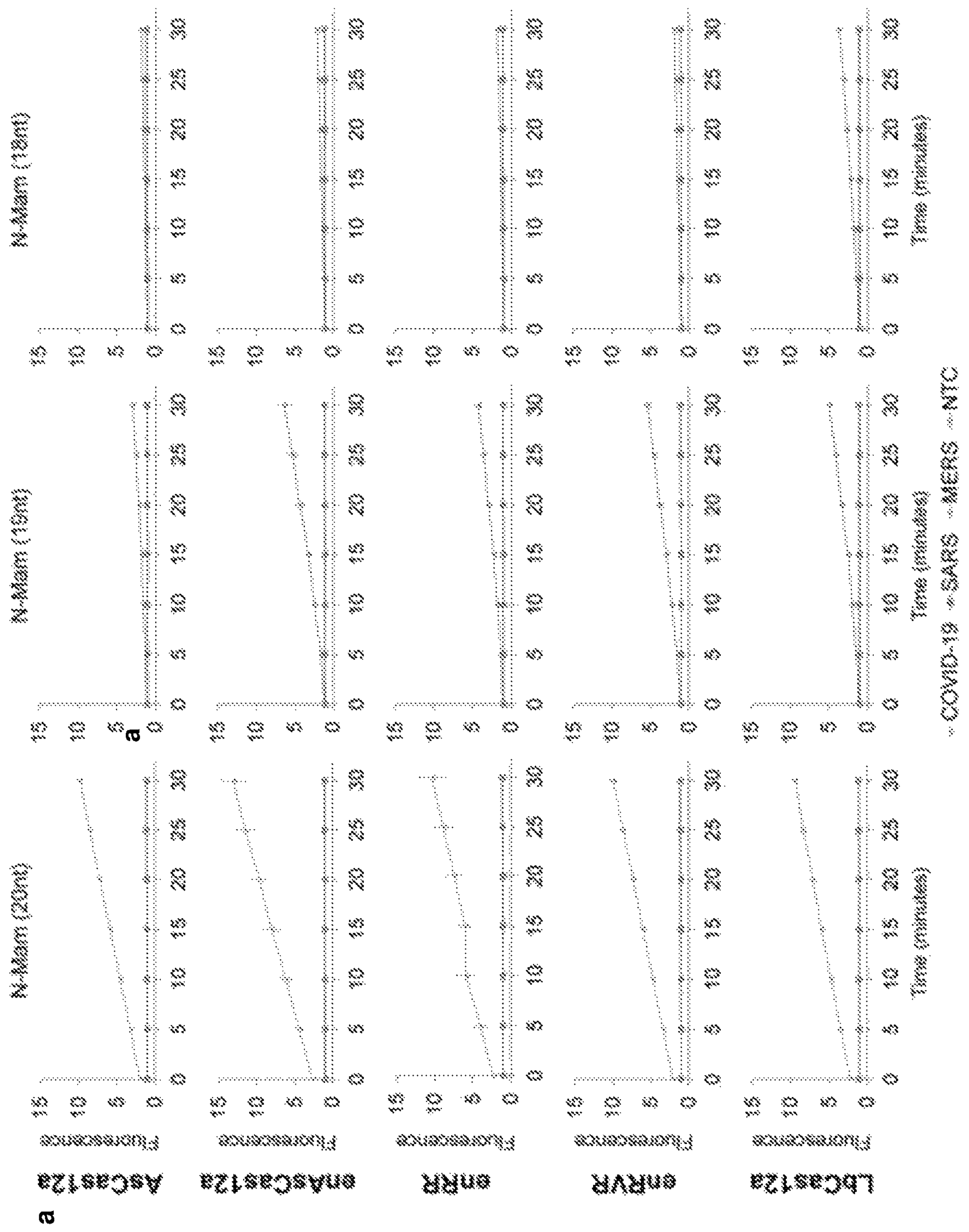
FIG. 4. Fluorescence intensity in the trans-cleavage assays.
Figure 4:
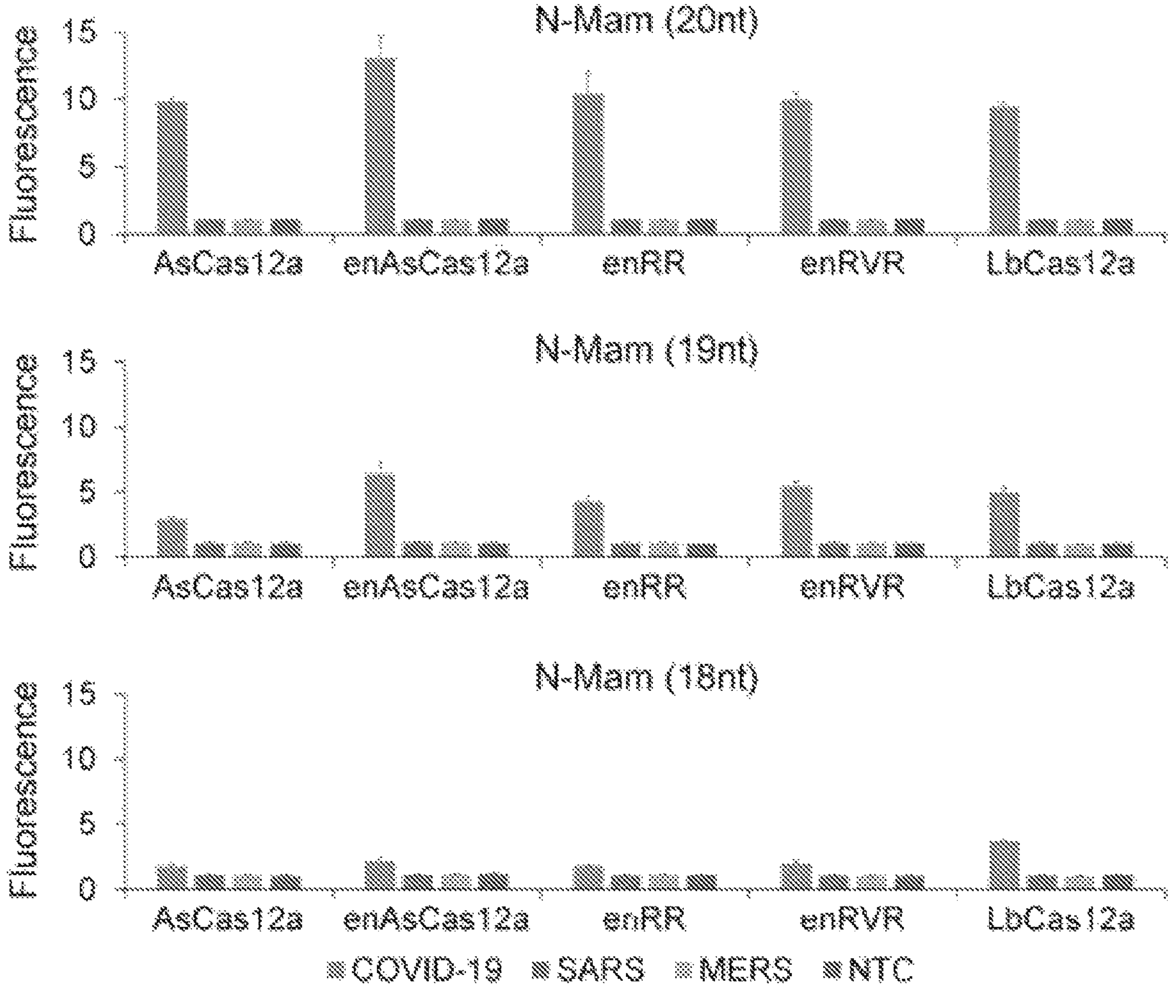
Figure 5:
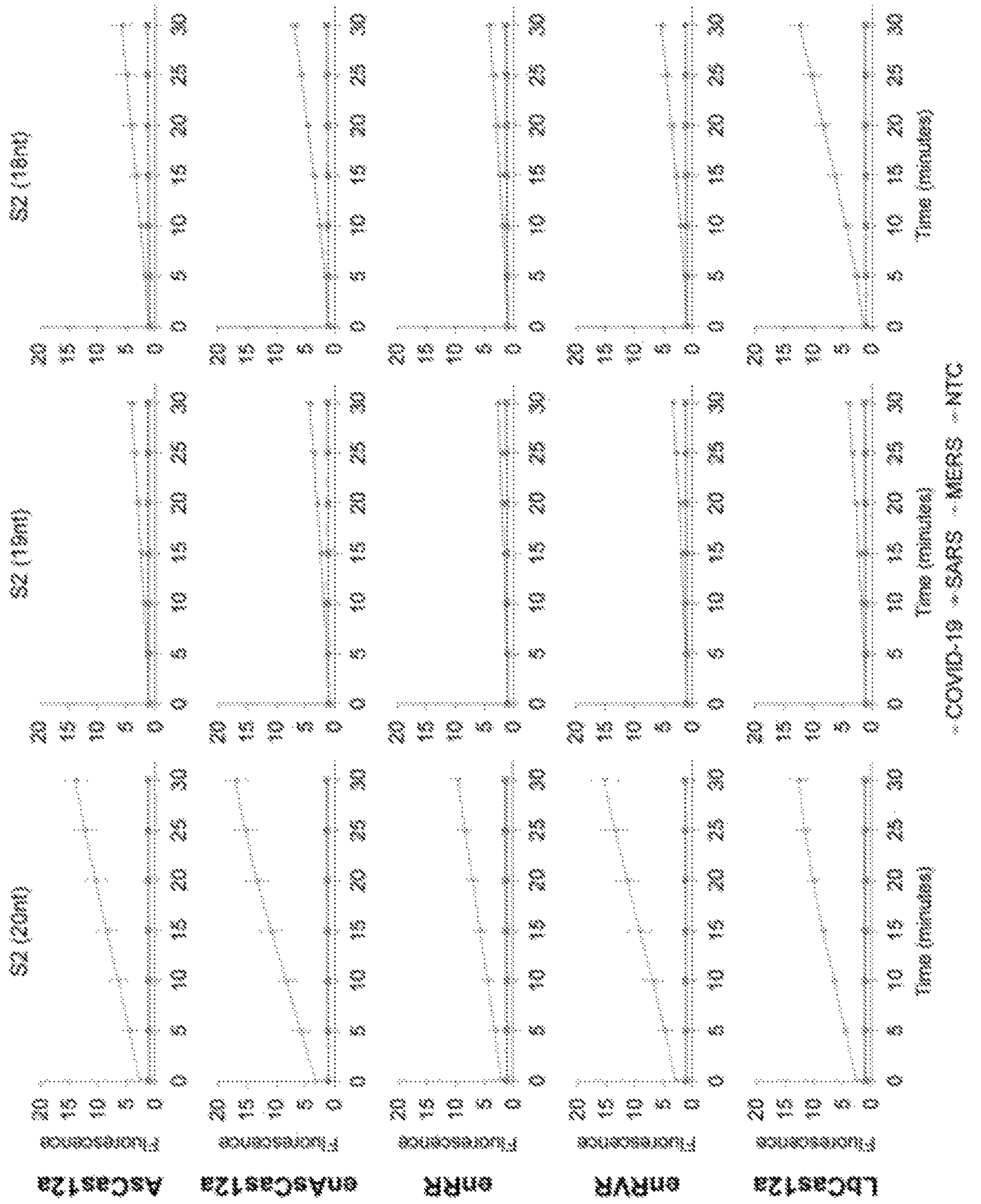
FIG. 5. Time courses of the fluorescence intensity in the trans-cleavage assays for various Cas12a nucleases complexed with perfect matched (PM) S2 gRNAs of three different spacer lengths. The assays were performed at 24° C. and 1E11 copies of purified DNA template were used as input. All the measurements were normalized to the no-template control (NTC) at the 0 min time point. Data represent mean±s.e.m. (n=3 [20nt] or 4 [18nt, 19nt] biological replicates).

The performance of various Cas12a RNP complexes in a fluorescence trans-cleavage assay (FIG. 1*a*) was evaluated and benchmarked against that deployed in the DETECTR system (Broughton, J. P. et al. (2020) Nat Biotechnol, doi:10.1038/s41587-020-0513-4), where wildtype LbCas12a was paired with a 20-nucleotide (nt) gRNA targeting the N-gene of SARS-CoV-2 (herein termed N-Mam gRNA) (FIG. 1*b*). To design new gRNAs, the genomes of SARS-CoV-2 and other related coronaviruses were aligned and six additional target sites (O1, O2, S1, S2, S3, and N1; complete ORF1ab, S and N genes of SARS-CoV-2, SARS-CoV and MERS-CoV are set forth in SEQ ID Nos. 17-25) were selected that not only contained the TTTV protospacer adjacent motif (PAM) for Cas12a, but were also highly divergent between the coronaviruses (data not shown). The corresponding DNA primer sequences for Also five different Cas12a enzymes were purified for testing. To assess the feasibility of a CRISPR-based diagnostic assay being deployed in a non-laboratory setting (e.g. a home setting), it has been initially carried out the cleavage reactions at room temperature using synthetic DNA fragments. Fluorescence was monitored over the course of 30 minutes in a microplate reader (FIG. 2-5). For the N-Mam gRNA, it has been observed that while LbCas12a could detect SARS-CoV-2 with minimal cross-reactivity for SARS-CoV or MERS-CoV as expected, the other four Cas12a enzymes performed similarly, with enAsCas12a yielding an even higher fluorescence signal than LbCas12a in the presence of the SARS-CoV-2 substrate (FIG. 4*b*). The N-Mam gRNA was also not the most ideal for LbCas12a. The collateral activity of LbCas12a complexed with the S3 gRNA was approximately double that of the same enzyme complexed with the N-Mam gRNA in the presence of SARS-CoV-2. The S2 gRNA also generated stronger fluorescence signals than the N-Mam gRNA when paired with LbCas12a as well as with AsCas12a, enAsCas12a, and enRVR. Among all the tested enzymes, enAsCas12a exhibited the highest collateral activity with the S2 gRNA in the presence of SARS-CoV-2. Overall, the minimum spacer length for a gRNA in this diagnostic assay appeared to be 20nt. When the spacer length has been shortened for either the N-Mam or the S2 gRNA to 18nt or 19nt, the collateral activity of all the Cas12a nucleases was reduced.

Figure 6:
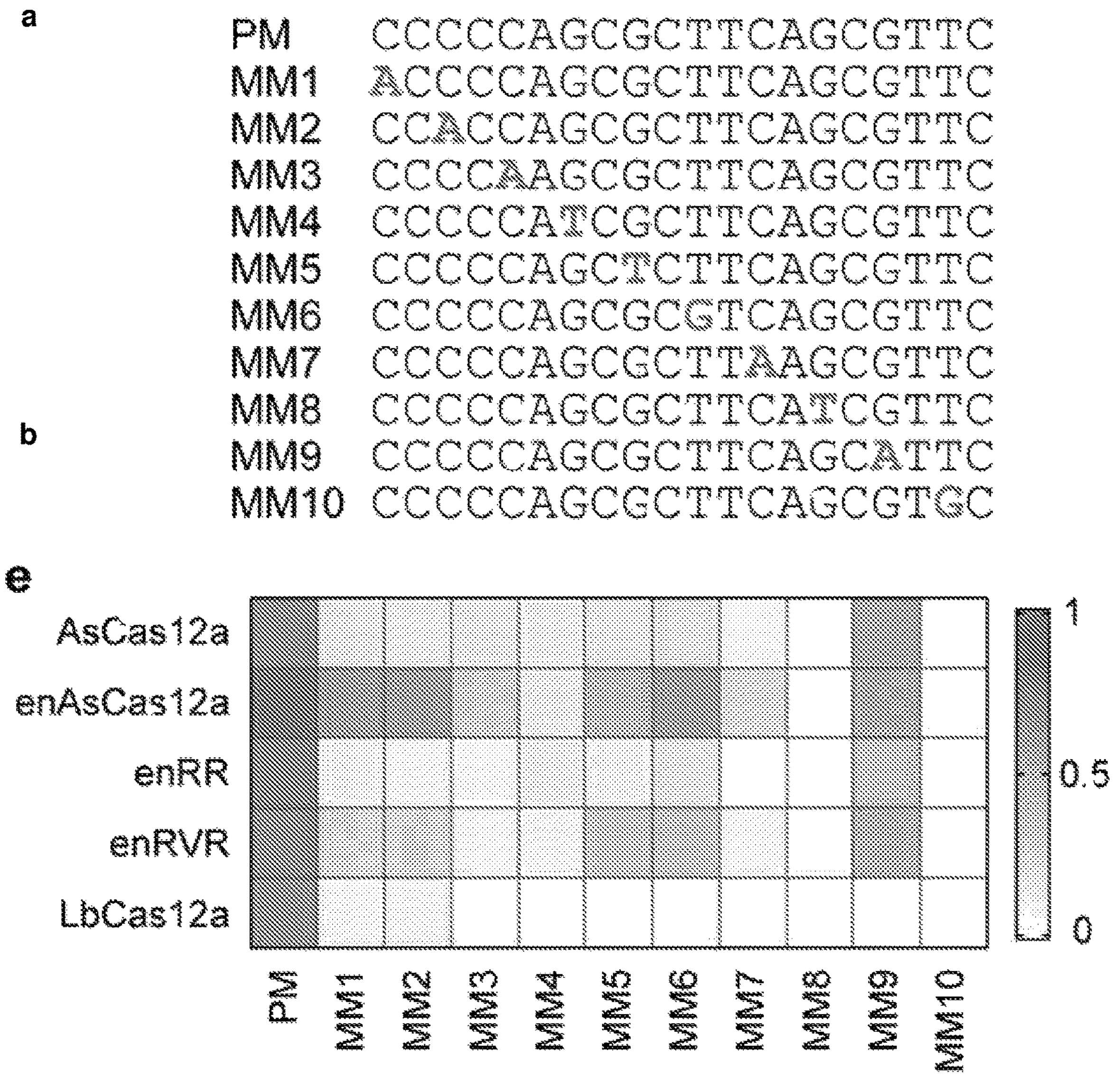
FIG. 6. Evaluation of different Cas12a-gRNA combinations at room temperature (24° C.).
Figure 7:
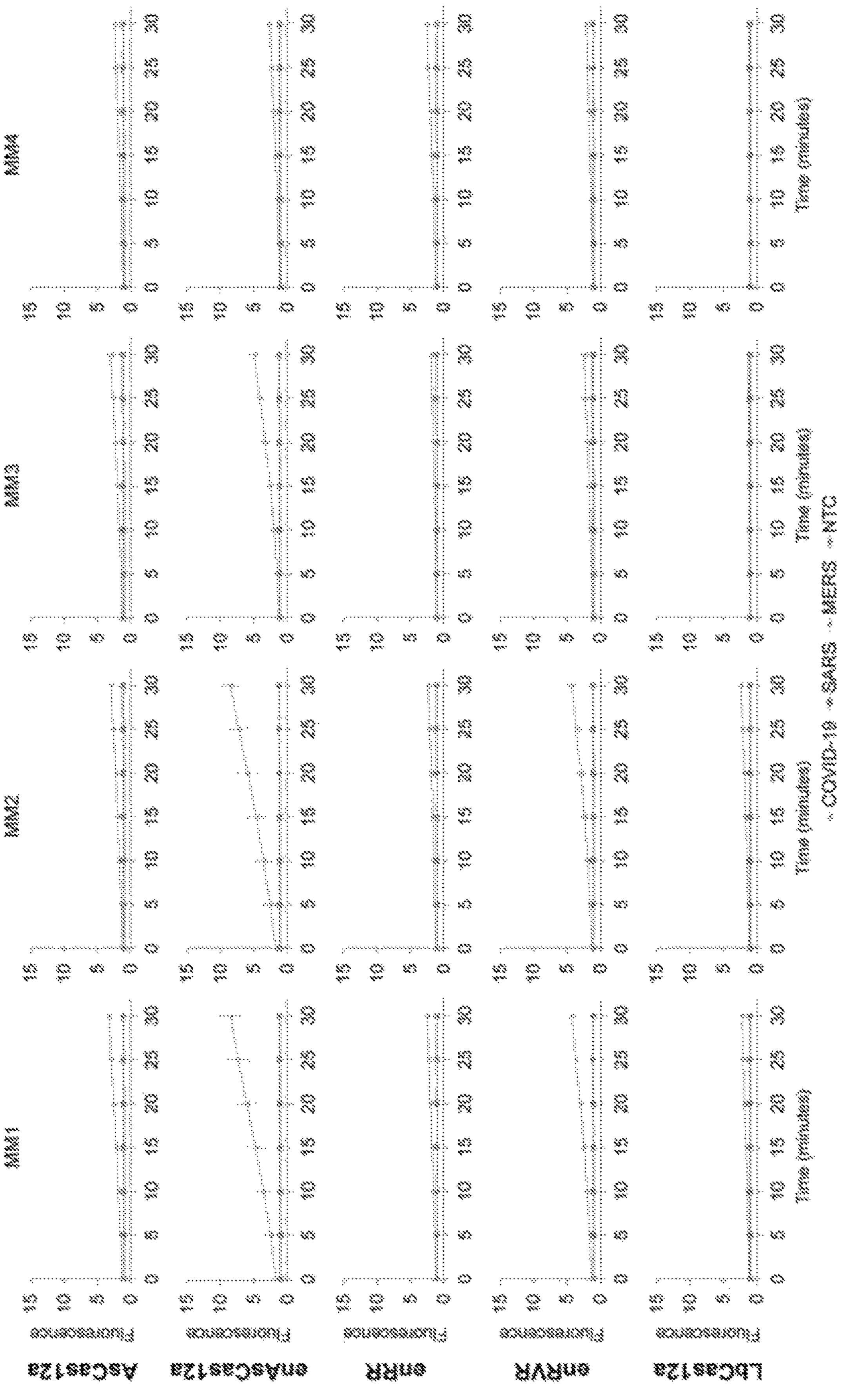
FIG. 7. Time courses of the fluorescence intensity in our trans-cleavage assays for various Cas12a nucleases complexed with mismatched (MM) N-Mam gRNAs of spacer length 20nt. The assays were performed at 24° C. and 1E11 copies of purified DNA template were used as input. Data represent mean±s.e.m. (n=3 [AsCas12a for MM5, MM6, MM8, MM9, and MM10; enAsCas12a; enRR; enRVR; LbCas12a] or 4 [AsCas12a for MM1, MM2, MM3, MM4, and MM7] biological replicates).
Figure 7:
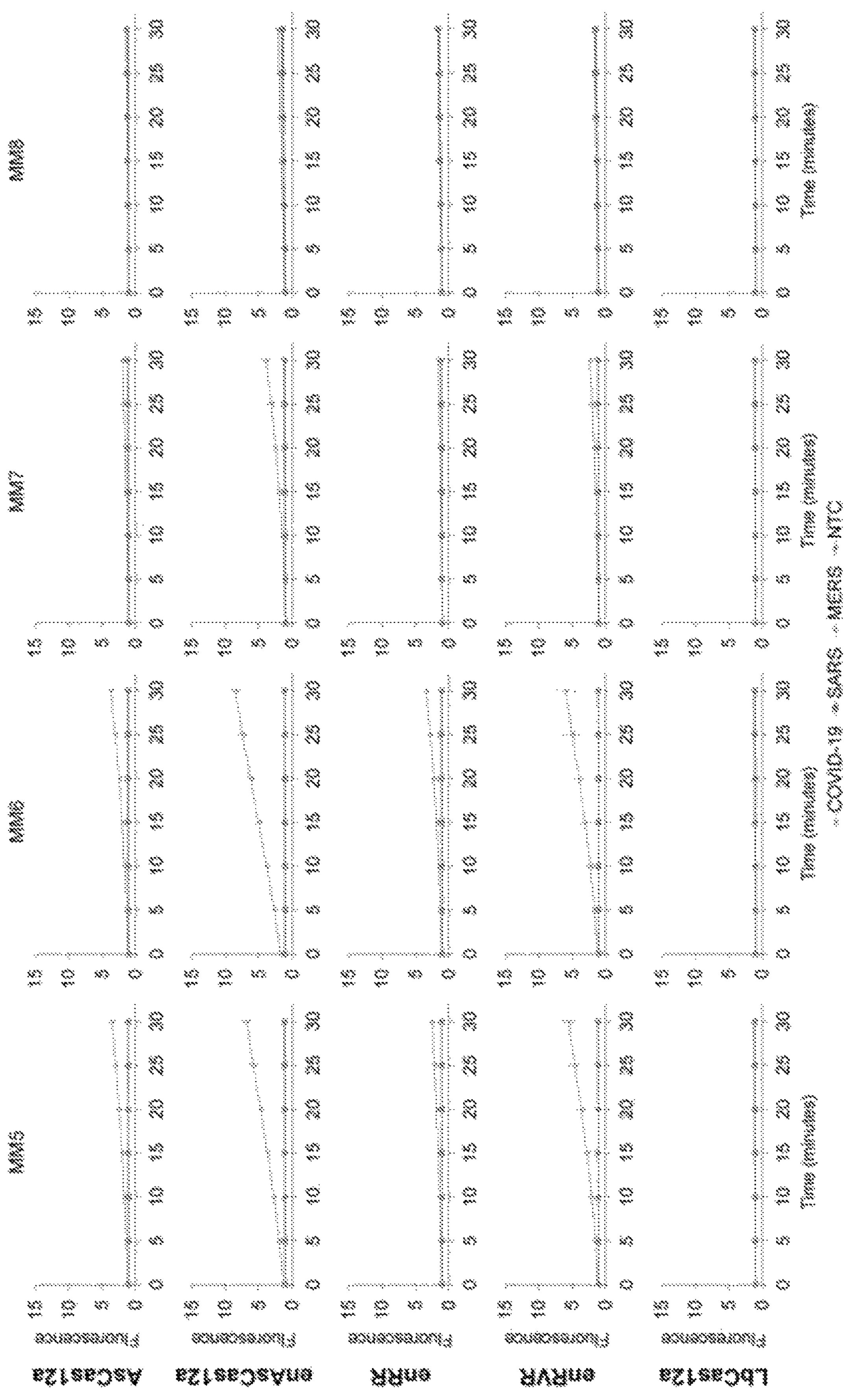
Figure 7:
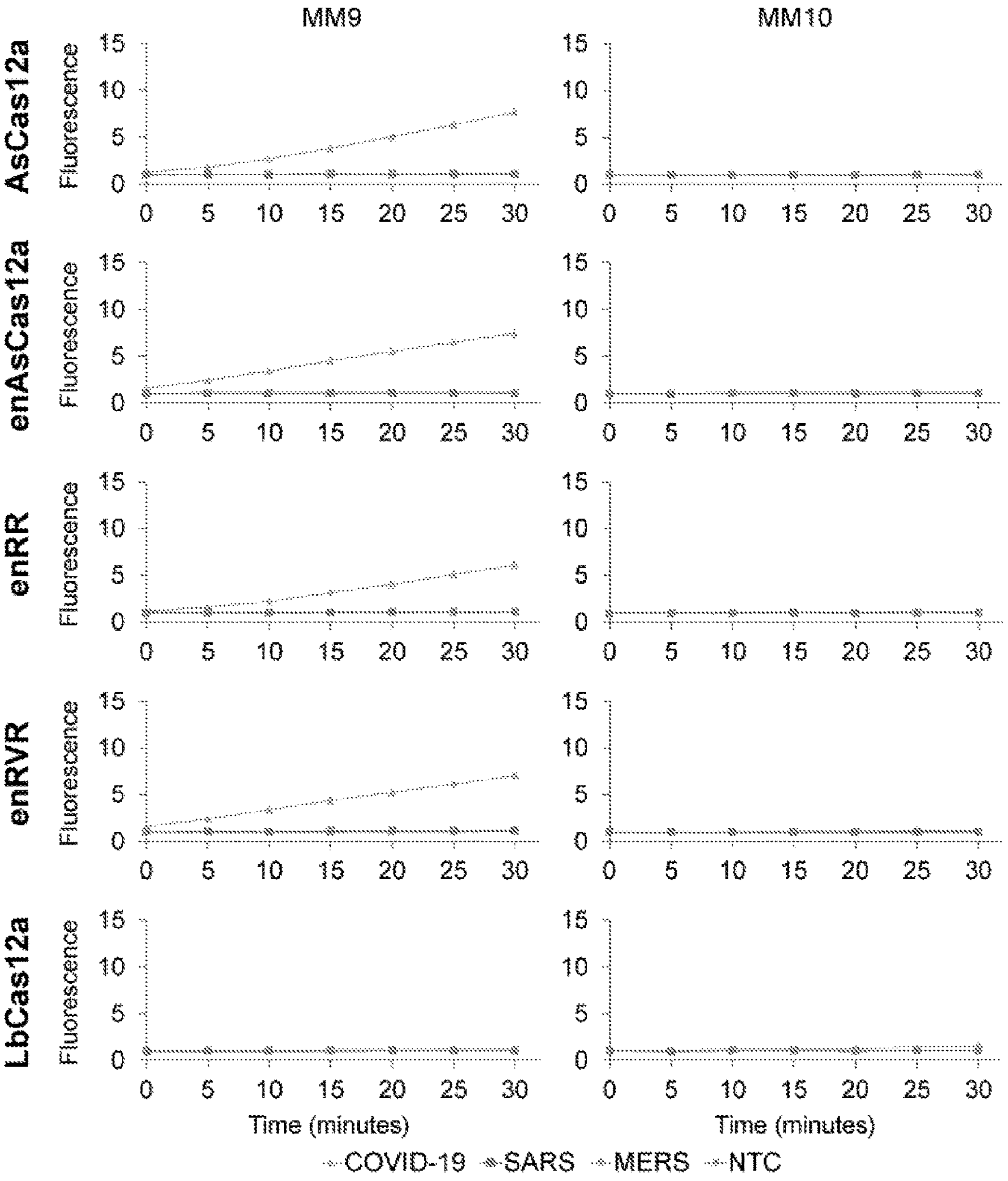
Figure 8:
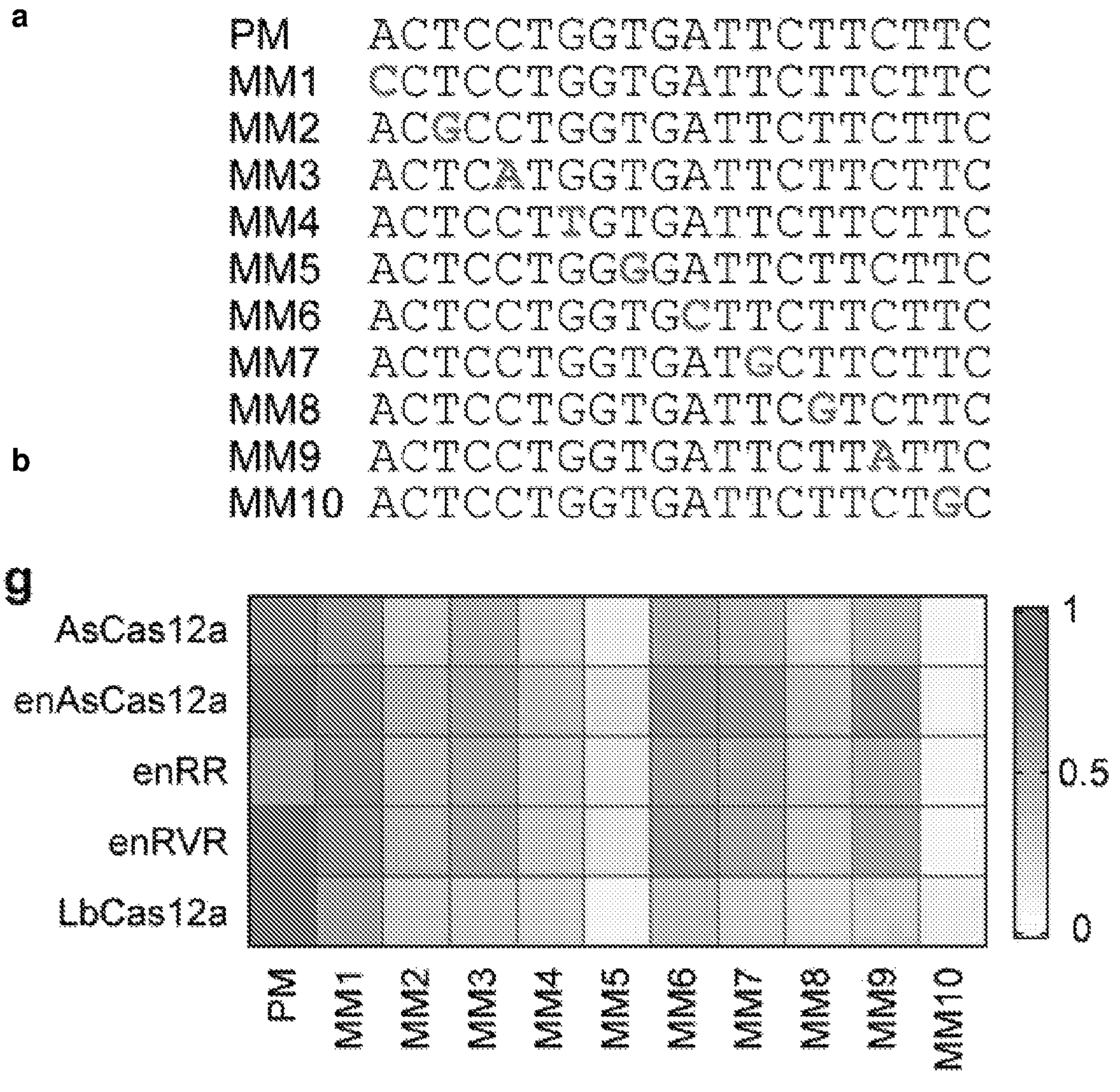
FIG. 8. Evaluation of different Cas12a-g RNA combinations at room temperature (24° C.).
Figure 9:
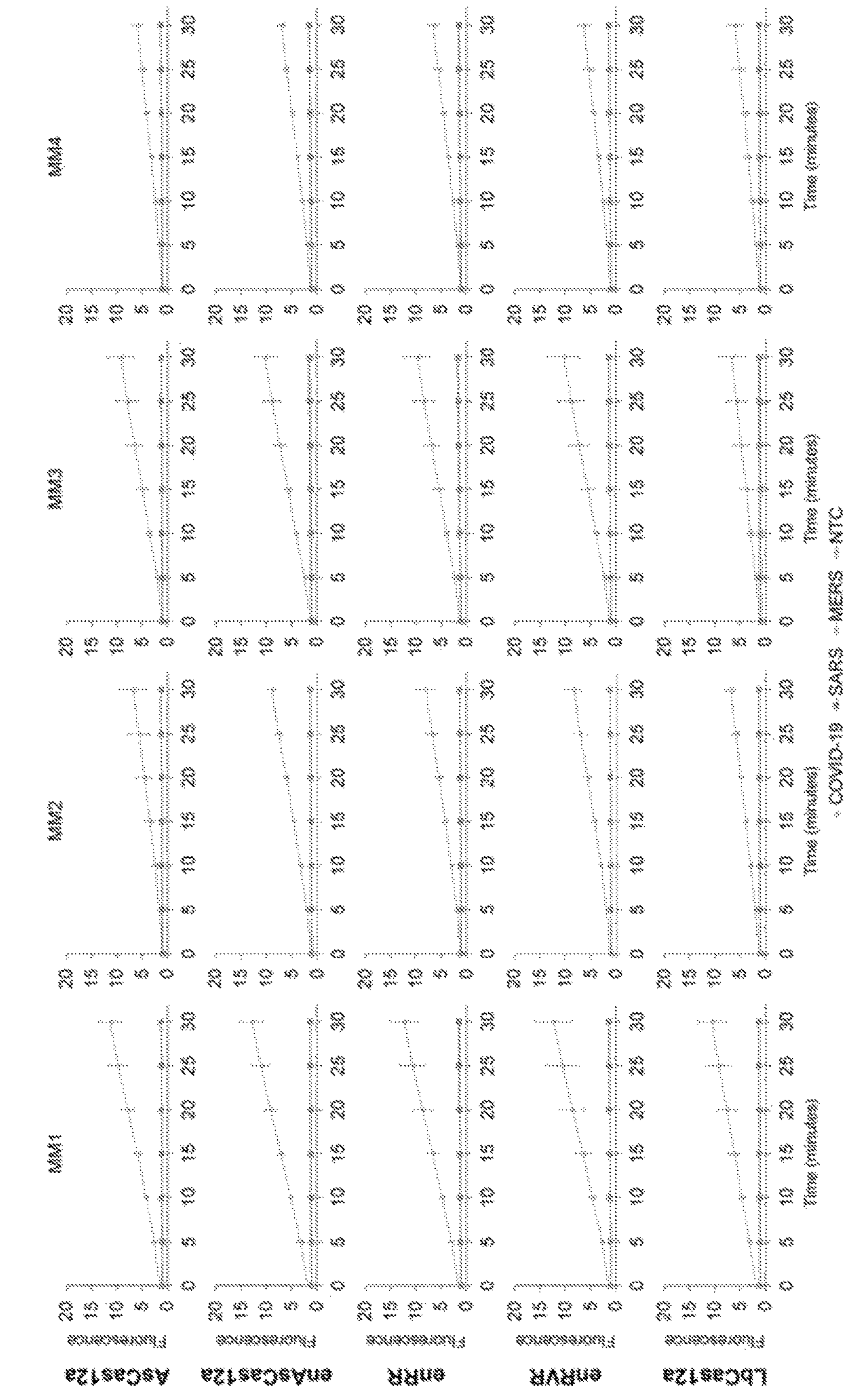
FIG. 9. Time courses of the fluorescence intensity in our trans-cleavage assays for various Cas12a nucleases complexed with mismatched (MM) S2 gRNAs of spacer length 20nt. The assays were performed at 24° C. and 1E11 copies of purified DNA template were used as input. Data represent mean±s.e.m. (n=2 biological replicates).
Figure 9:
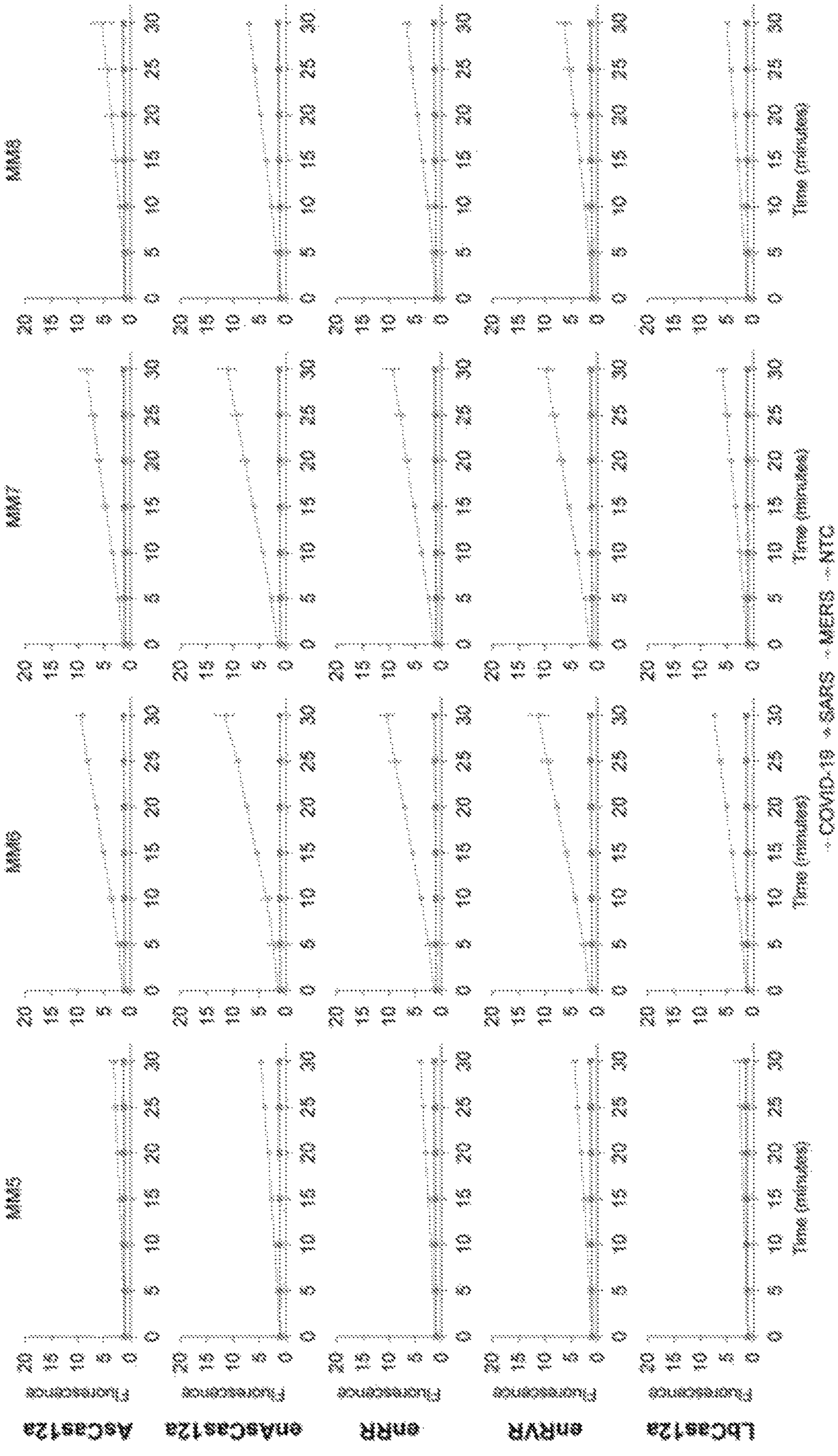
Figure 9:
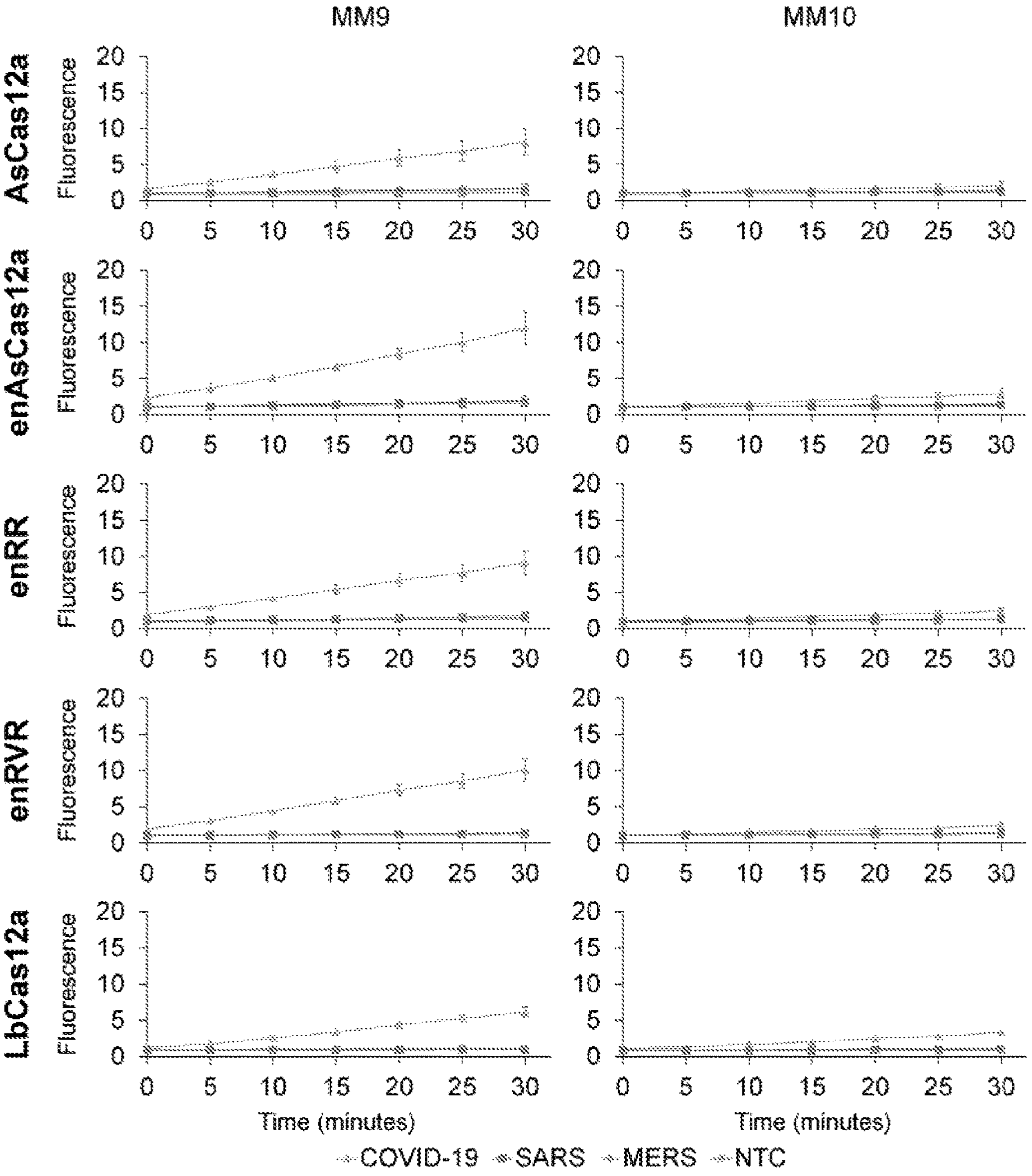
Figure 10:
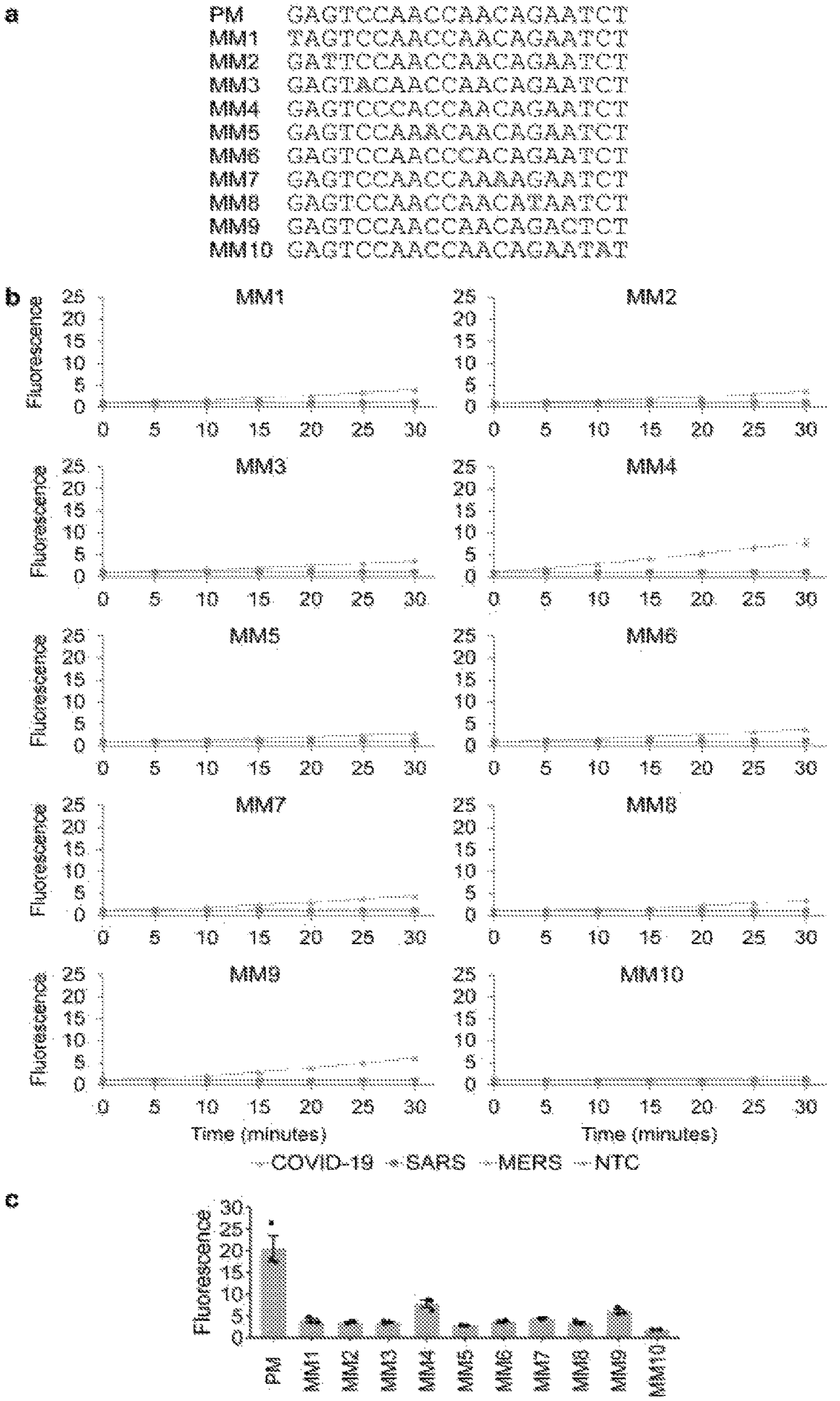
FIG. 10. Mismatch tolerance of LbCas12a at the S3 locus.

Next, it has been tested how mismatches at the gRNA-substrate interface may affect the fluorescence signal. Ten new gRNAs targeting the N-Mam locus, with each harbouring a single point mutation at variable locations along the spacer (FIG. 6*a*) have been generated. From the trans-cleavage assay, it has been found that LbCas12a was very sensitive to imperfect base pairing between the gRNA and the target substrate, as any mismatch along the spacer reduced the fluorescence output to near-background levels, while AsCas12a and its variants were able to tolerate some of the mismatches (FIG. 6*b*, 7). In particular, enAsCas12a was most tolerant of single nucleotide mismatches among the five tested enzymes. To verify the results, ten additional gRNAs targeting the S2 locus, with each harbouring a point mutation at different positions along the spacer (FIG. 8*a*) have been generated. Interestingly, it has been found that individual mismatches at the S2 locus affected the collateral activity of all the Cas12a endonucleases much less than those at the N-Mam locus (FIG. 8*b*, 9). Nevertheless, enAsCas12a again exhibited the highest tolerance for point mutations, while wildtype LbCas12a was again the most sensitive to imperfect base pairing between the gRNA and its target substrate. It has been further confirmed the poor mismatch tolerance of LbCas12a by generating more mismatched (MM) gRNAs targeting the S3 locus and finding that the collateral activity of LbCas12a was greatly diminished for all the new MM gRNAs (FIG. 10).

2. Further Characterization of enAsCas12a with S-Gene gRNAs

Figure 11:
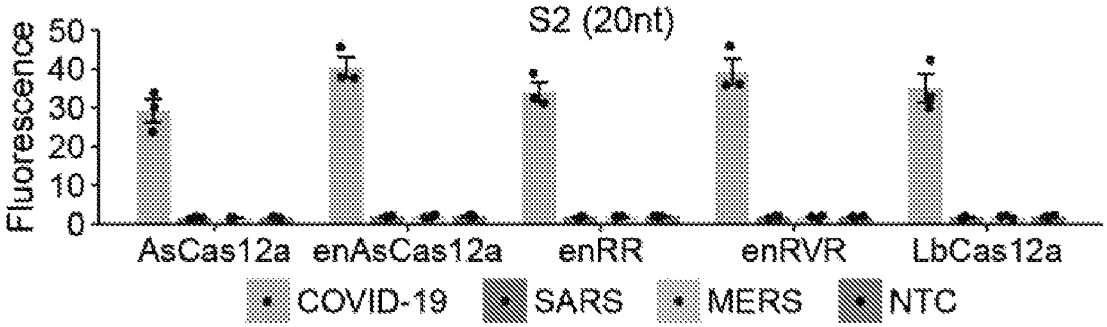
FIG. 11. Activity and mismatch tolerance of enAsCas12a with various S-gene-targeting gRNAs. The figure shows fluorescence measurements for a single S2 gRNA complexed with various Cas12a nucleases after 30 minutes of trans-cleavage reaction at 37° C. Compared to the earlier results obtained at 24° C., there was still no cross-reactivity for SARS-CoV or MERS-CoV at the higher temperature, but the fluorescence signal for SARS-CoV-2 was approximately twice as high. Data represent mean±s.e.m. (n=3 biological replicates).
Figure 12:
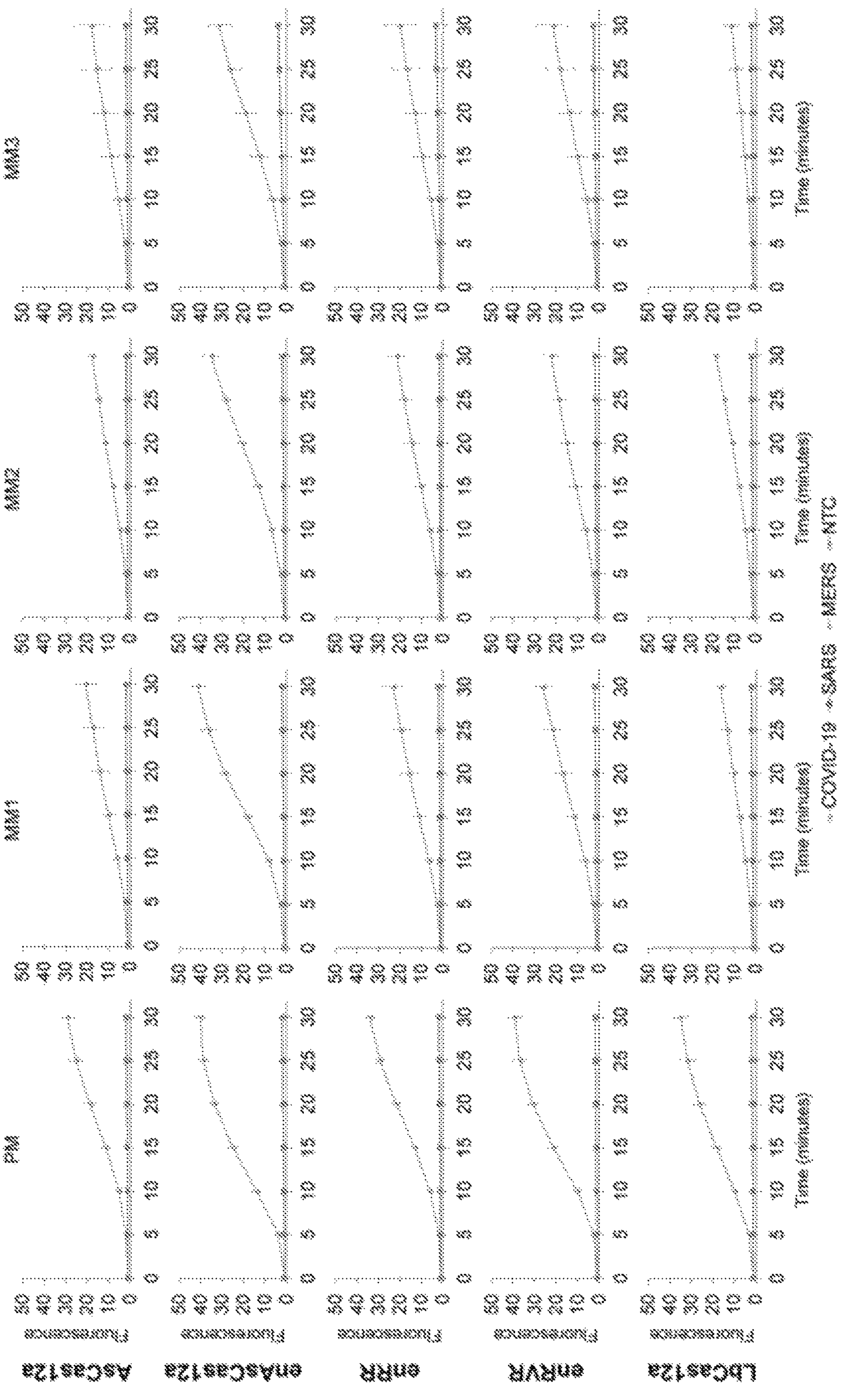
FIG. 12. Time courses of the fluorescence intensity in the trans-cleavage assays for various Cas12a nucleases complexed with either perfect matched (PM) or mismatched (MM) S2 gRNAs of spacer length 20nt. The assays were performed at 37° C. and 1E11 copies of purified DNA template were used as input. All the measurements were normalized to the no-template control (NTC) at the 0 min timepoint. It has been observed that when the Cas detection reaction was performed at 37° C., it proceeded around twice as fast as the same reaction at 24° C. (room temperature). Data represent mean±s.e.m. (n=3 biological replicates).
Figure 12:
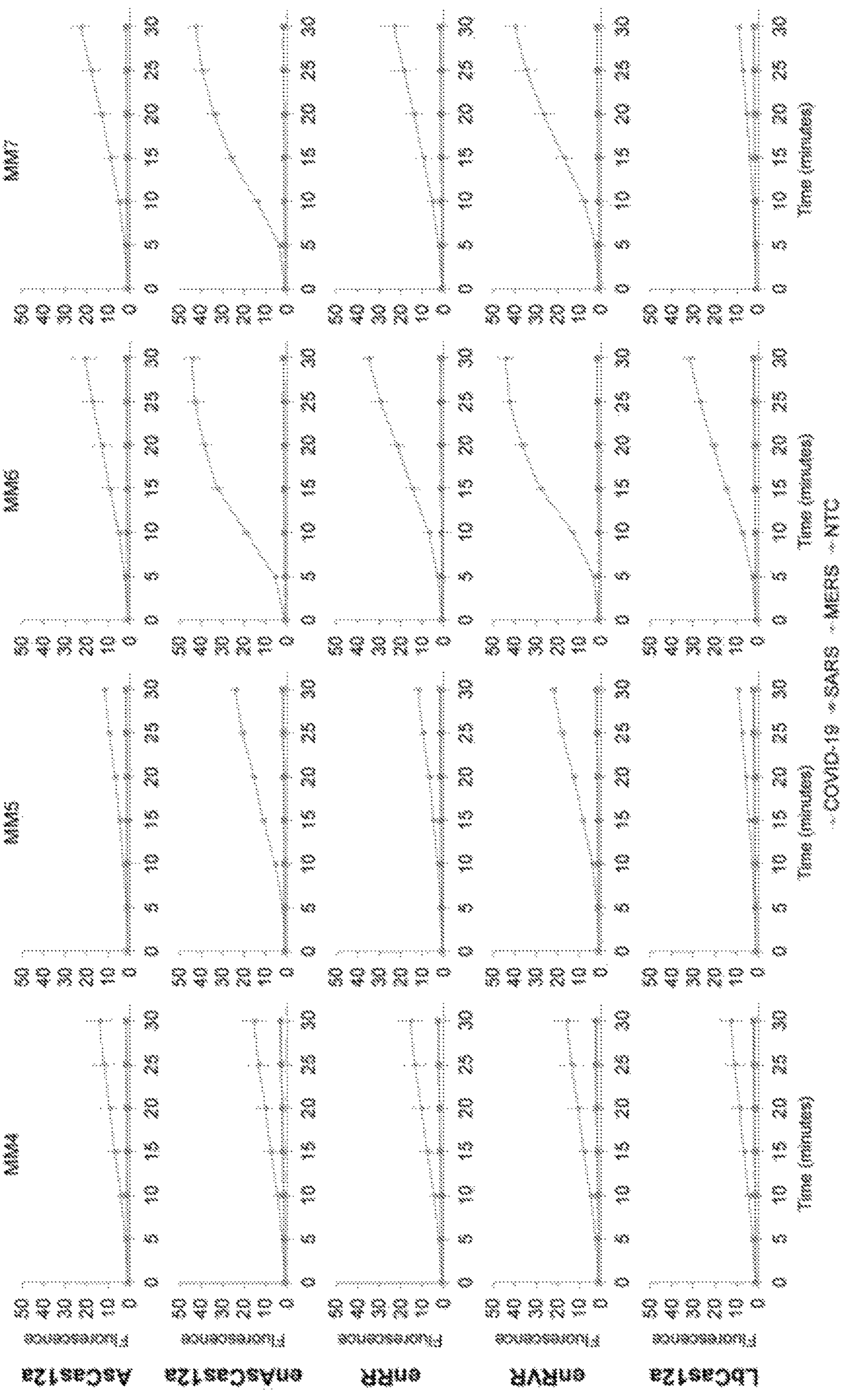
Figure 12:
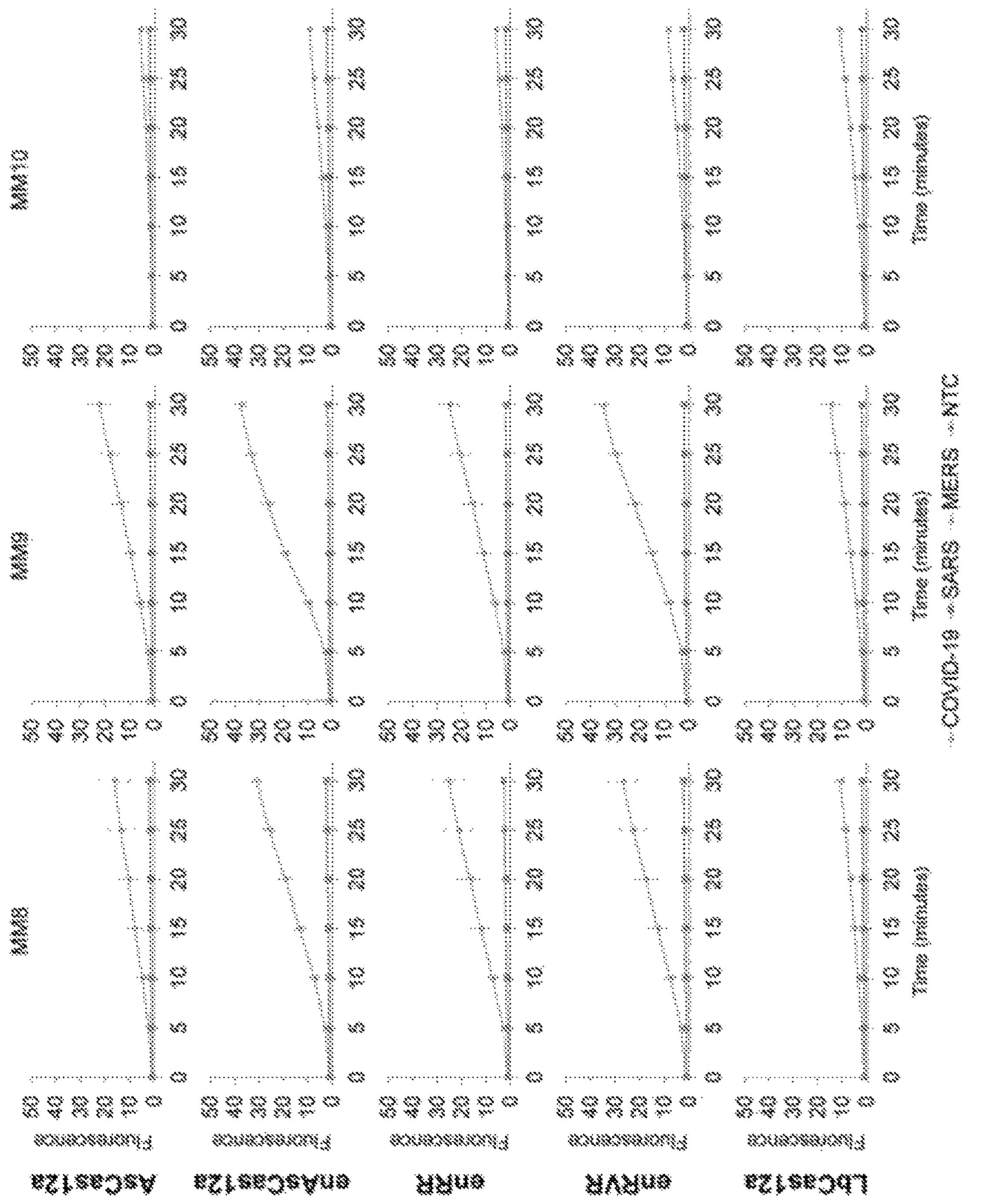
Figure 13:
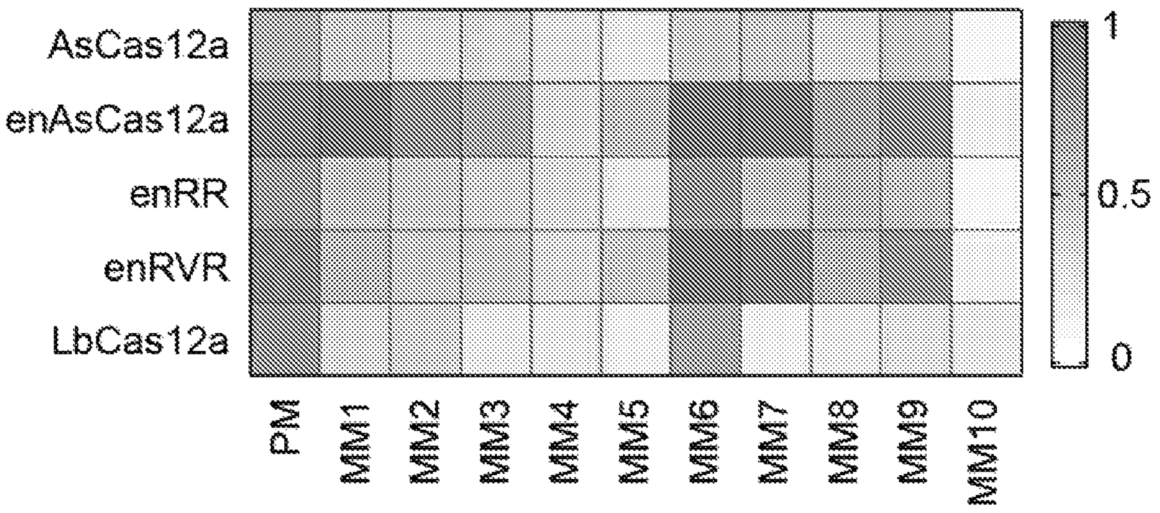
FIG. 13. Activity and mismatch tolerance of enAsCas12a with various S-gene-targeting gRNAs. The figure shows a heatmap showing the tolerance of various Cas12a enzymes to mismatches at the S2 target site when the trans-cleavage assay was performed at 37° C. The fluorescence readings are scaled between 0 and 1, where 1 is the highest measurement obtained and 0 is the background signal for NTC at the start of the experiment.

So far, the CRISPR-Cas detection had been performed at room temperature (24° C.) to simulate a non-laboratory setting. Now, it has to be found out if the diagnostic assay would perform substantially better at a more optimal reaction temperature (37° C.) and also if the observation of enAsCas12a being a more robust enzyme would still hold true at the higher temperature. Hence, the S2-targeting experiments have been repeated at 37° C. With the perfect matched (PM) gRNA, it has been observed that the fluorescence signal in the trans-cleavage assay increased around twice as fast at 37° C. in the presence of the intended SARS-CoV-2 template for all tested enzymes and reached much higher levels after 30 minutes of reaction, while showing little cross-reactivity for SARS-CoV and MERS-CoV (FIG. 11, 12). Furthermore, the activity profile in the presence of different point mutations remained similar, with enAsCas12a exhibiting the best mismatch tolerance as before (FIG. 12, 13). Hence, these results indicate that this CRISPR-based assay should be performed at 37° C. if a faster test result is desired and that enAsCas12a is a more suitable enzyme to use in a diagnostic test that is robust to viral genome mutations and intracellular RNA editing.

Figure 14:
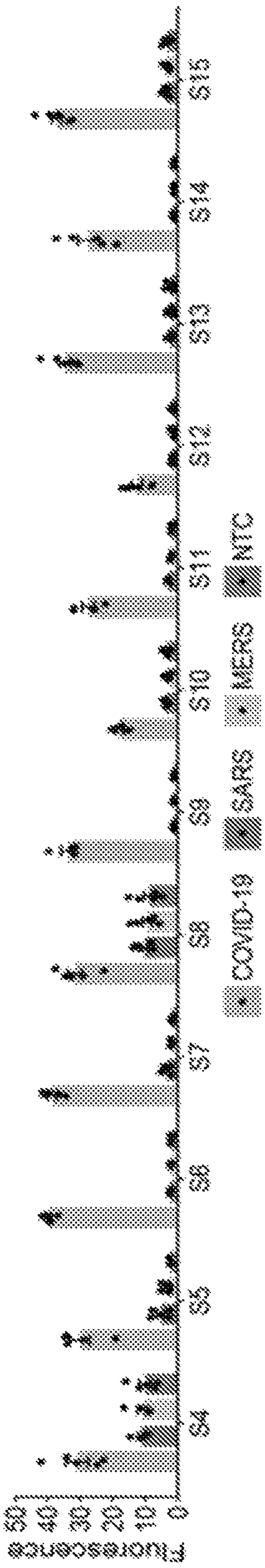
FIG. 14. Activity and mismatch tolerance of enAsCas12a with various S-gene-targeting gRNAs. The figure shows fluorescence measurements for enAsCas12a complexed with different gRNAs targeting the S-gene of SARS-CoV-2 after 30 minutes of cleavage reaction at 37° C. 1E11 copies of DNA were present in a 50 μl reaction. Two of the gRNAs (S4 and S8) triggered the collateral activity of enAsCas12a without a template. Data represent mean±s.e.m. (n=4 [S9], 5 [S4, S5, S6, S7, S11, S14], 6 [S8, S10, S12, S13], or 7 [S15] biological replicates).
Figure 15:
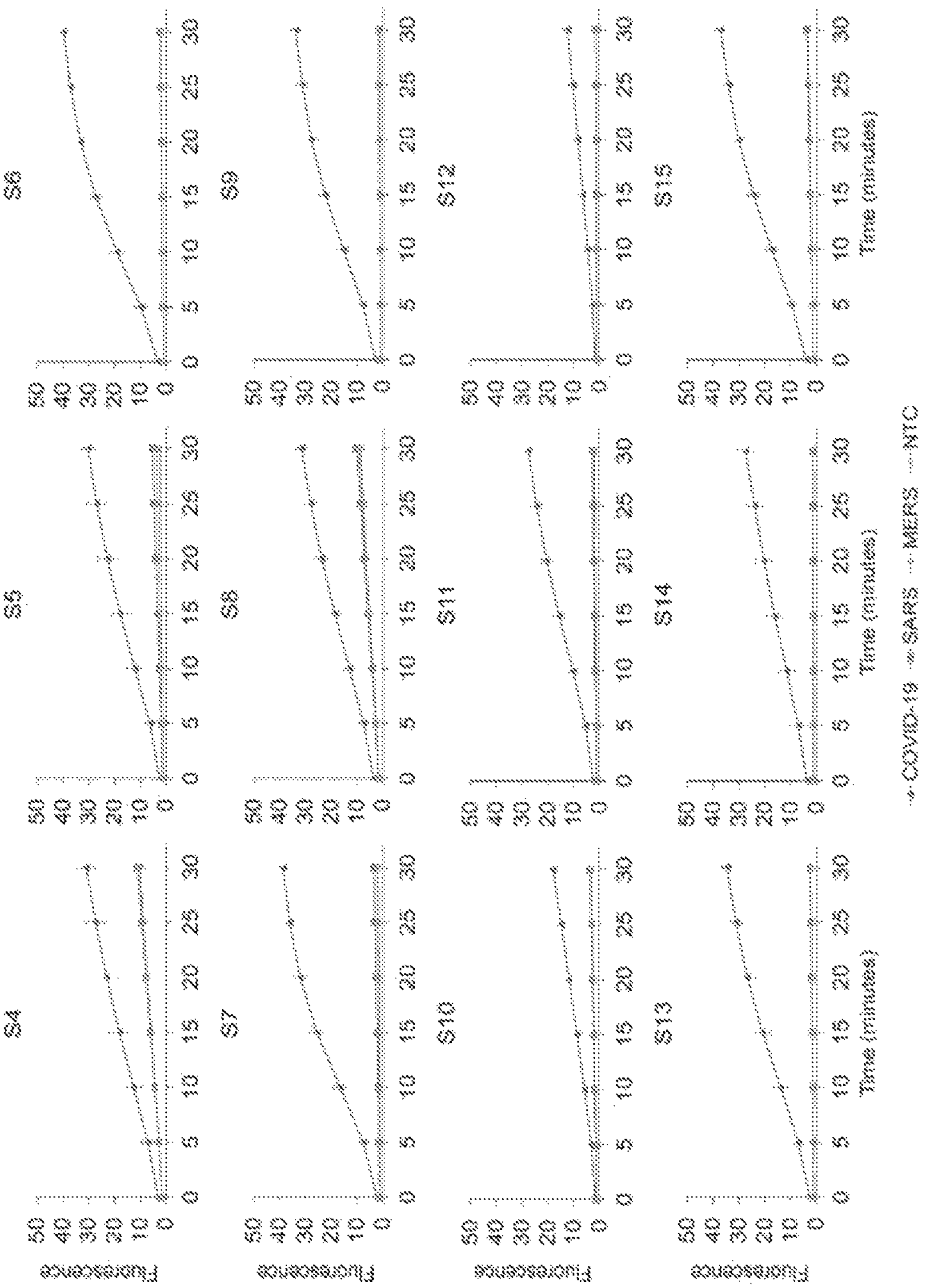
FIG. 15. Time courses of the fluorescence intensity in the trans-cleavage assays for enAsCas12a complexed with various gRNAs of spacer length 20nt. The gRNAs were designed to target the S-gene of SARS-CoV-2. The assays were performed at 37° C. and 1E11 copies of DNA were used as input. Data represent mean±s.e.m. (n=4 [S9], 5 [S4, S5, S6, S7, S11, S14], 6 [S8, S10, S12, S13], or 7 [S15] biological replicates).

Although enAsCas12a exhibited higher mismatch tolerance than the other tested nucleases, its activity could still be appreciably affected by mismatches at certain positions along the gRNA-target interface (such as MM10). Hence, to further enhance robustness of the assay against variant nucleotides, it has been sought to combine two or more gRNAs with this enzyme. The S2 gRNA worked well with enAsCas12a, but the engineered nuclease showed poor trans-cleavage activities with both the 51 and S3 gRNAs. Hence, it has been screened additional guides targeting the region surrounding the S2 locus, so that when the CRISPR detection module has been coupled with an isothermal amplification step, only one set of primers would be required. Based on genome sequences, each of the newly designed gRNAs was highly unique to SARS-CoV-2 (data not shown) and covered over 99.5% of the isolates annotated in GISAID with no mismatches and insertions or deletions (indels). From a fluorescence trans-cleavage assay, the S6 gRNA emerged as the most promising candidate because it exhibited the highest on-target activity for SARS-CoV-2 with little cross-reactivity for SARS-CoV and MERS-CoV (FIG. 14, 15).

Figure 16:
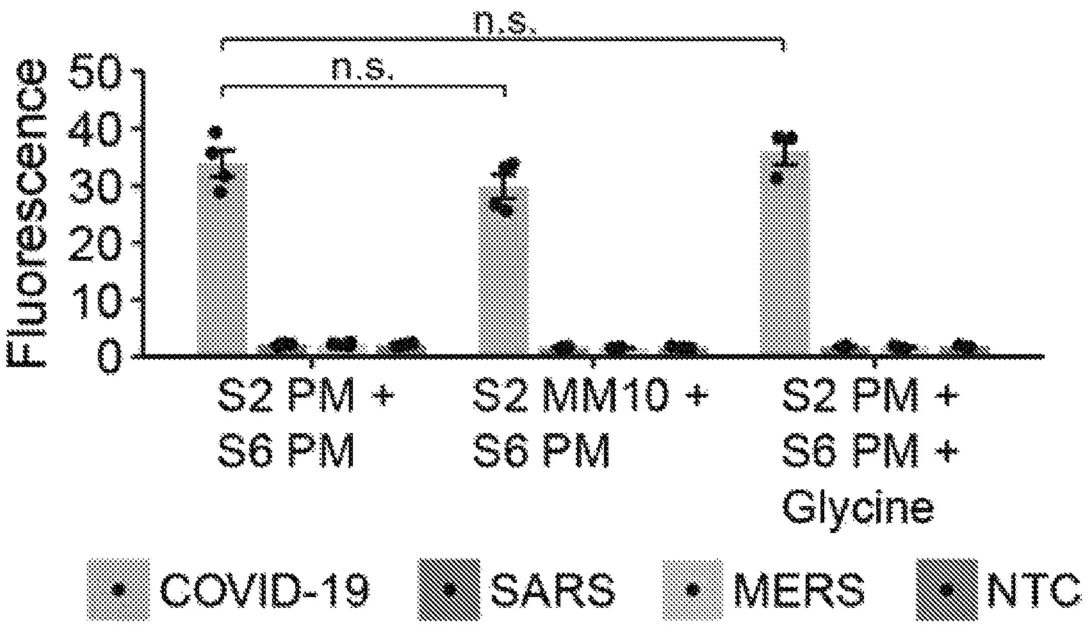
FIG. 16. Activity and mismatch tolerance of enAsCas12a with various S-gene-targeting gRNAs. The figure shows buffering the collateral activity of enAsCas12a against SNVs with a second gRNA. Fluorescence measurements here were taken after 30 minutes of cleavage reaction at 37° C. The S6 gRNA was used together with either the perfect matched (PM) or a mismatched (MM10) S2 gRNA in the absence or presence of 0.1 M glycine. Data represent mean±s.e.m. (n=3 [with glycine] or 4 [no glycine] biological replicates). (n.s.: not significant, P>0.2; two-sided Student's t-test).
Figure 17:
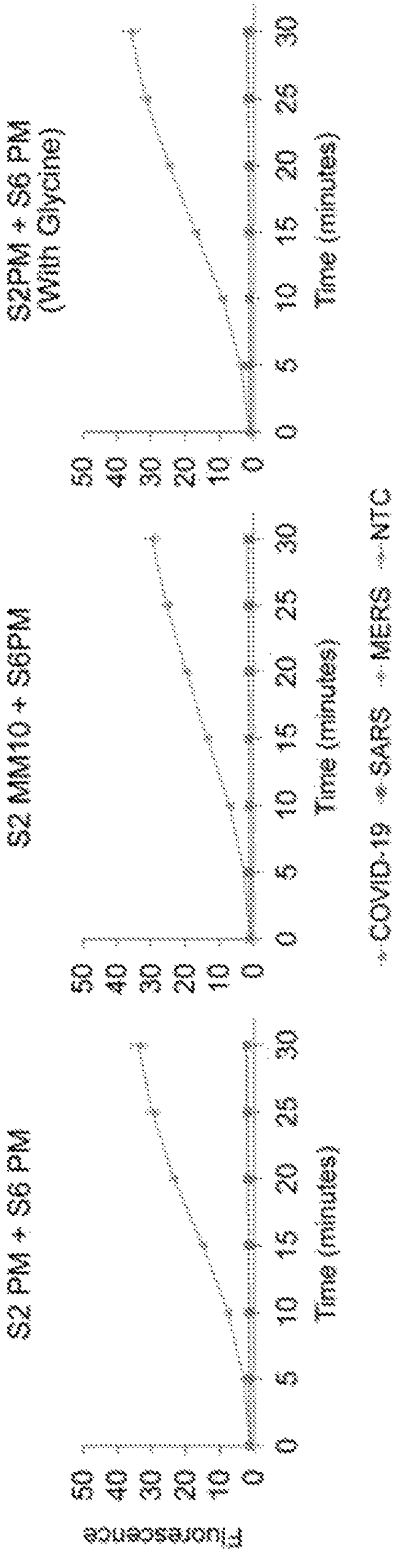
FIG. 17. Time courses of the fluorescence intensity in our trans-cleavage assays for enAsCas12a complexed with two different gRNAs, each of which had a spacer length of 20nt. Left and middle panels: no glycine was used. Right panel: 8 mM glycine was added. The assays were performed at 37° C. and 1E11 copies of purified DNA template were used as input. Data represent mean±s.e.m. (n=3 [with glycine] or 4 [no glycine] biological replicates).

Subsequently, it has been evaluated whether the newly identified S6 gRNA could rescue a mismatch at the S2 locus. To this end, the enAsCas12a nuclease has been assembled with both the S6 gRNA and either a perfect matched (PM) or a mismatched (MM10) S2 gRNA. From a fluorescence trans-cleavage assay with synthetic DNA as substrate, it has been found that there was no significant difference in collateral activity between S2 PM gRNA and S2 MM10 gRNA when the S6 gRNA was present ($P>0.2$, two-sided Student's t-test) (FIG. 16, 17). Furthermore, introduction of glycine, which was reported to improve the one-pot STOPCovid test (Joung et al. (2020) N Engl J Med 383, 1492-1494, doi: 10.1056/NEJMc2026172), into the reaction also did not affect the Cas detection module significantly.

Figure 18:
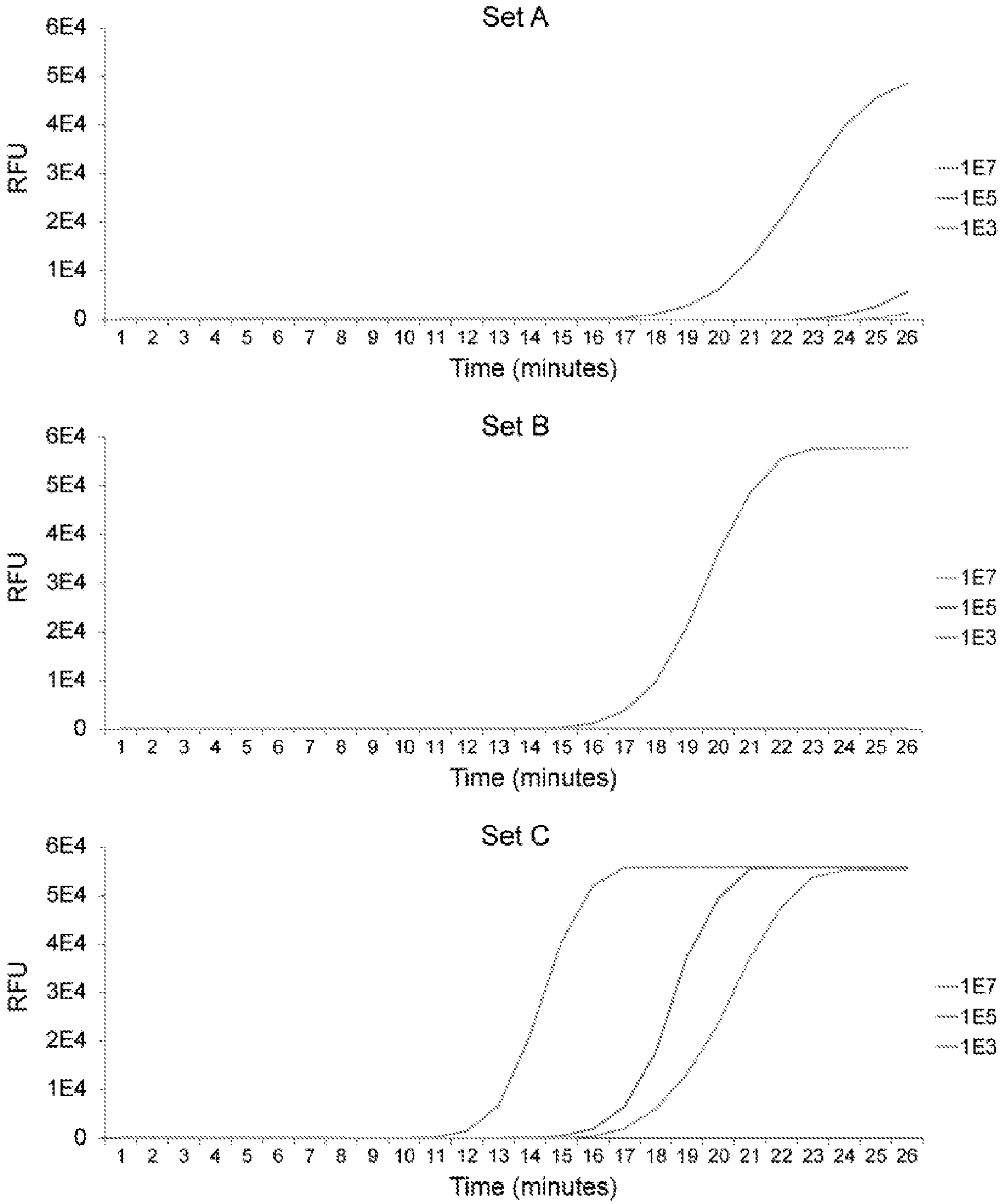
FIG. 18. Real-time monitoring of the RT-LAMP reaction performed at 65° C. for three different sets of primers targeting the S gene of SARS-CoV-2. Fluorescence signal was generated by the addition of a dye that was provided with the WarmStart LAMP kit (New England Biolabs). 1E3, 1E5, and 1E7 copies of synthetic SARS-CoV-2 RNA input were tested.
Figure 19:
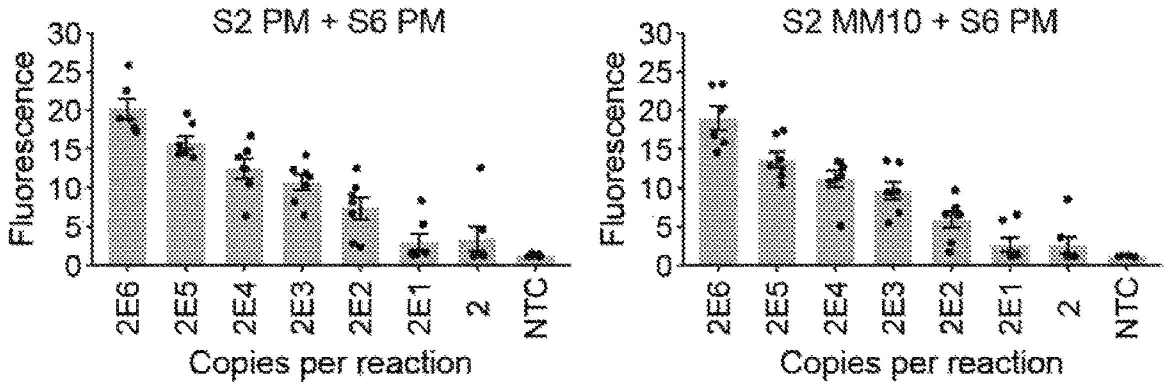
FIG. 19. Activity and mismatch tolerance of enAsCas12a with various S-gene-targeting gRNAs. The figure shows the analytical limit of detection (LoD) for enAsCas12a complexed with both the S6 gRNA and either the perfect matched (PM) or a mismatched (MM10) S2 gRNA. Different copies of SARS-CoV-2 RNA fragments were used as input to RT-LAMP, which was performed at 65° C. for 15 minutes using an initial set of LAMP primers (0.2 μM of each displacement primer, 1.6 μM of each internal primer, and 0.8 μM of each loop primer). The Cas detection reaction was then carried out at 37° C., with the fluorescence measurements here taken after 10 minutes. Data represent mean±s.e.m. (n=6 [2E6] or 7 [other copy numbers] biological replicates).
Figure 20:
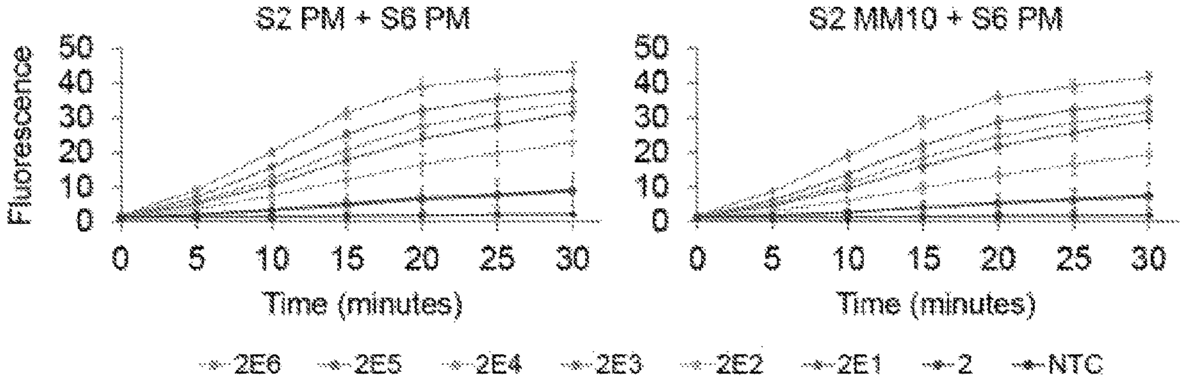
FIG. 20. Time courses of the fluorescence intensity in the trans-cleavage assays for enAsCas12a complexed with both the S6 gRNA and either the perfect matched (PM) or a mismatched (MM10) S2 gRNA. Before the Cas detection reaction, various copies of synthetic SARS-CoV-2 RNA fragments (see legend) were used as input to an RT-LAMP reaction, which was performed at 65° C. for 15 minutes with the initial set of LAMP primers (i.e. 0.2 μM of each displacement primer, 1.6 μM of each internal primer, and 0.8 μM of each loop primer). Subsequently, 4 μl LAMP products (out of 25 μl) were used for the trans-cleavage assays, which were performed at 37° C. Fluorescence measurements were taken using a microplate reader at five-minute intervals. Data represent mean±s.e.m. (n=6 [2E6] or 7 [other copy numbers] biological replicates).

Next, it has been sought to combine the RT-LAMP with the two-gRNA CRISPR detection module and to compare the assay sensitivity in the absence or presence of a mismatch at the S2 locus. Three sets of LAMP primers have been tested and it has been found one set that amplified well even with low amounts of input (FIG. 18). With this selected primer set, RT-LAMP has been carried out on variable copies of synthetic in vitro-transcribed (IVT) SARS-CoV-2 RNA templates at 65° C. for 15 minutes before using the amplified products immediately in the trans-cleavage assay. Overall, it has not been detected an obvious difference in sensitivity between the S2 PM gRNA and the S2 MM10 gRNA when the S6 gRNA was simultaneously deployed (FIG. 19, 20). Taken together, these results demonstrate that the use of two gRNAs can increase the robustness of CRISPR-Dx with respect to the presence of variant nucleotides.

3. Buffering the LAMP Reaction Against Variant Nucleotides

Figure 21:
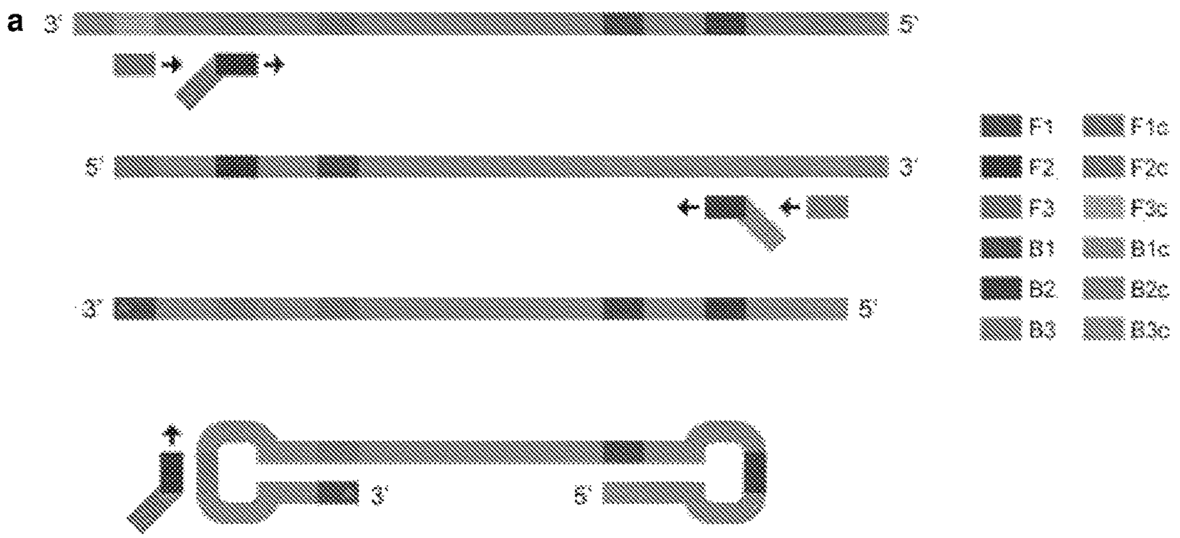
FIG. 21. Evaluating and enhancing the robustness of LAMP.
Figure 21:
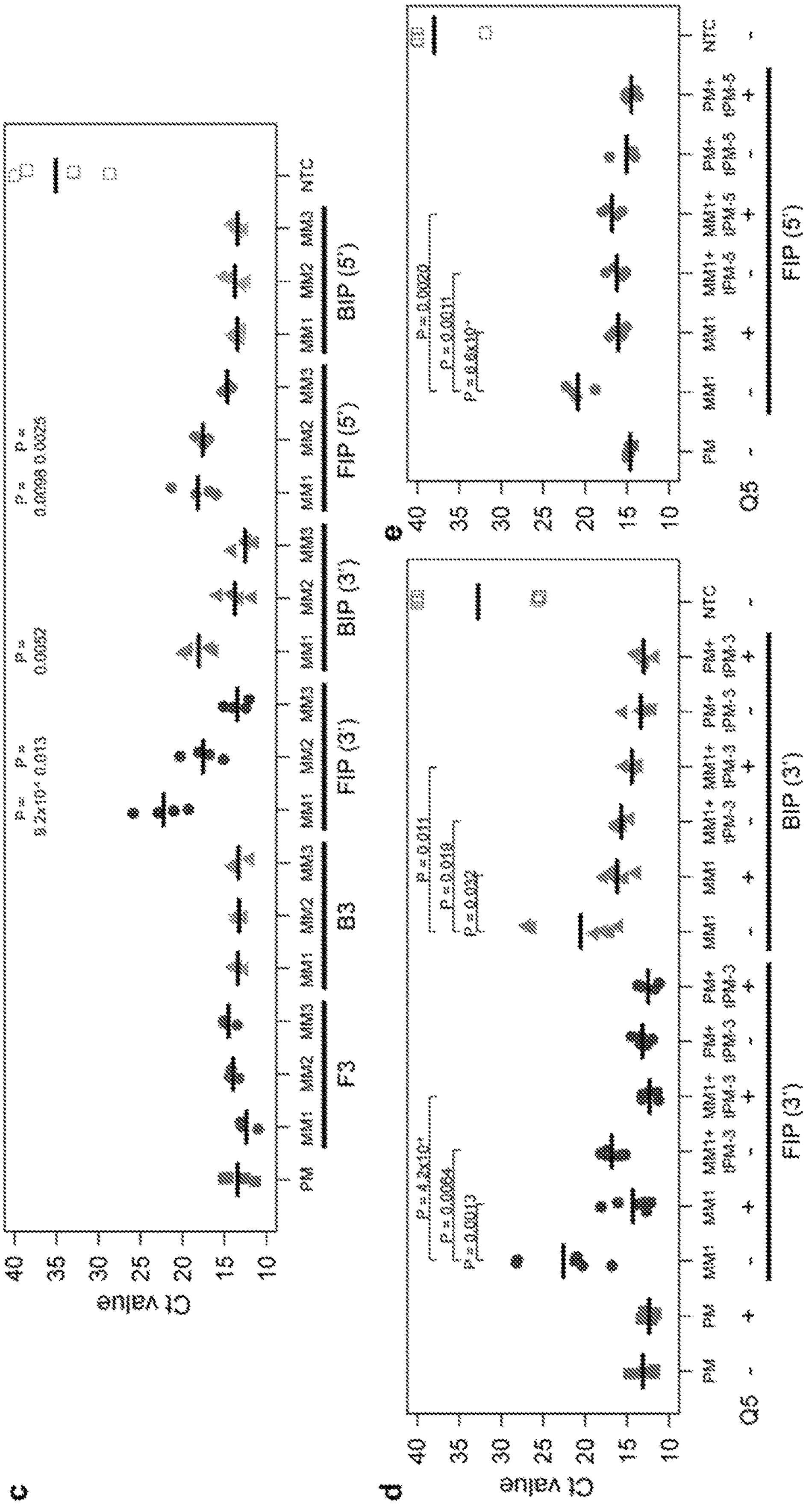

Besides the Cas detection module, mutations in or editing of the viral genome may also affect the isothermal amplification step. Hence, it has been sought to determine which LAMP primers were more susceptible to mismatches at their binding sites. The original method is based on two internal primers, known as FIP and BIP, and two displacement primers, known as F3 and B3, which collectively target six distinct regions in the DNA template (FIG. 21*a*). It has been hypothesized that mismatches at the 3' end of each primer may affect extension by the Bst DNA polymerase. Therefore, the RT-LAMP reaction has been tested with either perfect matched (PM) primers or primers with a mismatch (MM) positioned at the first, second, or third nucleotide from the 3'end (FIG. 21*b*). Moreover, since imperfect base pairing may also affect extension from the free 3' end of the dumbbell DNA generated during LAMP (FIG. 21*a*), it has been further tested the reaction with FIP or BIP primers carrying a mismatch at their 5' ends too (FIG. 21*b*). The RT-LAMP reaction was monitored in real-time with a fluorescent dye. These experiments revealed that mismatches in the two displacement primers did not affect the amplification step appreciably (FIG. 21*c*). In contrast, mismatches at the 3' ends of FIP and BIP as well as at the 5' end of FIP reduced the rate of amplification significantly ($P<0.05$, one-sided Student's t-test).

Next, it has been sought to develop or apply strategies to enhance the robustness of the LAMP reaction against potential variant nucleotides. It has been reasoned that since MM1 caused the greatest reduction in amplification efficiency, the use of a FIP or BIP primer that was truncated right at the end would avoid the most harmful mismatch altogether (FIG. 21*b*). Indeed, usage of a mixture of the original internal primers and the truncated primers (tPM-3 or tPM-5) led to a significant improvement in the amplification rate ($P<0.05$, one-sided Student's t-test) (FIG. 21*d, e*). Furthermore, it has been noted that the Bst DNA polymerase lacked a 3'-to-5' exonuclease activity and thus would encounter difficulty extending any DNA with mismatches at the 3' end. One possible solution was to add to the LAMP reaction a small amount of high-fidelity DNA polymerase, which possessed a proofreading capability and thus may help to remove any mismatched bases at the 3' end (Zhou et al. (2019) Front Microbiol 10, 1056, doi:10.3389/fmicb.2019.01056. Indeed, it has been found that addition of 0.15 U high-fidelity polymerase did result in a significant increase in the rate of reaction despite the presence of end mismatches in FIP or BIP ($P<0.05$, one-sided Student's t-test) (FIG. 21*d, e*). Notably, in the case of mismatches at the 3' ends of the internal primers, an even larger improvement in amplification efficiency was observed when the two strategies of truncated primers and high-fidelity DNA polymerase were used together (FIG. 21*d*). Collectively, the results indicate that the robustness of the LAMP reaction against variant nucleotides can be enhanced by utilizing two sets of internal primers (full-length and tPM-3) and a high-fidelity polymerase.

4. Strategies to Enhance the Sensitivity of LAMP

An important metric used to assess the performance of a diagnostic assay is its sensitivity. Although the assay contained features to handle SNVs in the viral genome, it has been noted that as the copy number decreased from 2E6 to 2, the test sensitivity declined monotonically as well (FIG. 19, 20). Hence, it has been sought to improve the sensitivity of the assay.

Figure 22:
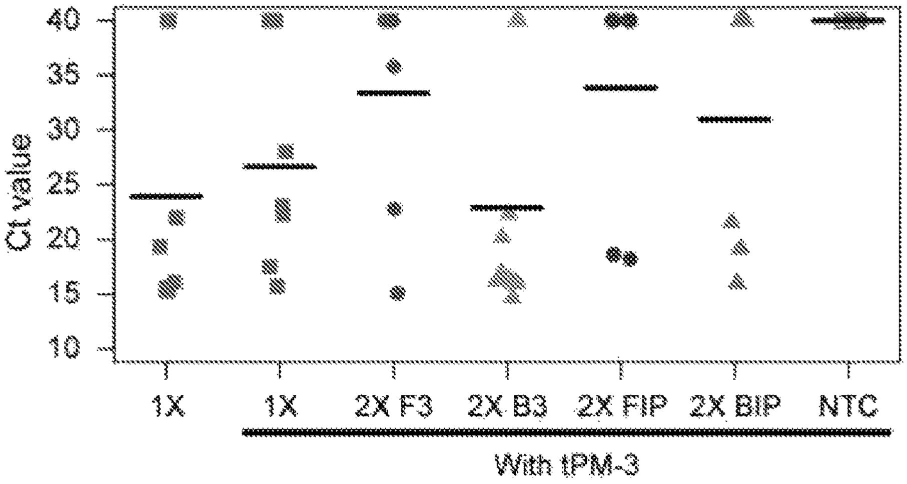
FIG. 22. Methods to improve sensitivity of LAMP. The figure shows a strip chart showing how LAMP sensitivity was affected by the concentration of primers used. Different concentrations of displacement primers and internal primers have bee tested. RT-LAMP was performed at 65° C. in a real-time instrument with 20 copies of RNA template corresponding to the S-gene of SARS-CoV-2. The black horizontal bars among the data points in the strip chart represent the mean (n=7 [1×, 2× F3, 2×FIP, 2×BIP], 10 [1× without tPM], 12 [2× B3], or 15 [NTC] biological replicates).

First, it has been tested how variations in the primer concentrations might affect the LAMP reaction. It has been focused on the displacement primers (F3 and B3) and the internal primers (FIP and BIP), which were part of the original LAMP setup. 20 copies of RNA template were used as input and the reaction was monitored in a real-time instrument with a fluorescent dye (FIG. 22). Overall, it has been observed that doubling the concentration of F3, FIP, or BIP worsened the performance of the CRISPR-Dx. In contrast, when the amount of B3 has been increased by twofold, the assay sensitivity improved marginally with 75% (9 out of 12) of the replicates showing successful amplification. This might be because the B3 primer given by the PrimerExplorer design software (https://primerexplorer.jp/e/) was suboptimal.

Figure 23:
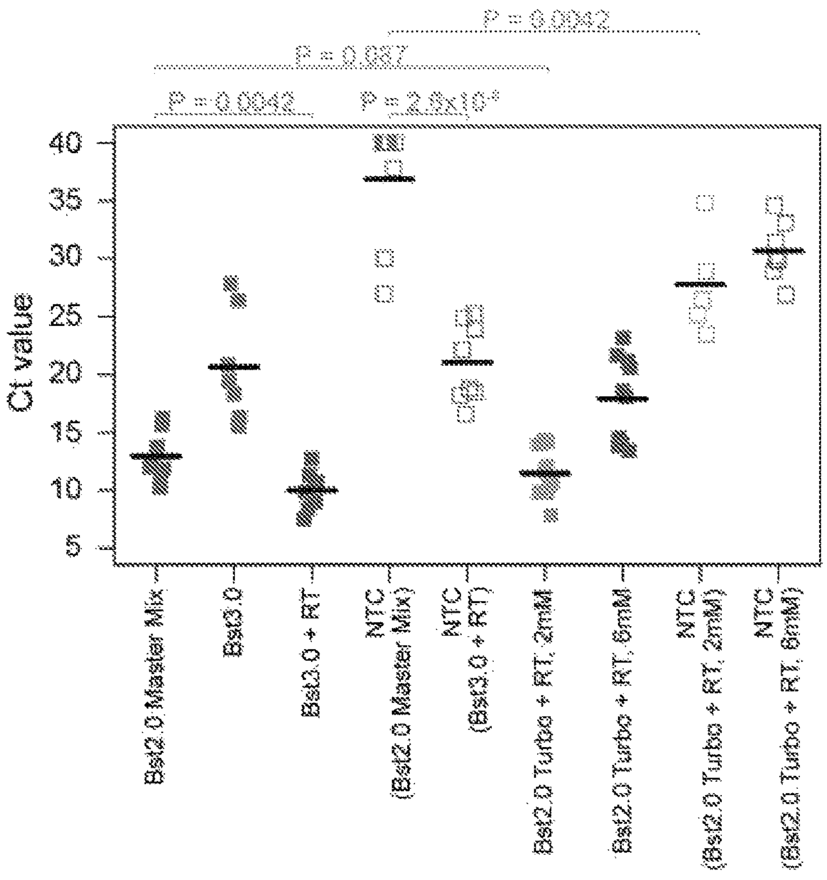
FIG. 23. Strip chart showing the performance of various Bst DNA polymerases in RT-LAMP reactions. Here, every reaction contained the displacement primers (0.2 μM each), the internal primers (1.6 μM each), the loop primers (0.8 μM each), and the swarm primers (1.6 μM each). For most of the work, it has been relied on the Bst2.0 mastermix, which contains a WarmStart reverse transcriptase to convert the RNA template into cDNA for the Bst2.0 enzyme to act on. Bst3.0 is an engineered DNA polymerase with enhanced reverse transcriptase activity, such that it is supposed to be capable of acting directly on RNA templates. In addition, the Saphir Bst2.0 Turbo Polymerase is supposed to give faster amplification rates as it contains an extra DNA-binding domain. The RT-LAMP reaction was carried out at 65° C. in a real-time instrument with 20,000 copies of synthetic RNA template. The black horizontal bars among the data points in the strip chart represent the mean (n=5 [NTC for 2 mM Turbo], 7 [Bst3.0, NTC for 6 mM Turbo], 8 [Master Mix, Bst3.0+RT, NTC for Master Mix, NTC for Bst3.0+RT], or 10 [2 mM Turbo, 6 mM Turbo] biological replicates). P values were calculated using one-sided Student's t-test.

Enzyme engineering may improve the performance of LAMP. Hence, second, it has been compared several different commercially available Bst polymerases, namely Bst2.0, Bst3.0 (a mutant polymerase with an intrinsic reverse transcriptase activity), and Turbo Bst (a polymerase fused to an extra DNA-binding domain), using the RT-LAMP setup (FIG. 23). While Bst3.0 alone performed worse than the original Bst2.0 master mix that had been used, Bst3.0 with a separate reverse transcriptase added significantly enhanced the kinetics of the reaction ($P<0.01$, one-sided Student's t-test). However, it has been observed that the combination of Bst3.0 and the additional reverse transcriptase was highly prone to false amplification, giving a fluorescence signal even in the absence of template. Moreover, it has been found that while Turbo Bst also improved the reaction kinetics marginally, it too was significantly more prone to false amplification than Bst2.0 ($P<0.01$, one-sided Student's t-test). Therefore, it has been retained the use of Bst2.0 master mix for subsequent experiments.

Third, it has been asked if the use of chemical additives might bolster the sensitivity of LAMP. A recent study showed that glycine and taurine could improve the kinetics of the one-pot STOPCovid test (Joung et al. (2020) N Engl J Med 383, 1492-1494, doi:10.1056/NEJMc2026172).

Figure 24:
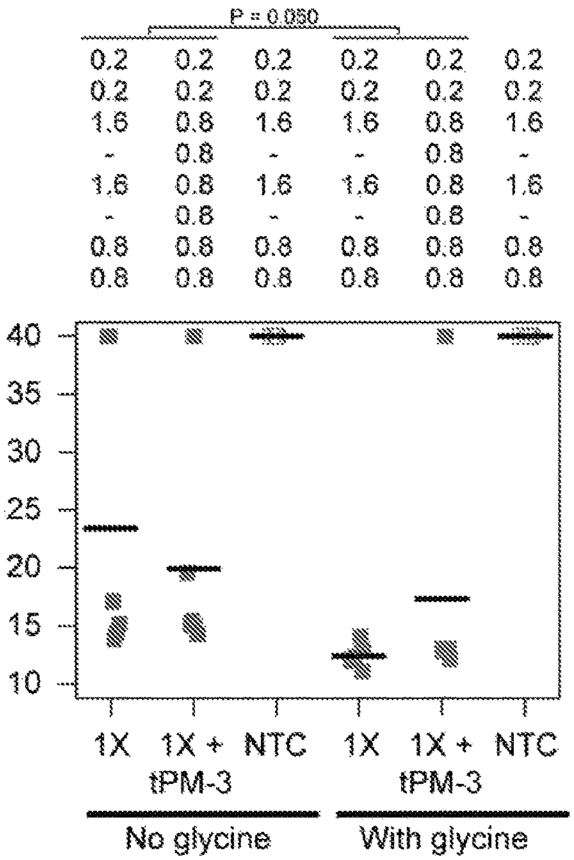
FIG. 24. Methods to improve sensitivity of LAMP. The figure shows a strip chart showing how LAMP sensitivity was altered by 0.1 M glycine. RT-LAMP was performed at 65° C. with 20 copies of RNA template. The black horizontal bars among the data points in the strip chart represent the mean (n=3 [NTC] or 6 [with template] biological replicates). P value was calculated using one-sided Student's t-test.
Figure 25:
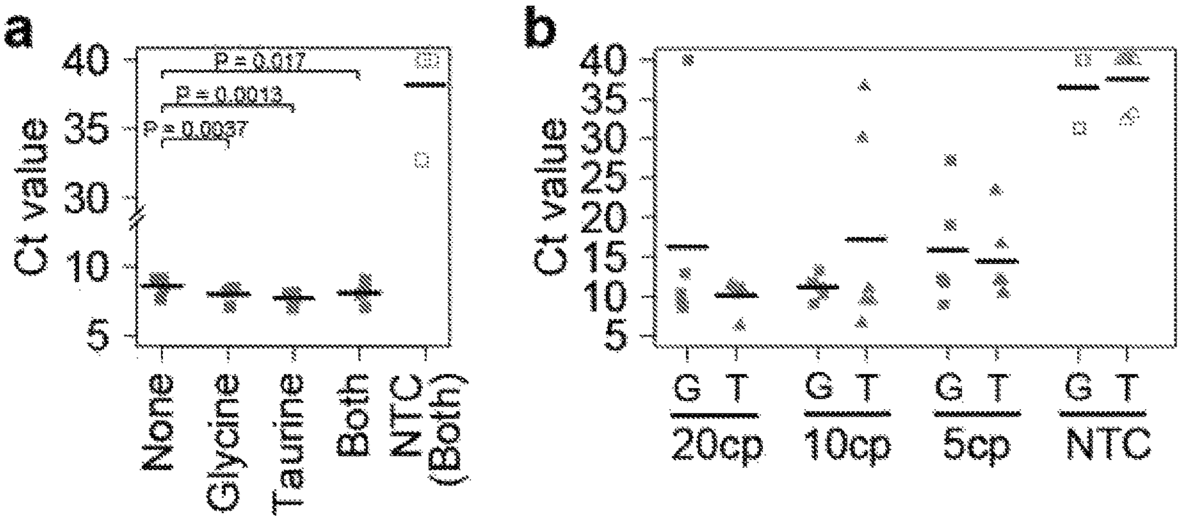
FIG. 25. Effect of glycine and taurine on RT-LAMP.

However, it is unclear if the improvement occurs in the RT-LAMP reaction or in the Cas detection module. To address the question, the RT-LAMP reaction has been performed only with or without either of the two chemicals. Overall, the data revealed that addition of glycine enhanced the sensitivity of RT-LAMP, with over 90% (11 out of 12) of the replicates showing successful amplification of 20 copies of viral template (FIG. 24). Addition of taurine also improved assay sensitivity in a similar manner to glycine, although usage of both chemicals together did not have a synergistic effect (FIG. 25). Besides glycine and taurine, another study reported that dimethyl sulfoxide (DMSO) increased the sensitivity and specificity of LAMP reactions (Wang et al. (2015) Molecules 20, 6048-6059, doi:10.3390/molecules20046048). The organosulfur compound is also often used in PCR to disrupt secondary structures of GC-rich templates. However, it has been found that both 2.5% and 5% DMSO exerted an inhibitory effect on LAMP instead (data not shown). Moving forward, glycine has been incorporated into the assay, since it is commonly found in laboratories.

Figure 26:
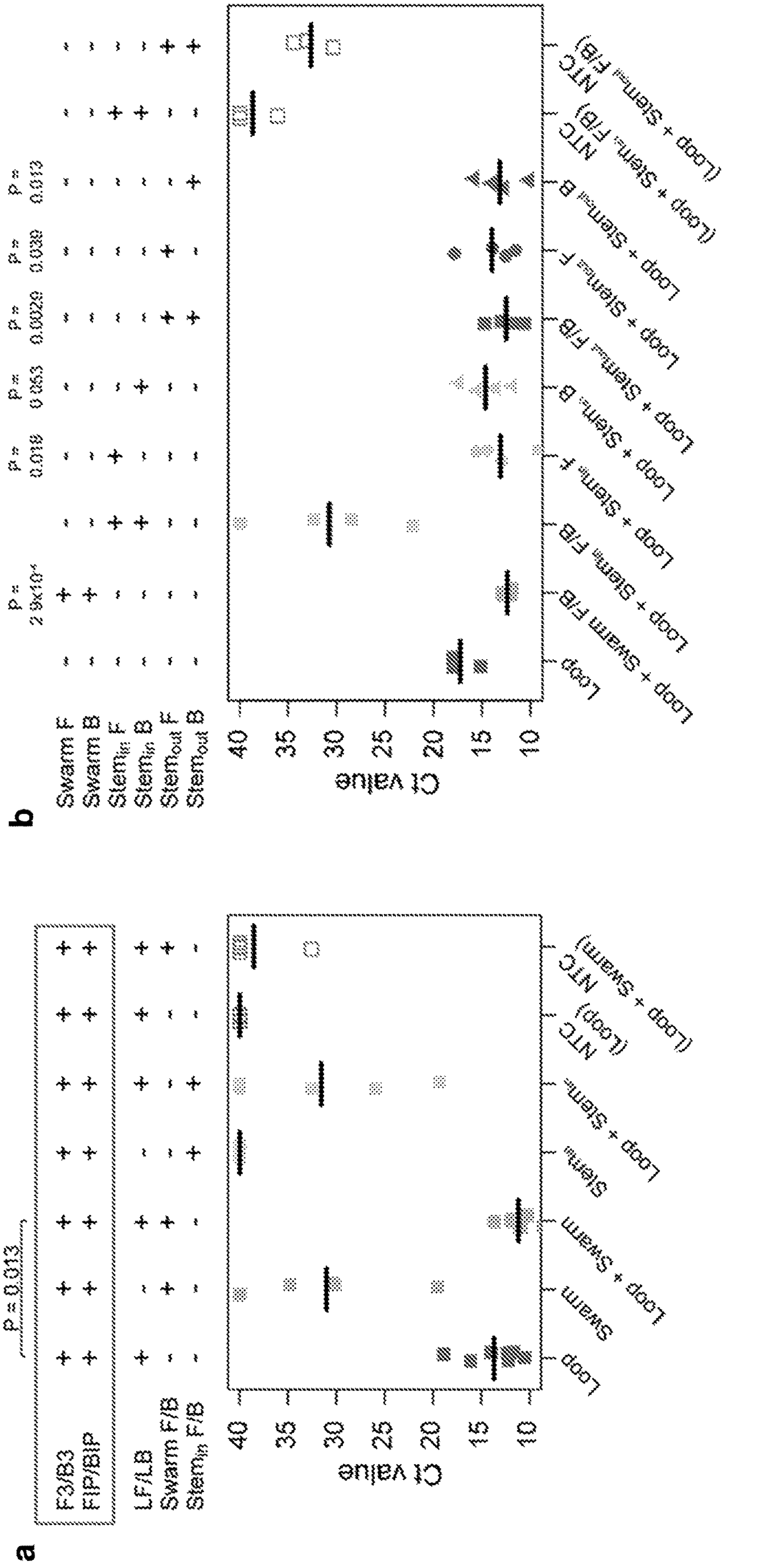
FIG. 26. Methods to improve sensitivity of LAMP.
Figure 27:
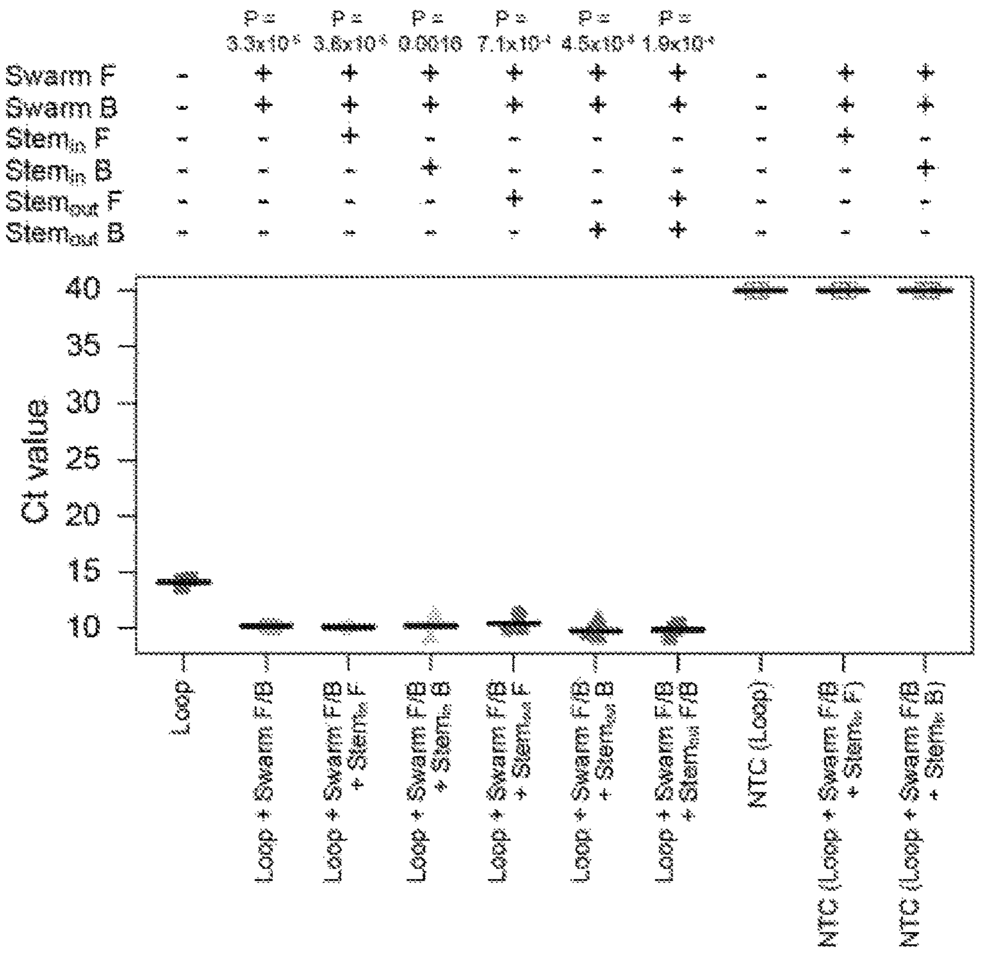
FIG. 27. Strip chart showing the impact of swarm and stem primers on the kinetics of the LAMP reaction. Here, every reaction contained the displacement primers (0.2 μM each), the internal primers (1.6 μM each), and the loop primers (0.8 μM each). Furthermore, it could also contain either two additional swarm primers or one or two additional stem primers (with the concentration of each extra primer being 1.6 μM). The RT-LAMP reaction was carried out at 65° C. in a real-time instrument with 20,000 copies of RNA template corresponding to the S-gene of SARS-CoV-2. The black horizontal bars among the data points in the strip chart represent the mean (n=3 biological replicates). P values were calculated using one-sided Student's t-test.

Fourth, it has been wondered if alternative LAMP reaction schemes would deliver higher sensitivities. Although the earliest LAMP method relied on four core primers (Notomi et al. (2000) Nucleic Acids Res 28, E63, doi:10.1093/nar/28.12.e63), subsequent studies described improvements in the method due to the addition of new primer sets. The most commonly added primer set is the "loop primers" (LF and LB), which target the single-stranded loop regions in the dumbbell structures generated during the reaction (Nagamine et al. (2002) Mol Cell Probes 16, 223-229, doi:10.1006/mcpr.2002.0415). The loop primers are provided with the four core primers by the PrimerExplorer design software. Furthermore, two other primer sets that may be added include the "stem primers", which target the single-stranded region between F1/F2/F3 and B1/B2/B3 (FIG. 21) (Gandelman et al. (2011) Int J Mol Sci 12, 9108-9124, doi:10.3390/ijms12129108), and the "swarm primers", which anneal to the template strand opposite to that of FIP or BIP so as to expose the binding sites for the internal primers (Martineau et al. (2017) Anal Chem 89, 625-632, doi:10.1021/acs.analchem.6b02578). Therefore, new stem primers and swarm primers in conjunction with the previous set of LAMP primers targeting the S-gene of SARS-CoV-2 have been tested. The data from our initial set of experiments indicated that although addition of stem primers ($Stem_{in}$) were detrimental to the RT-LAMP reaction possibly due to the short region available between F1/F2/F3 and B1/B2/B3, addition of swarm primers improved the reaction kinetics significantly ($P<0.05$, one-sided Student's t-test) (FIG. 26*a*). Notably, this improvement was only observed when the swarm primers were used with the core primers and the loop primers. When the loop primers were omitted, amplification occurred much later than the original RT-LAMP setup, indicating that the swarm primers could not substitute for the loop primers. Next, it has been examined the design of the stem primers ($Stem_{in}$) and noticed that they pointed towards each other with their 3' ends competing for binding to the template. Hence, each of the primers individually has been tested and also another pair of stem primers ($Stem_{out}$) that pointed away from each other have been evaluated. The results showed that one Stem primer alone as well as the $Stem_{out}$ primers were able to improve the kinetics of LAMP reaction to varying extents (FIG. 26*b*). Moreover, addition of one or two stem primers to the cocktail of core, loop, and swarm primers did not further improve the kinetics of LAMP (FIG. 27). Therefore, moving forward, it has not been continued to pursue the stem primers and it has been focused mainly on the loop and swarm primers. The final set of LAMP primers is highly specific to SARS-CoV-2 as shown by the sequence alignment of multiple coronaviral genomes (data not shown).

Figure 28:
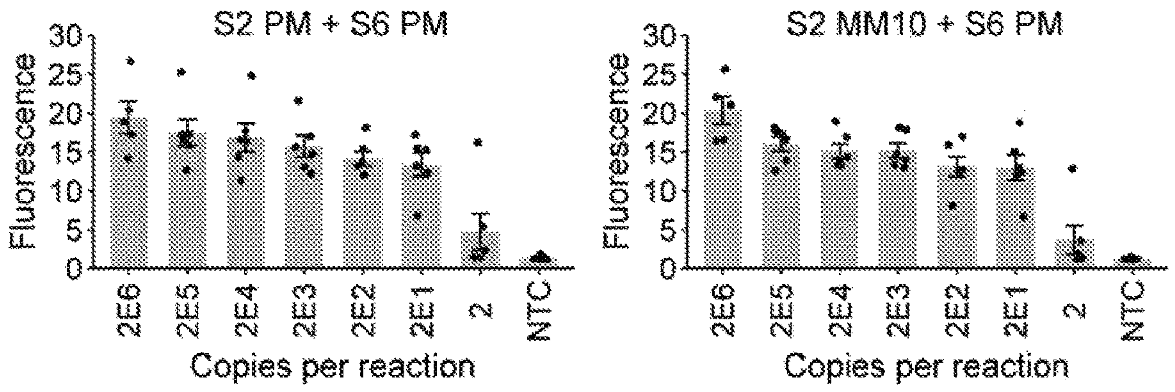
FIG. 28. Methods to improve sensitivity of LAMP. The figure shows an analytical LoD for enAsCas12a complexed with both the S6 gRNA and either the PM or the MM10 S2 gRNA. RT-LAMP was performed at 65° C. for 15 minutes under optimized conditions, which encompassed doubling the concentration of B3 to 0.4 μM, using both full-length and 1nt-truncated internal primers (1.6 μM each), including the swarm primers (1.6 μM each), and adding 0.15 U Q5 polymerase and 0.1 M glycine into each reaction. Fluorescence readings using a microplate reader after 10 minutes of cleavage reaction at 37° C. are shown. Data represent mean±s.e.m. (n=5 [2E6] or 6 [other copy numbers] biological replicates).
Figure 29:
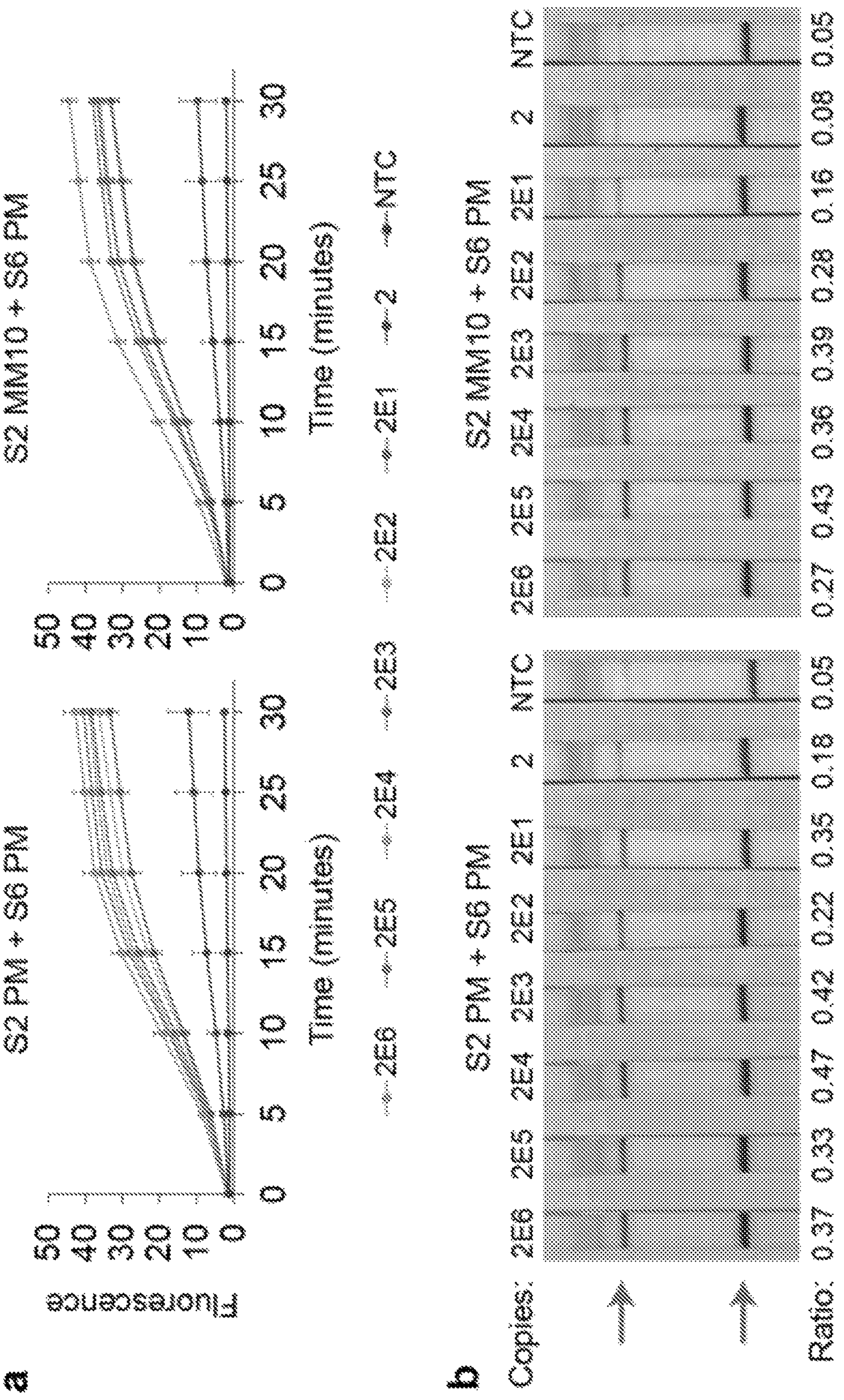
FIG. 29. Mismatch tolerance by a two-gRNA system.
Figure 30:
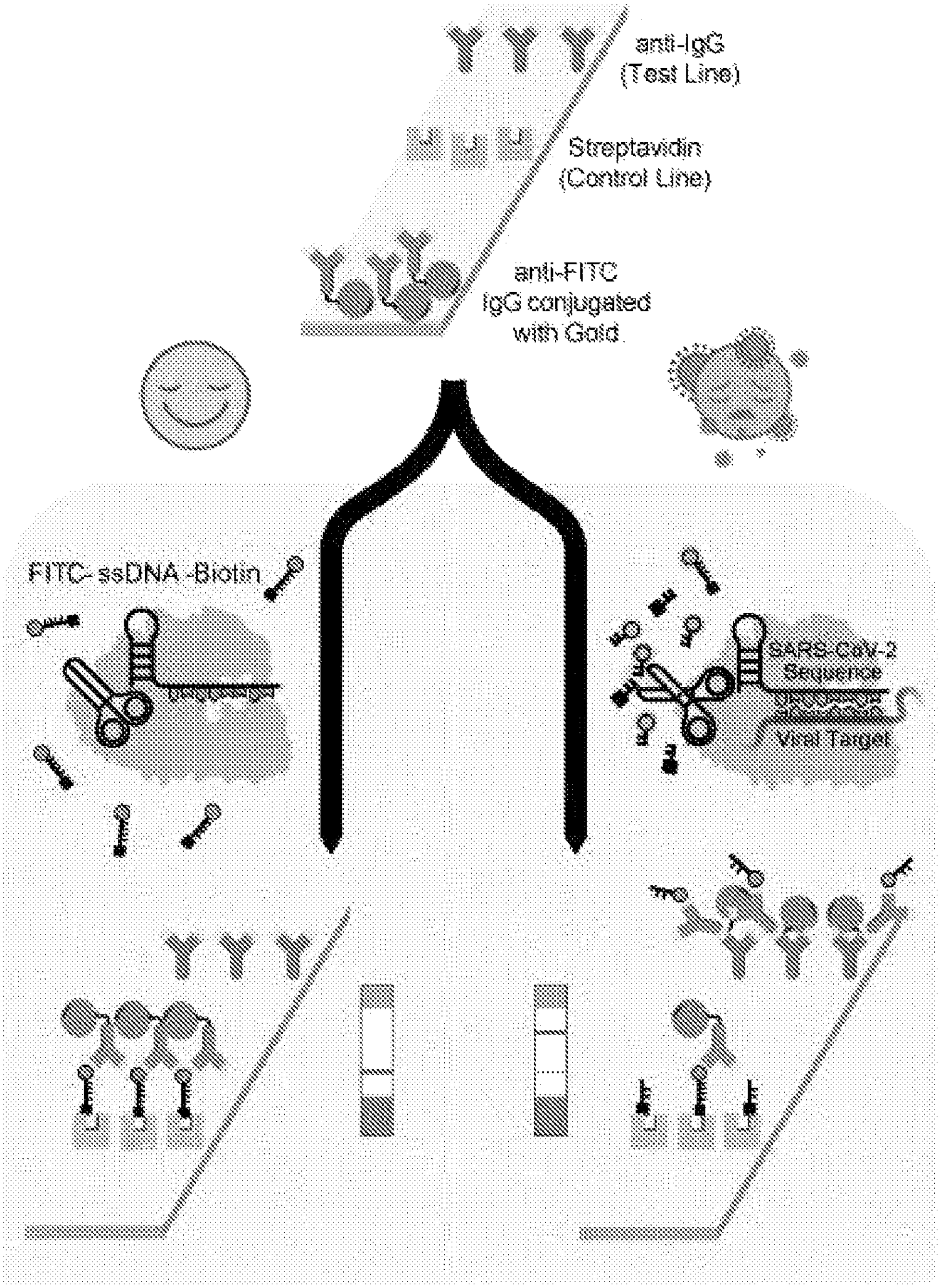
FIG. 30. Illustration of the operating principle of a lateral flow strip or dipstick. On each strip are gold-conjugated IgG antibodies against the fluorophore near the sample pad, streptavidin immobilized at the control line, and antibodies against IgG immobilized at the test line. In the case of a virus-free sample, the Cas nuclease remains inactive and thus the reporter, comprising a fluorophore linked to biotin by a short piece of single-stranded DNA (ssDNA), stays intact. When the reaction is loaded on the strip, the gold-conjugated IgG first binds to the fluorophore and then the entire IgG-reporter complex is captured at the control line due to the high affinity of streptavidin for biotin. Consequently, a dark band is observed at the control line. However, in the case of an infected sample, the Cas nuclease cleaves its viral target, becomes hyperactivated, and then proceeds to cut the linker between the fluorophore and biotin. Subsequently, when the reaction is loaded on the strip, the gold-conjugated IgG still binds to the fluorophore, but the gold will not be deposited at the control line as the fluorophore is now free of biotin. Instead, the IgG-fluorophore complex continues flowing along the strip to the test line, where it is captured by the anti-IgG antibodies there. Consequently, a dark band is observed at the test line.

It has been assessed if the optimized LAMP conditions together with the two-gRNA (S2 and S6) CRISPR detection module could improve assay sensitivity and accommodate point mutations. Unlike the original LAMP conditions without any swarm primers or glycine (FIG. 19, 20), it has been found that the fluorescence signal did not drop as much with decreasing amounts of RNA template when utilizing the optimized conditions (FIG. 28, 29*a*). The analytical limit of detection (LoD) was 20 copies per reaction with the optimized conditions, regardless of the absence or presence of a mismatch at the S2 locus. This sensitivity was further confirmed by a lateral flow assay (FIG. 29*b*), which is a convenient paper-based platform to read out the results (FIG. 30).

Figure 31:
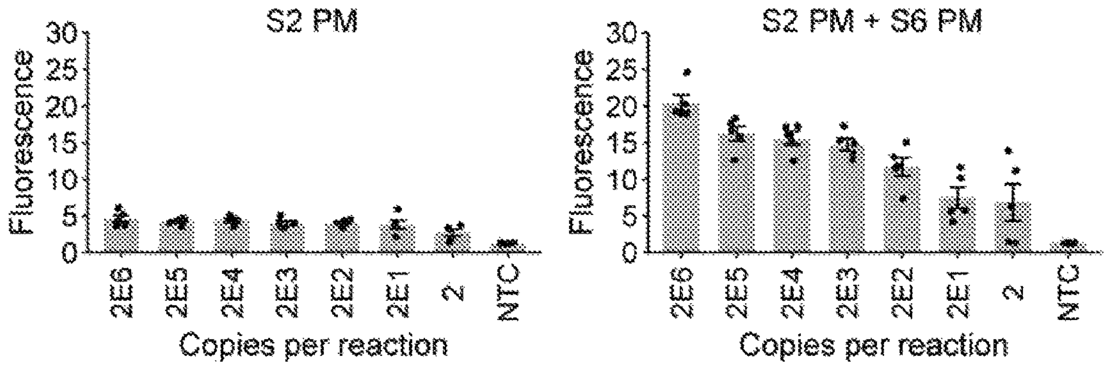
FIG. 31. Methods to improve sensitivity of LAMP. The figure shows an analytical LoD for enAsCas12a when a S254F mutation was present in the viral template. The nuclease was assembled either with the S2 gRNA alone or with both the S2 and S6 gRNAs. These gRNAs were designed to be perfect matched against the reference SARS-CoV-2 genome. RT-LAMP was performed at 65° C. for 15 minutes under optimized conditions. Fluorescence readings after 10 minutes of cleavage reaction at 37° C. are shown. Data represent mean±s.e.m. (n=5 biological replicates).
Figure 32:
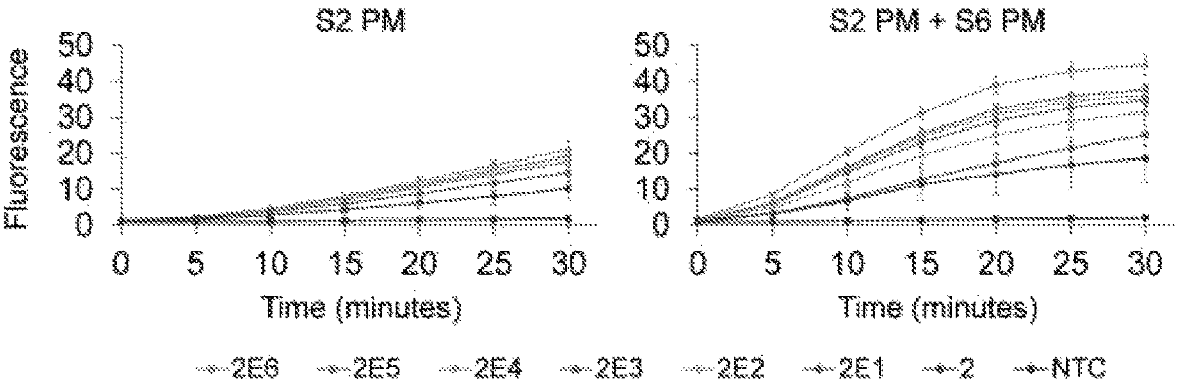
FIG. 32. Time courses of the fluorescence intensity in our trans-cleavage assays for enAsCas12a assembled either with the S2 gRNA alone or with both the S2 and S6 gRNAs. These guides were designed to be perfect matched against the reference SARS-CoV-2 genome. Before the Cas detection reaction, various copies of in vitro-transcribed SARS-CoV-2 RNA fragments (see legend) bearing a known S254F mutation in the S-gene were used as input to an RT-LAMP reaction, which was performed at 65° C. for 15 minutes under the optimized conditions. Subsequently, 4 μl LAMP products (out of 25 μl) were used for the trans-cleavage assays, which were performed at 37° C. Fluorescence measurements were taken at five-minute intervals using a microplate reader. Data represent mean±s.e.m. (n=5 biological replicates).
Figure 33:
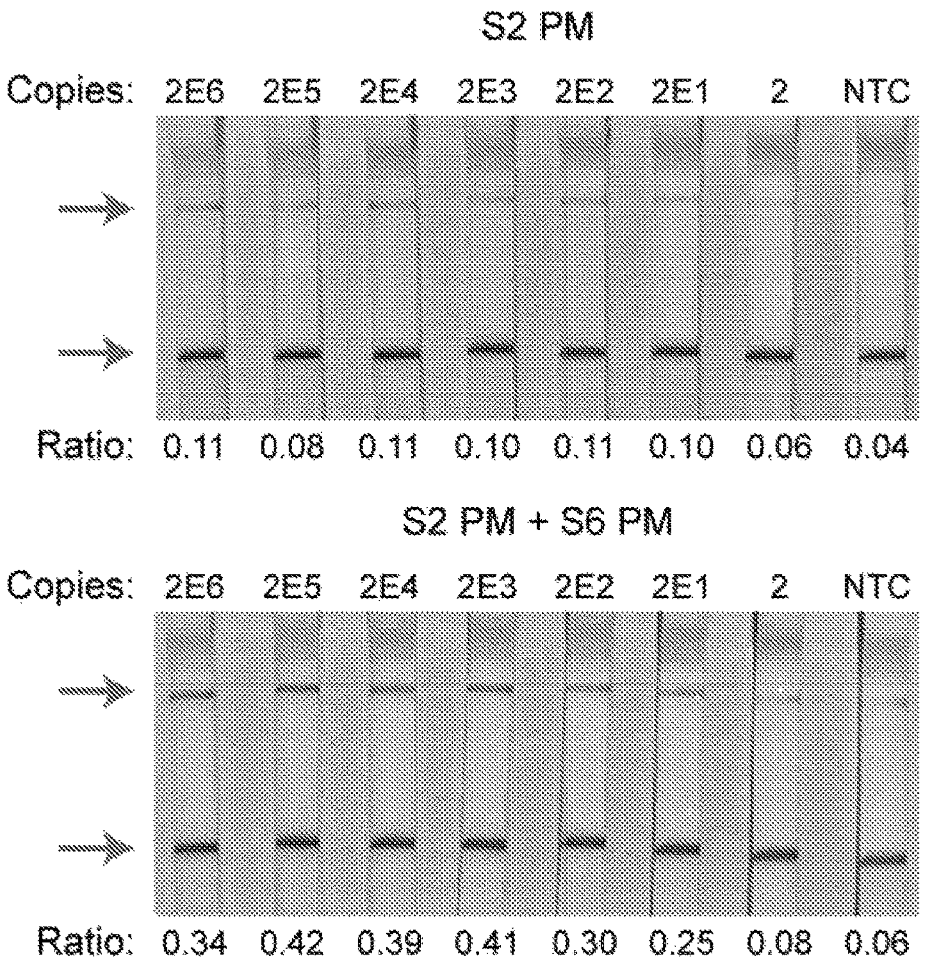
FIG. 33. Methods to improve sensitivity of LAMP. The figure shows similar experiments to FIG. 31, except that a different reporter was used and a dipstick was added to each sample tube after 10 minutes of cleavage reaction. Bands appeared on the dipsticks by 2 minutes. The higher arrow indicates the test bands, while the lower arrow indicates the control bands. Ratios of test band intensity to control band intensity are given under each dipstick.

Instead of artificially creating mismatches in the gRNA, it has been sought to evaluate the robustness of the assay with a real-life mutation in the target template using PM gRNAs. To this end, it has been selected a known S254F mutation in the S-gene (Yang et al. (2020) *Emerg Microbes Infect* 9, 1287-1299, doi:10.1080/22221751.2020.1773745; Koyama et al. (2020) *Pathogens* 9, doi:10.3390/pathogens9050324; Cavallo & Oliva, (2020) doi:10.1101/2020.06.08.140152; Devi et al. (2020) doi:10.21203/rs.3.rs-29557/v1), which may potentially interfere with the binding of the S2 gRNA. Upon targeting of the mutant viral RNA with enAsCas12a complexed to the S2 gRNA alone, low levels of fluorescence that are close to background for template amounts up to 2E6 copies (FIG. 31, 32) have been observed. In contrast, targeting of the S254F mutant template with both the S2 and S6 gRNAs yielded much higher fluorescence signals. These results have been further confirmed with a lateral flow assay, where a positive test outcome was clearly obtained with two gRNAs even when only 20 copies of the mutant template were present (FIG. 33). Collectively, the data indicate that the assay is robust against variant nucleotides in the viral target and can detect low copies of SARS-CoV-2.

5. Detection of Viral RNA in Total Human RNA Samples

Figure 34:
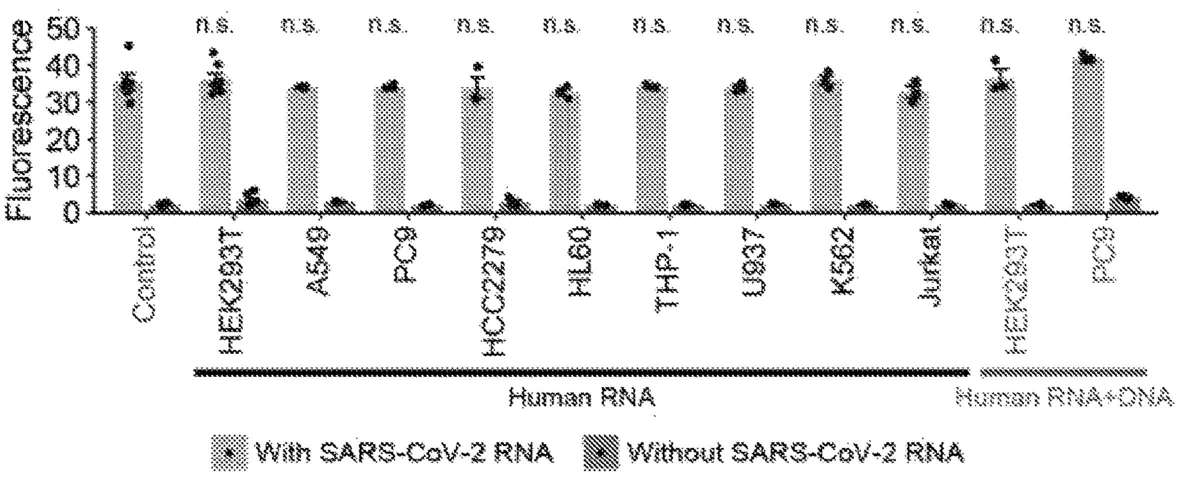
FIG. 34. Evaluation of the VaNGuard test under more realistic conditions. The figure shows that 20,000 copies of synthetic SARS-CoV-2 RNA fragments were spiked into 10 ng of total RNA extracted from different immortalized human cell lines to mimic infection in various cell types [HEK293T: adrenal precursor, A549: lung, PC9: lung, HCC2279: lung, HL60: blood (promyelocytes), THP-1: blood (monocytes), U937: blood (monocytes), K562: blood (granulocytes/erythrocytes), and Jurkat: blood (T cells)]. Pure synthetic viral RNAs were used as a control. The control or spiked RNA samples served as input to RT-LAMP, which was performed at 65° C. for 15 minutes. The Cas detection reaction was then carried out at 37° C., with fluorescence after 30 minutes shown. Data represent mean±s.e.m. (n=3 [all except control and HEK293T RNA], 6 [control], or 7 [HEK293T RNA] biological replicates). There was no significant loss of signal in the presence of human RNA (n.s.: not significant, P>0.2; one-sided Student's t-test).
Figure 35:
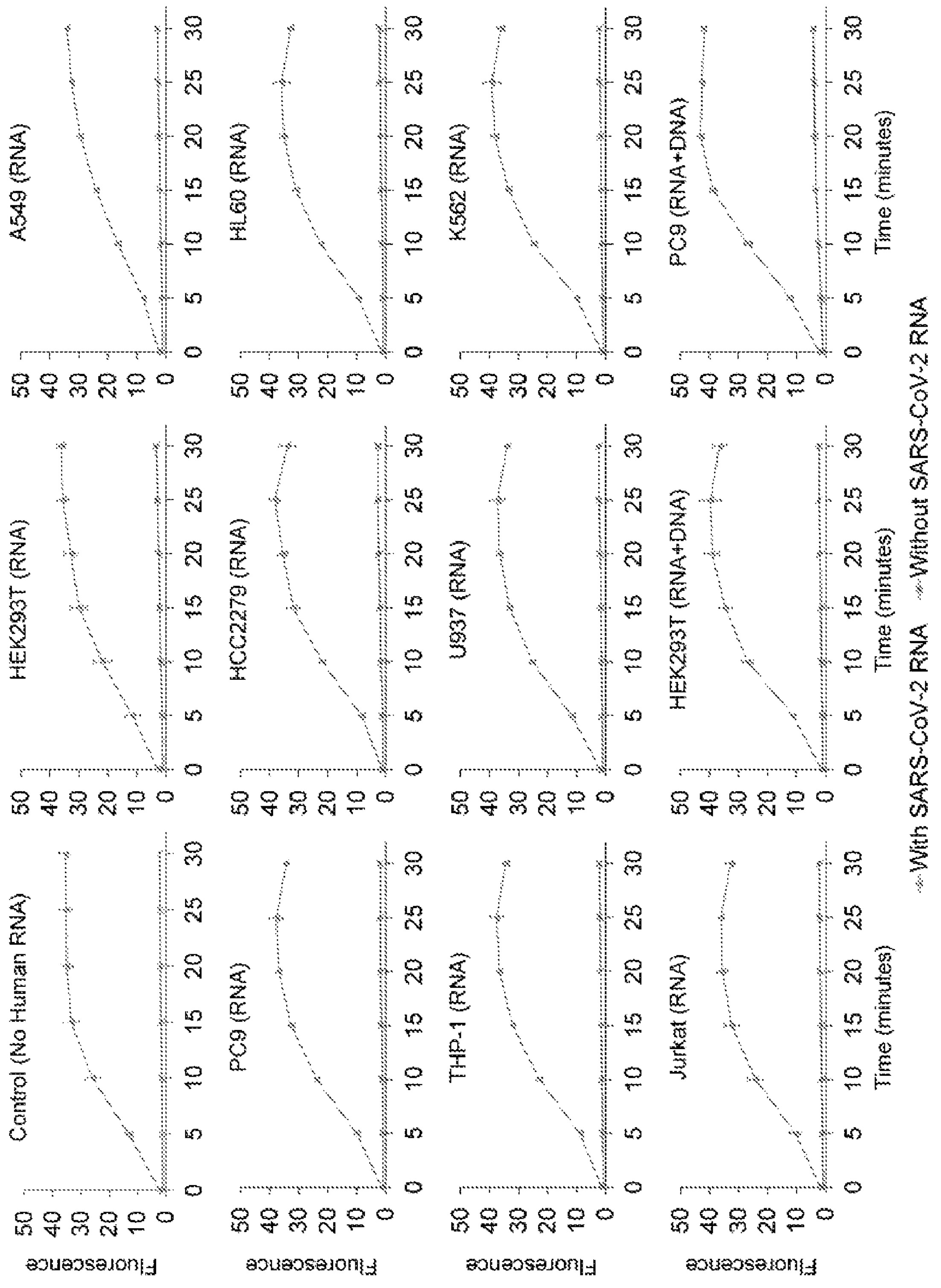
FIG. 35. Time courses of the fluorescence intensity in our trans-cleavage assays for 20,000 copies of synthetic wild-type SARS-CoV-2 RNA fragments spiked into 10 ng of total RNA from various immortalized human cell lines. Pure in vitro-transcribed viral RNA fragments (without any human RNA) were used as a control. The control or spiked RNA samples served as input to RT-LAMP, which was performed at 65° C. for 15 minutes under the optimized conditions. Subsequently, 4 μl LAMP products were used for the trans-cleavage assays, which were performed at 37° C. Fluorescence measurements were taken at five-minute intervals using a microplate reader. Data represent mean±s.e.m. (n=3 [all except control and HEK293T RNA], 6 [control], or 7 [HEK293T RNA] biological replicates).

Having evaluated the performance of the VaNGuard test with pure synthetic RNAs, next, it has been sought to evaluate the assay in more realistic situations. Specifically, it has been wondered if the SARS-CoV-2 RNA could still be detected in a large pool of human RNA. First, 20,000 copies of in vitro-transcribed viral RNA were spiked into 10 ng of total RNA extracted from various human cell lines and then performed RT-LAMP under optimized conditions followed by the fluorescence trans-cleavage assay with both the S2 and S6 gRNAs (FIG. 34, 35). The data revealed that the presence of a complex pool of human RNA did not significantly affect the fluorescence signal of the assay ($P>0.2$, one-sided Student's t-test). It has also been tested if the presence of human RNA and genomic DNA together might interfere with the detection of the virus, but did not observe any appreciable loss of fluorescence signal either.

Figure 36:
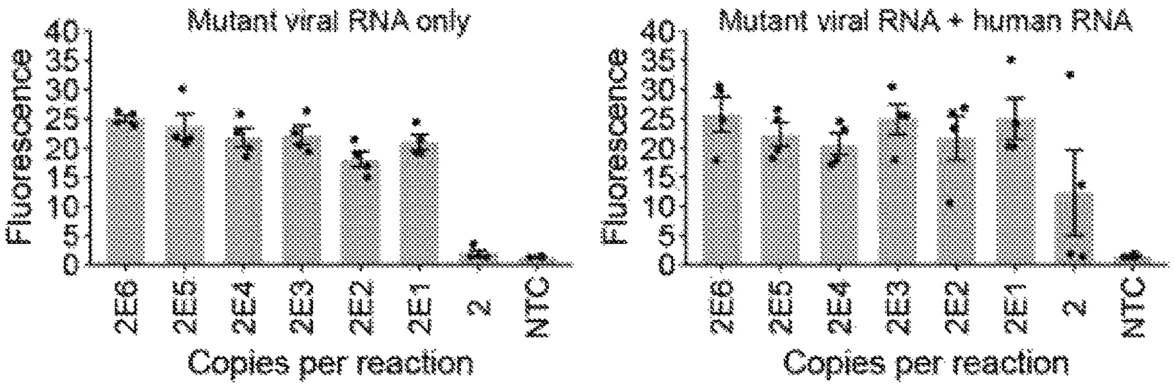
FIG. 36. Evaluation of the VaNGuard test under more realistic conditions. The figure shows an analytical LoD for a S254F N234N double mutant RNA template either by itself or mixed with 10 ng total human RNA from HCC2279 cells. Different copies of synthetic viral template (with or without human RNA) were used as input to RT-LAMP, which was performed at 65° C. for 15 minutes. The Cas detection reaction was then carried out at 37° C., with fluorescence after 10 minutes shown. Data represent mean±s.e.m. (n=4 biological replicates).
Figure 37:
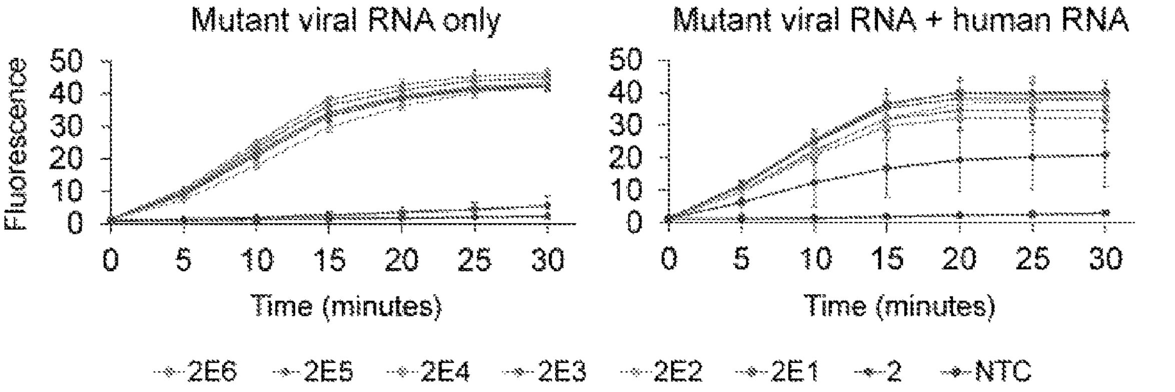
FIG. 37. Time courses of the fluorescence intensity in the trans-cleavage assays for a S254F N234N double mutant RNA template either by itself or mixed with 10 ng total human RNA from HCC2279 cells. A TCT-to-TTT mutation gave rise to the S254F amino acid change, while an AAC-to-AAT mutation was silent. Different copies of the in vitro-transcribed template (with or without human RNA) were used as input to the RT-LAMP reaction, which was performed at 65° C. for 15 minutes under optimized conditions. 4 μl LAMP products were then used for the trans-cleavage assays, which were performed at 37° C. Fluorescence measurements were taken at five-minute intervals using a microplate reader. Data represent mean±s.e.m. (n=4 biological replicates).

Second, it has been asked whether the presence of a complex pool of human RNA would affect the sensitivity of this assay for COVID-19, especially when the viral sequence had been mutated or edited. To this end, it has been generated a synthetic viral template harbouring not only the S254F mutation but also a second silent N234N mutation that had been found in at least ten sequenced SARS-CoV-2 isolates from around the world. While the former mutation could affect target recognition by the S2 gRNA, the latter mutation may affect target binding by the S6 gRNA. The sensitivity of the assay has been examined using this double mutant viral template either by itself or in a pool of total human RNA from the HCC2279 lung cell line. Encouragingly, it has been found that the LoD remained at 20 copies per reaction in both cases (FIG. 36, 37), underscoring the robustness of the VaNGuard test against known mutations in the viral RNA even in the presence of total human RNA.

Figure 38:
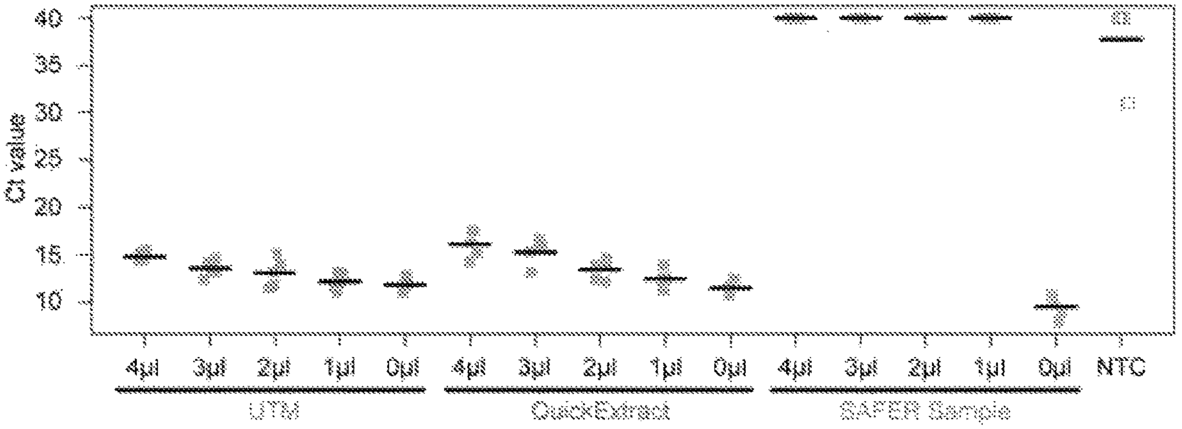
FIG. 38. Strip chart showing the effect of various sample collection media on RT-LAMP. It has been tested 1-4 μl of the widely used Universal Transport Medium (UTM), QuickExtract, and the SAFER Sample reagent. QuickExtract was heated at 95° C. for 5 minutes before use to denature the Proteinase K in the solution. The RT-LAMP reaction was carried out at 65° C. in a real-time instrument with 20,000 copies of RNA template. The black horizontal bars among the data points in the strip chart represent the mean (n=4 [SAFER 0-4 μl, NTC] or 5 [UTM 0-4 μl, QuickExtract 0-4 μl] biological replicates).
Figure 39:
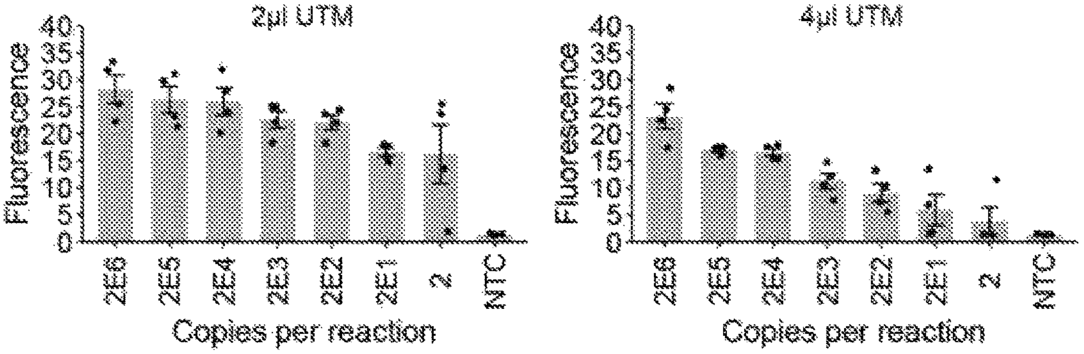
FIG. 39. Evaluation of the VaNGuard test under more realistic conditions. The figure shows an analytical LoD for purified synthetic wildtype SARS-CoV-2 RNA template in the presence of 2 μl or 4 μl UTM. Data represent mean±s.e.m. (n=4 biological replicates).
Figure 40:
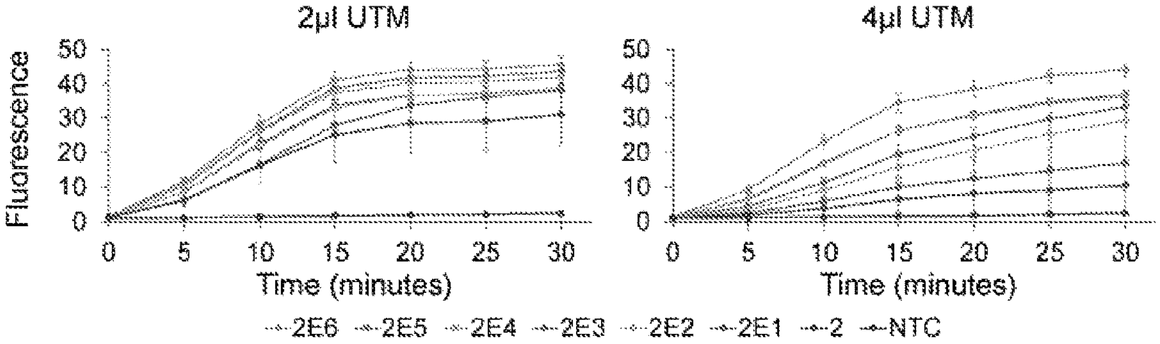
FIG. 40. Time courses of the fluorescence intensity in our trans-cleavage assays forpurified synthetic SARS-CoV-2 RNAs in the presence of 2 μl or 4 μl UTM. Various copies of in vitro-transcribed wildtype SARS-CoV-2 RNA fragments (see legend) in UTM were used as input to an RT-LAMP reaction, which was performed at 65° C. for 15 minutes under our optimized conditions. Next, 4 μl LAMP products (out of 25 μl) were used for the trans-cleavage assays, which were performed at 37° C. Fluorescence measurements were taken at five-minute intervals using a microplate reader. Data represent mean±s.e.m. (n=4 biological replicates).
Figure 41:
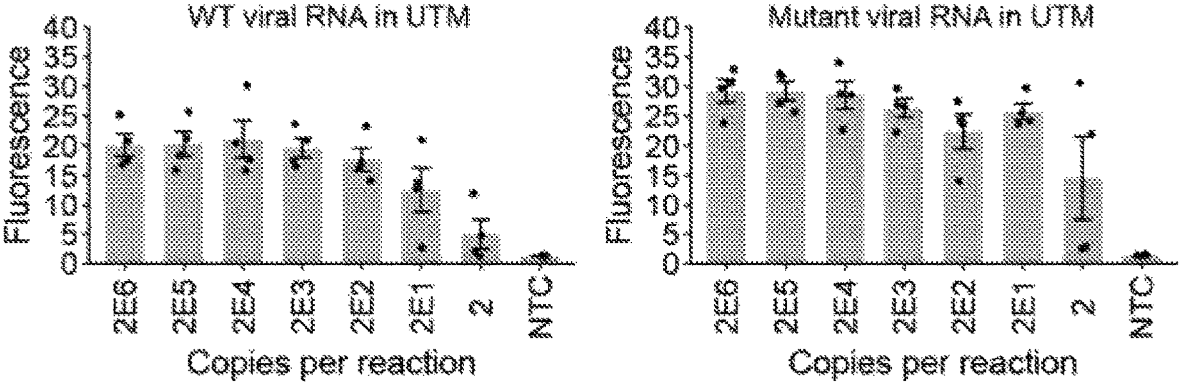
FIG. 41. Evaluation of the VaNGuard test under more realistic conditions. The figure shows an analytical LoD for wildtype (WT) or S254F N234N double mutant RNA template mixed with 10 ng total human RNA from HCC2279 cells in the presence of 2 μl UTM. Data represent mean±s.e.m. (n=4 biological replicates).
Figure 42:
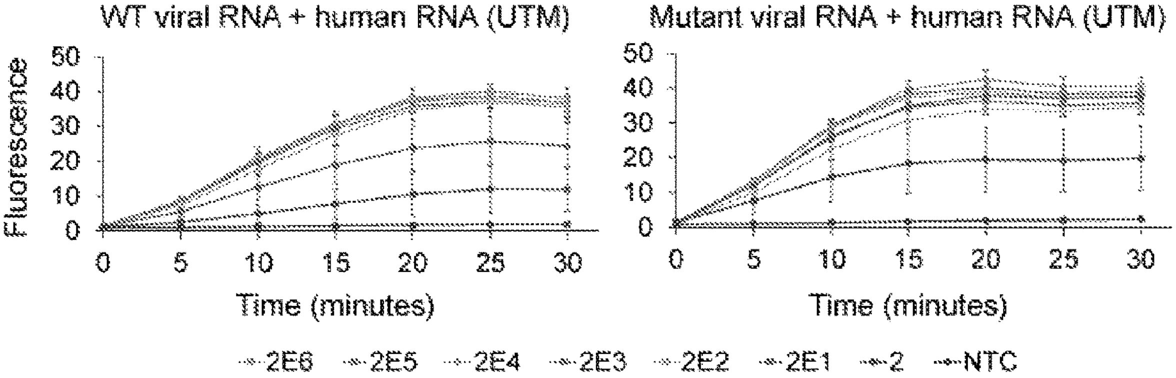
FIG. 42. Time courses of the fluorescence intensity in the trans-cleavage assays for either wildtype or S254F N234N double mutant RNA template mixed with 10 ng total human RNA from HCC2279 cells in the presence of 2 μl UTM. Different copies of the in vitro-transcribed template (see legend) mixed with human RNA in UTM were used as input to the RT-LAMP reaction, which was performed at 65° C. for 15 minutes under optimized conditions. 4 μl LAMP products (out of 25 μl) were then used for the trans-cleavage assays, which were performed at 37° C. Fluorescence measurements were taken at five-minute intervals using a microplate reader. Data represent mean±s.e.m. (n=4 biological replicates).

Third, since usage of patient samples directly without an extra RNA isolation step would reduce the time and cost of a diagnostic test, it has been examined whether various sample collection media may affect the performance of the assay (FIG. 38). Strikingly, just 1 μl of a commercially available SAFER Sample reagent was sufficient to block the RT-LAMP reaction completely. In contrast, up to 4 μl of Universal Transport Medium (UTM) could be tolerated with the kinetics of RT-LAMP reduced only marginally. The isothermal amplification reaction could also accommodate up to 4 μl of QuickExtract, albeit to a lesser extent than UTM. Nevertheless, when studying the impact of UTM on the entire RT-LAMP-CRISPR workflow, it has been observed that 4 μl of UTM clearly reduced the sensitivity of the VaNGuard test compared to just 2 μl of this widely used collection medium (FIG. 39, 40). Hence, it has been conclude that up to 2 μl (or less than 10% volume) of UTM may be added into this assay without any adverse consequence on its performance. Subsequently, the assay sensitivity has been examined using either wildtype or double mutant viral template mixed with total RNA from HCC2279 cells in 2 μl of UTM and found that the presence of two mutations in the gRNA binding sites still did not degrade the LoD of the assay (FIG. 41, 42). Altogether, these results suggest that patient samples in a small amount of UTM may be used directly in the VaNGuard test without affecting its robustness against SNVs in the template.

6. Reaction Conditions Affecting enAsCas12a Collateral Activity

Figure 43:
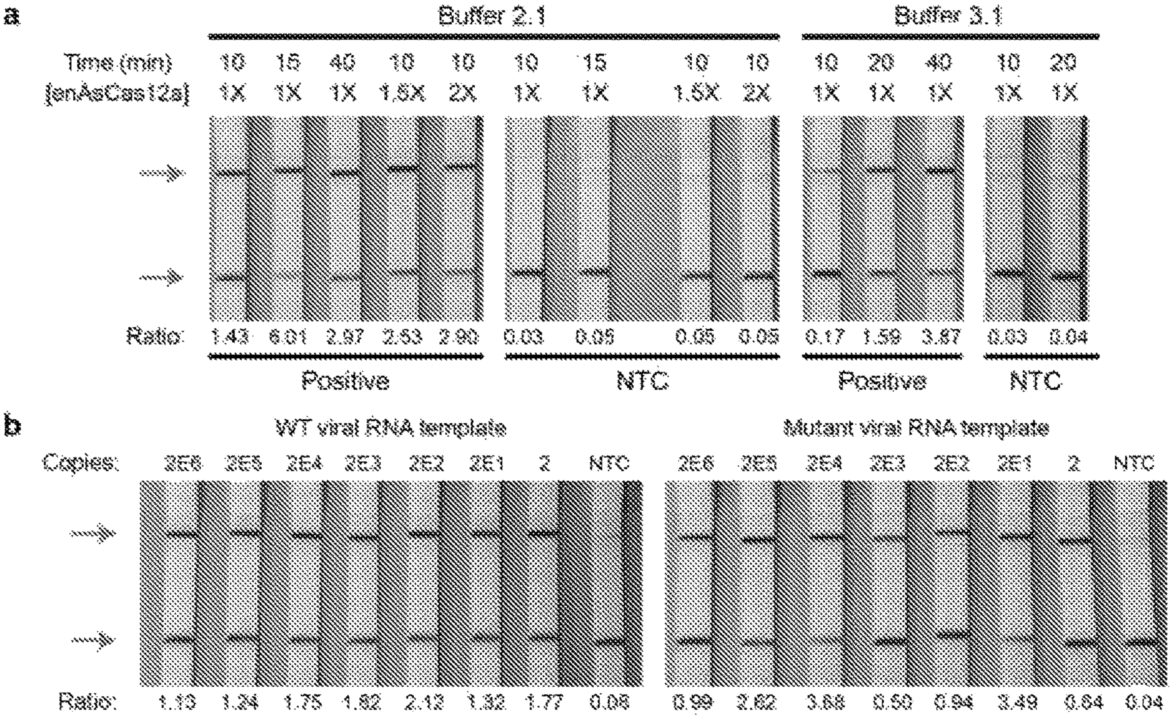
Figure 43:
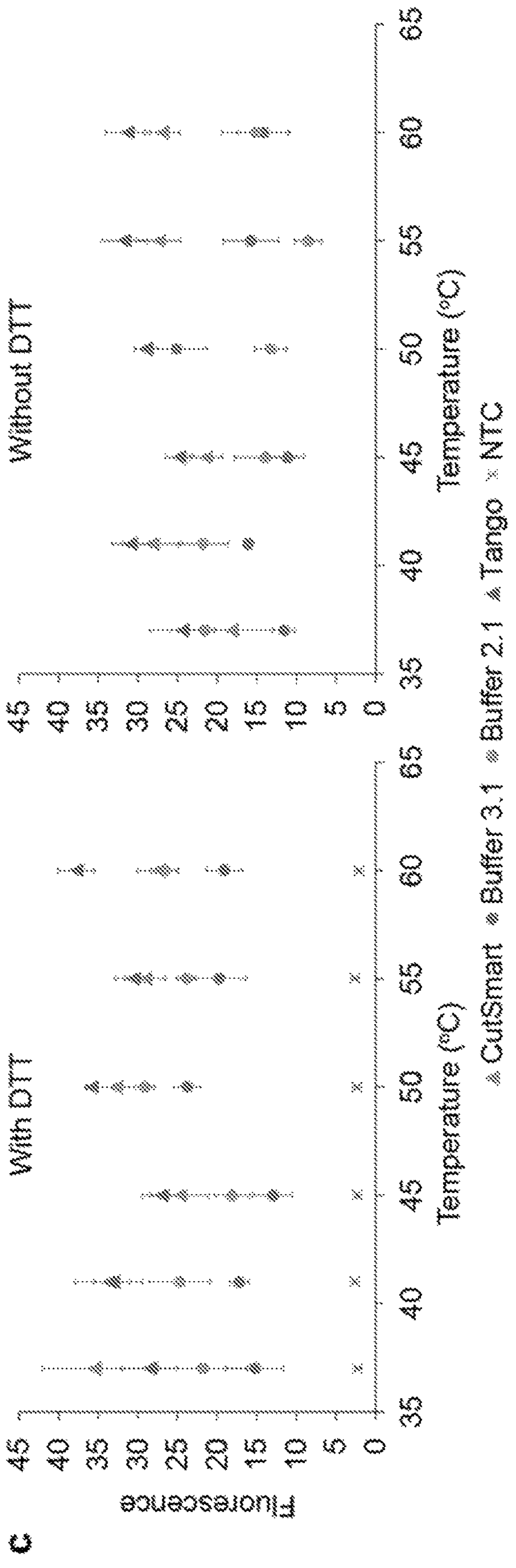

In earlier lateral flow assays, although positive test outcomes were obtained for samples with at least 20 copies of synthetic SARS-CoV-2 RNA, it has been noticed that the test bands were relatively weak compared to the control bands (FIG. 33, 29*b*). It has been hypothesized that a suboptimal buffer may have been used (Buffer 3.1) for the enAsCas12a-mediated assay. Hence, it has been tested an alternative reaction buffer (Buffer 2.1) together with different test durations and higher concentrations of the Cas12a RNP (FIG. 43*a*). Overall, it has been observed that reactions in the original buffer exhibited slower kinetics than reactions in the alternative buffer. For example, the intensity of the test band after 20 minutes in Buffer 3.1 was achieved by around 10 minutes in Buffer 2.1. Moreover, increasing the concentration of the Cas12a RNP by at least 50% also boosted the test signal. Hence, the sensitivity of the VaNGuard test has been re-evaluated using Buffer 2.1 and in vitro-transcribed SARS-CoV-2 RNA templates (FIG. 43*b*). Stronger test bands were observed from 2 to 2E6 copies of wildtype and S254F mutant viral templates with the Cas detection reaction performed for just 10 minutes.

Figure 44:
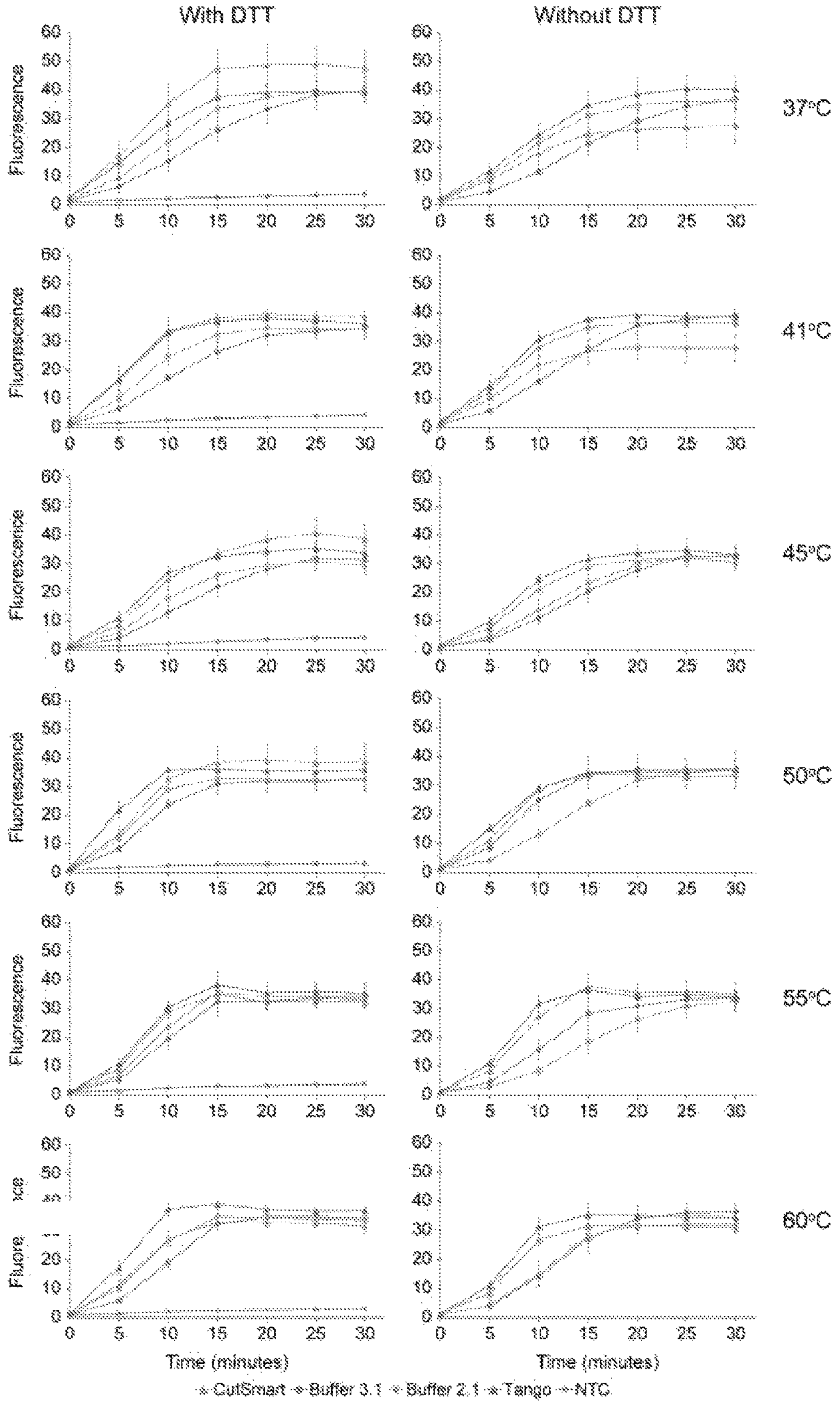
FIG. 44. Time courses of the fluorescence intensity in our trans-cleavage assays, which were carried out at different temperatures. Various buffer conditions were evaluated as well. Here, enAsCas12a was complexed with the S2 gRNA only. 2E11 copies of synthetic DNA template corresponding to the S-gene of SARS-CoV-2 were used and the reaction volume was 50 μl. Data represent mean±s.e.m. (n=3 [41° C., 45° C., 50° C., 55° C. Tango alone, 60° C. no DTT and NTC], 4 [37° C., 55° C. all but Tango alone], or 6 [60° C. with DTT] biological replicates).
Figure 45:
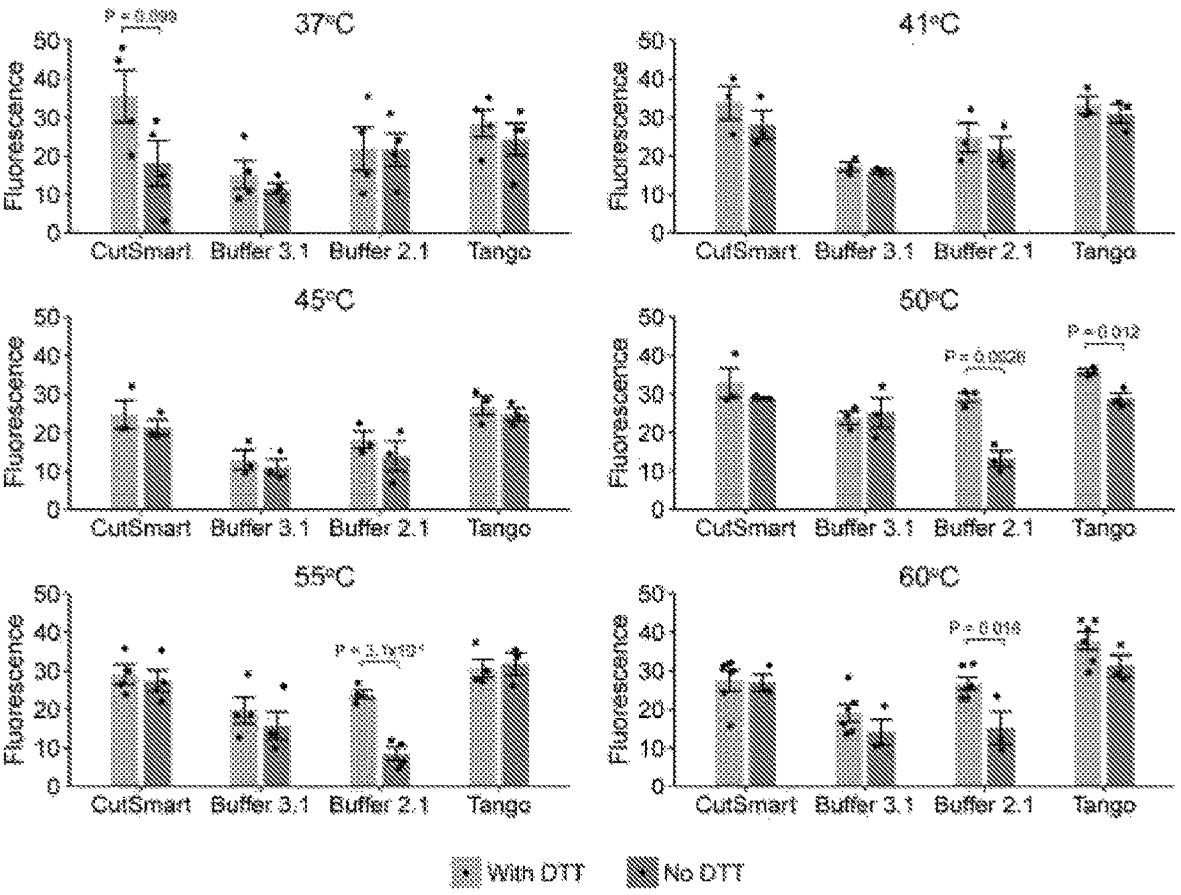
FIG. 45. Effect of DTT on the collateral activity of enAsCas12a at different temperatures. 2E11 copies of synthetic DNA corresponding to the S-gene of SARS-CoV-2 were used in the experiment together with enAsCas12a complexed with the S2 gRNA only. Fluorescence measurements here were taken using a microplate reader after 10 minutes of cleavage reaction. DTT significantly improved the activity of enAsCas12a in CutSmart buffer at 37° C. and in Buffer 2.1 at 50-60° C. Data represent mean±s.e.m. (n=3 [41° C., 45° C., 50° C., 55° C. Tango alone, 60° C. no DTT and NTC], 4 [37° C., 55° C. all but Tango alone], or 6 [60° C. with DTT] biological replicates). P values were calculated using two-sided Student's t-test.
Figure 46:
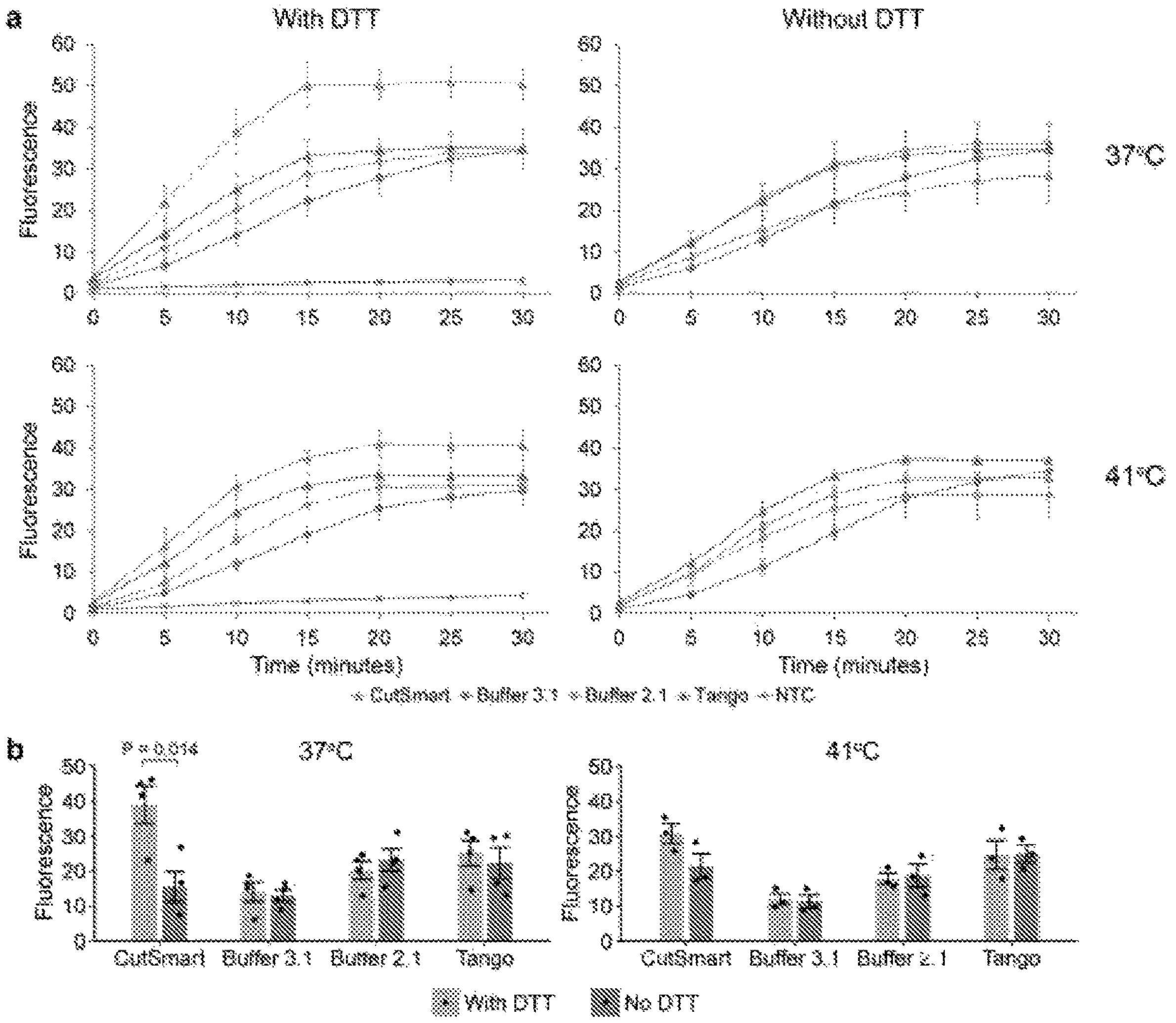
FIG. 46. Collateral activity of enAsCas12a complexed with the S6-targeting gRNA only in different reaction buffers.

Encouraged by these results, the reaction conditions under which purified enAsCas12a protein was active in vitro have been systematically investigated. Specifically, it has been tested four distinct buffers with or without dithiothreitol (DTT) over a range of temperatures using the S2 gRNA with enAsCas12a (FIG. 43*c*, 44). Unexpectedly, it has been found that enAsCas12a was active in the trans-cleave assay at all the temperatures tested. Overall, the engineered enzyme performed better in buffers containing acetate salts (CutSmart and Tango) than in buffers containing chloride salts (Buffer 2.1 and Buffer 3.1). At 37° C., CutSmart with DTT emerged as the best buffer to use with enAsCas12a, while at 60° C., Tango was the most suitable. Addition of DTT helped certain reaction conditions, for example CutSmart at 37° C. (FIG. 45). It has been further confirmed that DTT was required in the CutSmart buffer for enAsCas12a to function optimally at 37° C. using the S6 gRNA (FIG. 46).

Figure 47:
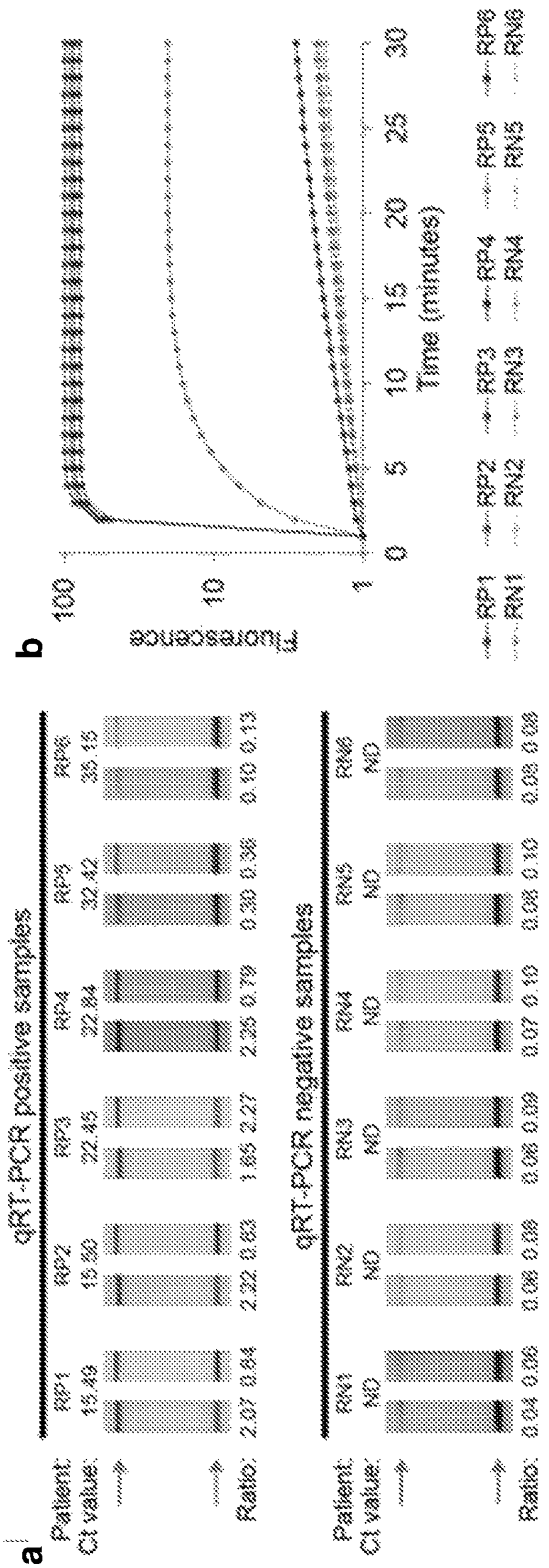

Subsequently, the diagnostic assay has been applied on a pilot set of leftover RNA samples extracted from patient nasopharyngeal (NP) swabs that had previously been analyzed by qRT-PCR in the hospital (FIG. 47*a*). Samples that exhibited a range of Ct values have been selected and the Cas detection step has been performed at 37° C. in CutSmart buffer with DTT. All the six samples that were negative in qRT-PCR analysis also turned out to be negative in the lateral flow assay, suggesting a specificity of 100% for the VaNGuard test. In addition, five out of the six infected samples gave obvious positive results on the dipsticks, with the remaining sample yielding a test band whose normalized intensity was only slightly above that of background. The results have been confirmed by repeating the test on the same set of patient samples using a fluorescence readout on the real-time instrument instead (FIG. 47*b*). Hence, the assay appeared to be able to detect SARS-CoV-2 in clinical RNA samples containing at least 93 copies of the virus, which corresponded to a cycle-threshold (Ct) value of 32.42 for the qRT-PCR kit used.

7. Engineering of Guides to Enhance the Sensitivity of Cas12a Detection

Figure 48:
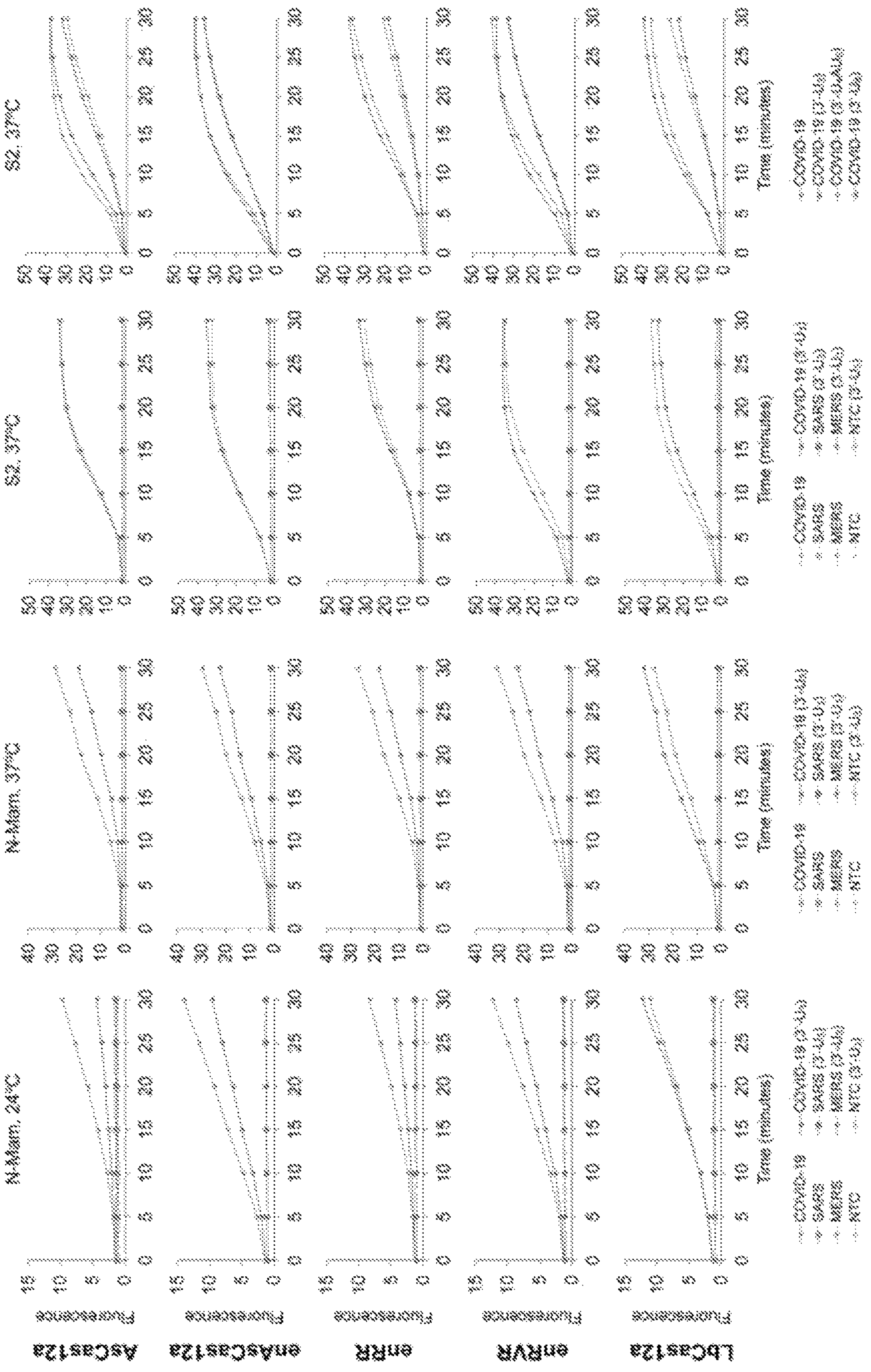
FIG. 48. Effect of extending gRNAs at their 3' end on the collateral activity of Cas12a enzymes. 1E11 copies of DNA template were used as input to the trans-cleavage assays. Fluorescence measurements were taken at five-minute intervals using a microplate reader and all the measurements were normalized to the no-template control (NTC) at the 0 min timepoint. A new N-Mam gRNA with aU33'-overhang has been generated and compared with the original unmodified gRNA at 24° C. and 37° C., but found that the 3'-extended gRNA yielded lower fluorescence signals for AsCas12a and its variants. Also new S2 gRNAs with a U3, U8, or U4AU63'-overhang have been generated and compared with the original unmodified gRNA at 37° C. The gRNA with a U33'-overhang gave similar fluorescence signals as the original gRNA, while the gRNA with a U8 or U4AU63'-overhang yielded poorer fluorescence output for all the tested Cas12a enzymes.

From the pilot evaluation with clinical samples, it has been observed that while the assay gave a positive test result for an infected sample with a Ct value of 32.42, the test band intensity and the fluorescence signal were weaker than those of samples with higher viral loads (FIG. 47*a, b*). Hence, it has been asked if the sensitivity of the Cas detection module could be enhanced. To this end, it has been sought to determine if modified gRNAs would boost the in vitro cell-free cleavage activity of the purified Cas12a RNPs, since previous studies had reported that such gRNAs could increase the cis- and trans-cleavage activity of Cas9 and Cas12a nucleases (Nguyen et al. (2020) Nat Commun 11, 4906, doi:10.1038/s41467-020-18615-1; Randar et al. (2015) Proc Natl Acad Sci USA 112, E7110-7117, doi: 10.1073/pnas.1520883112; Yin et al. (2017) Nat Biotechnol 35, 1179-1187, doi:10.1038/nbt.4005; Yin et al. (2018) Nat Chem Biol 14, 311-316, doi:10.1038/nchembio.2559; Mir et al. (2018) Nat Commun 9, 2641, doi:10.1038/s41467-018-05073-z; Bin Moon et al. (2018) Nat Commun 9, 3651, doi:10.1038/s41467-018-06129-w; Park et al. (2018) Nat Commun 9, 3313, doi:10.1038/s41467-018-05641-3; McMahon et al. (2018) Mol Ther 26, 1228-1240, doi: 10.1016/j.ymthe.2018.02.031). First, it has been tested if extensions of the gRNA at its 3' end would enhance the activity of the Cas12a enzymes. $U_3$, $U_8$, and $U_4AU_6$ extensions have been tried, but unlike previous work (Nguyen et al. (2020) Nat Commun 11, 4906, doi:10.1038/s41467-020-18615-1; Bin Moon et al. (2018) Nat Commun 9, 3651, doi:10.1038/s41467-018-06129-w), it has not been observed an appreciable or consistent improvement in activity (FIG. 48).

Figure 50:
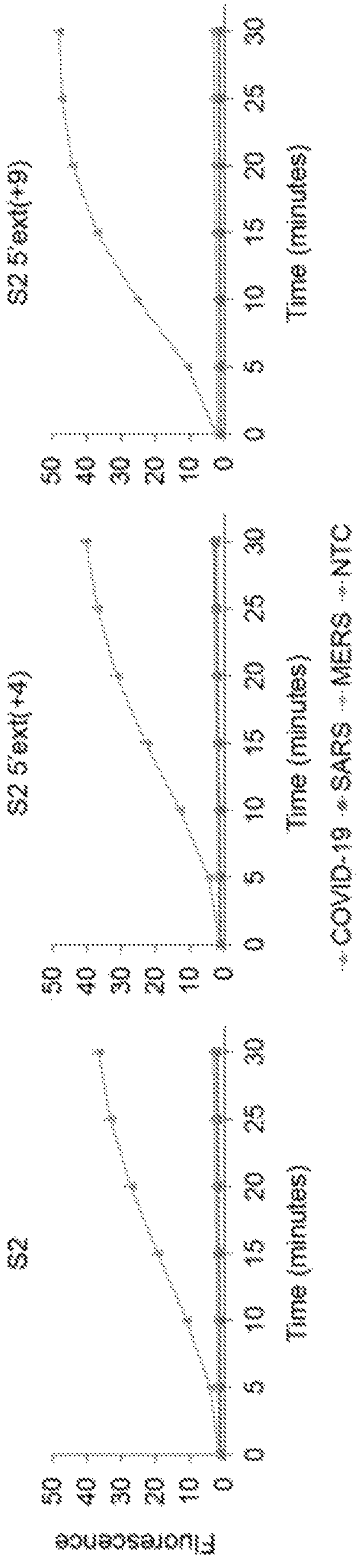
FIG. 50. Comparison of 5'-extended gRNAs with the original S2-targeting gRNA. To monitor the enAsCas12a-mediated cleavage reaction at 37° C., fluorescence measurements were taken at five-minute intervals using a microplate reader. 2E11 copies of synthetic DNA template were used. All readings were normalized to NTC at the 0 min timepoint. Data represent mean±s.e.m. (n=6 [S2 5'ext(+9)] or 11 [S2, S2 5'ext(+4)] biological replicates).

Second, it has been asked if extensions of the gRNA at its 5' end would increase the collateral activity of enAsCas12a. Such extensions had been reported to increase the gene editing efficiency of Cas12a in cells and in vivo (Park et al. (2018) Nat Commun 9, 3313, doi:10.1038/s41467-018-05641-3). The 5' end of the S2 gRNA has been extended by 4nt or 9nt (FIG. 49*a*). While the 4-nt extension did not improve the fluorescence signal in a trans-cleavage assay appreciably, the 9-nt extension did enhance the activity of enAsCas12a at 37° C. significantly ($P<0.001$, one-sided Student's t-test) (FIG. 49*b*, 50).

Figure 51:
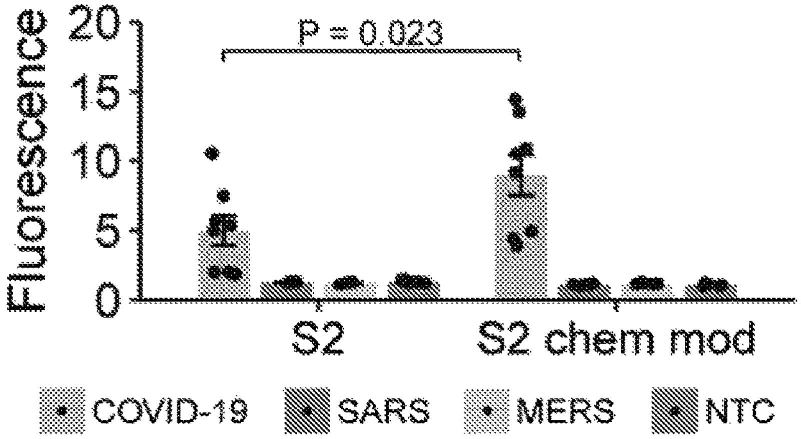
FIG. 51. Guide engineering to enhance the CRISPR detection module. The figure shows the comparison of a chemically modified gRNA with the original S2-targeting gRNA at 37° C. for enAsCas12a. Data represent mean±s.e.m. (n=3 [S2 SARS, S2 MERS], 6 [S2 chem mod SARS, S2 chem mod MERS], or 8 [COVID-19, NTC] biological replicates). P value was calculated using one-sided Student's t-test.
Figure 52:
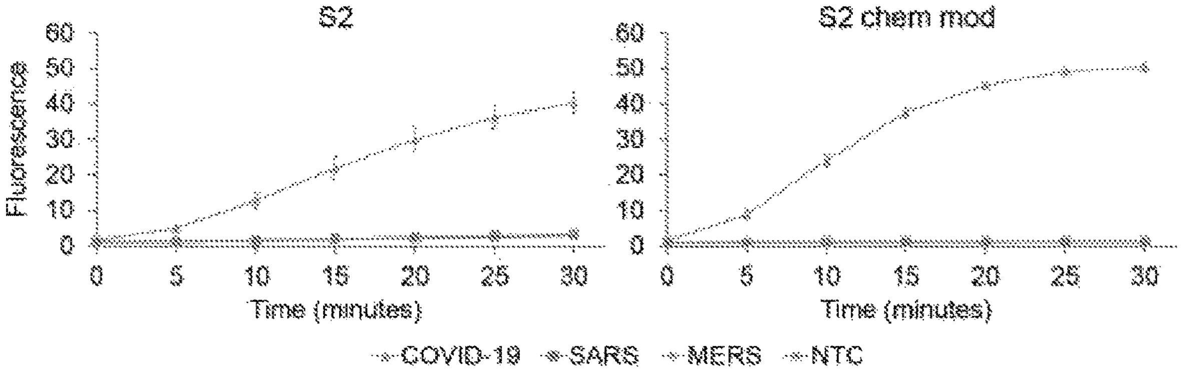
FIG. 52. Comparison of a chemically modified gRNA containing 2'-O-methyl ribonucleotides, 2'-deoxy-2'-fluororibonucleotides, and phosphorothioate bonds with the original S2-targeting gRNA. To monitor the enAsCas12a-mediated cleavage reaction at 37° C., fluorescence measurements were taken at five-minute intervals using a microplate reader. 2E11 copies of synthetic DNA template were used. All readings were normalized to NTC at the 0 min timepoint. Data represent mean±s.e.m. (n=3 [S2 SARS, S2MERS], 6 [S2 chem mod SARS, S2 chem mod MERS], or 8 [COVID-19, NTC] biological replicates).

Third, it has been asked if gRNAs bearing extra chemical modifications would yield higher collateral activities with enAsCas12a than regular gRNAs. Specifically, it has been examined a guide targeting the S2 locus that contained 2'-O-methyl RNA bases, 2'-fluoro bases, and phosphorothioate linkages at various positions (FIG. 49*a*). The design was based on prior work that showed that such a guide yielded higher Cas12a editing efficiency than a regular gRNA in human cells (McMahon et al. (2018) Mol Ther 26, 1228-1240, doi:10.1016/j.ymthe.2018.02.031). It has been found that the extra chemical modifications did boost the rate of the Cas detection reaction at 37° C. significantly ($P<0.05$, one-sided Student's t-test) (FIG. 51, 52).

Figure 53:
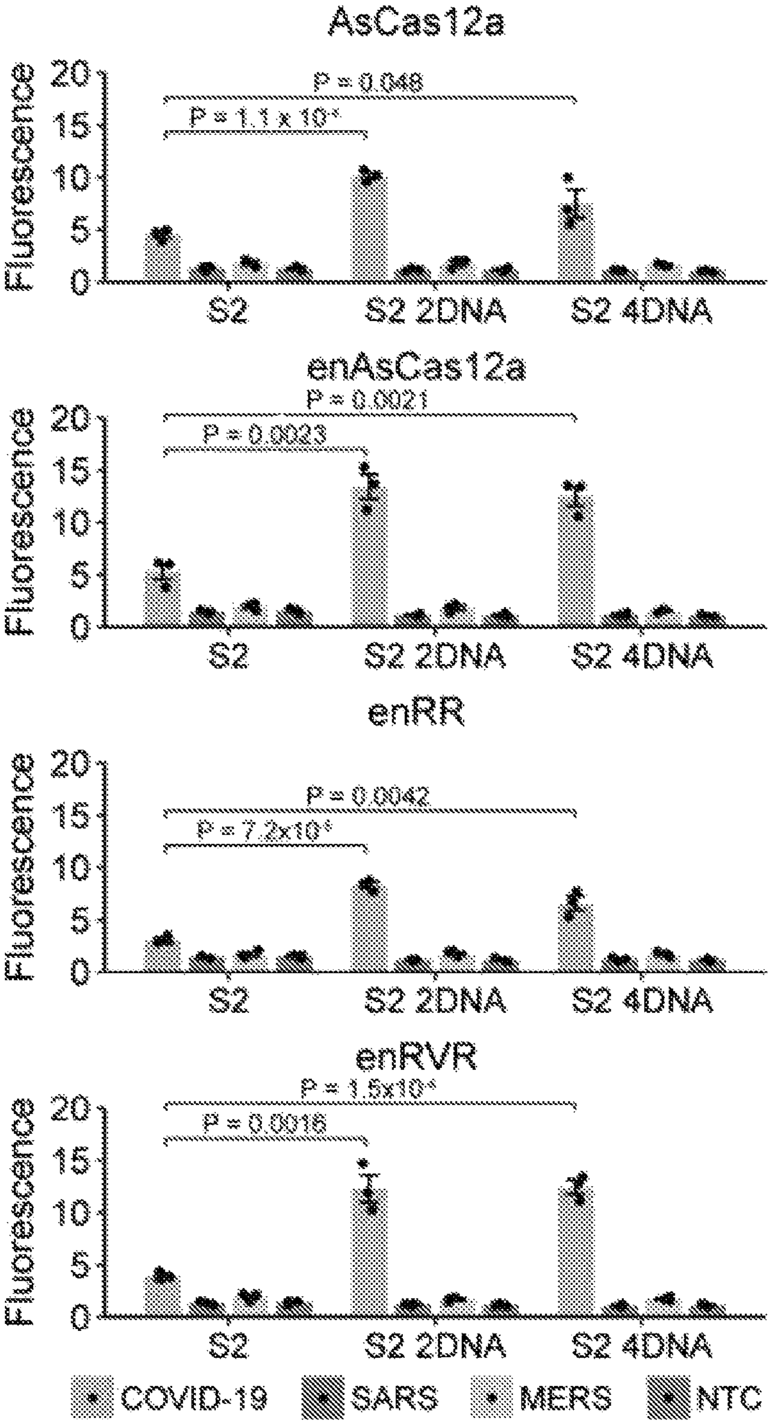
FIG. 53. Guide engineering to enhance the CRISPR detection module. The figure shows the comparison of DNA-RNA hybrid guides with the original S2-targeting gRNA at 37° C. for various Cas12a enzymes. Data represent mean±s.e.m. (n=3 biological replicates). P values were calculated using one-sided Student's t-test.
Figure 54:
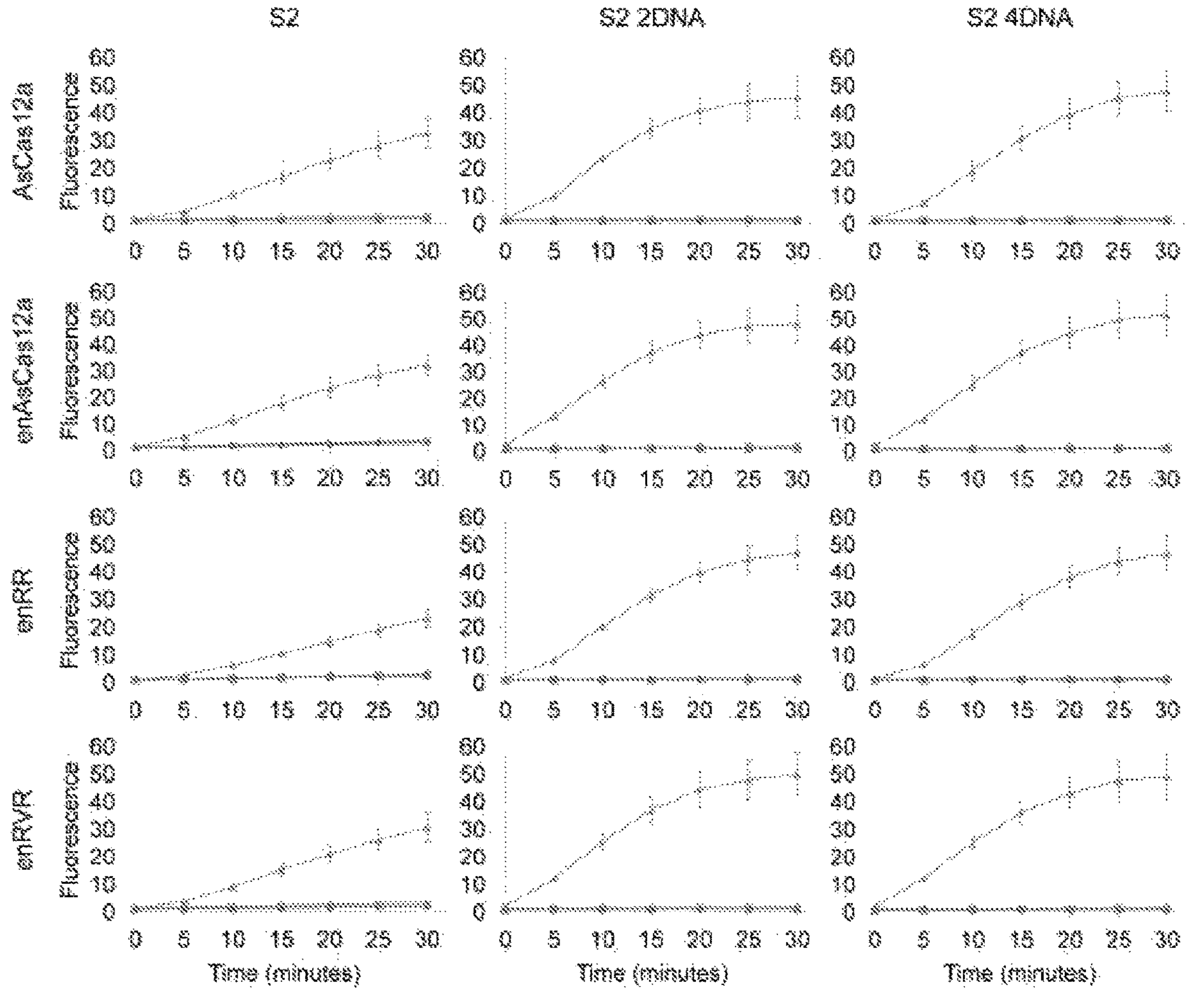
FIG. 54. Comparison of DNA-RNA hybrid guides with the original unmodified S2-targeting gRNA. To monitor the cleavage reaction at 37° C., fluorescence measurements were taken at five-minute intervals using a microplate reader. 2E11 copies of synthetic DNA template were used. All readings were normalized to NTC at the 0 min timepoint. Data represent mean±s.e.m. (n=3 biological replicates).

Fourth, it has been assessed if DNA-RNA hybrid guides would give higher collateral activities with AsCas12a and its engineered variants than regular guides that contained only RNA bases. To this end, S2-targeting guides that contained either two or four DNA base substitutions (FIG. 49*a*) have been generated. It has been started with changes at the 3' end of the guide because that region of the guide complexed with its target appeared to be disordered in a previously solved crystal structure and thus might be flexible (Yamano et al. (2016) Cell 165, 949-962, doi:10.1016/j.cell.2016.04.003). In addition, substitutions at positions 1 and 8 in the spacer have been tried as those positions had previously been shown to tolerate mismatches (Kleinstiver et al. (2016) Nat Biotechnol 34, 869-874, doi:10.1038/nbt.3620). At 37° C., both hybrid guides (with two or four DNA bases) were able to significantly increase the collateral activity of AsCas12a and its engineered variants relative to the original gRNA with no DNA bases ($P<0.05$, one-sided Student's t-test) (FIG. 53, 54).

Figure 55:
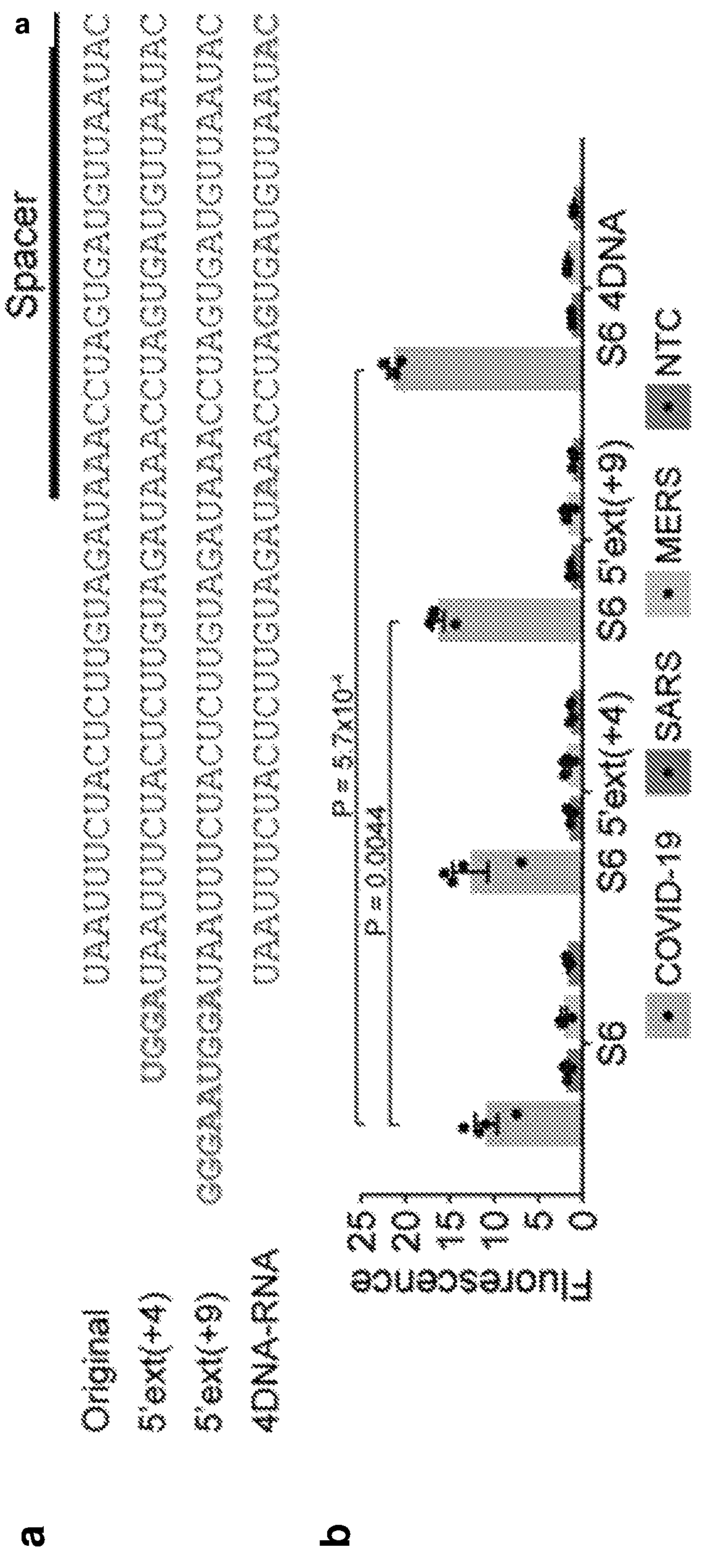
FIG. 55. Guide engineering to enhance the CRISPR detection module.
Figure 56:
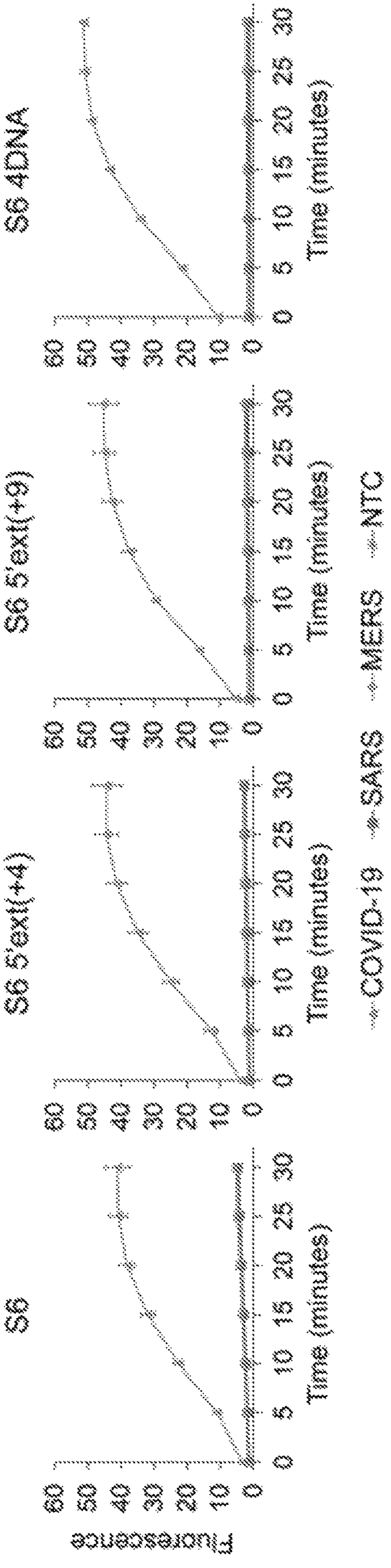
FIG. 56 shows a comparison of 5'-extended gRNAs and a DNA-RNA hybrid guide with the original S6-targeting gRNA. To monitor the enAsCas12a-mediated cleavage reaction at 37° C., fluorescence measurements were taken at five-minute intervals using a microplate reader. 2E11 copies of synthetic DNA template were used. All readings were normalized to NTC at the start of the experiment. Data represent mean±s.e.m. (n=3 [S6 4DNA] or 4 [S6, S6 5'ext (+4), S6 5'ext(+9)] biological replicates).
Figure 60:
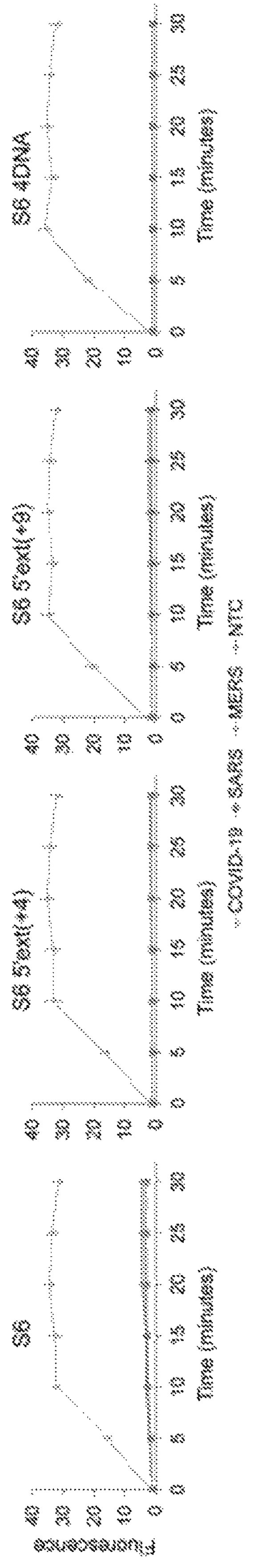
FIG. 60. Comparison of 5'-extended gRNAs and a DNA-RNA hybrid guide with the original S6-targeting gRNA. To monitor the enAsCas12a-mediated cleavage reaction at 60° C., fluorescence measurements were taken at five-minute intervals using a microplate reader. The trans-cleavage assays were performed in Tango buffer. 2E11 copies of synthetic DNA template were used. All readings were normalized to NTC at the 0 min timepoint. Data represent mean±s.e.m. (n=3 biological replicates).

It has been sought to verify the effects of guide modifications using a different target site, the S6 locus. To this end, three new S6-targeting guides—one gRNA with a 4-nt 5' extension, one gRNA with a 9-nt 5' extension, and one hybrid guide with four DNA base substitutions (FIG. 55*a*) have been generated. It has been decided not to pursue the chemically modified gRNA because it was much more expensive than a hybrid DNA-RNA guide but did not perform better. Overall, it has been found that the results from a trans-cleavage assay performed at 37° C. for the S6 locus mirrored those for the S2 locus (FIG. 55*b*, 60). Extending the gRNA by 9nt at the 5' end or replacing four RNA bases with DNA bases significantly increased the collateral activity of enAsCas12a ($P<0.01$, one-sided Student's t-test).

Figure 57:
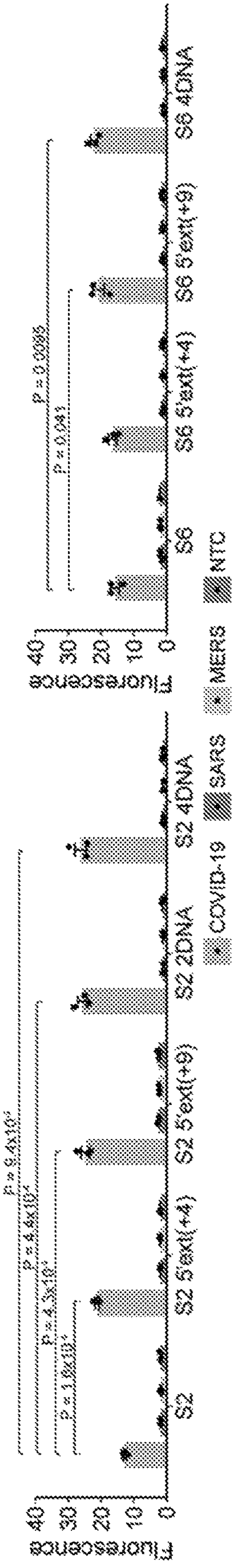
FIG. 57. Guide engineering to enhance the CRISPR detection module. The figure shows a comparison of 5'-extended gRNAs and DNA-RNA hybrid guides with the corresponding unmodified gRNAs at 60° C. for enAsCas12a. The S2-targeting and S6-targeting guides were tested separately. Fluorescence measurements here were taken after 5 minutes of cleavage reaction with 2E11 copies of synthetic DNA. Data represent mean±s.e.m. (n=3 biological replicates). P values were calculated using one-sided Student's t-test.
Figure 58:
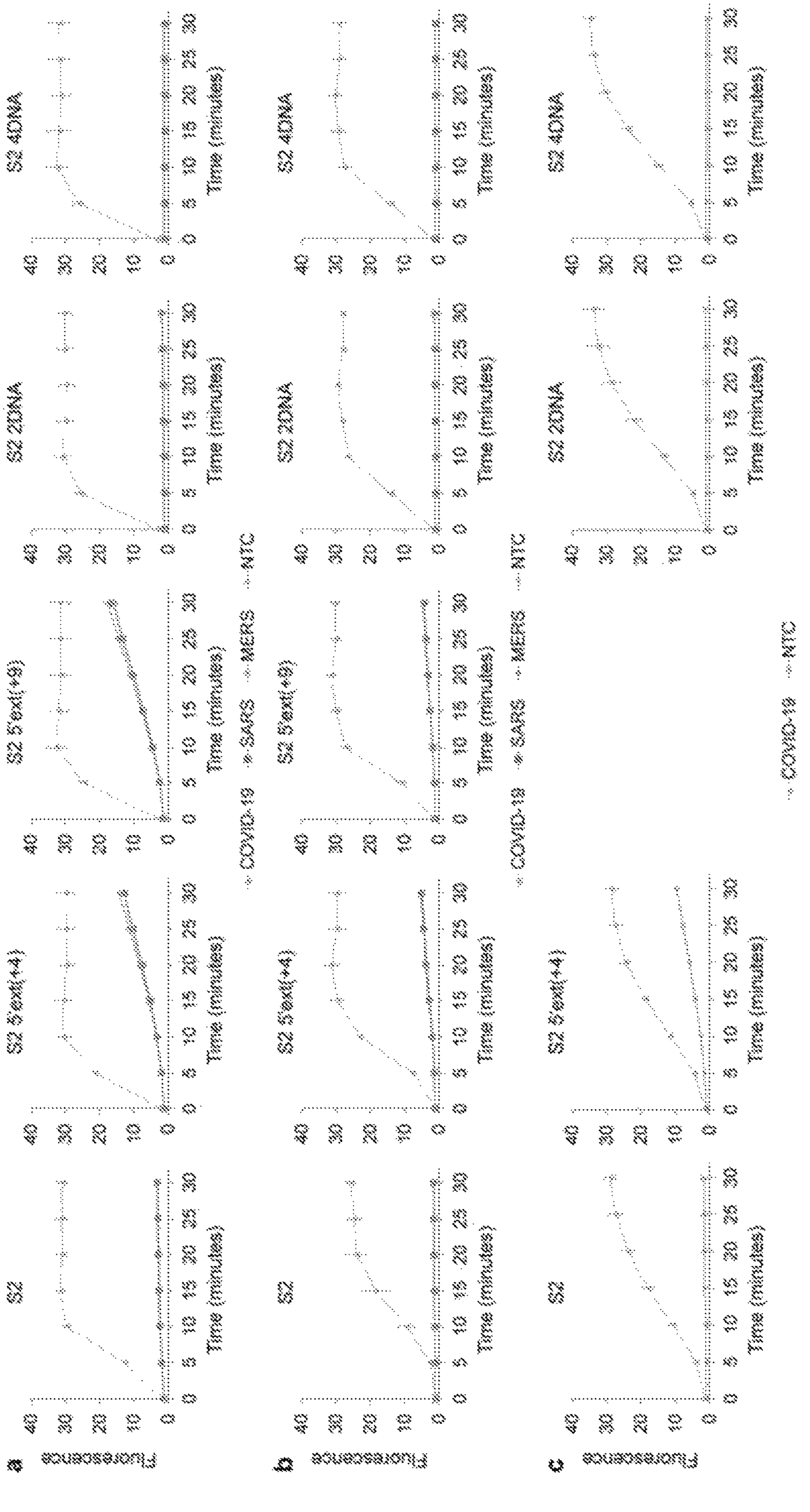
FIG. 58. Comparison of 5'-extended gRNAs and DNA-RNA hybrid guides with the original S2-targeting gRNA. To monitor the enAsCas12a-mediated cleavage reaction at 60° C., fluorescence measurements were taken at five-minute intervals using a microplate reader. The trans-cleavage assays were performed in (a) Tango buffer, (b) Buffer 3.1 with DTT, or (c) CutSmart buffer with DTT. 2E11 copies of synthetic DNA template were used. All readings were normalized to NTC at the 0 min timepoint. Data represent mean±s.e.m. (n=3 biological replicates).

Since enAsCas12a appeared to be active over a wide range of temperatures, next, it has been sought to evaluate the modified guides at 60° C. For the S2-targeting set of guides, it has been observed that both gRNAs with 5' extensions as well as both hybrid DNA-RNA guides exhibited faster reaction kinetics with enAsCas12a than the original unmodified gRNA; by 5 minutes, they generated significantly higher fluorescence signals in a trans-cleavage assay ($P<0.001$, one-sided Student's t-test) (FIG. 57, 58). Unexpectedly, however, the two gRNAs with 5' extensions triggered the collateral activity of enAsCas12a even in the absence of a template, as shown by the obvious increase in background signal by 30 minutes of reaction time (FIG. 58, 59). Similar results were obtained with three different reaction buffers. Moving forward, these two gRNAs have been dropped from further consideration. For the S6-targeting set of guides, the results obtained at 60° C. mirrored those obtained at 37° C. (FIG. 57, 59, 60). Both the gRNA with a 9-nt 5' extension and the hybrid guide increased the rate of reaction significantly ($P<0.05$, one-sided Student's t-test) and there was no unexpected triggering of enAsCas12's collateral activity in the absence of a template.

Figure 61:
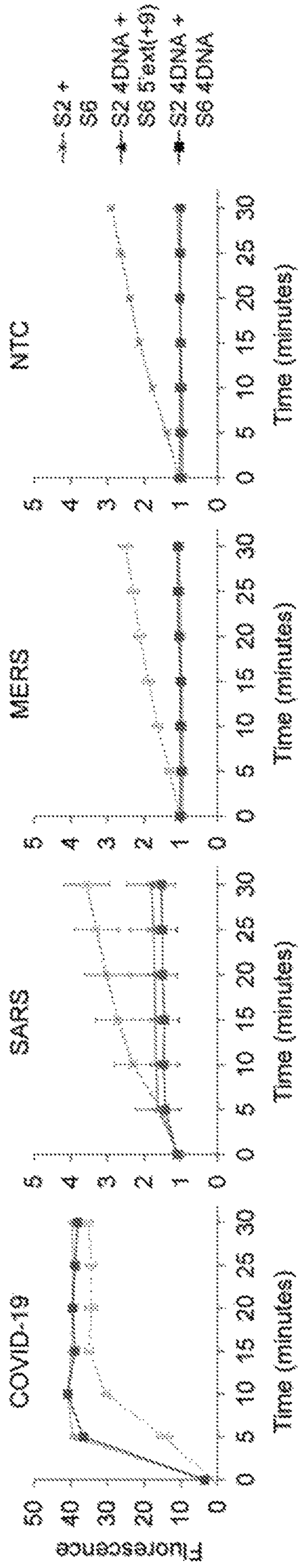
FIG. 61. Guide engineering to enhance the CRISPR detection module. The figure shows the evaluation of the two-gRNA CRISPR module using unmodified and modified guides. Fluorescence measurements were taken every 5 minutes using a microplate reader. The enAsCas12a-mediated cleavage reaction was performed at 60° C. with 2E11 copies of synthetic DNA. Data represent mean±s.e.m. (n=3 [S2+S6 negative controls, S2 4DNA+S6 5'ext(+9)] or 5 [S2+S6 COVID-19, S2 4DNA+S6 4DNA] biological replicates).

Subsequently, it has been asked how simultaneous deployment of two modified guides together with enAsCas12a would improve the CRISPR detection module. The original set of unmodified S2 and S6 gRNAs has been benchmarked against the S2 hybrid guide containing four DNA bases combined with either the S6 gRNA extended by 9nt at its 5' end or the S6 hybrid guide containing four DNA bases (FIG. 61). In the presence of the intended SARS-CoV-2 template, each set of modified guides exhibited faster reaction kinetics than the original set of unmodified gRNAs, with the fluorescence signal saturating within 5 minutes. Furthermore, it has been observed that the modified guides completely suppressed any collateral activity of enAsCas12a in the absence of a template or in the presence of the closely related SARS-CoV and MERS-CoV templates. Collectively, these results demonstrate that the use of modified guides can increase the rate of the Cas detection reaction and effectively curb any off-target activity.

8. Evaluation of a Quasi-One-Pot Reaction with Clinical RNA Samples

Figure 62:
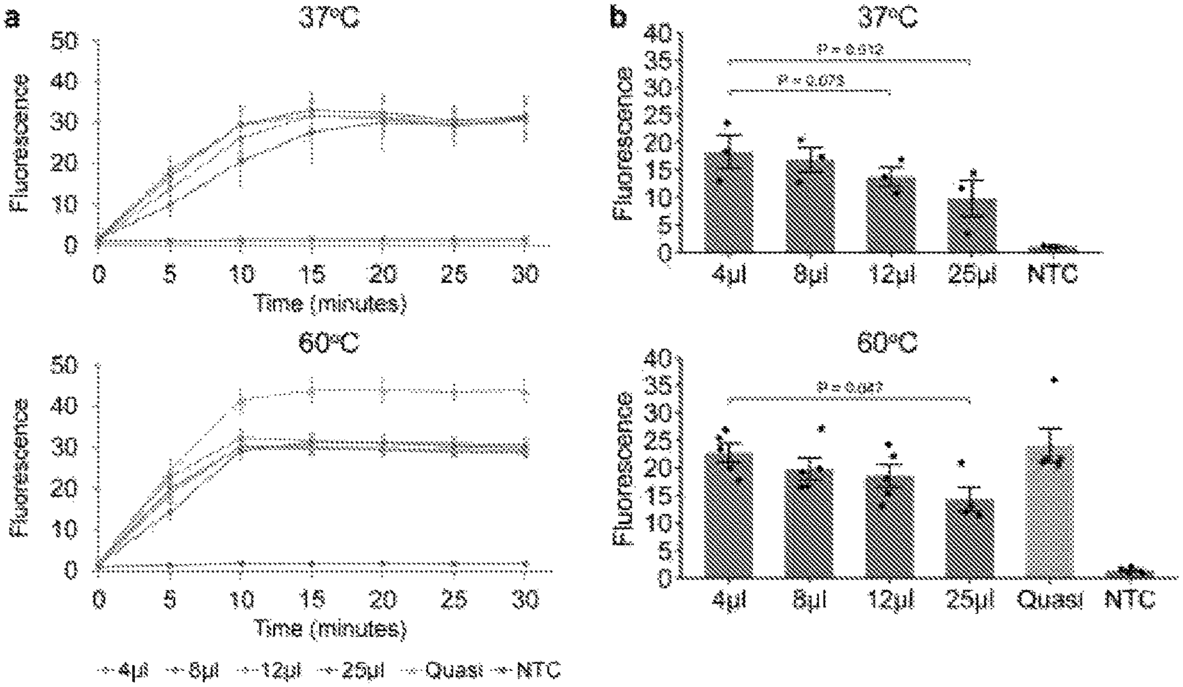
FIG. 62. Effect of different volumes of LAMP products on the CRISPR module.

It has been wondered how the complete RT-LAMP-CRISPR workflow could be improved. So far, it had been transferred only 4 μl of LAMP products into 46 μl of CRISPR reaction mix to minimize a change in buffer of the Cas detection step. However, the LAMP reaction itself had a total volume of 25 μl, which was not being utilized fully. Hence, it has been tested if the CRISPR reaction was able to tolerate a larger amount of unpurified LAMP products, while keeping its final volume constant at 50 μl (FIG. 62). It has been found that the kinetics of the CRISPR reaction gradually became slower with an increasing amount of LAMP products in it. The fluorescence signal for a setup containing the entire 25 μl LAMP mix in the CRISPR reaction (i.e. the LAMP products were diluted 1:1) was significantly lower than that for the original workflow at both 37° C. and 60° C. ($P<0.05$, one-sided Student's t-test). This suggested that some unknown factor in the LAMP mix might be partially inhibitory to the enAsCas12a enzyme and had to be diluted out. Then, it has been tested an alternative setup where instead of transferring LAMP products into the CRISPR reaction, 50 μl of CRISPR reaction mix have been added into the LAMP reaction tube instead (i.e. the LAMP products were diluted 1:2). This not only enabled utilizing all the LAMP products but also helped to minimize human error and cross-contamination, since nothing was taken out of the LAMP reaction tube. Encouragingly, it has been found that the alternative setup exhibited similar reaction kinetics to the original workflow and gave an even higher fluorescence signal at saturation.

Figure 63:
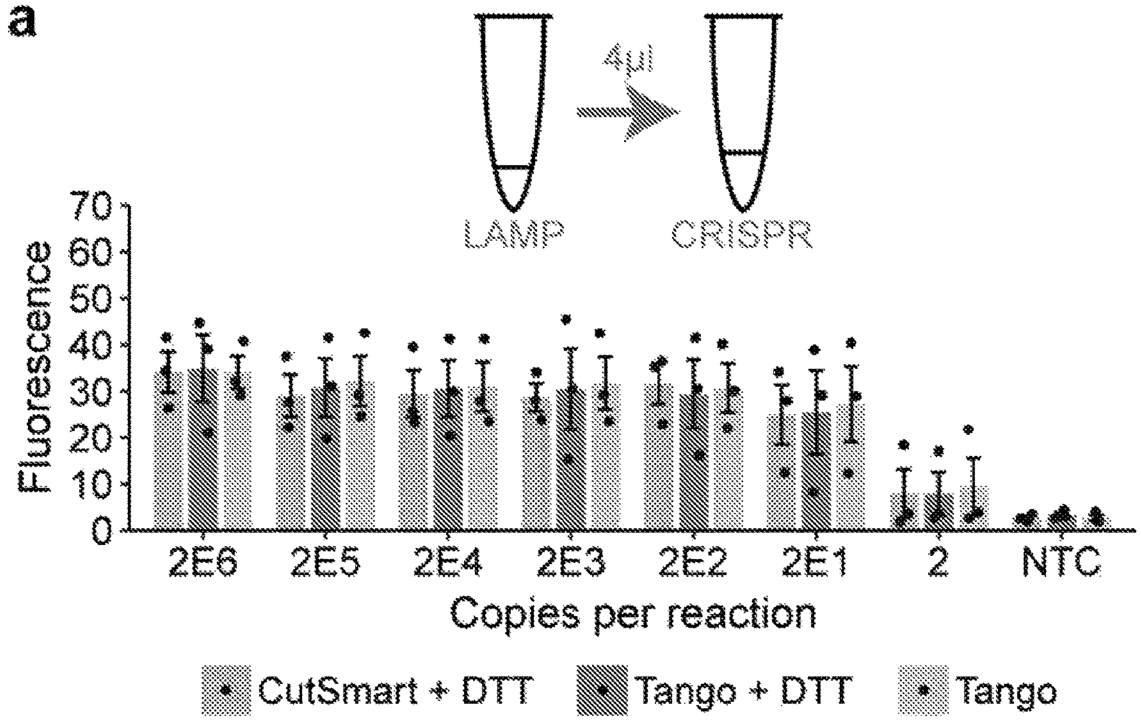
FIG. 63. Implementation of a quasi-one-pot reaction.
Figure 63:
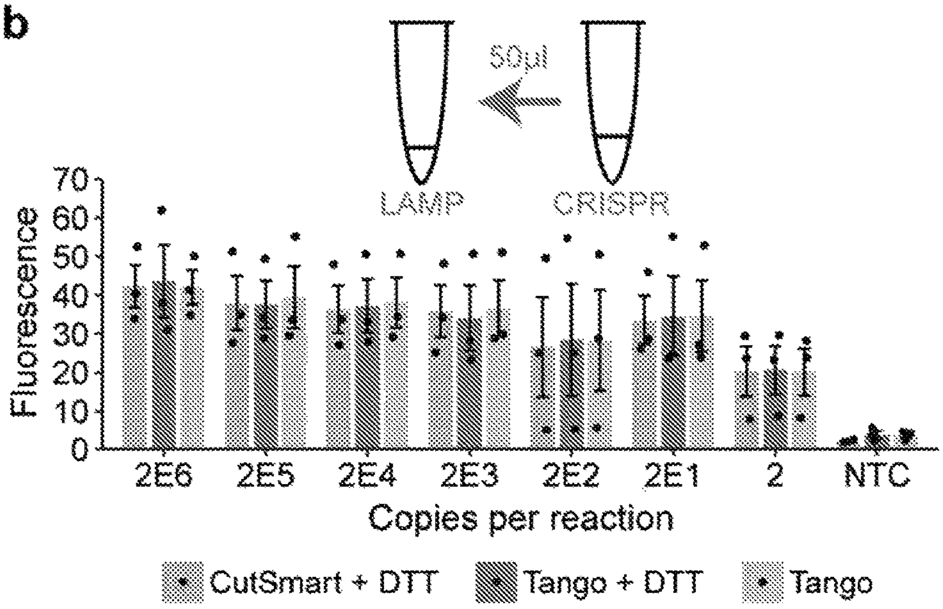
Figure 64:
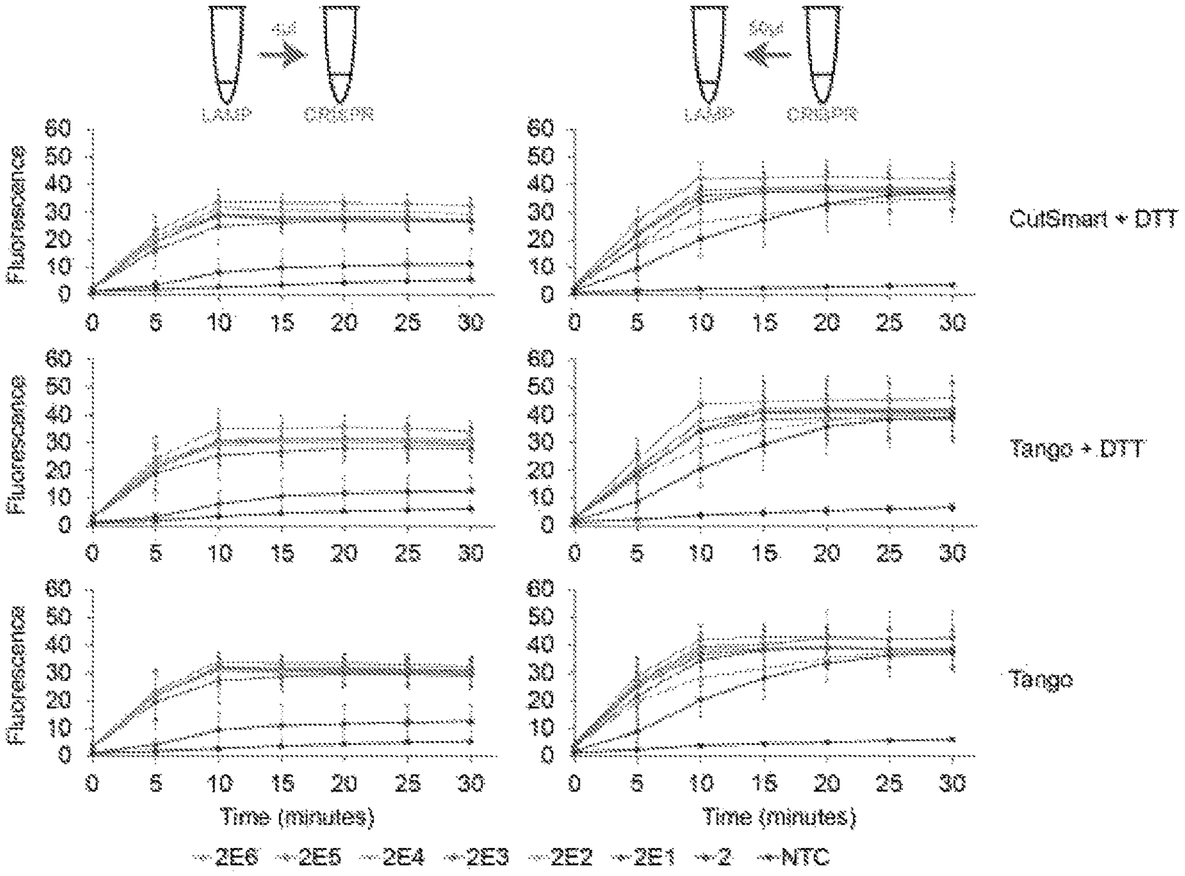
FIG. 64. Analytical LoD of the assay based on either the original workflow (left) or when all LAMP products were utilized (right). Different copies of in vitro transcribed SARS-CoV-2 RNA (see legend) were used as input to the RT-LAMP reaction, which was performed at 65° C. for 15 minutes. Subsequently, the Cas detection reaction was carried out at 60° C., with the fluorescence measurements taken at 5-minute intervals using a microplate reader. Data represent mean±s.e.m. (n=3 biological replicates).
Figure 65:
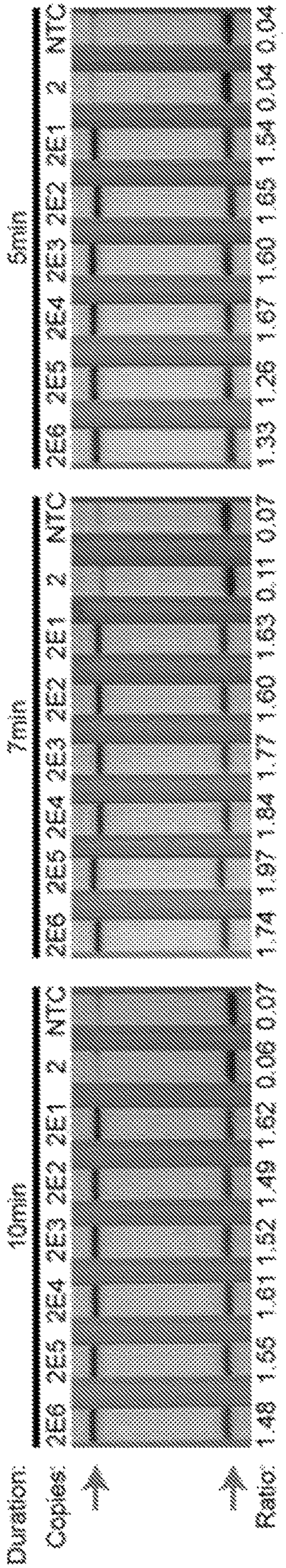
FIG. 65. Analytical LoD of synthetic wildtype SARS-CoV-2 RNA by enAsCas12a complexed with both the S2 4DNA hybrid guide and the S6 9nt 5'-extended gRNA in the presence of 2 μl UTM. Different copies of synthetic viral template in clean UTM were used as input to the RT-LAMP reaction, which was performed at 65° C. for 15 minutes. Next, 50 μl of CRISPR reaction mix in Tango buffer was added directly into each LAMP reaction tube. The trans-cleavage assay was then carried out at 60° C. for 5, 7, or 10 minutes before a dipstick was inserted into each tube. Bands appeared on the dipsticks by 2 minutes. The higher arrow indicates the test bands, while the lower arrow indicates the control bands. Strong test bands were detected from 2E1 to 2E6 copies of viral RNA even with only 5 minutes of cleavage reaction time.

Subsequently, it has been sought to compare the LoD of the original workflow and the alternative setup using synthetic SARS-CoV-2 RNA (FIG. 63*a*, 63*b*, 64). RT-LAMP was performed at 65° C., while the Cas detection reaction was performed at 60° C. While only 1 out of 3 replicates showed successful amplification of 2 copies of viral template in the original workflow, all replicates were successful in the alternative setup. The experiments have been repeated with different buffers for the CRISPR reaction and similar results have been obtained. Furthermore, it has been verified that a small amount of UTM could be tolerated even when all the LAMP products were utilized in the downstream Cas detection step (FIG. 65). Hence, moving forward, the alternative setup has been adopted, where 50 μl of enAsCas12a RNPs in Tango buffer was added directly into the LAMP reaction tube after completion of isothermal amplification.

Figure 66:
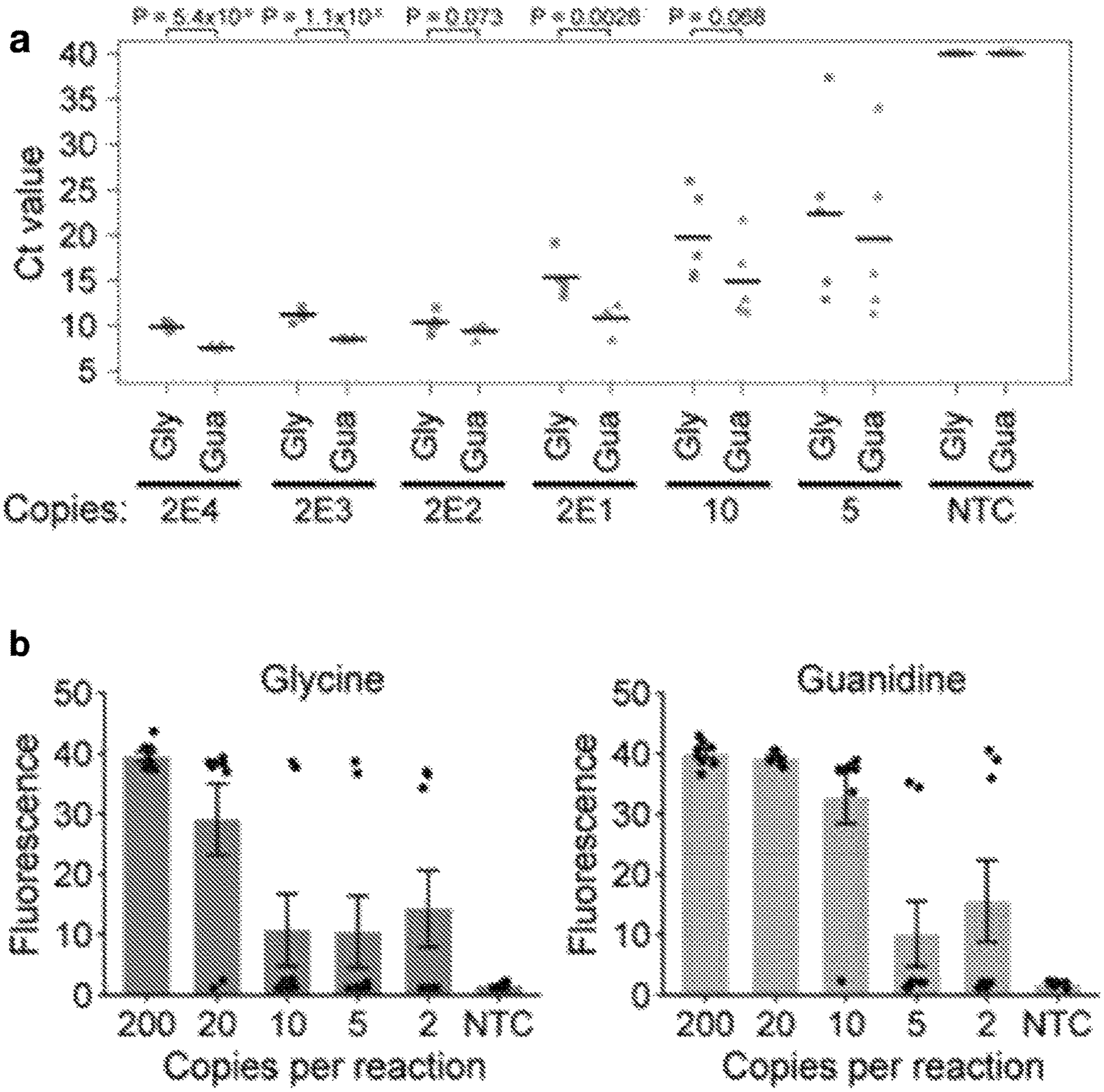
FIG. 66. Implementation of a quasi-one-pot reaction.
Figure 67:
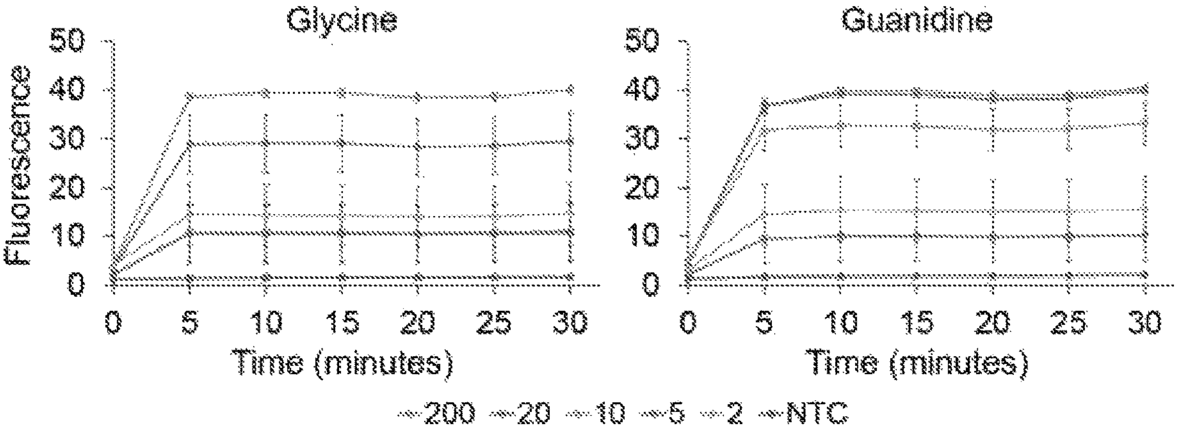
FIG. 67. Comparison of the assay sensitivity between glycine and guanidine. Different copies of synthetic SARS-CoV-2 RNA fragments were used as input to RT-LAMP, which was performed at 65° C. for 15 minutes. Subsequently, 50 μl CRISPR reagents were added directly into the LAMP reaction tube and the Cas detection reaction was then carried out at 60° C., with fluorescence measurements taken at 5-minute intervals using a microplate reader. Data represent mean±s.e.m. (n=8 biological replicates).
Figure 68:
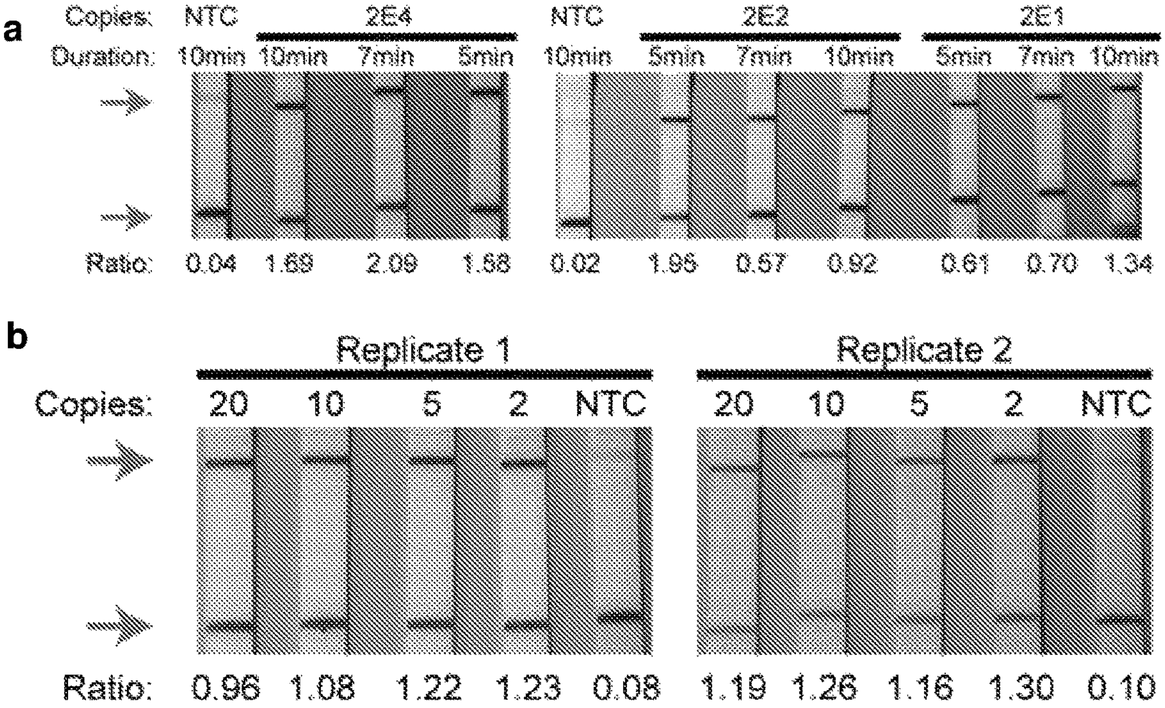
FIG. 68. Implementation of a quasi-one-pot reaction.

While the project was ongoing, another study was published reporting that the speed and sensitivity of LAMP could be enhanced by guanidine (Zhang et al. (2020) *Biotechniques* 69, 178-185, doi:10.2144/btn-2020-0078). Hence, it has been sought to determine whether guanidine or glycine, which has been incorporated into this CRISPR-Dx earlier (FIG. 22), would be better for the assay. First, RT-LAMP was performed alone and it has been found that guanidine increased the reaction rate more appreciably than glycine (FIG. 66*a*). Next, the entire assay has been performed with either guanidine or glycine in the reaction mix and it has been observed that the assay with guanidine appeared to be more sensitive (FIG. 66*b*, 67). Guanidine enabled 10 viral copies to be detected in 7 out of 8 replicates, while glycine enabled successful detection in only 2 out of 8 replicates. Hence, glycine has been replaced with guanidine in the assay and the speed and sensitivity of the updated test using dipsticks (FIG. 68*a, b*) could be confirmed.

Figure 69:
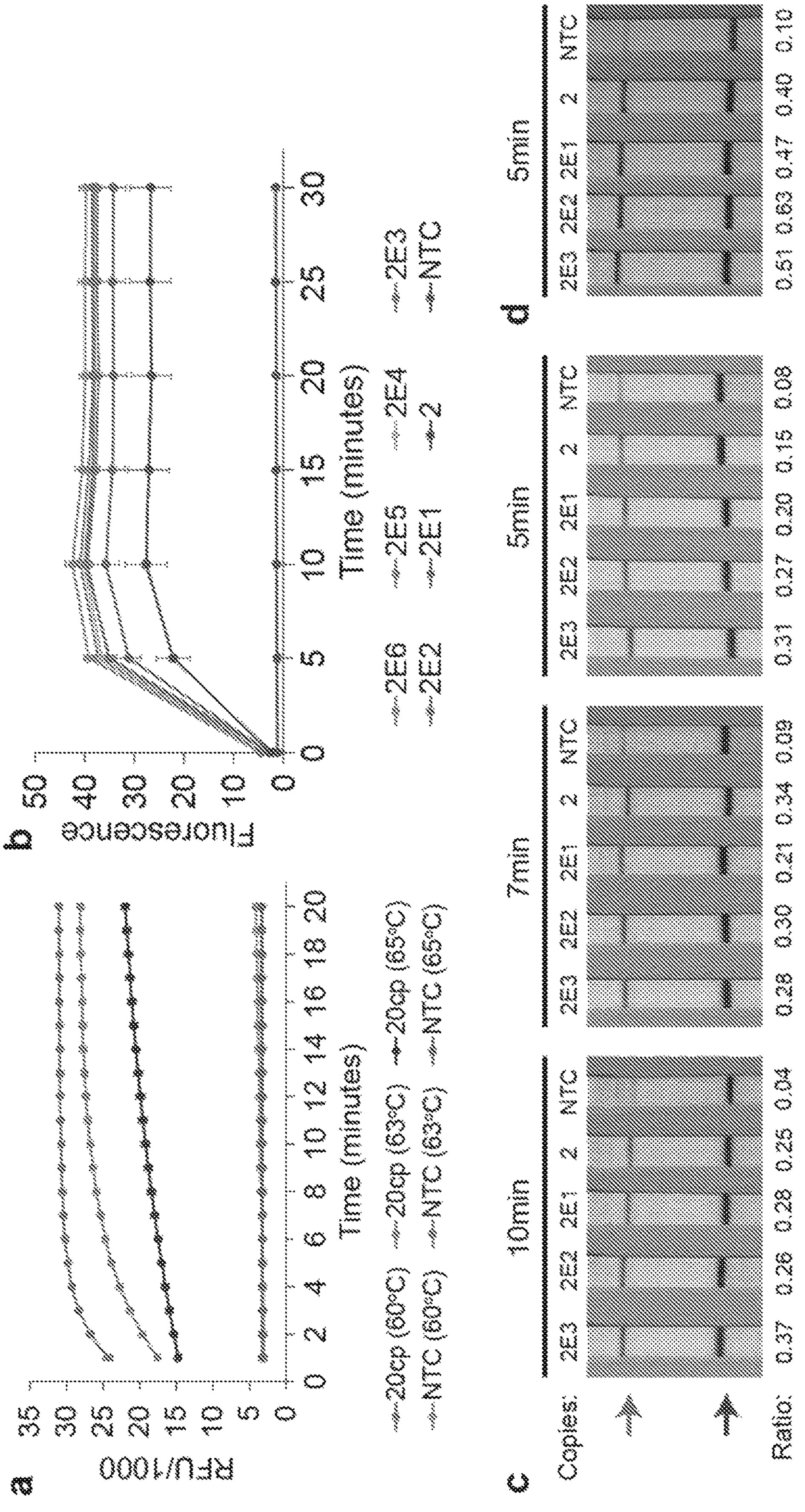
FIG. 69. Demonstration of a quasi-one-pot reaction where RT-LAMP and the Cas detection step were performed at similar temperatures.

The surprising robustness of enAsCas12a to temperature afforded an opportunity to perform the entire RT-LAMP-CRISPR workflow in a single temperature step. RT-LAMP had hitherto been performed at 65° C., while the Cas detection reaction had only been tested up till 60° C. Therefore, it has been wondered if both stages could be carried out at the same temperature. First, the CRISPR reaction has been tested at 60, 63, and 65° C. and it has been observed that while the fluorescence readout only decreased slightly at 63° C., the drop in signal was more appreciable at 65° C. (FIG. 69*a*). Next, it has been evaluated the sensitivity of the assay with RT-LAMP performed at a slightly lower temperature of 63° C., while maintaining the CRISPR step at 60° C. 14 out of 15 replicates showed successful amplification of 20 copies of synthetic viral template (FIG. 69*b*). Finally, it has been tested if the whole workflow could be performed with just one heat block set at either 63° C. or 60° C. The duration of RT-LAMP was extended from 15 to 22 minutes to accommodate for the somewhat sub-optimal temperature faced by the isothermal amplification reaction. Remarkably, the lateral flow assays revealed that positive test results could be obtained within 5 minutes of CRISPR reaction even with only 2 copies of synthetic viral template in the sample (FIG. 69*c*, 69*d*). The single heat block setup has been termed "quasi-one-pot", where the enAsCas12a RNPs were added directly into the LAMP reaction tube without the sample changing temperature. Notably, the entire assay can be completed within 30 minutes (22 minutes for RT-LAMP, 5 minutes for the trans-cleavage reaction, and 2 minutes for bands to develop on the dipsticks).

Figure 70:
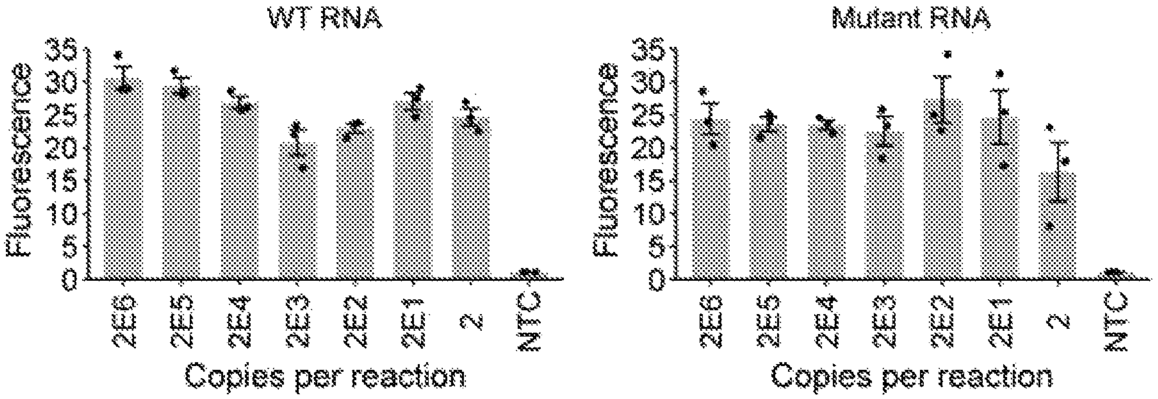
FIG. 70. Implementation of a quasi-one-pot reaction. The figure shows an analytical LoD for WT or S254F N234N double mutant RNA template using a quasi-one-pot reaction. The enAsCas12a enzyme was complexed with both the S2 and S6 hybrid guides. Fluorescence measurements here were taken after 5 minutes of trans-cleavage reaction. Data represent mean±s.e.m. (n=3 biological replicates).
Figure 71:
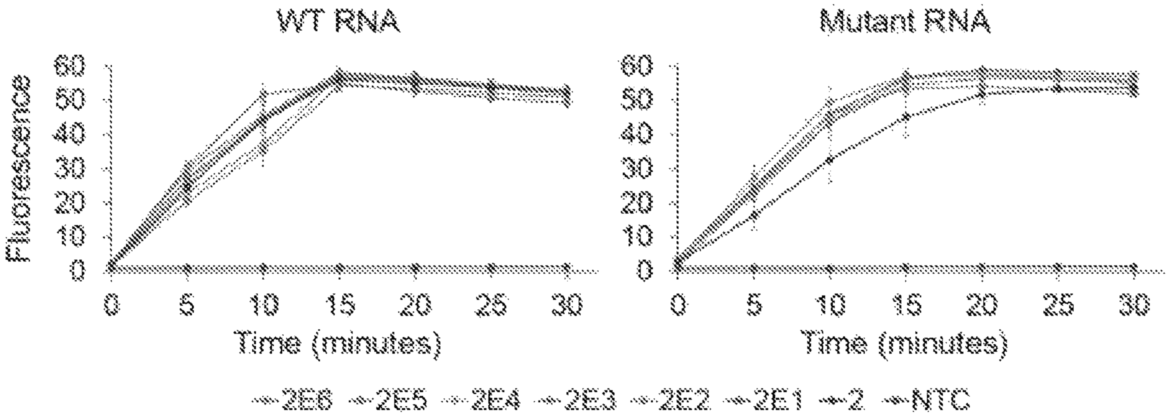
FIG. 71. Detection of a real-life mutant SARS-CoV-2 sequence using a quasi-one-pot reaction. The enAsCas12a enzyme was complexed with both the S2 and S6 hybrid guides. Different copies of synthetic SARS-CoV-2 RNA fragments (see legend) were used as input. The fluorescence measurements were taken at 5-minute intervals using a microplate reader. All readings were normalized to NTC at the start of the experiment. The analytical LoD for the wildtype template and the S254F N234N double mutant template appeared to be similar. Data represent mean±s.e.m. (n=3 biological replicates).
Figure 72:
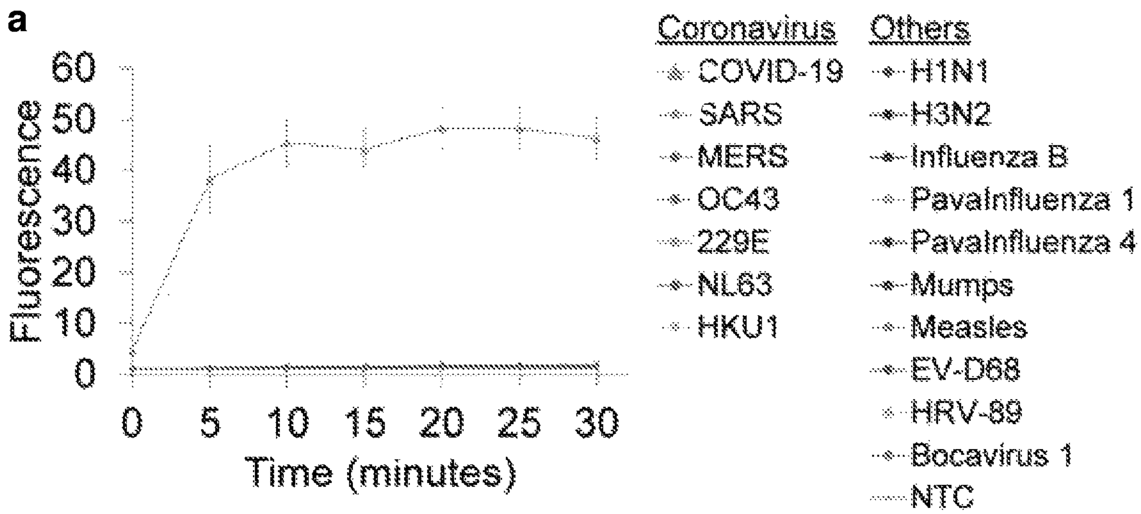
FIG. 72. Implementation of a quasi-one-pot reaction.
Figure 72:
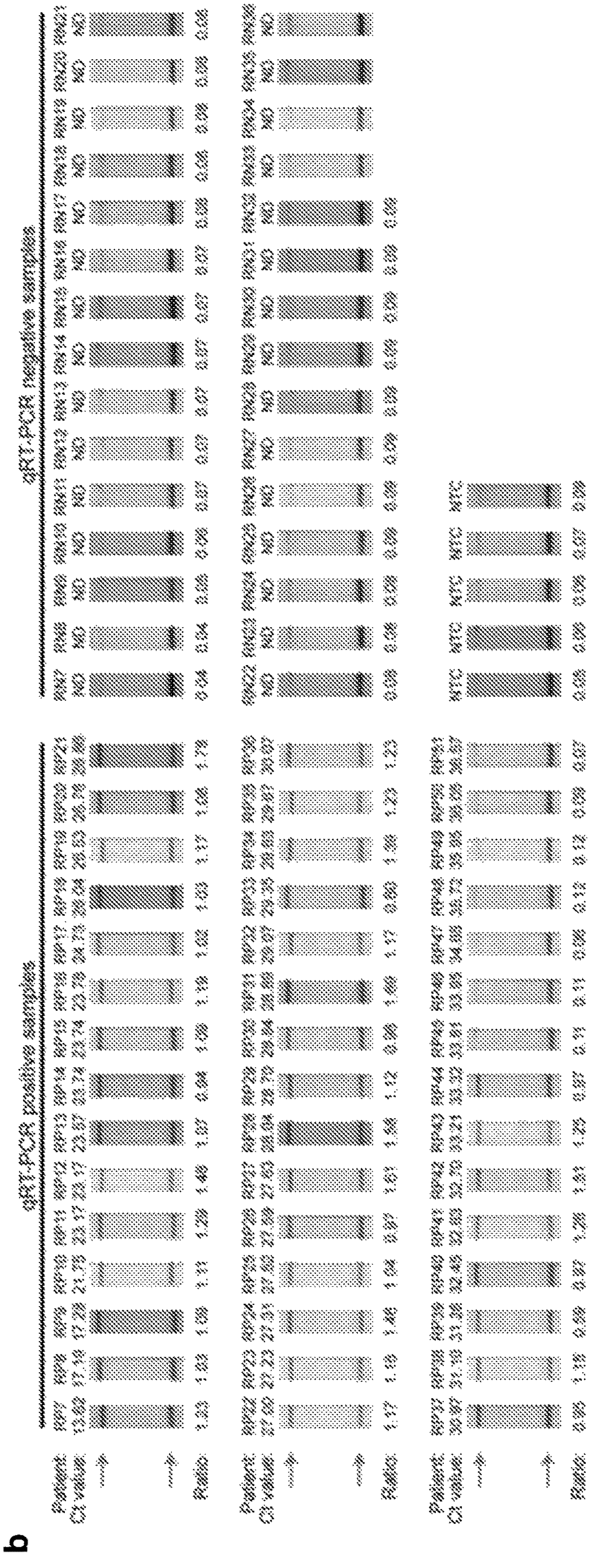
Figure 72:
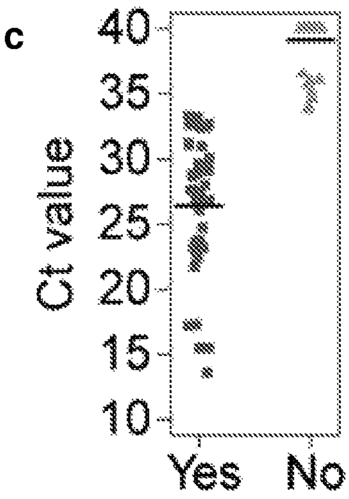

It has been asked if the quasi-one-pot setup would still be robust to SNVs at the target sites but yet exhibit exquisite specificity for SARS-CoV-2. To this end, the mismatch tolerance of the optimized assay has been examined (enAsCas12a complexed with two DNA-RNA hybrid guides) and it has been found that it showed similar sensitivity for the wildtype and the S254F N234N double mutant template (FIG. 70, 71). The assay has been further tested against a set of coronaviruses and other respiratory viruses, including influenza viruses, paramyxoviruses, and enteroviruses. Fluorescence was detected only for SARS-CoV-2 over the course of 30 minutes, thereby confirming the specificity of the test (FIG. 72*a*).

Subsequently, the CRISPR-Dx has been subjected to clinical evaluation with RNA samples isolated from patient NP swabs, which had previously been analyzed by qRT-PCR in the hospital. These samples came from 45 patients with COVID-19 and 30 uninfected individuals. Similar to the earlier pilot test (FIG. 47*a, b*), all samples that were negative by qRT-PCR also emerged negative in the lateral flow assay, confirming a 100% specificity for the assay (FIG. 72*b*). In addition, the VaNGuard test returned an unambiguous positive result for clinical samples that had a Ct value of 33.32 or lower in qRT-PCR analysis (FIG. 72*b, c*). Hence, based on these clinical RNA samples, the assay exhibited a LoD of 50 copies per reaction or 2 copies per microliter.

9. Direct Application of VaNGuard Test on Unpurified Clinical Samples

Figure 73:
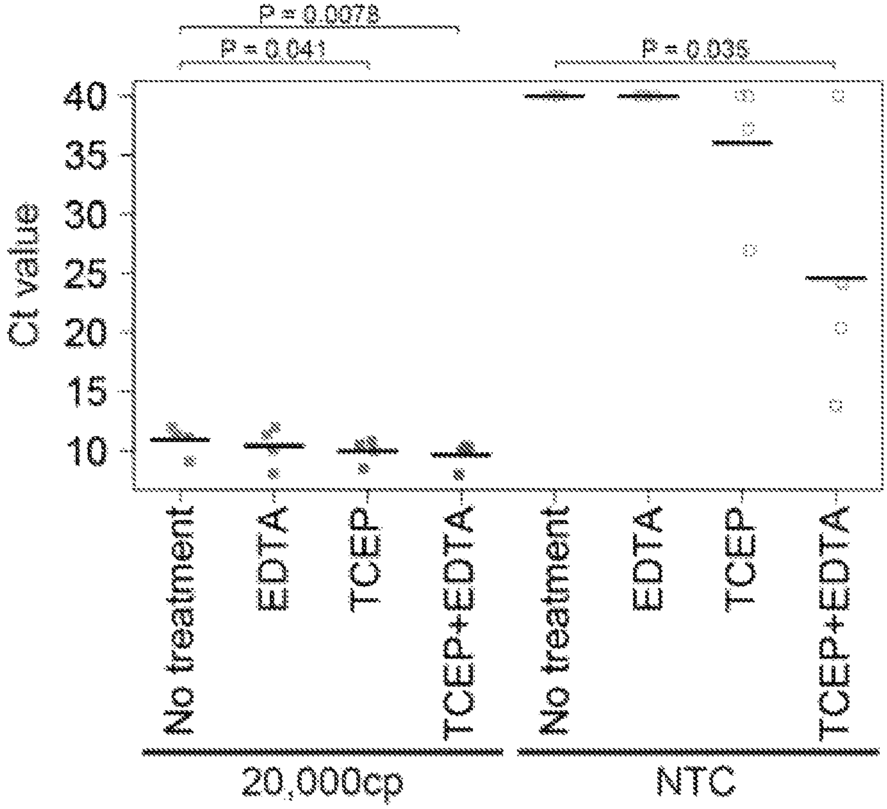
FIG. 73. Impact of TCEP and EDTA on RT-LAMP. The isothermal amplification reaction was performed at 65° C. for 15 minutes with our full set of primers (including the swarm primers and the truncated primers) in the presence or absence of 2.5 mM TCEP or 1 mM EDTA. 20,000 copies of synthetic SARS-CoV-2 RNA were used as input. Addition of TCEP and EDTA significantly improved the kinetics of RT-LAMP, but it also caused non-specific amplification. Data represent mean±s.e.m. (n=4 biological replicates). P values were calculated using one-sided Student's t-test.

An important consideration for rapid diagnostic tests is whether they can accept patient samples directly. RNA extraction usually takes at least 15 minutes and adds complexity to the workflow, thereby increasing the waiting time and making the test less usable by untrained professionals. Hence, it has been asked if the assay could be used on patient samples directly without an additional RNA isolation step. One problem with patient samples is the presence of RNases that can rapidly degrade the viral RNA that is to be detected. To inactivate RNases, first, the Hudson protocol (Myhrvold et al. (2018) Science 360, 444-448, doi:10.1126/science.aas8836) has been tried, but it has been found that addition of TCEP and EDTA triggered spurious template-free amplification at Ct values less than 25 in most of the replicates (FIG. 73).

Figure 74:
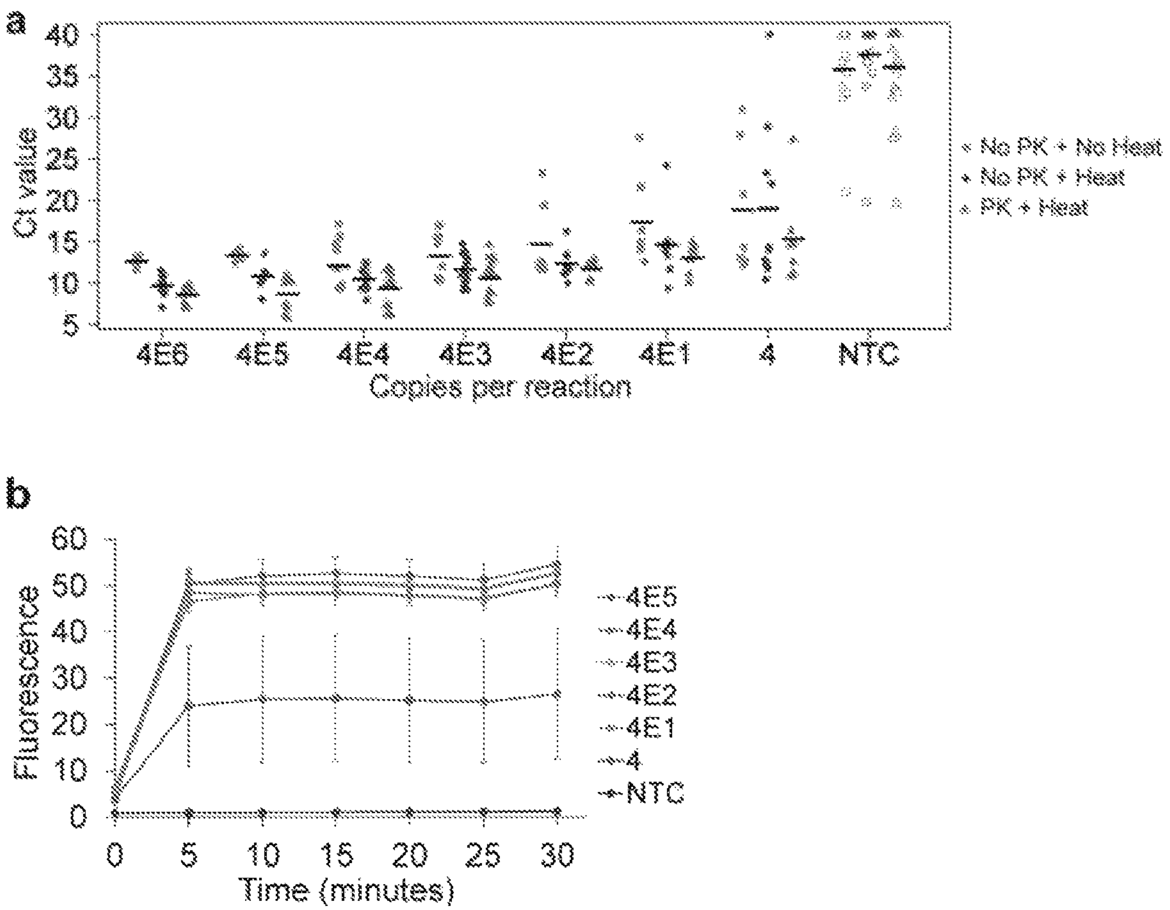
FIG. 74. Application of the VaNGuard assay on crude samples.
Figure 74:
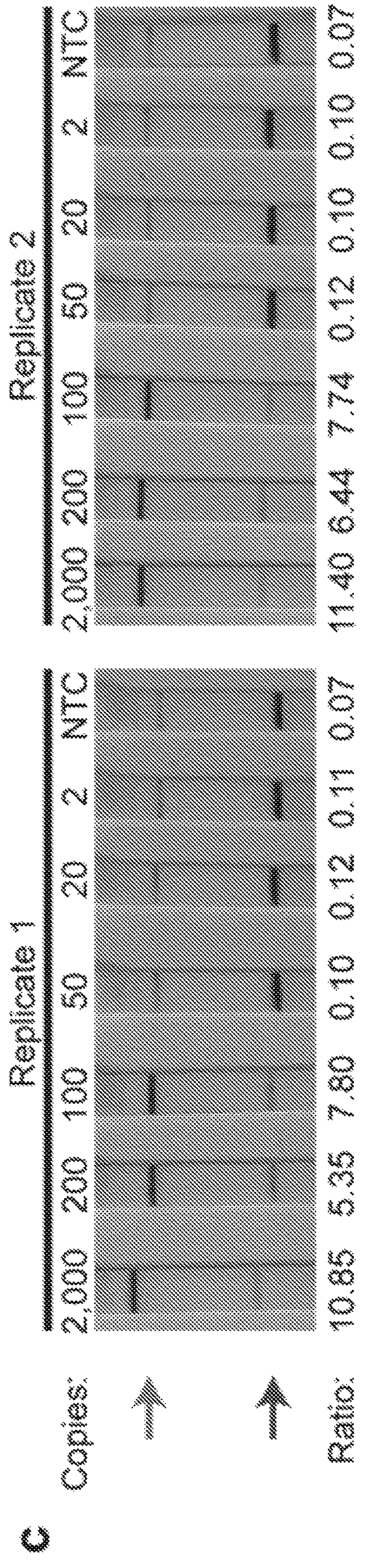
Figure 74:
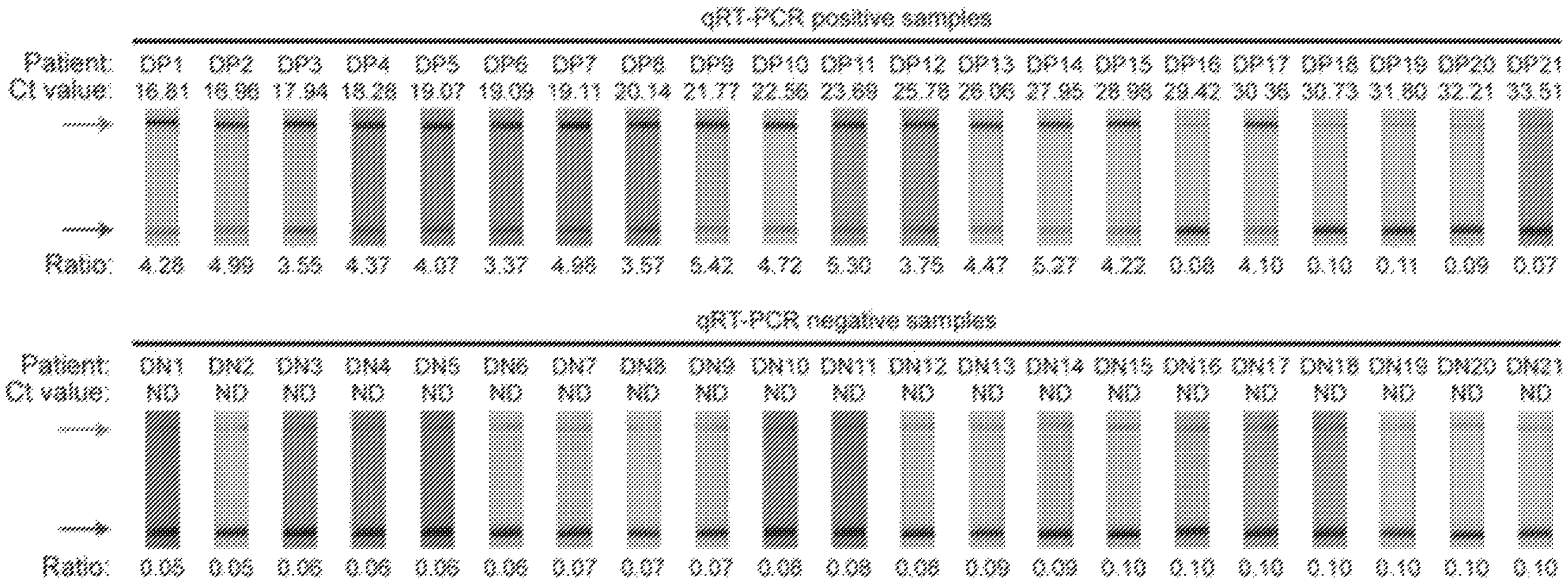
Figure 74:
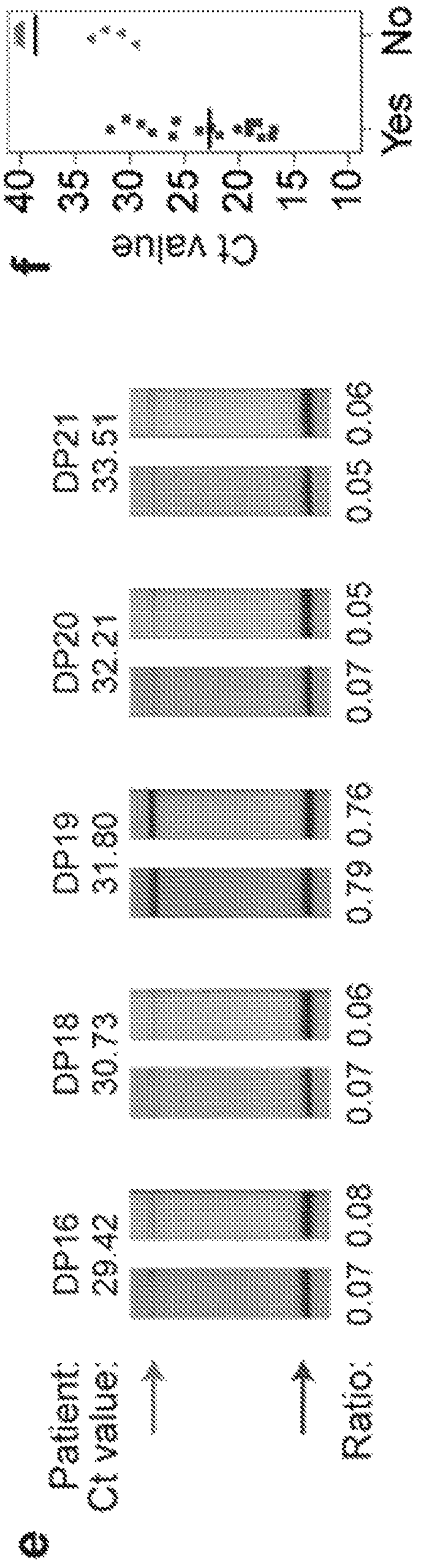

Other options have been explored for RNase inactivation, namely proteinase K treatment and heat (Lalli et al. (2020) Clin Chem, doi:10.1093/clinchem/hvaa267; Vogels, et al. (2020), doi:10.1101/2020.08.03.20167791). As simulation, it has been generated a lentivirus that expressed the relevant S-gene fragment from SARS-CoV-2 and spiked different amounts of it into human saliva. Then, the RT-LAMP reaction has been performed on the contrived specimens, which were left untreated, heated at 95° C. for 5 minutes only, or treated with both proteinase K and heat (FIG. 74*a*). In agreement with recent studies (Lalli et al. (2020) Clin Chem, doi:10.1093/clinchem/hvaa267; Vogels, et al. (2020), doi:10.1101/2020.08.03.20167791), it has been found that treatment with both proteinase K and heat appeared to improve the speed and sensitivity of RT-LAMP. Next, it has been assessed the LoD of the CRISPR-Dx using the contrived specimens as input. The samples were pre-treated with proteinase K and heat. Notably, the assay was able to detect 40 copies of the lentivirus in all replicates (FIG. 74*b*). Importantly, omission of an RNA extraction step did not affect the speed of the test, with the fluorescence signal saturating after 5 minutes of CRISPR reaction.

Next, it has been asked if this assay could detect SARS-CoV-2 virions in sample collection medium. To this end, it has been spiked different amounts of the virus produced by Vero E6 cells into clinically negative UTM, which had previously been used to collect swabs from healthy individuals. After proteinase K and heat treatment, the assay has been applied on these contrived specimens and it has been observed clear test bands on the dipsticks for 100 or more copies of SARS-CoV-2 (FIG. 74*c*).

Subsequently, it has been sought to evaluate the assay using clinical NP swabs directly without any RNA extraction. 21 samples from patients with COVID-19 infection and another 21 samples from healthy controls have been obtained. Part of these samples had previously undergone RNA extraction and qRT-PCR testing in a diagnostic laboratory, so it was possible to compare the test results of this study with the Ct values given by the laboratory. The samples have been treated with proteinase K and heat before performing the lateral flow assay (FIG. 74*d*). Expectedly, all the clinically negative specimens also turned out to be negative in the VaNGuard test, verifying its 100% specificity. In addition, the test returned an unambiguous positive result for clinical samples that had a Ct value of 28.98 or lower, which corresponded to 1000 or more copies per reaction. Curiously, it has been also observed that while the test appeared to have missed a sample with Ct value of 29.42, it correctly flagged another sample with Ct value of 30.36. Hence, to increase the likelihood of detecting the virus, the five clinically positive samples that had been misclassified with double the reaction volume and twice the amount of sample input (FIG. 74*e*) have been re-tested. However, the test correctly identified only one extra sample, which had a Ct value of 31.80. Overall, unlike the earlier clinical evaluation with purified RNA samples (FIG. 72*b, c*), the boundary for the Ct value between a positive and a negative outcome in the test was not as clear-cut for the crude NP swab samples (FIG. 74*f*). For Ct values between 29 and 32, the assay may return a positive or a negative result. This ambiguity may be due to the unknown and potentially complex sample matrix (for example, mucus from the nose), which can vary from specimen to specimen and exert some inhibitory effect on the assay enzymes. Moreover, the extent of viral RNA recovery during the purification process in the diagnostic laboratory may not be perfectly consistent especially for samples with low viral loads. Therefore, a specimen that actually had a higher viral load in the original NP swab might end up having a poorer Ct value due to greater sample loss. Taken together, these results indicate that although more challenging, the VaNGuard test can be applied directly on patient samples without additional RNA purification, with a LoD of 1000 copies per reaction or 40 copies per microliter. As the swabs used in this study were collected in 3 ml of UTM and only 2 μl were taken for the test, the sensitivity may be better if the swabs had been collected in a smaller volume of medium.

10. Incorporating a Human Internal Control Within the Same Reaction

Figure 75:
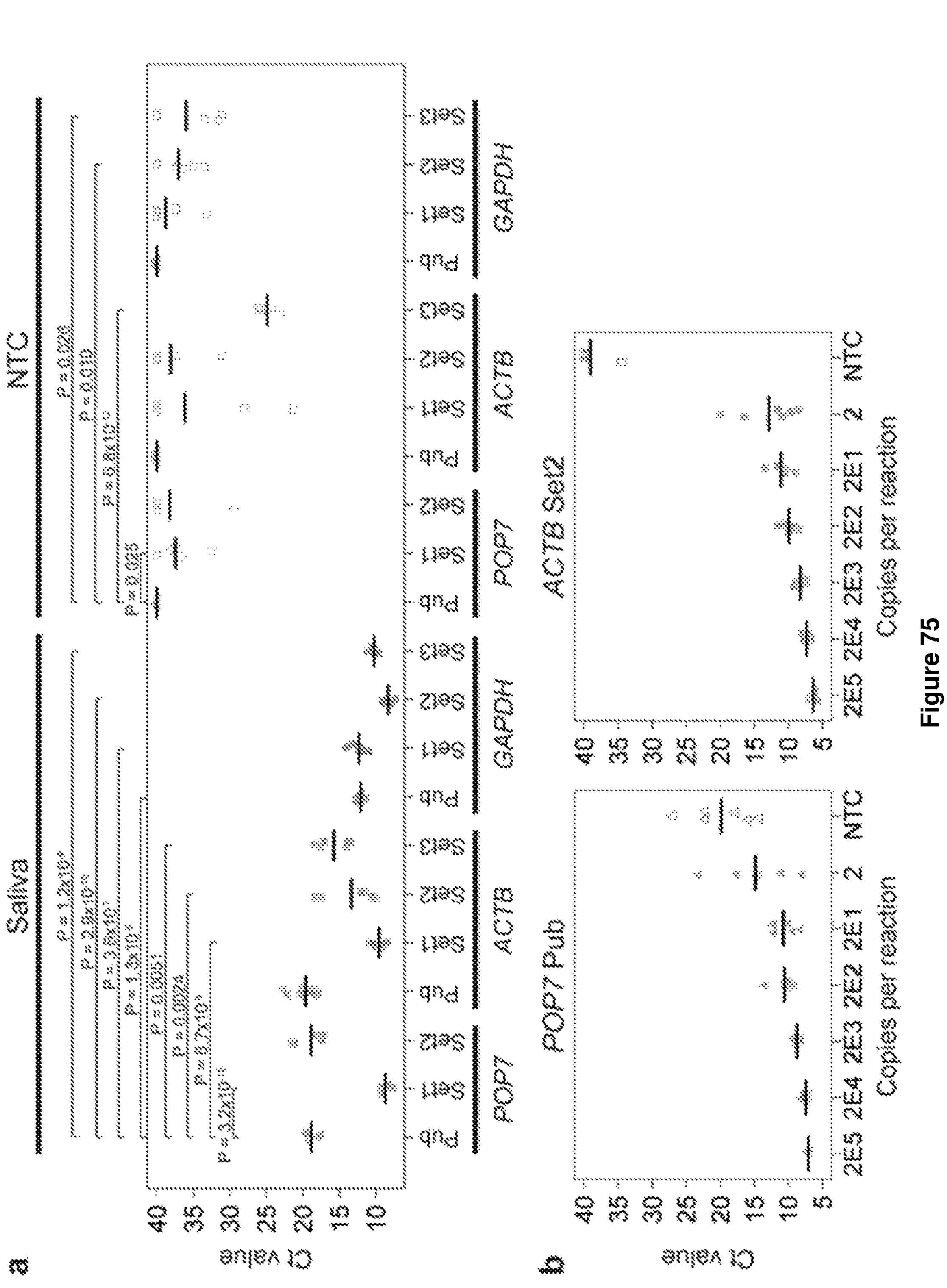
FIG. 75. Development of a human internal control for our VaNGuard test.

A diagnostic test for COVID-19 should include a human internal control to verify that a negative result is due to an absence of the virus and not simply due to insufficient sample input. To this end, it has been sought to identify a suitable set of LAMP primers targeting some housekeeping gene to use in this assay. Three primers sets against POP7, four primer sets against ACTB, and four primer sets against GAPDH, have been screened using heat-treated human saliva as sample input (FIG. 75*a*). All primer sets gave amplification products successfully, albeit at different rates. Furthermore, a few primer sets also yielded spurious by-products without a template.

Figure 76:
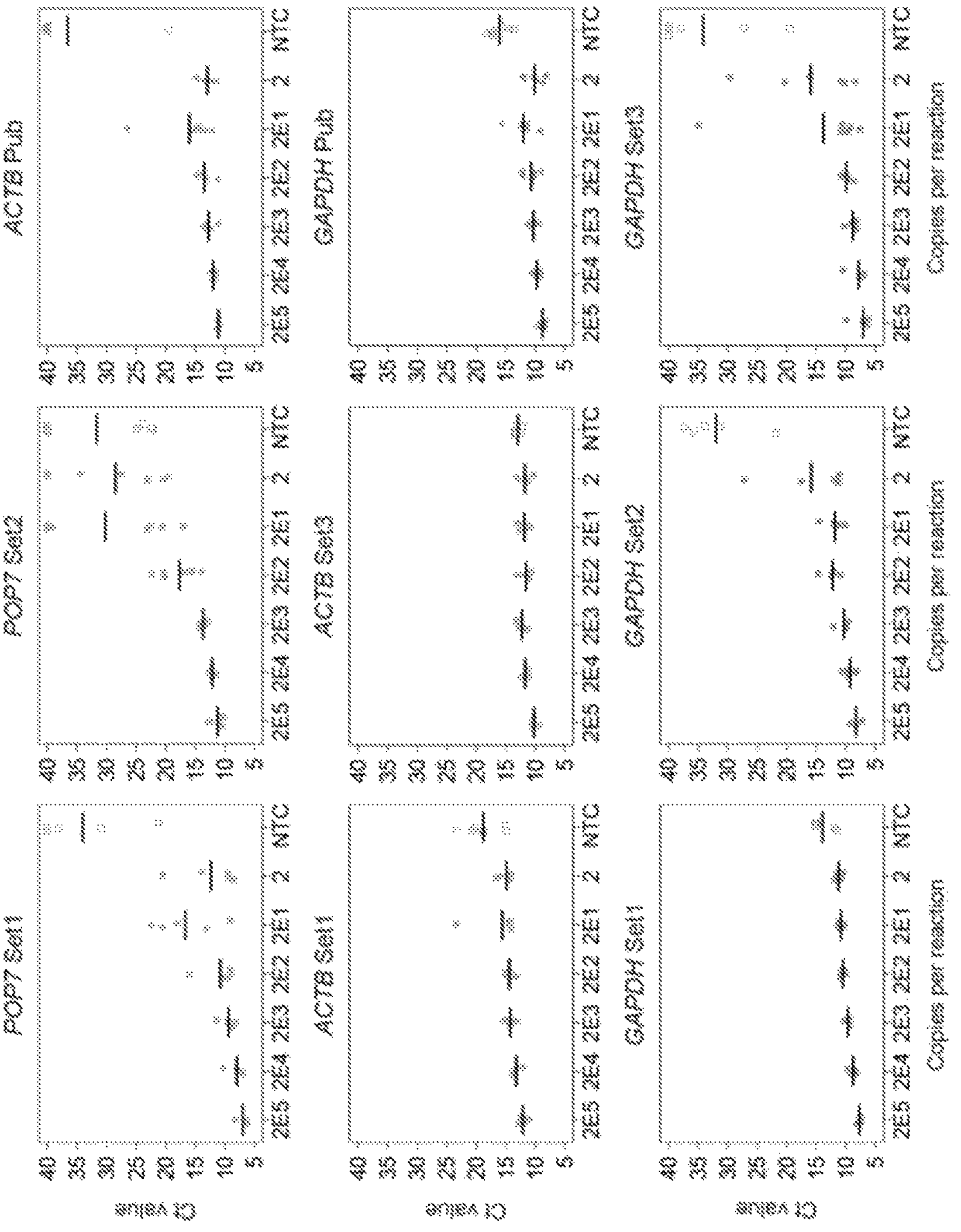
FIG. 76. Strip chart showing the effect of different sets of human primers targeting POP7, ACTB, or GAPDHon isothermal amplification of the SARS-CoV-2 S-gene. Different copies of synthetic SARS-CoV-2 RNA were used as sample input to RT-LAMP, which was performed at 65° C. over 40 minutes in a real-time instrument. The black horizontal bars among the data points in the strip chart represent the mean (n=3 [POP7Set1 2E5, GAPDHSet2 2E5], 5 [POP7Set1 all except 2E5, GAPDHSet2 all except 2E5], 6 [ACTBPub and Set3, GAPDHPub and Set1+3], 7 [ACTBSet1], or 8[POP7Set2] biological replicates).

Ideally, the internal control should be built into the same reaction tube as the COVID-19 test. Hence, next it has been evaluated if the human primers would interfere with the SARS-CoV-2 primers in the RT-LAMP reaction (FIG. 75*b*, 76). Variable copies of synthetic viral RNA template were used. Interestingly, it has been observed that a few primer sets, such as the POP7-targeting primers deployed in the DETECTR system (Broughton et al. (2020) *Nat Biotechnol*, doi:10.1038/s41587-020-0513-4), caused non-specific amplification. It has been selected an ACTB-targeting primer set to proceed with because it did not trigger any serious mis-amplification without template and our SARS-CoV-2 LAMP primers continued to amplify well in its presence even at low copy numbers of viral RNA.

Figure 77:
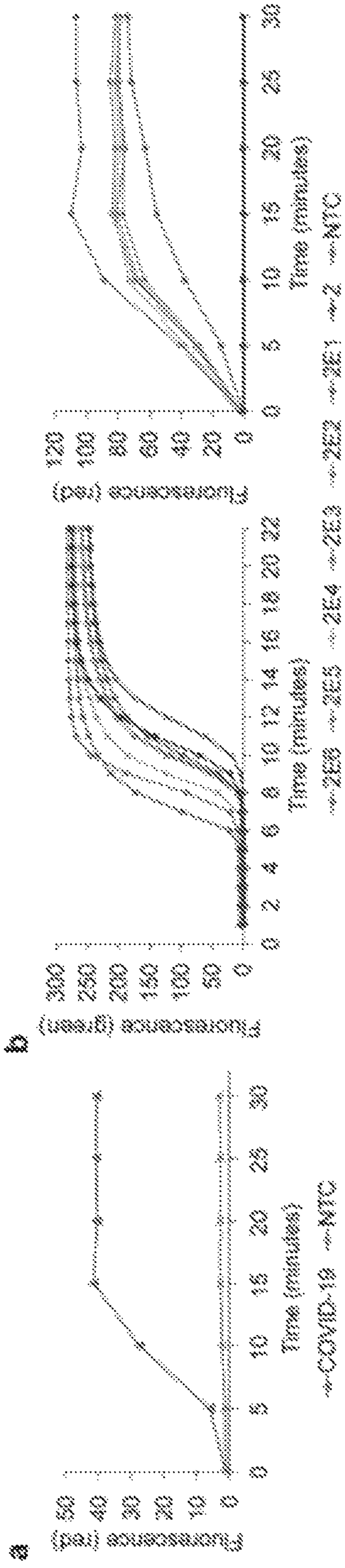
FIG. 77. Trans-cleavage assays with a Cy5-quencher reporter.

To incorporate an internal control within the same reaction tube as the COVID-19 test, a fluorescence readout has to be used instead of dipsticks and two colours are required to distinguish SARS-CoV-2 amplicons from human amplicons. It has been first replaced the green fluorophore (FAM) in the CRISPR reporter with a red fluorophore (Cy5) and it has been verified that the signal was similar (FIG. 77*a*). Then, it has been checked the sensitivity of the assay using synthetic viral RNA spiked into heat-treated saliva. The reaction mix contained a generic green DNA-binding dye and the Cy5-reporter. Encouragingly, it has been observed that the assay could detect 20 or more copies of viral RNA even with concomitant amplification of human ACTB (FIG. 77*b*). Furthermore, green, but not red, fluorescence was detected for the no-template control reaction as desired.

Figure 78:
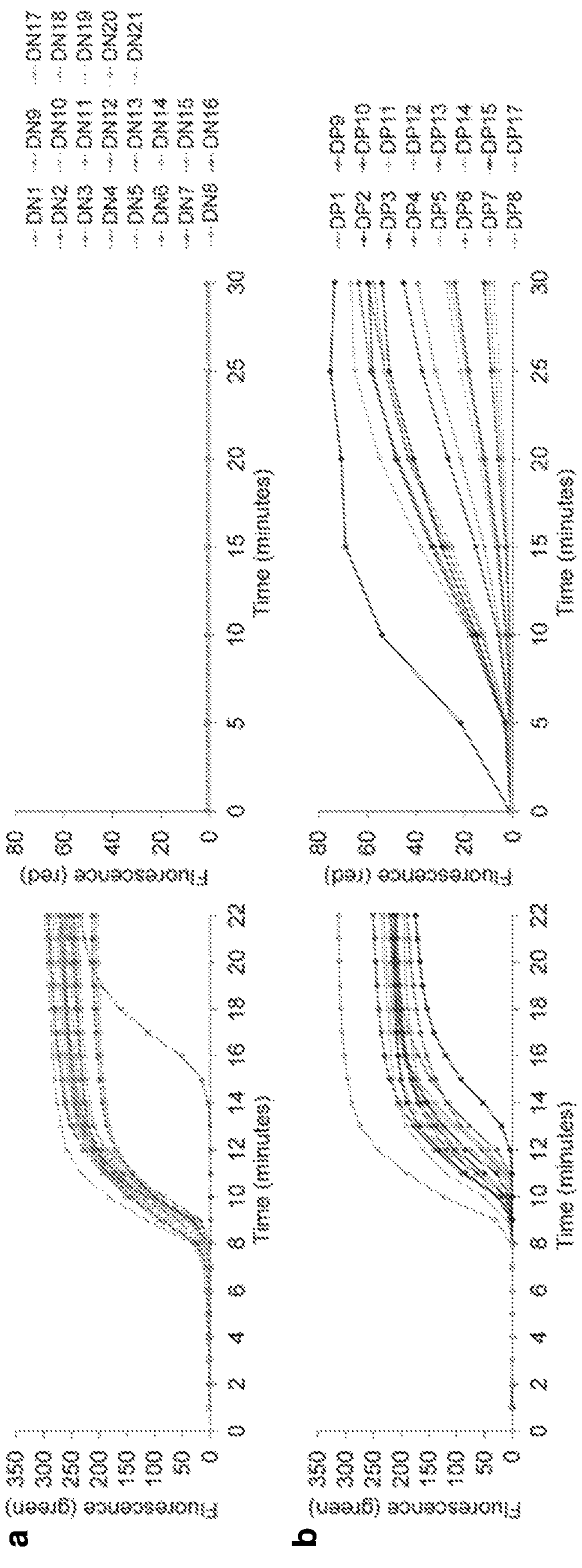
FIG. 78. Development of a human internal control for our VaNGuard test. The figures show the evaluation of the prototype VaNGuard assay containing a human internal control using (a) clinically negative and (b) clinically positive NP swab samples. The green fluorescence originates from a generic DNA-binding dye, while the red fluorescence originates from a Cy5-quencher reporter specific for SARS-CoV-2. Each sample was treated with proteinase K and heat before 2 μl was used as input to the quasi-one-pot reaction.

Subsequently, it has been sought to evaluate the assay with the internal control on unpurified clinical samples. To this end, it has been utilized the same set of NP swabs that was evaluated earlier using dipsticks (FIG. 74*d-f*). For all the qRT-PCR negative samples, amplification was observed for human ACTB but not for the S-gene of SARS-CoV-2 as expected (FIG. 78*a*). For the qRT-PCR positive samples, it has been focused on those that had been classified correctly in the original assay. Amplification was observed in both the green and red channels for every sample (FIG. 78*b*). However, the CRISPR reaction kinetics for many samples was slower than expected.

Figure 79:
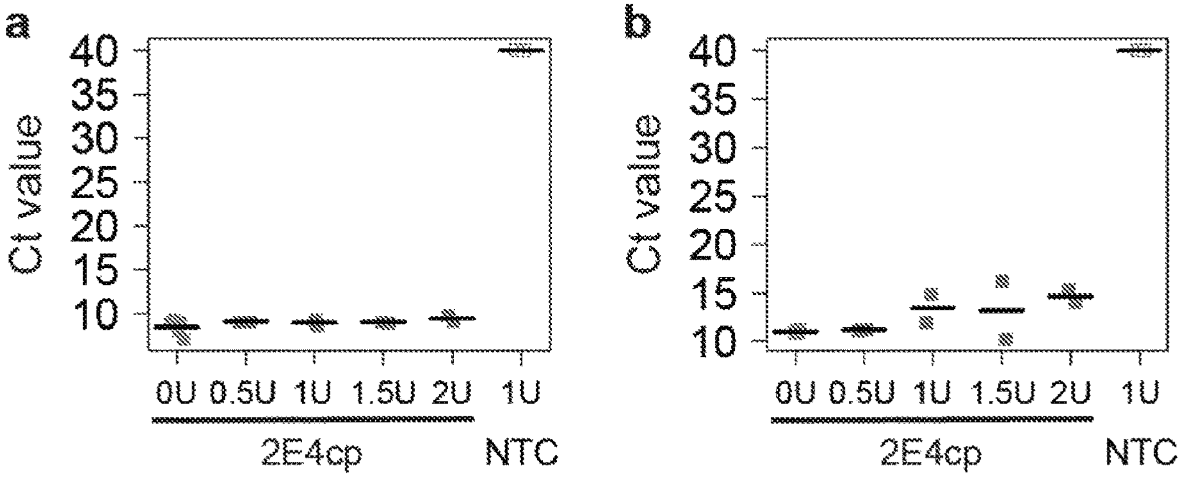
FIG. 79. Effect of pyrophosphatase on RT-LAMP.
Figure 80:
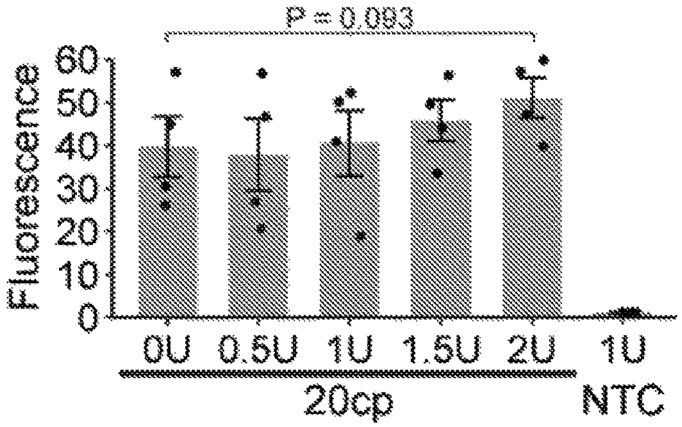
FIG. 80. Development of a human internal control for our VaNGuard test. The figure shows 20 copies of synthetic SARS-CoV-2 RNA that were used as input to the quasi-one-pot reaction with different amounts of pyrophosphatase added during the Cas detection step. The fluorescence measurements here were taken after 5 minutes of trans-cleavage reaction. Data represent mean±s.e.m. (n=4 biological replicates). P value was calculated using one-sided Student's t-test.
Figure 81:
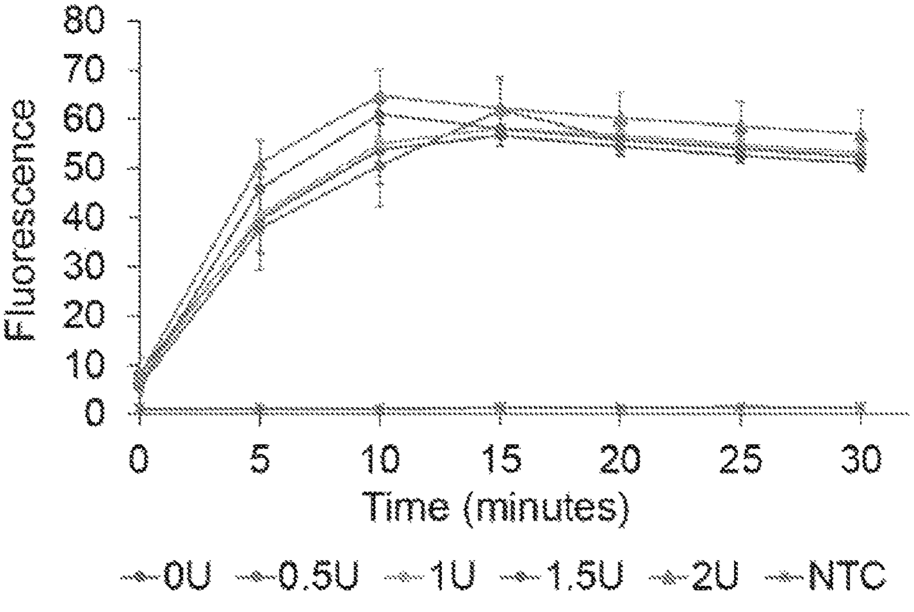
FIG. 81. Effect of pyrophosphatase on the CRISPR module. 20 copies of synthetic SARS-CoV-2 RNA were used as input to the quasi-one-pot reaction with different amounts (0-2 U) of pyrophosphatase added during the Cas detection step. Fluorescence measurements were taken at 5-minute intervals of the trans-cleavage reaction using a microplate reader. Data represent mean±s.e.m. (n=4 biological replicates).
Figure 82:
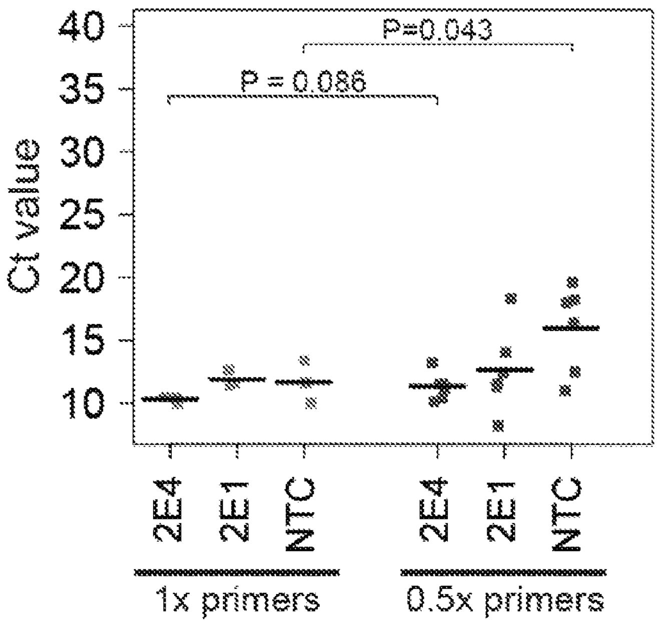
FIG. 82. Effect of halving the amount of human LAMP primers on amplification efficiency. 2E1 or 2E4 copies of synthetic SARS-CoV-2 RNA spiked into heat-treated saliva were used as sample input to RT-LAMP, whose reaction mix contained a green DNA-binding dye, the human LAMP primers, and the SARS-CoV-2 LAMP primers. The black horizontal bars among the data points in the strip chart represent the mean (n=3 biological replicates, with each biological replicate of 0.5× primers performed in two technical replicates). P values were calculated using one-sided Student's t-test.
Figure 83:
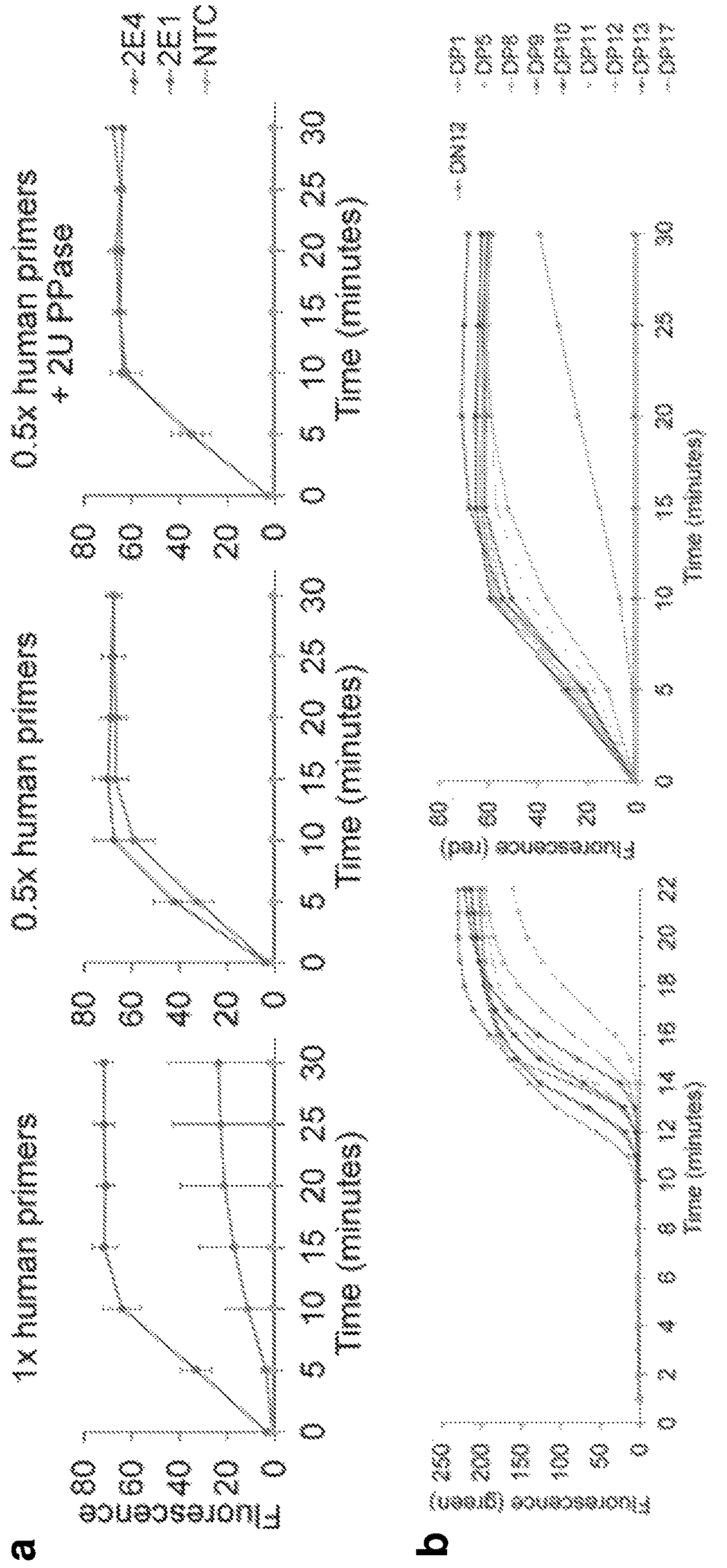
FIG. 83. Development of a human internal control for our VaNGuard test.

It has been sought to improve the assay with the internal control, using synthetic viral RNA spiked into heat-treated saliva in the troubleshooting experiments. During the LAMP reaction, a large amount of pyrophosphate is produced, causing magnesium to precipitate out of solution. It has been wondered whether this would reduce the concentration of magnesium ions available for reaction over time or whether the pyrophosphate was inhibitory to the CRISPR reaction. Hence, it has been tested if addition of a thermostable pyrophosphatase would improve the VaNGuard test. While addition of up to 2 U pyrophosphatase did not appear to improve RT-LAMP (FIG. 79), it did appreciably enhance the kinetics of the Cas detection reaction (FIG. 80, 81). Next, it has been hypothesized that the human primers were competing with the SARS-CoV-2 primers for LAMP reagents. Hence, it has been investigated the effect of halving the amount of human ACTB primers in the assay. Overall, reduction in the concentration of the human primers led to a perceivably slower rate of green fluorescence generation presumably due to less efficient amplification of ACTB (FIG. 82). Nevertheless, it did not prevent any of the replicates from amplifying successfully within the RT-LAMP duration of 22 minutes. In addition, it has been discovered that usage of less human primers clearly enhanced the sensitivity of the assay for SARS-CoV-2 (FIG. 83*a*). Further addition of 2 U pyrophosphatase in the Cas detection reaction also enhanced the kinetics of the reaction.

Finally, it has been wondered how the improved version of the assay with internal control would perform on real patient samples. The clinically positive NP swabs that yielded weaker-than-expected red fluorescence signals in the earlier dual-colour assay (FIG. 78*b*) have been re-evaluated. Additionally, DN12 has been re-analysed as it previously showed later amplification of ACTB than the other clinically negative samples (FIG. 78*a*) and thus it has been concerned that halving the amount of human primers might prevent the internal control from working in this specimen. The re-test revealed that adjustment of LAMP primer concentrations and addition of 2 U pyrophosphatase enabled more robust detection of SARS-CoV-2 in every clinically positive NP swab (FIG. 83*b*). Furthermore, amplification was still observed for the human ACTB gene, but not for the S-gene of SARS-CoV-2, in DN12. Taken together, the results demonstrate that the VaNGuard test containing an internal control within the same reaction can be successfully applied on crude clinical samples without RNA extraction.

11. Conclusion

A novel CRISPR-based assay has been developed. To bolster the robustness of this test against unexpected variant nucleotides introduced by evolutionary pressures or RNA editing, several distinct strategies have been implemented. First, several Cas12a enzymes have been tested and it has been found that enAsCas12a exhibited the highest tolerance for SNVs at the gRNA-target interface. Second, it has been demonstrated that the use of two gRNAs (S2 and S6) with enAsCas12a further enhanced the robustness of the assay. Third, truncated primers and a high-fidelity polymerase have been incorporated into the RT-LAMP reaction. With all these strategies in place, it has been showed that this VaNGuard test was able to detect low copies of viral RNA that harboured known mutations in some SARS-CoV-2 isolates from around the world.

Besides robustness to SNVs in the viral genome, this VanGuard test also possesses other strengths. It has been found that the use of modified gRNAs, in particular hybrid DNA-RNA guides, accelerated the Cas detection reaction and suppressed any residual background activity to negligible levels. In addition, it has been discovered that enAsCas12a exhibited surprising robustness to reaction temperature and was active from 37° C. to over 60° C. This enabled the performance of RT-LAMP and the Cas detection reaction in a single heat block at the same temperature. Furthermore, to maximize the real-world utility of the test, it has been demonstrated that it could be applied directly on crude clinical samples without any RNA extraction and it has been also successfully incorporated an internal control into the same reaction tube through the optimization of LAMP primer concentrations and the use of pyrophosphatase to reduce the built-up of pyrophosphate. The optimized VaNGuard test exhibits high specificity for SARS-CoV-2 and does not show any cross-reactivity with 16 other coronaviruses or respiratory viruses. To facilitate the interpretation of test results by a layperson, a mobile phone app has been developed to analyse dipsticks (data not shown) as well as designed and built a cheap do-it-yourself device from discarded cartons that allowed fluorescence signals from the trans-cleavage assay to be readily visualized using light from a mobile phone (data not shown). Overall, the cost of running the VaNGuard test is under S$10 per sample (data not shown), which is around US$7.30 or €6.20. Bulk of the cost comes from the LAMP mastermix and the dipstick.

Figure 59:
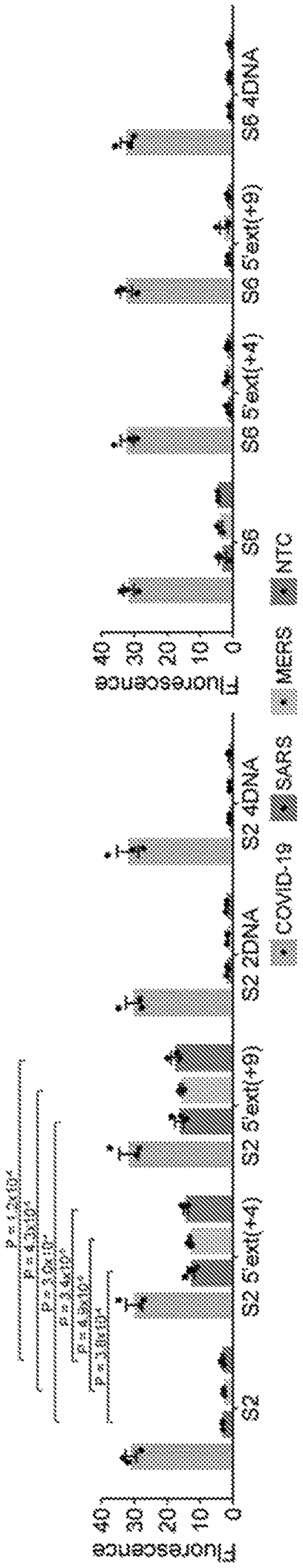
FIG. 59. Guide engineering to enhance the CRISPR detection module. The figure shows the comparison of 5'-extended gRNAs and DNA-RNA hybrid guides with the corresponding unmodified gRNAs at 60° C. for enAsCas12a. The S2-targeting and S6-targeting guides were tested separately. Fluorescence measurements here were taken after 30 minutes of cleavage reaction with 2E11 copies of synthetic DNA. Data represent mean±s.e.m. (n=3 biological replicates). P values were calculated using one-sided Student's t-test.

While this project was ongoing, a paper was published reporting that gRNAs with 3' extensions, but not 5' extensions, yielded more collateral cleavage in vitro than their unmodified counterparts (Nguyen et al. (2020) Nat Commun 11, 4906, doi:10.1038/s41467-020-18615-1). However, it has been obtained opposite results in this work. Specifically, it has been found that gRNAs with UA-rich 3' extensions did not consistently enhance the trans-cleavage activity of Cas12a and in fact often gave poorer assay performance (FIG. 48). In contrast, the S2 and S6 gRNAs with 9-nt 5' extensions produced appreciably more collateral cleavage instead (FIG. 49*b*, 55*b*, 57), although it had been observed that the 5' extended S2 gRNA triggered spurious template-free amplification at 60° C. for some unknown reason (FIG. 59). Considering all the results, it has been speculated that gRNA extensions, regardless of whether they are at the 3' end or the 5' end, might disrupt RNA structure in unexpected ways and thus may not represent a generalizable strategy to enhance the efficiency of the CRISPR-Cas detection module in diagnostic applications. Consequently, in the final VaNGuard test, it has been adopted guides whose overall sequences remained unchanged compared to wildtype but instead contained DNA nucleotide substitutions at specific locations within the spacer.

Figure 84:
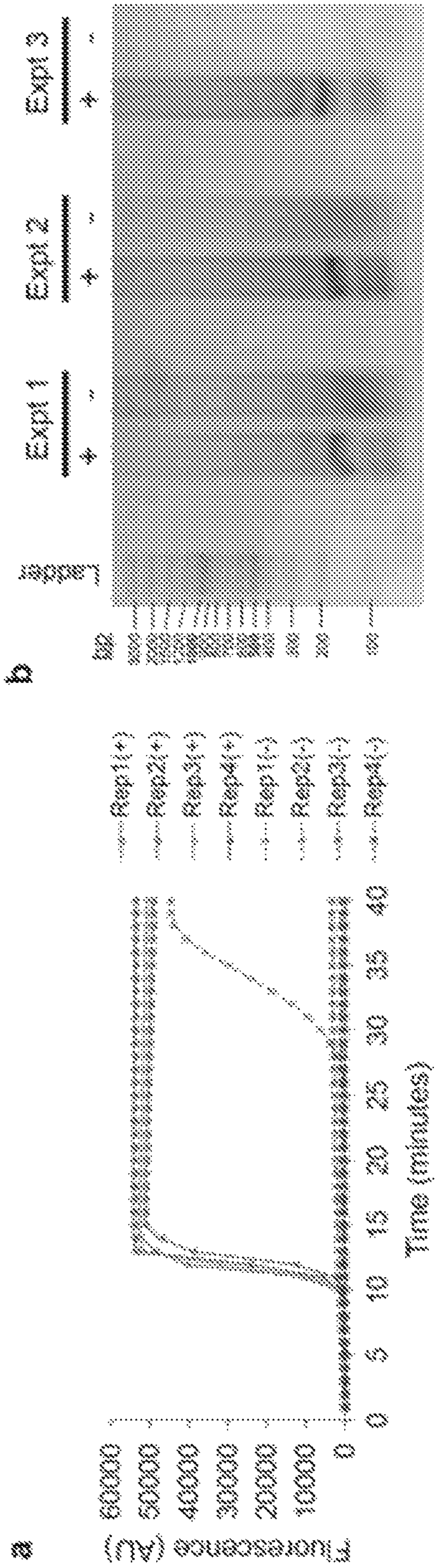
FIG. 84. Spurious amplification in LAMP.
Figure 85:
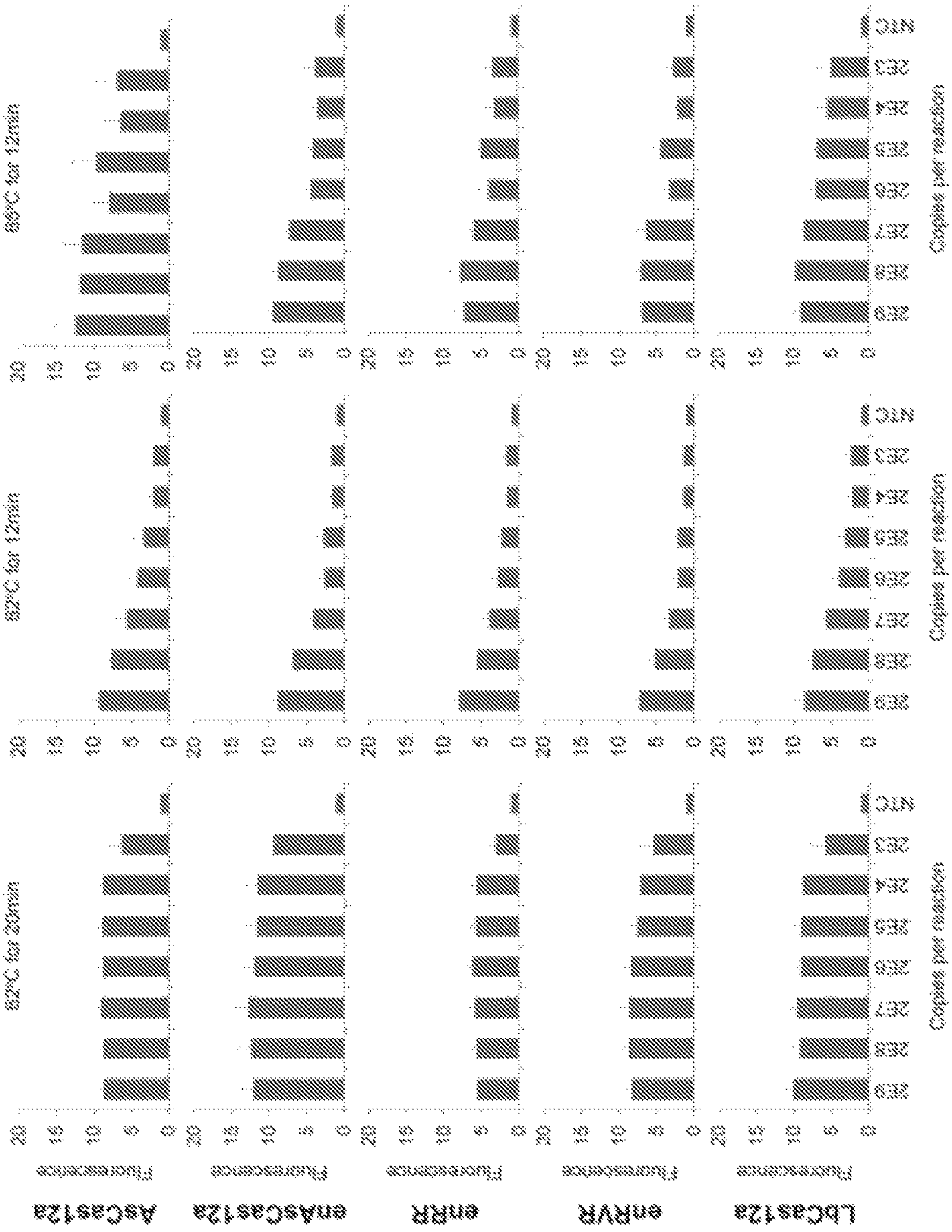
FIG. 85. Analytic limit of detection (LoD) under various LAMP reaction conditions. Different copies of synthetic SARS-CoV-2 RNA fragments were used as input and the volume of each RT-LAMP reaction was 25 μl. The fluorescence readings here were taken after 10 minutes of cleavage reaction. Data represent mean±s.e.m. (62° C. for 20 min: n=4-7 biological replicates; 62° C./65° C. for 12 min: n=3 biological replicates).
Figure 86:
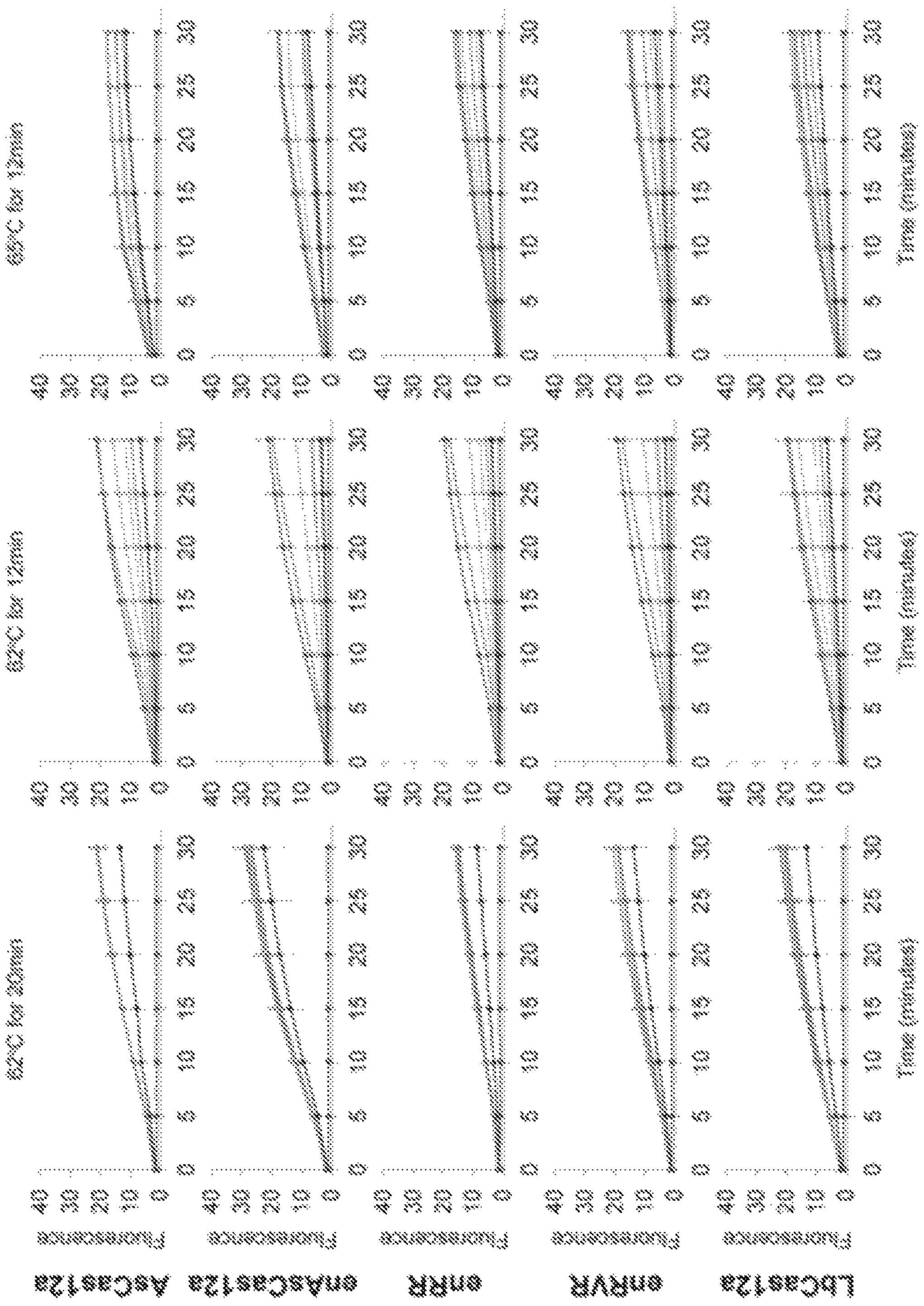
FIG. 86. Time courses of the fluorescence intensity in our trans-cleavage assays for various Cas12a nucleases complexed with perfect matched (PM) N-Mam gRNAs of spacer length 20nt. Before the Cas detection reaction, various copies of in vitro transcribed SARS-CoV-2 RNA fragments (see legend) were used as input to an RT-LAMP reaction performed under three different conditions (62° C. for 20 minutes, 62° C. for 12 minutes, and 65° C. for 12 minutes). Subsequently, 4 μl LAMP products (out of 25 μl) were used for the cleavage assays, which were performed at 24° C. Data represent mean±s.e.m. (62° C. for 20 min: n=4-7 biological replicates; 62° C./65° C. for 12 min: n=3 biological replicates).
Figure 87:
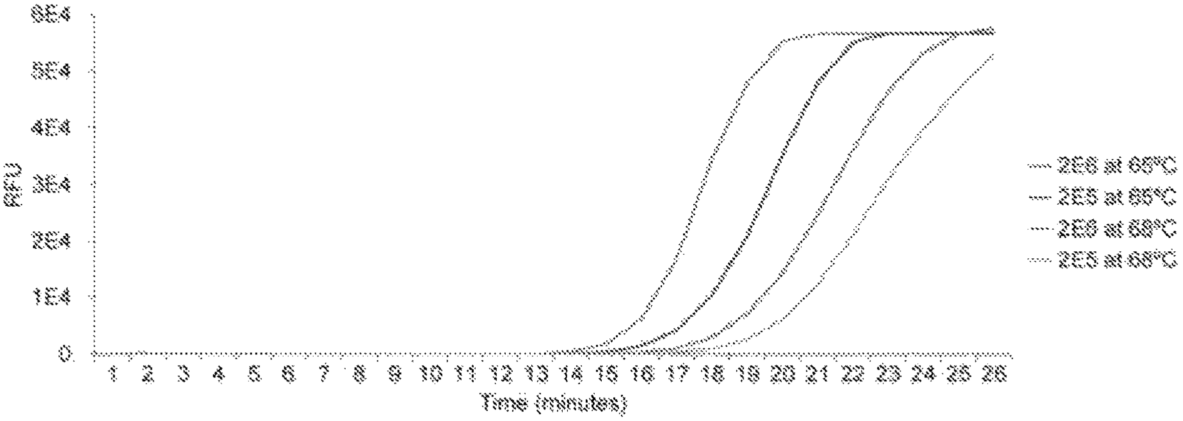
FIG. 87. Real-time monitoring of the RT-LAMP reaction performed at two different temperatures, 65° C. and 68° C. Fluorescence signal was generated by the addition of a dye that was provided with the WarmStart LAMP kit (New England Biolabs). 2E5 and 2E6 copies of synthetic SARS-CoV-2 RNA input were tested.
Figure 88:
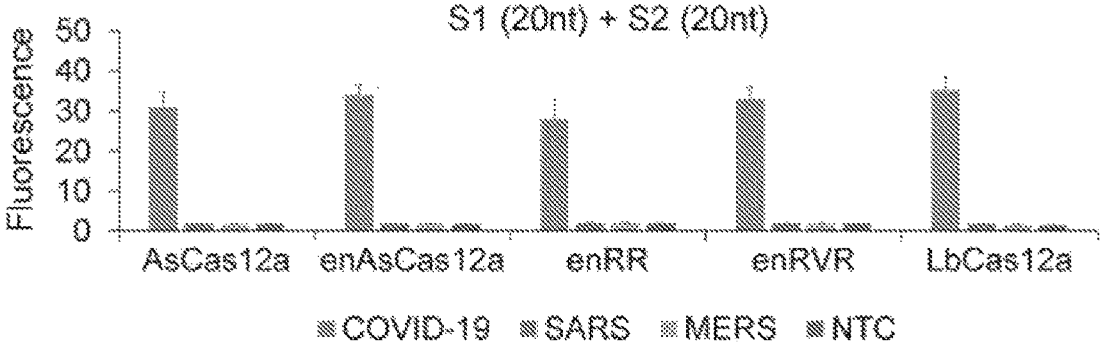
FIG. 88. Fluorescence measurements for two PM gRNAs (S1 and S2) after 30 minutes of cleavage reaction at 37° C. No cross-reactivity for SARS-CoV or MERS-CoV was observed. Data represent mean±s.e.m. (n=3 biological replicates).
Figure 89:
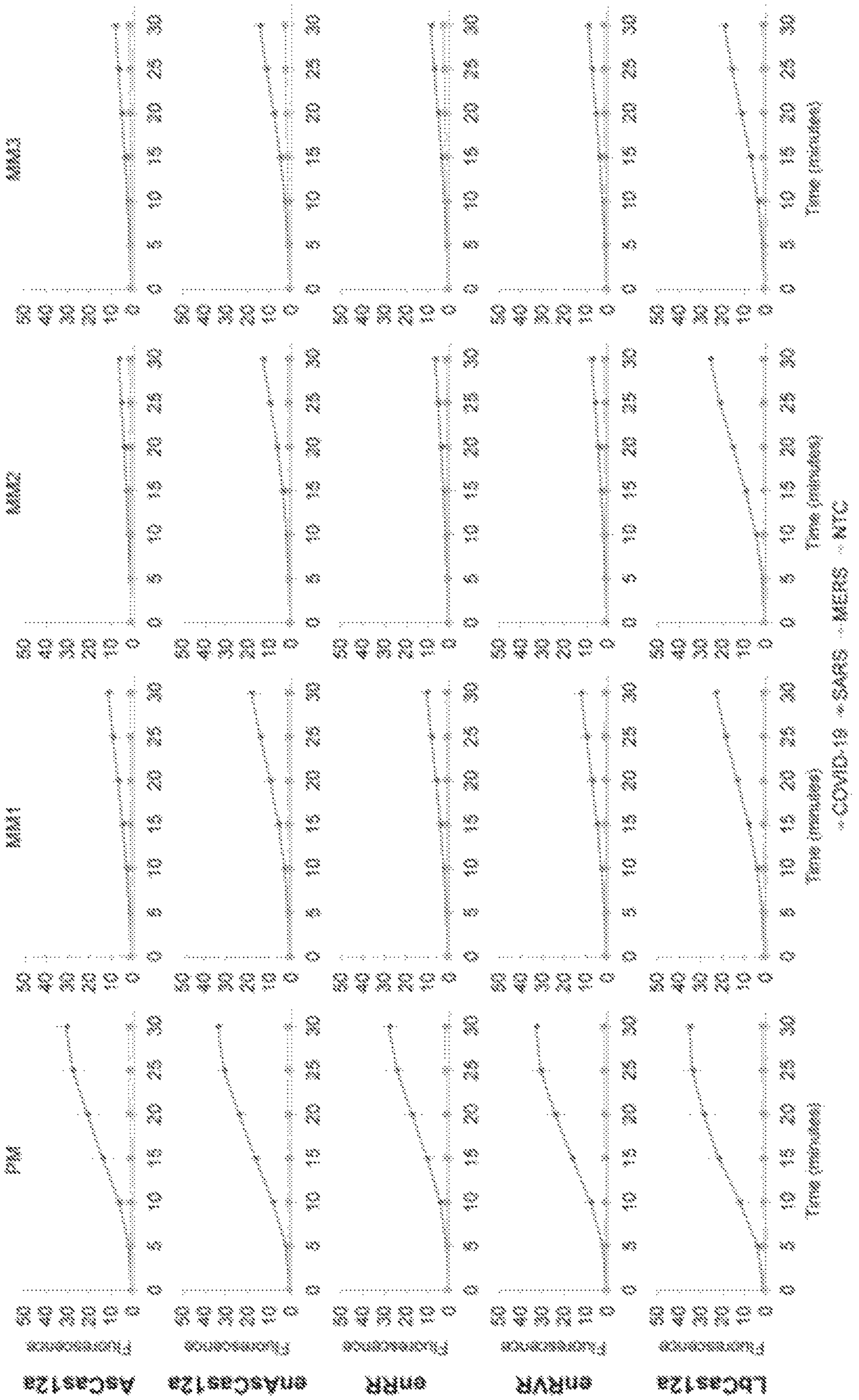
FIG. 89. Time courses of the fluorescence intensity in the trans-cleavage assays for various Cas12a nucleases assembled with two gRNAs—S1 PM gRNA and S2 PM or MM gRNA. All the guides tested here have a spacer length of 20nt. The assays were performed at 37° C. and approximately 1E11 copies of purified DNA template were used as input. Data represent mean±s.e.m. (n=3 biological replicates).
Figure 89:
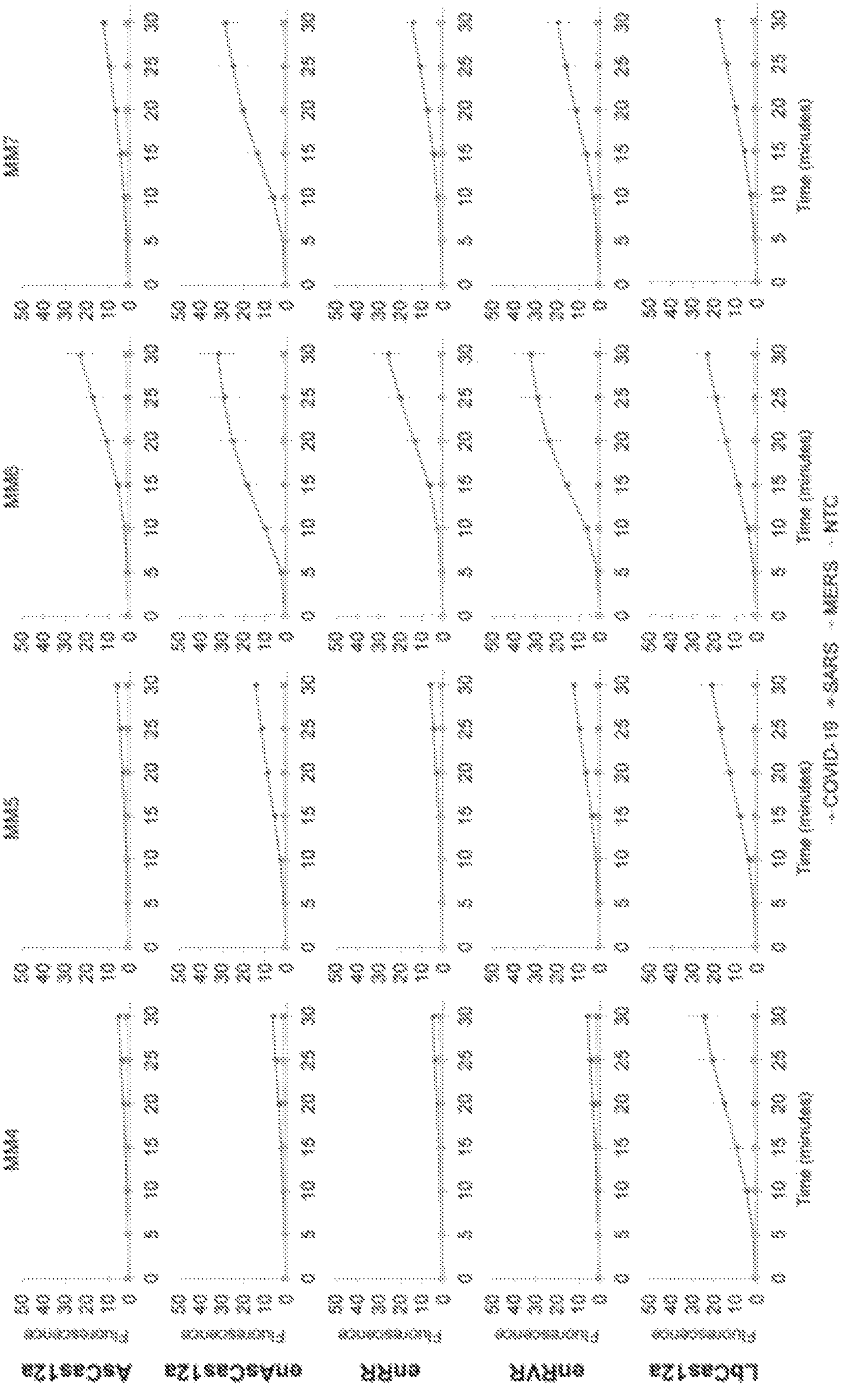
Figure 89:
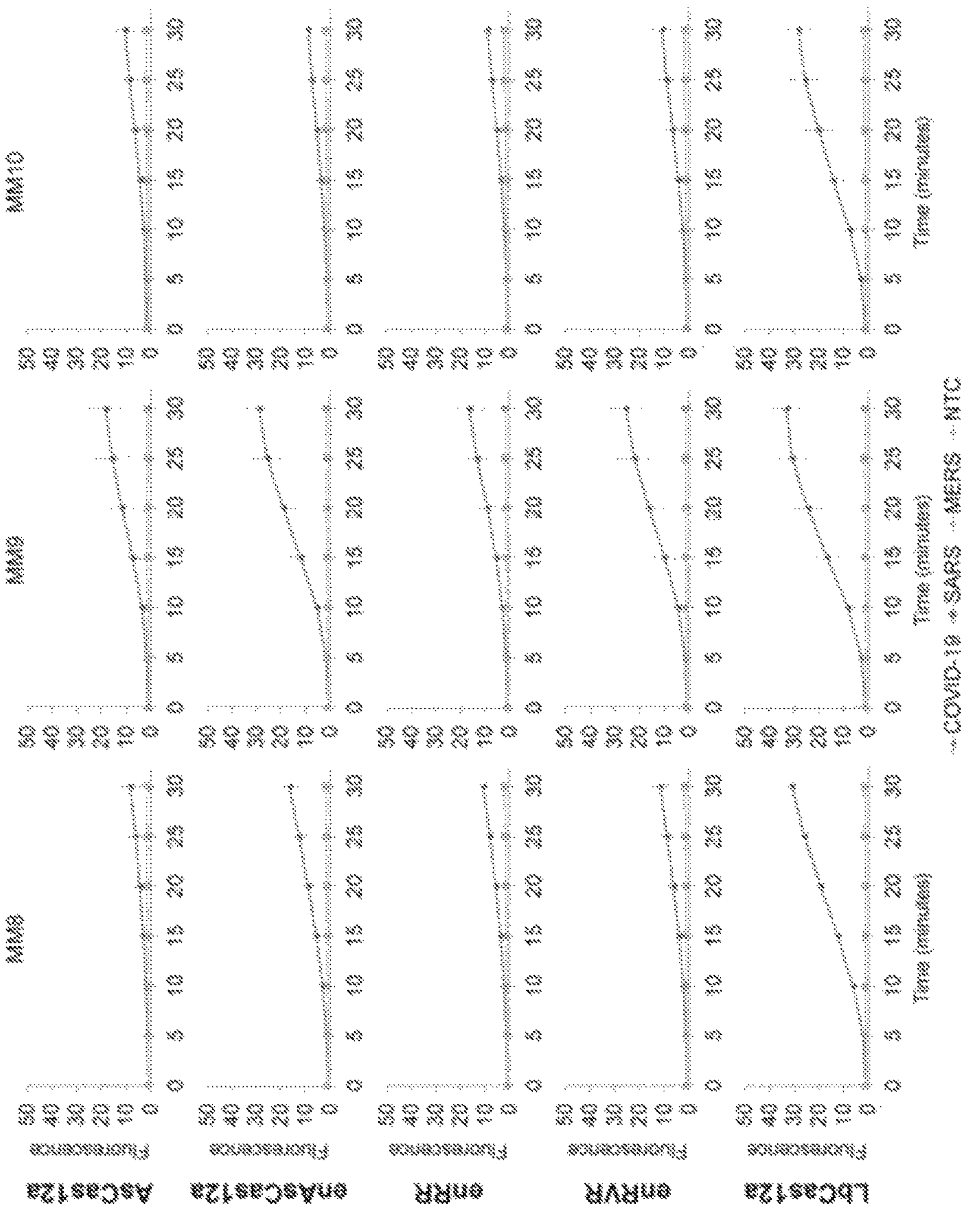
Figure 90:
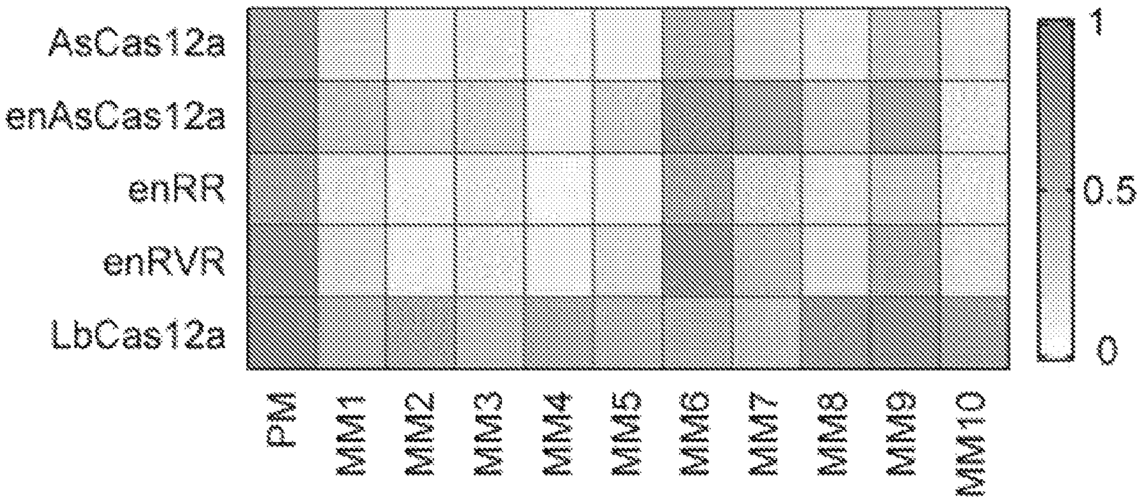
FIG. 90. Heatmap showing how the addition of a second perfect matched S1 gRNA changed the tolerance of various Cas12a enzymes to mismatched S2 gRNAs. The trans-cleavage assay was performed at 37° C., with the fluorescence readings scaled between 0 and 1.

It has been noted that diagnostic assays can be constructed out of isothermal amplification methods alone without coupling them to a separate CRISPR-Cas detection module. Such assays typically rely on the use of a turbidimeter to measure the extent of magnesium precipitation, labelled primers, or special dyes that sense pH changes, react with amplification by-products, or bind to double-stranded DNA. Due to their relative simplicity, numerous RT-LAMP-only diagnostic assays for COVID-19 have been developed and even commercialized. However, isothermal amplification frequently produces non-specific products without a template, giving rise to false positive results (FIG. 84). Hence, the Cas detection step provides a valuable specificity check that rules out these undesirable false positives. Although one may also utilize an alternative sequence-specific detection probe that is distinct from the LAMP primers as a specificity check (Bhadra et al. (2020) doi:10.1101/2020.04.13.039941), the probe itself is not involved in any amplification process. In contrast, the CRISPR-Cas detection system is capable of signal amplification because each hyperactivated Cas nuclease can proceed to cleave numerous reporter molecules.

In conclusion, rapid diagnostic tests are essential to minimize viral transmission and reopen the societies safely. The availability of different types of rapid tests diversifies supply chains, thereby helping to mitigate the risk of test shortages. CRISPR-Dx has emerged as one major type of rapid test. This work here provides strategies for enhancing the robustness and speed of CRISPR-based assays and can also be adopted to fight disease X in the future.

Example 2

1. Evaluation of RT-LAMP Parameters

Figure 91:
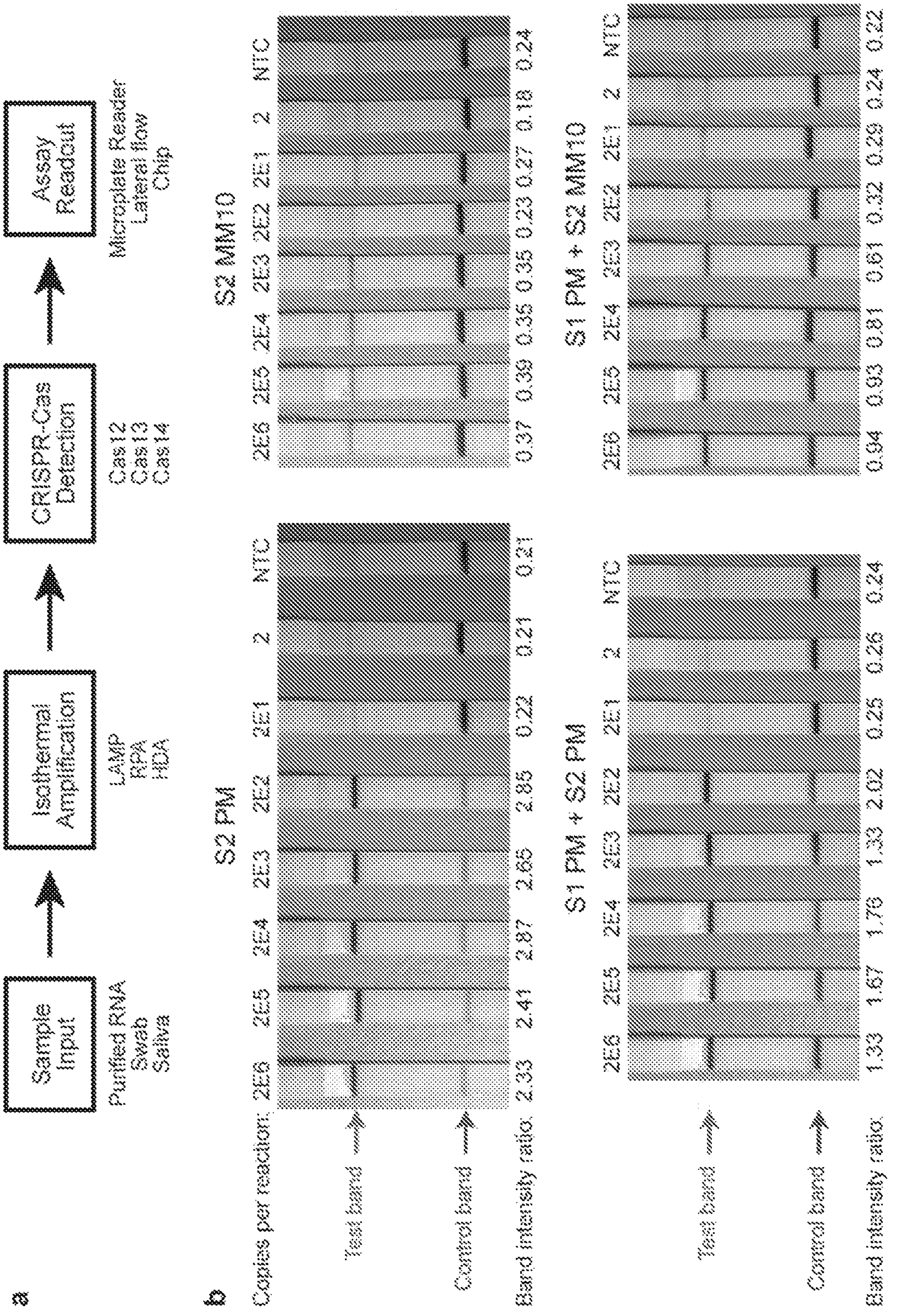
FIG. 91. Implementation of our VaNGuard assay on lateral flow strips.
Figure 92:
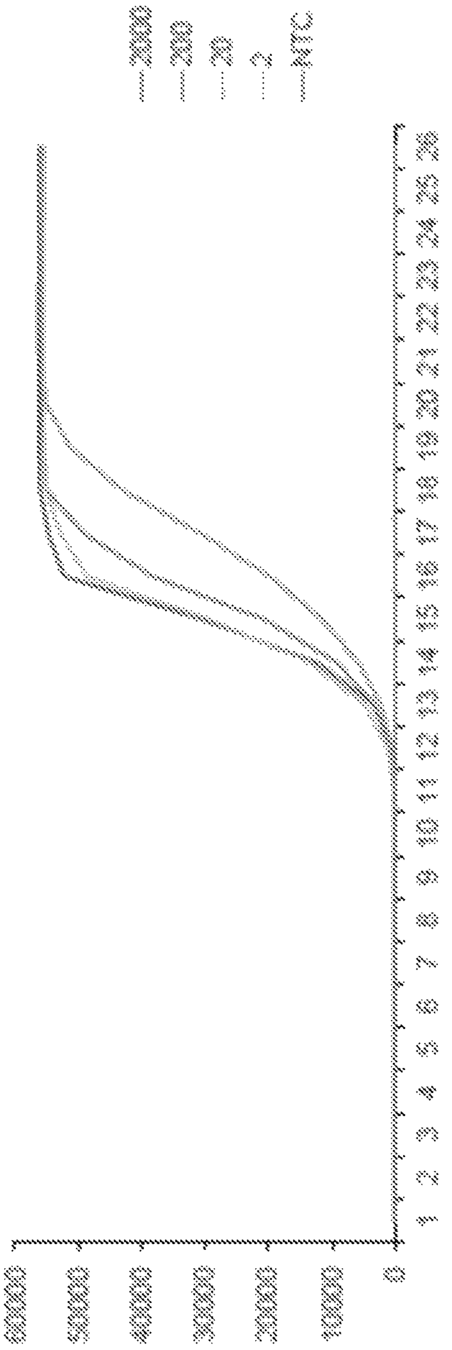
FIG. 92. Rapid diagnostic assay based on RT-LAMP. A set of primers targeting the S-gene of SARS-CoV-2 has been designed. These included two displacement primers (F3/B3), two internal primers (FIP/BIP), and two loop primers (LF/LB). A fluorescent dye similar to SYBR Green I was added to enable monitoring the progress of the reaction. The RT-LAMP reaction has been performed at 65° C. in a real-time instrument, with fluorescence measured every minute. The data showed that this experimental setup could detect 2-2,000 copies of a synthetic RNA fragment of the S-gene in a 25 μl reaction volume. No amplification was observed for a no-template control (NTC).

To enhance sensitivity, CRISPR-Cas detection is typically combined with an isothermal amplification step, of which there are several options. Due to supply chain issues in the ongoing pandemic, reverse transcription loop-mediated isothermal amplification (RT-LAMP) (Notomi et al. (2000) Nucleic Acids Res 28, E63, doi:10.1093/nar/28.12.e63) is the method-of-choice for COVID-19 applications. In the DETECTR assay, the RT—LAMP reaction was performed at 62° C. for 20-30 minutes (Broughton et al. (2020) Nat Biotechnol, doi:10.1038/s41587-020-0513-4). Therefore, it has been first carried out RT-LAMP at 62° C. for 20 minutes on synthetic in vitro-transcribed (IVT) SARS-CoV-2 RNA templates and then it has been used the amplified products in our fluorescence trans-cleavage assay (FIG. 91). For all the tested enzymes, the viral sequence was consistently and clearly detected in every replicate when 20,000 or more copies of RNA were used as input to RT-LAMP. However, in contrast to the published report (Broughton et al. (2020) Nat Biotechnol, doi:10.1038/s41587-020-0513-4), when 2,000 copies of RNA were used in a 25 μl RT-LAMP reaction (i.e. 80 copies per μl) instead, the viral sequence was detected in only around half the replicates for all the Cas enzymes, including LbCas12a.

Subsequently, it has been asked how the sensitivity of the CRISPR-based assay would be affected if we varied the parameters of the LAMP reaction (FIG. 91, 92). When the duration of LAMP has been decreased from 20 to 12 minutes, it has been observed that the fluorescence signal showed an exponential decay with every 10-fold reduction in RNA copy number, indicating that the analytic limit of detection (LoD) became poorer if the amplification step was performed for too short a period of time. Interestingly however, when the reaction temperature has been increased from 62° C. to 65° C. while keeping the duration at 12 minutes, it was possible to partially recover the fluorescence signal. Further increase in temperature from 65° C. to 68° C. caused a deterioration in the performance of our CRISPR-Dx (FIG. 93). Hence, these results suggest that 65° C. is the optimal temperature for LAMP and that the amplification reaction is sensitive to small variations in temperature.

2. Multiplex Cas12a Targeting

Besides searching for Cas-gRNA pairs that are not only specific for SARS-CoV-2 but are also tolerant of mismatches at the binding site, another strategy to enhance robustness is to incorporate two or more distinct gRNAs into the detection module. As a proof-of-concept, it has been sought to buffer the collateral activity of LbCas12a, which appeared to be more sensitive to imperfect base pairing at the gRNA-target interface than AsCas12a and its engineered variants. Moreover, LbCas12a protein is commercially available and can be readily bought by diagnostic laboratories that do not have the ability to purify their own enzymes. To keep all the target sites within the same LAMP products, the S2 gRNA can be paired with either the S1 or the S3 gRNA, as both worked well with LbCas12a (see FIG. 3, 10). Then it has been tried to design LAMP primers using the online software PrimerExplorer V5. However, it could not be found any set of primers that would produce an amplicon smaller than 500 bp that contained both the S2 and S3 loci. In contrast, many primer sets could be obtained for S1 and S2. Hence, it has been decided to perform the multiplexed targeting experiments with the S1 and S2 gRNAs.

Using a synthetic DNA fragment of the SARS-CoV-2 S gene as substrate, it has been first assessed the collateral activity of the five purified Cas12a enzymes when they were combined with both the S1 and S2 gRNAs. All five nucleases exhibited robust activity with perfect matched (PM) gRNAs (FIG. 94, 95). However, it has been noted that addition of the S1 gRNA caused a small but obvious reduction in the trans-cleavage activity of the three AsCas12a variants, while that of LbCas12a remained approximately the same. This was likely because the S1 gRNA would compete with the S2 gRNA for the Cas proteins but only LbCas12a exhibited strong activity with the S1 gRNA (FIG. 3, 10). Subsequently, it has been profiled the activity of the Cas12a nucleases when the S1 PM gRNA was used together with each one of the S2 MM gRNAs (FIG. 95, 96). Strikingly, it has been now observed that LbCas12a exhibited the best overall tolerance for mismatches, while AsCas12a and its engineered variants became more sensitive to the mismatches.

3. Towards a Point-of-Care Test

To broaden the use cases of the diagnostic assay, it has been sought to develop a portable point-of-care test (POCT). After the CRISPR-Cas trans-cleavage reaction has taken place, the results can be read out in different ways (FIG. 91*a*). While a microplate reader is useful for high throughput screening of samples in a centralized facility, it is not amenable to non-laboratory settings like ports of entry, workplaces, schools, public spaces, and homes. Hence, it has been decided to visualize the results of our assay on a lateral flow strip (see FIG. 30). Here, the reporter molecule consists of a fluorescent dye (fluorescein) linked to biotin by a short piece of ssDNA. An anti-fluorescein antibody conjugated to gold binds to the dye on the strip. When the viral substrate is absent, the reporter is intact and captured by streptavidin at the control line. However, when the viral target is present, the reporter is cleaved and the fluorescein-antibody complex migrates to the test line where it is captured by an immobilized secondary antibody.

The RT-LAMP reaction has been performed at 65° C. for 15 minutes followed by the CRISPR-Cas trans-cleavage reaction at 37° C. for 10 minutes before adding a lateral flow strip to the reaction tube. Bands appeared at either the test line or the control line within two minutes (FIG. 91*b*). Hence, in total, the entire assay took slightly under 30 minutes to complete. Here, it has been focused on LbCas12a to demonstrate the utility of multiplex targeting. The S2 gRNA (PM or MM10) was used in the assay with or without a second S1 PM gRNA. Different copy numbers of the synthetic SARS-CoV-2 RNA template have been also tested. Overall, it has been found that the lateral flow assays gave results that mirrored those from a microplate reader. When the S2 PM gRNA was used alone or in conjunction with the S1 PM gRNA, dark bands appeared at the test line in the presence of at least 200 copies of template in the reaction mix. Expectedly, without any multiplexing, introduction of a mismatch at the S2 gRNA-target interface dramatically reduced the intensity of the test bands and worsened the analytic LoD to 2,000 copies per reaction. Importantly, addition of the S1 PM gRNA was able to partially restore the intensity of the test bands. Quantification of the test and control band intensities further provided a more objective measure of whether the intended target was detected or not. In the case of a mismatch at the S2 locus but perfect base pairing at the S1 locus, it can be noted that 200 copies per reaction gave a positive test result based on the ratio of the test to control band intensities. In the future, a web or mobile phone application can be developed to distinguish such borderline cases.

4. Conclusion

CRISPR-Dx has the potential to meet society's need for such a diagnostic test. The entire workflow consists of four main modules (FIG. 91*a*). First is the sample input. Although purified RNA is ideal for performance, the process of RNA extraction will take up precious time, increase cost, and stress the supply chain. Therefore, there is great interest in developing assays that can directly handle patient samples, including nasopharyngeal swabs and saliva. The second module is the isothermal amplification step, which is commonly implemented to enhance the sensitivity of CRISPR-Dx. LAMP (Notomi et al. (2000) Nucleic Acids Res 28, E63, doi:10.1093/nar/28.12.e63) is the method-of-choice in the current pandemic climate, as its reagents are readily available from several suppliers, but other approaches can also be used, including recombinase polymerase amplification (RPA) (Piepenburg et al. (2006) PLoS Biol 4, e204, doi:10.1371/journal.pbio.0040204) and helicase-dependent amplification (HDA) (Vincent et al. (2004) EMBO Rep 5, 795-800, doi:10.1038/sj.embor.7400200. The third module is the CRISPR-Cas detection system. Most CRISPR-Dx rely on an indiscriminate collateral activity possessed by some Cas nucleases, including Cas12, Cas13, and Cas14 family members. Lastly, the fourth module is the assay readout. While our work here has demonstrated the use of a microplate reader (for high-throughput testing) and a lateral flow strip (for POCT), another possibility is a graphene-based field-effect transistor, whose high sensitivity has been reported to obviate the need for a pre-amplification step (Hajian et al. (2019) Nat Biomed Eng 3, 427-437, doi:10.1038/s41551-019-0371-x (2019). Overall, the cost of running a CRISPR-based test per sample is under S$9, which is around US$6.40 or €5.80 and is similar to that of an off-the-shelf pregnancy test. The bulk of the cost comes from the LAMP mastermix and the dipstick.

While promising, current CRISPR-Dx assays for COVID-19 have not taken into account viral evolution and RNA editing. Alarmingly, mutations in the SARS-CoV-2 genome have been observed at the target sites of multiple existing qRT-PCR diagnostic tests (Wang (2020) arXiv e-prints, arXiv:2005.02188 <https://ui.adsabs.harvard.edu/abs/2020arXiv200502188W>). Moreover, RNA editing mediated by the ADAR and APOBEC enzymes can also impact upon the performance of COVID-19 diagnostics. Hence, in this work, it has been sought to bolster the robustness of CRISPR-Dx against unexpected variant nucleotides introduced by evolutionary pressures or RNA editing. Starting from the DETECTR platform (Chen et al. (2018) Science 360, 436-439, doi:10.1126/science.aar6245; Broughton et al. (2020) Nat Biotechnol, doi:10.1038/s41587-020-0513-4), several different natural and engineered Cas12a enzymes have been tested and it has been found that enAsCas12a exhibited the highest tolerance for single mismatches at the gRNA-target interface. Importantly, high specificity for SARS-CoV-2 was still maintained with enAsCas12a, as no cross-reactivity for two other closely related coronaviruses SARS-CoV and MERS-CoV was observed. Also additional gRNAs have been screended and it has been discovered that all the tested nucleases, except en RR, exhibited higher trans-cleavage activity with the S2 gRNA than with the N-Mam gRNA. Hence, these results indicate that enCas12a complexed with the S2 gRNA will serve as a more sensitive and robust SARS-CoV-2 detection system than the published LbCas12a and N-Mam gRNA pair. Nevertheless, enCas12a is not yet a commercially available enzyme. Hence, it has been demonstrated that a multiplex targeting strategy could also be utilized to enhance the robustness of CRISPR-Dx. For example, the LbCas12a nuclease, which is readily bought, may be combined with both the 51 and S2 gRNAs to increase the robustness of viral detection.

It has been noted that diagnostic assays can be constructed out of isothermal amplification methods alone without coupling them to a separate CRISPR-Cas detection module. Such assays typically rely on the use of a turbidimeter to measure the extent of magnesium precipitation, labelled primers, or special dyes that sense pH changes, react with amplification by-products, or bind to double-stranded DNA (dsDNA). Due to their relative simplicity, over a dozen LAMP-only diagnostic assays for COVID-19 have been developed so far (Lu et al. (2020) Virol Sin, doi:10.1007/s12250-020-00218-1; Baek et al. (2020) Emerg Microbes Infect 9, 998-1007, doi:10.1080/22221751.2020.1756698; Huang et al. (2020) Microb Biotechnol, doi:10.1111/1751-7915.13586; Yan et al. (2020) Clin Microbiol Infect 26, 773-779, doi:10.1016/j.cmi.2020.04.001; Sun et al. (2020) Lab Chip 20, 1621-1627, doi:10.1039/d0lc00304b; Yu, L. et al. (2020) Clin Chem, doi:10.1093/clinchem/hvaa102; Park et al. (2020) J Mol Diagn, doi:10.1016/j.jmoldx.2020.03.006; Song et al. doi:10.26434/chemrxiv.11860137.v1; Bhadra et al. (2020) doi:10.1101/2020.04.13.039941; Lalli et al. (2020) doi:10.1101/2020.05.07.20093542; Lamb et al. (2020) doi:10.1101/2020.02.19.20025155; Zhang, Y. et al. (2020) doi:10.1101/2020.02.26.20028373 (2020); Ben-Assa et al. (2020), doi:10.1101/2020.04.22.20072389; Dao et al. (2020) doi:10.1101/2020.05.05.20092288; Butler et al. (2020) doi:10.1101/2020.04.20.048066). However, isothermal amplification frequently produces spurious non-specific products, which can give rise to false positive results. Although this problem may be circumvented by the use of a sequence-specific detection probe that is distinct from the LAMP primers (Bhadra et al. (2020) doi:10.1101/2020.04.13.039941), the probe itself is not involved in any amplification process. In contrast, CRISPR-Dx confers two distinct rounds of specificity. The first round comes from primer-specific isothermal amplification such as LAMP, while the second round comes from gRNA-specific Cas detection. Furthermore, the CRISPR-Cas detection system is also capable of signal amplification because each hyperactivated Cas nuclease can proceed to cleave numerous reporter molecules. Hence, CRISPR-Dx can function like a photomultiplier tube and the assay duration can potentially be shortened if all the reagents are in a single-pot and the conditions are optimal for every reaction.

In conclusion, CRISPR-Dx can serve as a rapid, specific, sensitive, and affordable approach for the detection of SARS-CoV-2. This work here has further provided two different strategies, namely the use of enCas12a and multiplex targeting, to enhance the robustness of the assay. It can be implemented in a high-throughput format through the use of a microplate reader or deployed as a POCT through the use of a lateral flow strip to enable halting viral transmission and reopen our society safely.

Methods

1. Plasmids and Oligonucleotides

The pET28b-T7-Cas12a-NLS-6×His expression plasmids were gifts from Keith Joung and Benjamin Kleinstiver (Addgene plasmid #114069 [AsCas12a], #114070 [LbCas12a], #114072 [enAsCas12a], #114075 [enRVR], and #114077 [enRR]) (Dao et al. (2020) doi:10.1101/2020.05.05.20092288). DNA oligonucleotides, custom reporters for the trans-cleavage assays, and gene fragments (ORF1AB, S, and N) for the three coronaviruses SARS-CoV-2, SARS-CoV, and MERS-CoV were synthesised by Integrated DNA Technologies. PCR fragments of the S-gene and T2A-eGFP were cloned into a lentiviral vector using the NEBuilder HiFi DNA Assembly Kit (NEB).

2. Cas12a Expression and Purification

The Cas12a expression plasmids were transformed into *Escherichia coli* BL21 (DE3) and stored as glycerol stocks. Starter cultures were grown in LB broth with 50 μg/ml kanamycin at 37° C. for 16 h and diluted 1:50 into 400 ml LB-kanamycin broth until an $OD_{600}$ of 0.4-0.6 was reached. Cultures were then induced with 1 mM isopropyl β-D-1-thiogalactopyranoside (IPTG) and incubated at 25° C. for another 16 h. Subsequently, cells were harvested by centrifugation at 3,220 g for 20 min and resuspended in lysis buffer [50 mM HEPES, 500 mM NaCl, 2 mM $MgCl_2$, 20 mM imidazole, 1% Triton X-100, 1 mM DTT, 0.005 mg/ml lysozyme (Vivantis), 1× Halt Protease Inhibitor Cocktail (Thermo Fisher Scientific)], followed by sonication at high power for 10 cycles of 30 s ON/OFF (Bioruptor Plus; Diagenode). Lysates were clarified by centrifugation at 10,000 g for 15 min. The supernatants were pooled, loaded onto a gravity flow column packed with Ni-NTA agarose (Qiagen), and rotated for 2 h at 4° C. The column was washed twice with 5 ml wash buffer (50 mM Tris, 300 mM NaCl and 30 mM imidazole). Five elutions were performed with 500 μl elution buffer (50 mM Tris, 300 mM NaCl, and 200 mM imidazole) and analysed by SDS-PAGE. The final gel filtration step was performed with a HiLoad 16/600 Superdex 200 pg column (GE Healthcare) on a fast protein liquid chromatography purification system (ÄKTA Explorer; GE Healthcare), which was eluted with storage buffer (50 mM Tris, 300 mM NaCl, and 1 mM DTT). Fractions containing Cas12a were collected, analysed by SDS-PAGE, and concentrated to around 500 μl with Vivaspin 20, 50,000 MWCO concentrator units (Sartorius). Glycerol was added to a final concentration of 20%. Protein concentrations were measured with the Quick Start Bradford Protein Assay (Bio-Rad) before the purified proteins were aliquoted and stored at −80° C. For example 2, EnGen Lba Cas12a was purchased from New England Biolabs (NEB) for comparison.

3. gRNA Design

Complete genomes of SARS-CoV-2 (accession MN908947.3), SARS-CoV (accession NC_004718.3), MERS-CoV (accession NC_019843.3), CoV 0043 (accession NC_006213.1), CoV 229E (accession NC_002645.1), CoV NL63 (accession JX504050.1), and CoV HKU1 (accession KF686346.1) were retrieved from NCBI (https://www.ncbi.nlm.nih.gov/) and aligned with MUSCLE (https://www.ebi.ac.uk/Tools/msa/muscle/) using default settings. Potential target sites (20nt spacers) in the ORF1AB, S, and N genes were selected from non-conserved regions containing a TTTV PAM (with V being A, C or G). Potential targets were filtered after a specificity check on BLASTn (https://blast.ncbi.nlm.nih.gov/Blast.cgi) to remove non-specific candidates. Truncated gRNAs were generated by shortening their spacers to 18nt and 19nt lengths at the 3' end.

4. In Vitro Transcription (IVT) of gRNAs

Templates for gRNA synthesis were designed with the following sequence order: T7 promoter-Cas12a scaffold-spacer. Top strand DNA oligos consisting of the T7 promoter (5'-TAATACGACTCACTATAGG-3') (SEQ ID NO:26) and scaffold (5'-TAATTTCTACTCTTGTAGAT-3' (SEQ ID NO:258) for AsCas12a and its variants; 5'-AATTTC-TACTAAGTGTAGAT-3' (SEQ ID NO:259) for LbCas12a) were annealed to the bottom strand and extended by Q5 High-Fidelity DNA polymerase (NEB). IVT of the dsDNA products was performed with the HiScribe T7 Quick High Yield RNA Synthesis kit (NEB) at 37° C. overnight. Following DNase I digestion, gRNAs were purified with the RNA Clean & Concentrator-5 kit (ZYMO Research), analysed by 2% TAE-agarose gel electrophoresis to assess RNA integrity, measured with NanoDrop 2000, and stored at −20° C.

5. Synthesis of DNA and RNA Templates

Gene fragments (gBlocks) were cloned into pCR-Blunt II-TOPO vector using the Zero Blunt TOPO PCR Cloning kit (Invitrogen) and their sequences were verified by Sanger sequencing. The vectors were used as templates for PCR with Q5 High-Fidelity DNA polymerase (NEB) and the products were gel extracted and purified with the PureNA Biospin Gel Extraction kit (Research Instruments). DNA concentrations were measured using NanoDrop 2000 and all the DNA samples were stored at 4° C. To generate RNA templates for RT-LAMP assays, the forward primers used for PCR were appended with the T7 promoter sequence. After PCR amplification with the gBlock-TOPO vectors as template, IVT was performed as described for gRNA generation.

6. Fluorescence Trans-Cleavage Assay

Cas ribonucleoprotein (RNP) complexes were pre-assembled with 65 nM AsCas12a/LbCas12a, 195 nM gRNA, and 200 nM custom ssDNA fluorophore-quencher (FQ) reporter in reaction buffer (1× NEBuffer 3.1 plus 0.4 mM DTT) for 30 minutes at room temperature. Subsequently, the cleavage reaction was initiated by adding 3 nM DNA template (approximately 1E11 copies) to a total volume of 50 μl and then transferred to a 96-well microplate (Costar). Fluorescence intensities were measured with either the Infinite M1000 Pro (Tecan) or the Spectramax M5 plate reader (Molecular Devices) for 30 minutes at room temperature, with measurement intervals of 5 minutes ($\lambda_{ex}$: 485 nm; $\lambda_{em}$: 535 nm).

7. RT-LAMP Reaction

For Example 1, synthetic SARS-CoV-2 RNA templates were serially diluted and amplified using the WarmStart LAMP Kit (NEB). 10× S-gene LAMP primer mix was prepared with concentration of 2 μM for F3, 4 μM for B3, 8 μM for FIP(PM), BIP(PM), FIP(tPM-3), BIP(tPM-3), LF, and LB, and 16 μM for swarm F1c and swarm B1c. The RT-LAMP reaction containing 12.5 μl WarmStart LAMP Mastermix, 2.5 μl 10× S-gene primer mix, 2.5 μl 0.4M guanidine HCl, 2.5 μl Q5 High-Fidelity Polymerase (0.06 U/μL), and 5 μl synthetic RNA was then setup for a total reaction volume of 25 μl. Subsequently, the reaction tube was incubated at 65° C. for 22 mins. For the assay with the internal control, RT-LAMP reactions also contained 0.5 μl LAMP dye (NEB) and primers targeting human ACTB with final concentration of 0.1 μM for F3 and B3, 0.8 μM for FIP and BIP, and 0.4 μM for LF and LB.

For Example 2, synthetic SARS-CoV-2 RNA templates were serially diluted and amplified by RT-LAMP using the WarmStart LAMP Kit (NEB). LAMP primers were added to a final concentration of 0.2 μM for F3 and B3, 1.6 μM for FIP and BIP, and 0.8 μM for LF and LB. The optimal temperature for RT-LAMP was found to be 65° C. Subsequently, 4 μl RT-LAMP products were used as templates for the trans-cleavage assay, instead of 3 nM PCR-amplified DNA template.

8. Quasi-One-Pot Trans-Cleavage Assay (Example 1)

For the lateral flow readout, the following components were combined together: 9 μl 541 nM Cas12a RNP, 7.5 μl 10× Tango buffer, 13.5 μl 500 nM FITC-biotin reporter, and 20 μl water. This 50 μl Cas12a reaction mix was then added directly into the 25 μl RT-LAMP reaction tube. Next, the reaction was incubated at 60° C. for at least 5 mins. Subsequently, 75 μl HybriDetect assay buffer (Milenia Biotec) was added to the reaction and a HybriDetect (Milenia Biotec) dipstick was inserted directly into the solution in an upright position. The dipstick was incubated in the reaction tube for 2 mins at room temperature before inspection.

For the fluorescence readout, the following components were combined together, 9 μl 541 nM Cas12a RNP, 7.5 μl 10× Tango buffer, 1.5 μl 10 μM Cy5/FAM-Quencher reporter, and 32 μl water. This 50 μl Cas12a reaction mix was then added directly into the 25 μl RT-LAMP reaction tube. Next, the reaction was incubated at 60° C. for 30 mins and the fluorescence intensity was measured every 5 mins using the Infinite M1000 Pro (Tecan), the Spectramax M5 plate reader (Molecular Devices), or the EnSpire Multimode Plate Reader (PerkinElmer).

9. Lateral Flow Readout (Example 2)

500 nM of custom ssDNA biotin reporter was used instead of the FQ reporter. The Cas12a detection reaction was performed at 37° C. for 10 minutes. Subsequently, 50 μL HybriDetect assay buffer (Milenia Biotec) was added to the reaction and a HybriDetect (Milenia Biotec) dipstick was inserted directly into the solution in an upright position. The dipstick was incubated in the reaction for 2 minutes at room temperature before inspection.

10. Evaluations with SARS-CoV-2 Samples

Heat-inactivated SARS-CoV-2 (ATCC VR-1986HK) was diluted into clinically negative Universal Transport Medium (UTM) (Copan) based on the droplet digital PCR (ddPCR) quantification provided by the vendor. Ethics approval for the use of leftover RNA patient samples was given by the National Healthcare Group Domain Specific Review Board (NHG-DSRB) (Study Reference Number: 2020/00867). For the NP swab samples, the research was waived for review by the A*STAR Institutional Review Board as the overall intent of the work was to develop a diagnostic assay to contribute to ongoing surveillance efforts, and control and preventive measures for the COVID-19 pandemic in Singapore. 8.3 µl of each NP swab sample was treated with 1 µl Proteinase K (NEB) and vortexed for 1 min at room temperature. The treated sample was then heated at 95° C. for 5 mins before 2 µl was used for RT-LAMP. A step-by-step protocol describing the VaNGuard test can be found at Protocol Exchange (Ooi et al. (2021) Protoc. Exch. https://doi.org/10.21203/rs.3.pex-1373/v1).

11. Data Availability

Whole genomes of SARS-CoV-2, SARS-CoV, MERS-CoV, CoV 0043, CoV 229E, CoV NL63, and CoV HKU1 are available in GenBank under the accession numbers MN908947.3, NC_004718.3, NC_019843.3, NC_006213.1, NC_002645.1, JX504050.1, and KF686346.1 respectively.

TABLE 1

| gRNA | PAM | Spacer (5'-3') | IDT oligo sequence (5'-3') | SEQ ID NO: |
|---|---|---|---|---|
| | | | PCR for sgRNA synthesis | |
| | | | Top strand | |
| AsCas12a-Top | | | TAATACGACTCACTATAGGtAATTTCTACTCTTGTAGAT | SEQ ID NO: 27 |
| LbCas12a-Top | | | TAATACGACTCACTATAGGtAATTTCTACTAAGTGTAGAT | SEQ ID NO: 28 |
| | | | Bottom strand, 20-nt spacer | |
| As-O1 | TTTG | TGCACCACTCACTGTCTTTT | AAAAGACAGTGAGTGGTGCAATCTACAAGAGTAGAAATTaCCTATAGTGAGTC | SEQ ID NO: 29/30 |
| As-O2 | TTTA | CAACCATCTGTAGGTCCCAA | TTGGGACCTACAGATGGTTGATCTACAAGAGTAGAAATTaCCTATAGTGAGTC | SEQ ID NO: 31/32 |
| As-S1 | TTTA | CTTGCTTTACATAGAAGTTA | TAACTTCTATGTAAAGCAAGATCTACAAGAGTAGAAATTaCCTATAGTGAGTC | SEQ ID NO: 33/34 |
| As-S2 | TTTG | ACTCCTGGTGATTCTTCTTC | GAAGAAGAATCACCAGGAGTATCTACAAGAGTAGAAATTACCTATAGTGAGTC | SEQ ID NO: 35/36 |
| As-S3 | TTTA | GAGTCCAACCAACAGAATCT | AGATTCTGTTGGTTGGACTCATCTACAAGAGTAGAAATTACCTATAGTGAGTC | SEQ ID NO: 37/38 |
| As-S4 | TTTC | AAACTTTACTTGCTTTACAT | ATGTAAAGCAAGTAAAGTTTATCTACAAGAGTAGAAATTACCTATAGTGAGTC | SEQ ID NO: 39/40 |
| As-S5 | TTTA | CATAGAAGTTATTTGACTCC | GGAGTCAAATAACTTCTATGATCTACAAGAGTAGAAATTaCCTATAGTGAGTC | SEQ ID NO: 41/42 |
| As-S6 | TTTG | AAACCTAGTGATGTTAATAC | GTATTAACATCACTAGGTTTATCTACAAGAGTAGAAATTaCCTATAGTGAGTC | SEQ ID NO: 43/44 |
| As-S7 | TTTG | CCAATAGGTATTAACATCAC | GTGATGTTAATACCTATTGGATCTACAAGAGTAGAAATTaCCTATAGTGAGTC | SEQ ID NO: 45/46 |
| As-S8 | TTTA | GAACCATTGGTAGATTTGCC | GGCAAATCTACCAATGGTTCATCTACAAGAGTAGAAATTaCCTATAGTGAGTC | SEQ ID NO: 47/48 |
| As-S9 | TTTC | GGCTTTAGAACCATTGGTAG | CTACCAATGGTTCTAAAGCCATCTACAAGAGTAGAAATTACCTATAGTGAGTC | SEQ ID NO: 49/50 |
| As-S10 | TTTA | ATAGAAAAGTCCTAGGTTGA | TCAACCTAGGACTTTTCTATATCTACAAGAGTAGAAATTaCCTATAGTGAGTC | SEQ ID NO: 51/52 |
| As-S11 | TTTC | TGAGAGAGGGTCAAGTGCAC | GTGCACTTGACCCTCTCTCAATCTACAAGAGTAGAAATTaCCTATAGTGAGTC | SEQ ID NO: 53/54 |
| As-S12 | TTTG | TTTCTGAGAGAGGGTCAAGT | ACTTGACCCTCTCTCAGAAAATCTACAAGAGTAGAAATTaCCTATAGTGAGTC | SEQ ID NO: 55/56 |
| As-S13 | TTTC | AACGTACACTTTGTTTCTGA | TCAGAAACAAAGTGTACGTTATCTACAAGAGTAGAAATTaCCTATAGTGAGTC | SEQ ID NO: 57/58 |
| As-S14 | TTTC | TACAGTGAAGGATTTCAACG | CGTTGAAATCCTTCACTGTAATCTACAAGAGTAGAAATTaCCTATAGTGAGTC | SEQ ID NO: 59/60 |
| As-S15 | TTTA | GTGCGTGATCTCCCTCAGGG | CCCTGAGGGAGATCACGCACATCTACAAGAGTAGAAATTaCCTATAGTGAGTC | SEQ ID NO: 61/62 |
| As-N1 | TTTC | AAAGATCAAGTCATTTTGCT | AGCAAAATGACTTGATCTTTATCTACAAGAGTAGAAATTaCCTATAGTGAGTC | SEQ ID NO: 63/64 |
| As-N-Mam | TTTG | CCCCCAGCGCTTCAGCGTTC | GAACGCTGAAGCGCTGGGGGATCTACAAGAGTAGAAATTaCCTATAGTGAGTCGT | SEQ ID NO: 65/66 |
| Lb-O1 | TTTG | TGCACCACTCACTGTCTTTT | AAAAGACAGTGAGTGGTGCAATCTACACTTAGTAGAAATTaCCTATAGTGAG | SEQ ID NO: 67/68 |
| Lb-O2 | TTTA | CAACCATCTGTAGGTCCCAA | TTGGGACCTACAGATGGTTGATCTACACTTAGTAGAAATTACCTATAGTGAG | SEQ ID NO: 69/70 |
| Lb-S1 | TTTA | CTTGCTTTACATAGAAGTTA | TAACTTCTATGTAAAGCAAGATCTACACTTAGTAGAAATTaCCTATAGTGAG | SEQ ID NO: 71/72 |
| Lb-S2 | TTTG | ACTCCTGGTGATTCTTCTTC | GAAGAAGAATCACCAGGAGTATCTACACTTAGTAGAAATTACCTATAGTGAG | SEQ ID NO: 73/44 |
| Lb-S3 | TTTA | GAGTCCAACCAACAGAATCT | AGATTCTGTTGGTTGGACTCATCTACACTTAGTAGAAATTaCCTATAGTGAG | SEQ ID NO: 75/76 |
| Lb-N1 | TTTC | AAAGATCAAGTCATTTTGCT | AGCAAAATGACTTGATCTTTATCTACACTTAGTAGAAATTaCCTATAGTGAG | SEQ ID NO: 77/78 |
| Lb-N-Mam | TTTG | CCCCCAGCGCTTCAGCGTTC | GAACGCTGAAGCGCTGGGGGATCTACACTTAGTAGAAATTaCCTATAGTGAGTCG | SEQ ID NO: 79/80 |
| | | | Bottom strand, 18-nt spacer | |
| 18-As-S2 | | ACTCCTGGTGATTCTTCT | AGAAGAATCACCAGGAGTATCTACAAGAGTAGAAATTACCTATAGTGAGTCG | SEQ ID NO: 81/82 |
| 18-Lb-S2 | | ACTCCTGGTGATTCTTCT | AGAAGAATCACCAGGAGTATCTACACTTAGTAGAAATTaCCTATAGTGAGTC | SEQ ID NO: 83/84 |
| 18-As-N-Mam | | CCCCCAGCGCTTCAGCGT | ACGCTGAAGCGCTGGGGGATCTACAAGAGTAGAAATTaCCTATAGTGAGT | SEQ ID NO: 85/86 |
| 18-Lb-N-Mam | | CCCCCAGCGCTTCAGCGT | ACGCTGAAGCGCTGGGGGATCTACACTTAGTAGAAATTaCCTATAGTGAG | SEQ ID NO: 87/88 |
| | | | Bottom strand, 19-nt spacer | |
| 19-As-S2 | | ACTCCTGGTGATTCTTCTT | AAGAAGAATCACCAGGAGTATCTACAAGAGTAGAAATTaCCTATAGTGAG | SEQ ID NO: 89/90 |
| 19-Lb-S2 | | ACTCCTGGTGATTCTTCTT | AAGAAGAATCACCAGGAGTATCTACACTTAGTAGAAATTaCCTATAGTGA | SEQ ID NO: 91/92 |
| 19-As-N-Mam | | CCCCCAGCGCTTCAGCGTT | AACGCTGAAGCGCTGGGGGATCTACAAGAGTAGAAATTaCCTATAGTGAGTCGT | SEQ ID NO: 93/94 |
| 19-Lb-N-Mam | | CCCCCAGCGCTTCAGCGTT | AACGCTGAAGCGCTGGGGGATCTACACTTAGTAGAAATTaCCTATAGTGAGTCG | SEQ ID NO: 95/96 |

TABLE 1-continued

| gRNA | PAM | Spacer (5'-3') | IDT oligo sequence (5'-3') | SEQ ID NO: |
|---|---|---|---|---|
| | | | Bottom strand, N-Mam gRNA mismatches | |
| As-N-MamMM1 | | **A**CCCCAGCGCTTCAGCGTTC | GAACGCTGAAGCGCTGGGGTATCTACAAGAGTAGAAATTaCCTATAGTGA | SEQ ID NO: 97/98 |
| As-N-MamMM2 | | CC**A**CCAGCGCTTCAGCGTTC | GAACGCTGAAGCGCTGGTGGATCTACAAGAGTAGAAATTaCCTATAGTGA | SEQ ID NO: 99/100 |
| As-N-MamMM3 | | CCCC**A**AGCGCTTCAGCGTTC | GAACGCTGAAGCGCTTGGGGATCTACAAGAGTAGAAATTaCCTATAGTGA | SEQ ID NO: 101/102 |
| As-N-MamMM4 | | CCCCCA**T**CGCTTCAGCGTTC | GAACGCTGAAGCGATGGGGGATCTACAAGAGTAGAAATTaCCTATAGTGA | SEQ ID NO: 103/104 |
| As-N-MamMM5 | | CCCCCAGC**T**CTTCAGCGTTC | GAACGCTGAAGAGCTGGGGGATCTACAAGAGTAGAAATTaCCTATAGTGA | SEQ ID NO: 105/106 |
| As-N-MamMM6 | | CCCCCAGCGCGTCAGCGTTC | GAACGCTGACGCGCTGGGGGATCTACAAGAGTAGAAATTaCCTATAGTGA | SEQ ID NO: 107/108 |
| As-N-MamMM7 | | CCCCCAGCGCTTAAGCGTTC | GAACGCTTAAGCGCTGGGGGATCTACAAGAGTAGAAATTaCCTATAGTGA | SEQ ID NO: 109/110 |
| As-N-MamMM8 | | CCCCCAGCGCTTCATCGTTC | GAACGATGAAGCGCTGGGGGATCTACAAGAGTAGAAATTaCCTATAGTGA | SEQ ID NO: 111/112 |
| As-N-MamMM9 | | CCCCCAGCGCTTCAGCATTC | GAATGCTGAAGCGCTGGGGGATCTACAAGAGTAGAAATTaCCTATAGTGA | SEQ ID NO: 113/114 |
| As-N-MamMM10 | | CCCCCAGCGCTTCAGCGTGC | GCACGCTGAAGCGCTGGGGGATCTACAAGAGTAGAAATTACCTATAGTGAGTCGT | SEQ ID NO: 115/116 |
| Lb-N-MamMM1 | | **A**CCCCAGCGCTTCAGCGTTC | GAACGCTGAAGCGCTGGGGTATCTACACTTAGTAGAAATTaCCTATAGTG | SEQ ID NO: 117/118 |
| Lb-N-MamMM2 | | CC**A**CCAGCGCTTCAGCGTTC | GAACGCTGAAGCGCTGGTGGATCTACACTTAGTAGAAATTaCCTATAGTG | SEQ ID NO: 119/120 |
| Lb-N-MamMM3 | | CCCC**A**AGCGCTTCAGCGTTC | GAACGCTGAAGCGCTTGGGGATCTACACTTAGTAGAAATTaCCTATAGTG | SEQ ID NO: 121/122 |
| Lb-N-MamMM4 | | CCCCCA**T**CGCTTCAGCGTTC | GAACGCTGAAGCGATGGGGGATCTACACTTAGTAGAAATTaCCTATAGTG | SEQ ID NO: 123/124 |
| Lb-N-MamMM5 | | CCCCCAGC**T**CTTCAGCGTTC | GAACGCTGAAGAGCTGGGGGATCTACACTTAGTAGAAATTaCCTATAGTG | SEQ ID NO: 125/126 |
| Lb-N-MamMM6 | | CCCCCAGCGCGTCAGCGTTC | GAACGCTGACGCGCTGGGGGATCTACACTTAGTAGAAATTACCTATAGTG | SEQ ID NO: 127/128 |
| Lb-N-MamMM7 | | CCCCCAGCGCTTAAGCGTTC | GAACGCTTAAGCGCTGGGGGATCTACACTTAGTAGAAATTACCTATAGTG | SEQ ID NO: 129/130 |
| Lb-N-MamMM8 | | CCCCCAGCGCTTCATCGTTC | GAACGATGAAGCGCTGGGGGATCTACACTTAGTAGAAATTaCCTATAGTG | SEQ ID NO: 131/132 |
| Lb-N-MamMM9 | | CCCCCAGCGCTTCAGCATTC | GAATGCTGAAGCGCTGGGGGATCTACACTTAGTAGAAATTaCCTATAGTG | SEQ ID NO: 133/134 |
| Lb-N-MamMM10 | | CCCCCAGCGCTTCAGCGTGC | GCACGCTGAAGCGCTGGGGGATCTACACTTAGTAGAAATTACCTATAGTGAGTCG | SEQ ID NO: 135/136 |
| | | | Bottom strand, S-2 gRNA mismatches | |
| As-S2-MM1 | | **C**CTCCTGGTGATTCTTCTTC | GAAGAAGAATCACCAGGAGGATCTACAAGAGTAGAAATTACCTATAGTGAGTCGT | SEQ ID NO: 137/138 |
| As-S2-MM2 | | AC**G**CCTGGTGATTCTTCTTC | GAAGAAGAATCACCAGGCGTATCTACAAGAGTAGAAATTACCTATAGTGAGTCGT | SEQ ID NO: 139/140 |
| As-S2-MM3 | | ACTC**A**TGGTGATTCTTCTTC | GAAGAAGAATCACCATGAGTATCTACAAGAGTAGAAATTACCTATAGTGAGTCGT | SEQ ID NO: 141/142 |
| As-S2-MM4 | | ACTCCT**T**GTGATTCTTCTTC | GAAGAAGAATCACAAGGAGTATCTACAAGAGTAGAAATTACCTATAGTGAGTCGT | SEQ ID NO: 143/144 |
| As-S2-MM5 | | ACTCCTGG**G**GATTCTTCTTC | GAAGAAGAATCCCCAGGAGTATCTACAAGAGTAGAAATTACCTATAGTGAGTCGT | SEQ ID NO: 145/146 |
| As-S2-MM6 | | ACTCCTGGTG**C**TTCTTCTTC | GAAGAAGAAGCACCAGGAGTATCTACAAGAGTAGAAATTACCTATAGTGAGTCGT | SEQ ID NO: 147/148 |
| As-S2-MM7 | | ACTCCTGGTGAT**G**CTTCTTC | GAAGAAGCATCACCAGGAGTATCTACAAGAGTAGAAATTACCTATAGTGAGTCGT | SEQ ID NO: 149/150 |
| As-S2-MM8 | | ACTCCTGGTGATTC**G**TCTTC | GAAGACGAATCACCAGGAGTATCTACAAGAGTAGAAATTACCTATAGTGAGTCGT | SEQ ID NO: 151/152 |
| As-S2-MM9 | | ACTCCTGGTGATTCTT**A**TTC | GAATAAGAATCACCAGGAGTATCTACAAGAGTAGAAATTACCTATAGTGAGTCGT | SEQ ID NO: 153/154 |
| As-S2-MM10 | | ACTCCTGGTGATTCTTCTGC | GCAGAAGAATCACCAGGAGTATCTACAAGAGTAGAAATTACCTATAGTGAGTCGT | SEQ ID NO: 155/156 |
| Lb-S2-MM1 | | **C**CTCCTGGTGATTCTTCTTC | GAAGAAGAATCACCAGGAGGATCTACACTTAGTAGAAATTACCTATAGTGAGTCG | SEQ ID NO: 157/158 |
| Lb-S2-MM2 | | AC**G**CCTGGTGATTCTTCTTC | GAAGAAGAATCACCAGGCGTATCTACACTTAGTAGAAATTACCTATAGTGAGTCG | SEQ ID NO: 159/160 |
| Lb-S2-MM3 | | ACTC**A**TGGTGATTCTTCTTC | GAAGAAGAATCACCATGAGTATCTACACTTAGTAGAAATTACCTATAGTGAGTCG | SEQ ID NO: 161/162 |
| Lb-S2-MM4 | | ACTCCT**T**GTGATTCTTCTTC | GAAGAAGAATCACAAGGAGTATCTACACTTAGTAGAAATTACCTATAGTGAGTCG | SEQ ID NO: 163/164 |
| Lb-S2-MM5 | | ACTCCTGG**G**GATTCTTCTTC | GAAGAAGAATCCCCAGGAGTATCTACACTTAGTAGAAATTACCTATAGTGAGTCG | SEQ ID NO: 165/166 |
| Lb-S2-MM6 | | ACTCCTGGTG**C**TTCTTCTTC | GAAGAAGAAGCACCAGGAGTATCTACACTTAGTAGAAATTACCTATAGTGAGTCG | SEQ ID NO: 167/168 |
| Lb-S2-MM7 | | ACTCCTGGTGAT**G**CTTCTTC | GAAGAAGCATCACCAGGAGTATCTACACTTAGTAGAAATTACCTATAGTGAGTCG | SEQ ID NO: 169/170 |
| Lb-S2-MM8 | | ACTCCTGGTGATTC**G**TCTTC | GAAGACGAATCACCAGGAGTATCTACACTTAGTAGAAATTACCTATAGTGAGTCG | SEQ ID NO: 171/172 |
| Lb-S2-MM9 | | ACTCCTGGTGATTCTT**A**TTC | GAATAAGAATCACCAGGAGTATCTACACTTAGTAGAAATTACCTATAGTGAGTCG | SEQ ID NO: 173/174 |
| Lb-S2-MM10 | | ACTCCTGGTGATTCTTCT**G**C | GCAGAAGAATCACCAGGAGTATCTACACTTAGTAGAAATTACCTATAGTGAGTCG | SEQ ID NO: 175/176 |
| | | | Bottom strand, S-3 gRNA mismatches | |
| As-S3-MM1 | | **T**AGTCCAACCAACAGAATCT | AGATTCTGTTGGTTGGACTAATCTACAAGAGTAGAAATTaCCTATAGTGA | SEQ ID NO: 177/178 |
| As-S3-MM2 | | GA**T**TCCAACCAACAGAATCT | AGATTCTGTTGGTTGGAATCATCTACAAGAGTAGAAATTaCCTATAGTGA | SEQ ID NO: 179/180 |

TABLE 1-continued

| gRNA | PAM | Spacer (5'-3') | IDT oligo sequence (5'-3') | SEQ ID NO: |
|---|---|---|---|---|
| As-S3-MM3 | | GAGT**A**CAACCAACAGAATCT | AGATTCTGTTGGTTGTACTCATCTACAAGAGTAGAAATTaCCTATAGTGA | SEQ ID NO: 181/182 |
| As-S3-MM4 | | GAGTCC**C**ACCAACAGAATCT | AGATTCTGTTGGTGGGACTCATCTACAAGAGTAGAAATTaCCTATAGTGA | SEQ ID NO: 183/184 |
| As-S3-MM5 | | GAGTCCAA**A**CAACAGAATCT | AGATTCTGTTGTTTGGACTCATCTACAAGAGTAGAAATTaCCTATAGTGA | SEQ ID NO: 185/186 |
| As-S3-MM6 | | GAGTCCAACC**C**ACAGAATCT | AGATTCTGTGGGTTGGACTCATCTACAAGAGTAGAAATTaCCTATAGTGA | SEQ ID NO: 187/188 |
| As-S3-MM7 | | GAGTCCAACCAA**A**AGAATCT | AGATTCTTTTGGTTGGACTCATCTACAAGAGTAGAAATTaCCTATAGTGA | SEQ ID NO: 189/190 |
| As-S3-MM8 | | GAGTCCAACCAACA**T**AATCT | AGATTATGTTGGTTGGACTCATCTACAAGAGTAGAAATTACCTATAGTGA | SEQ ID NO: 191/192 |
| As-S3-MM9 | | GAGTCCAACCAACAGA**C**TCT | AGAGTCTGTTGGTTGGACTCATCTACAAGAGTAGAAATTaCCTATAGTGA | SEQ ID NO: 193/194 |
| As-S3-MM10 | | GAGTCCAACCAACAGAAT**A**T | ATATTCTGTTGGTTGGACTCATCTACAAGAGTAGAAATTaCCTATAGTGA | SEQ ID NO: 195/196 |
| Lb-S3-MM1 | | **T**AGTCCAACCAACAGAATCT | AGATTCTGTTGGTTGGACTAATCTACACTTAGTAGAAATTaCCTATAGTG | SEQ ID NO: 197/198 |
| Lb-S3-MM2 | | GA**T**TCCAACCAACAGAATCT | AGATTCTGTTGGTTGGAATCATCTACACTTAGTAGAAATTaCCTATAGTG | SEQ ID NO: 199/200 |
| Lb-S3-MM3 | | GAGT**A**CAACCAACAGAATCT | AGATTCTGTTGGTTGTACTCATCTACACTTAGTAGAAATTaCCTATAGTG | SEQ ID NO: 201/202 |
| Lb-S3-MM4 | | GAGTCC**C**ACCAACAGAATCT | AGATTCTGTTGGTGGGACTCATCTACACTTAGTAGAAATTaCCTATAGTG | SEQ ID NO: 203/204 |
| Lb-S3-MM5 | | GAGTCCAA**A**CAACAGAATCT | AGATTCTGTTGTTTGGACTCATCTACACTTAGTAGAAATTaCCTATAGTG | SEQ ID NO: 205/206 |
| Lb-S3-MM6 | | GAGTCCAACC**C**ACAGAATCT | AGATTCTGTGGGTTGGACTCATCTACACTTAGTAGAAATTaCCTATAGTG | SEQ ID NO: 207/208 |
| Lb-S3-MM7 | | GAGTCCAACCAA**A**AGAATCT | AGATTCTTTTGGTTGGACTCATCTACACTTAGTAGAAATTaCCTATAGTG | SEQ ID NO: 209/210 |
| Lb-S3-MM8 | | GAGTCCAACCAACA**T**AATCT | AGATTATGTTGGTTGGACTCATCTACACTTAGTAGAAATTACCTATAGTG | SEQ ID NO: 211/212 |
| Lb-S3-MM9 | | GAGTCCAACCAACAGA**C**TCT | AGAGTCTGTTGGTTGGACTCATCTACACTTAGTAGAAATTaCCTATAGTG | SEQ ID NO: 213/214 |
| Lb-S3-MM10 | | GAGTCCAACCAACAGAAT**A**T | ATATTCTGTTGGTTGGACTCATCTACACTTAGTAGAAATTaCCTATAGTG | SEQ ID NO: 215/216 |
| PCR for dsDNA substrate synthesis (F = forward; R = reverse) | | | | |
| SARS2-O-F | | | GCTTTGGGCTAAGCGCAA | SEQ ID NO: 217 |
| SARS2-S-F | | | AAACAGGGTAATTTCAAAAATCT | SEQ ID NO: 218 |
| SARS2-N-F | | | CTTCTAAGAAGCCTCGGC | SEQ ID NO: 219 |
| SARS-O-F | | | GCTTTGGGCTAAGCGTAA | SEQ ID NO: 220 |
| SARS-S-F | | | AAGTCAGGTAATTTTAAACACTTAC | SEQ ID NO: 221 |
| SARS-N-F | | | CATCTAAAAAGCCTCGCCA | SEQ ID NO: 222 |
| MERS-O-F | | | ACTCTATGCTAAGCGTGC | SEQ ID NO: 223 |
| MERS-S-F | | | AATTCCTATACTTCTTTTGCCACTT | SEQ ID NO: 224 |
| MERS-N-F | | | CTAAAAATAAGATGCGCCACAAG | SEQ ID NO: 225 |
| SARS2-O-R | | | CAATGAATTCATCCATAGCTAATTCTAAGA | SEQ ID NO: 226 |
| SARS2-S-R | | | TGGCGTTAAAAACTTCACCA | SEQ ID NO: 227 |
| SARS2-N-R | | | GTTGAGTCAGCACTGCTCAT | SEQ ID NO: 228 |
| SARS-O-R | | | GTATGAATTCATCCATAGCGAG | SEQ ID NO: 229 |
| SARS-S-R | | | GGGAATTTAGTAGCATTAAAAACC | SEQ ID NO: 230 |
| SARS-N-R | | | GTTGAATCAGCAGAAGCTCC | SEQ ID NO: 231 |
| MERS-O-R | | | TAATGAAAACATCACTATCAAAAGAT | SEQ ID NO: 232 |
| MERS-S-R | | | GGAGGTGTGCCAGACAGA | SEQ ID NO: 233 |
| MERS-N-R | | | ATTGGACCAGGCTGAACAC | SEQ ID NO: 234 |
| PCR for RNA substrate synthesis | | | | |
| T7-SARS2-O-F | | | TAATACGACTCACTATAGGGCTTTGGGCTAAGCGCAA | SEQ ID NO: 235 |
| T7-SARS2-S-F | | | TAATACGACTCACTATAGGAAACAGGGTAATTTCAAAAATCT | SEQ ID NO: 236 |
| T7-SARS2-N-F | | | TAATACGACTCACTATAGGCTTCTAAGAAGCCTCGGC | SEQ ID NO: 237 |
| RT-LAMP | | | | |
| N-Mam F3 | | | AACACAAGCTTTCGGCAG | SEQ ID NO: 238 |
| N-Mam B3 | | | GAAATTTGGATCTTTGTCATCC | SEQ ID NO: 239 |
| N-Mam FIP | | | TGCGGCCAATGTTTGTAATCAGCCAAGGAAATTTTGGGGAC | SEQ ID NO: 240 |

TABLE 1-continued

| gRNA | PAM | Spacer (5'-3') | IDT oligo sequence (5'-3') | SEQ ID NO: |
|---|---|---|---|---|
| N-Mam BIP | | | CGCATTGGCATGGAAGTCACTTTGATGGCACCTGTGTAG | SEQ ID NO: 241 |
| N-Mam LF | | | TTCCTTGTCTGATTAGTTC | SEQ ID NO: 242 |
| N-Mam LB | | | ACCTTCGGGAACGTGGTT | SEQ ID NO: 243 |
| S2 F3 | | | TTAATTTAGTGCGTGATCTCC | SEQ ID NO: 244 |
| S2 B3 | | | AGCATCTGTAATGGTTCCAT | SEQ ID NO: 245 |
| S2 FIP (SetA) not selected | | | GCAAGTAAAGTTTGAAACCTAGCTCAGGGTTTTTCGGCT | SEQ ID NO: 246 |
| S2 FIP (SetB) not selected | | | AAGCAAGTAAAGTTTGAAACCTACTCAGGGTTTTTCGGCT | SEQ ID NO: 247 |
| S2 FIP (SetC) selected | | | TGTAAAGCAAGTAAAGTTTGAAACCCTCAGGGTTTTTCGGCT | SEQ ID NO: 248 |
| S2 BIP | | | TGGACAGCTGGTGCTAATAGAAAAGTCCTAGGTTGAAG | SEQ ID NO: 249 |
| S2 LF | | | GGCAAATCTACCAATGGTTCTAA | SEQ ID NO: 250 |
| S2 LB | | | GCAGCTTATTATGTGGGTTAT | SEQ ID NO: 251 |
| S2 Swarm F1c | | | TGTAAAGCAAGTAAAGTTTGAAACC | SEQ ID NO: 252 |
| S2 Swarm B1c | | | TGGACAGCTGGTGCT | SEQ ID NO: 253 |
| S2 StemF_in | | | AGAAGTTATTTGACTCCTGGTG | SEQ ID NO: 254 |
| S2 StemB_in | | | CCTGAAGAAGAATCACCAGG | SEQ ID NO: 255 |
| S2 StemF_out | | | CACCAGGAGTCAAATAACTTCT | SEQ ID NO: 256 |
| S2 StemB_out | | | ACTCCTGGTGATTCTTCTTCA | SEQ ID NO: 257 |
| | | | Reporter | |
| Custom ssDNA FQ reporter | | | /56-FAM/TTATT/3IABKFQ/ | |
| Custom ssDNA biotin reporter | | | /56-FAM/TTATTATT/3Bio/ | |

The inventions illustratively described herein may suitably be practiced in the absence of any element or elements, limitation or limitations, not specifically disclosed herein. Thus, for example, the terms “comprising”, “including”, “containing”, etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and sub-generic groupings falling within the generic disclosure also form part of the invention.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. A method for detecting the presence or amount of a target nucleic acid in a sample, comprising:

(a) amplifying the target nucleic acid using loop-mediated isothermal amplification (LAMP) to obtain an amplicon thereof;

(b) contacting the target nucleic acid and the amplicon with a nucleic acid detection system, said nucleic acid detection system comprising (1) at least one Cas12a enzyme, (2) at least one gRNA, and (3) at least one detection reagent, wherein the at least one gRNA comprises at least two different gRNAs that bind to two different, non-overlapping target sequences in the same target nucleic acid;

wherein the at least one gRNA comprises a 5'-terminal extension of at least 2, or at least one chemical modification of a nucleotide selected from 2'-O-methyl RNA, 2'-fluoro base nucleotide and phosphorothioate linkage, or the at least one gRNA is a DNA-RNA hybrid and comprises at least 1 DNA nucleotide, in the spacer sequence, the rest being RNA nucleotides;

wherein the Cas12a enzyme is an engineered AsCas12a variant that retains Cas12a functionality and comprises the amino acid sequence set forth in SEQ ID NO:1; and wherein said at least one gRNA comprises a spacer sequence of at least 20 nucleotides in length that specifically recognizes and binds a target sequence in the target nucleic acid, under conditions that allow binding of the complex of the Cas12a enzyme and the at least two different gRNAs to the target sequence and resultant activation of the Cas12a enzyme;

wherein the activated Cas12a enzyme generates, by interaction with the at least one detection reagent, a detectable, and optionally quantifiable, signal; and (c) detecting said detectable signal.

2. The method of claim 1, wherein the target nucleic acid is DNA, RNA or a viral nucleic acid.

3. The method of claim 1, wherein the amplicon is a DNA amplicon.

4. The method of claim 1, wherein the LAMP method comprises the use of two internal primers (FIP and BIP), two displacement primers (F3 and B3) and optionally two loop primers (LF and LB).

5. The method of claim 4, wherein the LAMP method further comprises the use of:

at least one swarm primer set or at least one stem primer set; and/or

3' or 5' truncated internal primers that differ from the internal primers by a truncation of one nucleotide at the 3' or 5' end of their target-complementary sequence; and/or a high fidelity DNA polymerase with a proofreading capability.

6. The method of claim 1, wherein amplification is carried out: (1) in the presence of glycine, taurine or guanidine; and/or (2) at a temperature of 60 to 65° C.; and/or (3) for a time period of 10 to 60 minutes.

7. The method of claim 4, wherein the target nucleic acid is SARS-CoV-2 RNA or a DNA amplicon thereof and the first internal primer (FIP) has the nucleotide sequence set forth in SEQ ID NO:4, the second internal primer (BIP) has the nucleotide sequence set forth in SEQ ID NO:5, the first displacement primer (F3) has the nucleotide sequence set forth in SEQ ID NO:6, and/or the second displacement primer (B3) has the nucleotide sequence set forth in SEQ ID NO:7.

8. The method of claim 4, wherein the target nucleic acid is SARS-CoV-2 RNA or a DNA amplicon thereof and the LAMP method comprises the use of loop primers, wherein the first loop primer (LF) has the nucleotide sequence set forth in SEQ ID NO: 8 and/or the second loop primer (LB) has the nucleotide sequence set forth in SEQ ID NO:9.

9. The method of claim 4, wherein the target nucleic acid is SARS-CoV-2 RNA or a DNA amplicon thereof and the LAMP method comprises the use of swarm primers, wherein the first swarm primer has the nucleotide sequence set forth in SEQ ID NO:10 and/or the second swarm primer has the nucleotide sequence set forth in SEQ ID NO:11.

10. The method of claim 1, wherein the Cas12a enzyme consists of the amino acid sequence set forth in SEQ ID NO:1 (enAsCas12a).

11. The method of claim 1, wherein the target nucleic acid is SARS-CoV-2 RNA or a DNA amplicon thereof and said spacer sequence of the at least one gRNA comprises or consists of the nucleotide sequence ACUCCUG-GUGAUUCUUCUUC (SEQ ID NO:12), AAACC-UAGUGAUGUUAAUAC (SEQ ID NO:13) or a variant thereof that shares at least 85% sequence identity with SEQ ID NO:12 or 13.

12. The method of claim 1, wherein the target nucleic acid is SARS-CoV-2 RNA or a DNA amplicon thereof and the SARS-COV-2 target sequence comprises or consists of the nucleotide sequence GAAGAAGAAUCACCAGGAGU (SEQ ID NO: 14) or GUAUUAACAUCACUAGGUUU (SEQ ID NO:15) or a variant thereof that shares at least 85% sequence identity with SEQ ID NO:14 or 15.

13. The method of claim 1, wherein the target nucleic acid is SARS-CoV-2 RNA or a DNA amplicon thereof and the first gRNA comprises a spacer sequence comprising or consisting of the nucleotide sequence ACUCCUG-GUGAUUCUUCUUC (SEQ ID NO: 12) or a variant thereof having at least 85% sequence identity to SEQ ID NO:12, and the second gRNA comprises a spacer sequence comprising or consisting of the nucleotide sequence AAAC-CUAGUGAUGUUAAUAC (SEQ ID NO:13) or a variant thereof having at least 85% sequence identity to SEQ ID NO: 13.

14. The method of claim 1, wherein the at least one gRNA comprises:

a 5'-terminal extension of at least 2, or at least one chemical modification of a nucleotide selected from 2'-O-methyl RNA, 2'-fluoro base nucleotide and phosphorothioate linkage.

15. The method of claim 1, wherein the at least one gRNA is a DNA-RNA hybrid and comprises at least 1 DNA nucleotide, in the spacer sequence, the rest being RNA nucleotides, wherein the DNA nucleotides are located (1) at the 3' terminus of the spacer sequence, and/or (2) at position 1 and/or (3) at any one of positions 2-12 of the spacer sequence.

16. The method of claim 1, wherein the detection step (b) is conducted at a temperature of at least 37° C.

17. The method of claim 1, wherein the detection reagent is an oligonucleotide that upon cleavage by the activated Cas12a enzyme generates a detectable signal, wherein the oligonucleotide (1) is an ssDNA molecule; and/or (2) comprises a donor fluorophore/acceptor or fluorophore/quencher pair, wherein upon cleavage of the oligonucleotide, the (donor) fluorophore generates a detectable signal.

18. The method of claim 1, wherein step (a) is performed in a reaction vessel, and the contacting of step (b) comprises adding the nucleic acid detection system into the reaction vessel.

19. The method of claim 18, wherein steps (a) and (b) are performed at substantially the same temperature, preferably at 60° C. or 63° C.

* * * * *